US012767637B2

(12) United States Patent
Neamati et al.

(10) Patent No.: US 12,767,637 B2
(45) Date of Patent: Oct. 20, 2026

(54) MITOCHONDRIAL TARGETING COMPOUNDS FOR THE TREATMENT OF ASSOCIATED DISEASES

(71) Applicant: The Regents of the University of Michigan, Ann Arbor, MI (US)

(72) Inventors: Nouri Neamati, Ann Arbor, MI (US); Ding Xue, Ann Arbor, MI (US); Yibin Xu, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 802 days.

(21) Appl. No.: 17/927,094

(22) PCT Filed: May 25, 2021

(86) PCT No.: PCT/US2021/034052
§ 371 (c)(1),
(2) Date: Nov. 22, 2022

(87) PCT Pub. No.: WO2021/242753
PCT Pub. Date: Dec. 2, 2021

(65) Prior Publication Data

US 2023/0212122 A1 Jul. 6, 2023

Related U.S. Application Data

(60) Provisional application No. 63/029,979, filed on May 26, 2020.

(51) Int. Cl.

| | |
|---|---|
| ***C07D 207/00*** | (2006.01) |
| ***A61K 31/395*** | (2006.01) |
| ***A61K 31/40*** | (2006.01) |
| ***A61P 35/00*** | (2006.01) |
| ***C07C 311/21*** | (2006.01) |
| ***C07D 207/48*** | (2006.01) |
| ***C07D 211/96*** | (2006.01) |
| ***C07D 401/04*** | (2006.01) |
| ***C07D 401/06*** | (2006.01) |
| ***C07D 401/12*** | (2006.01) |
| ***C07D 413/04*** | (2006.01) |
| ***C07D 413/14*** | (2006.01) |

(52) U.S. Cl.
CPC .......... *C07D 211/96* (2013.01); *C07C 311/21* (2013.01); *C07D 401/04* (2013.01); *C07D 401/06* (2013.01); *C07D 401/12* (2013.01); *C07D 413/04* (2013.01); *C07D 413/14* (2013.01)

(58) Field of Classification Search
CPC .. C07D 207/00; C07D 207/48; A61K 31/395; A61K 31/40; A61P 35/00
See application file for complete search history.

(56) References Cited

U.S. PATENT DOCUMENTS

| | | | |
|---|---|---|---|
| 3,867,391 A | 2/1975 | Holland | |
| 6,143,776 A | 11/2000 | Erlanson | |
| 8,642,660 B2 * | 2/2014 | Goldfarb | A61K 31/122 514/18.9 |
| 8,722,742 B2 * | 5/2014 | Reyes | A61K 31/16 514/315 |
| 11,241,427 B2 * | 2/2022 | Koos | A61K 31/198 |
| 2010/0204226 A1 | 8/2010 | Bembenek et al. | |
| 2011/0065686 A1 | 3/2011 | Mazola Reyes et al. | |
| 2011/0237559 A1 | 9/2011 | Boyle et al. | |
| 2014/0179736 A1 | 6/2014 | Schwab et al. | |
| 2017/0073331 A1 | 3/2017 | Kim et al. | |
| 2018/0093953 A1 | 4/2018 | Kim et al. | |
| 2020/0131119 A1 | 4/2020 | Nuri et al. | |

FOREIGN PATENT DOCUMENTS

| | | |
|---|---|---|
| CA | 2394095 | 6/2011 |
| WO | 2018/192461 | 10/2018 |

OTHER PUBLICATIONS

Ryan et al. (Chemical Biology & Drug Design (2017), 90(6), 1190-1205). Abstract.*
Extended Search Report, EP Patent Application No. 21812275.2, dated Aug. 12, 2024, 8 pages.
International Search Report and Written Opinion for PCT/US2021/034052. Mailed Nov. 5, 2021. 16 pages.
Beier et al., Essential role of mitochondrial energy metabolism in Foxp3+ T-regulatory cell function and allograft survival. FASEB J. Jun. 2015;29(6):2315-26.
Birsoy et al., An Essential Role of the Mitochondrial Electron Transport Chain in Cell Proliferation Is to Enable Aspartate Synthesis. Cell. Jul. 30, 2015;162(3):540-51.
Birsoy et al., Metabolic determinants of cancer cell sensitivity to glucose limitation and biguanides. Nature. Apr. 3, 2014;508(7494):108-12.
Bridges et al., Effects of metformin and other biguanides on oxidative phosphorylation in mitochondria. Biochem J. Sep. 15, 2014;462(3):475-87.
Diskin et al., Metabolic Modulation in Macrophage Effector Function. Front Immunol. Feb. 19, 2018;9:270. 17 pages.
Dykens et al., Biguanide-induced mitochondrial dysfunction yields increased lactate production and cytotoxicity of aerobically-poised HepG2 cells and human hepatocytes in vitro. Toxicol Appl Pharmacol. Dec. 1, 2008;233(2):203-10.
Farge et al., Chemotherapy-Resistant Human Acute Myeloid Leukemia Cells Are Not Enriched for Leukemic Stem Cells but Require Oxidative Metabolism. Cancer Discov. Jul. 2017;7(7):716-735.

(Continued)

*Primary Examiner* — Bruck Kifle
(74) *Attorney, Agent, or Firm* — Casimir Jones, S.C.; Robert A. Goetz

(57) ABSTRACT

Mitochondrial targeting compounds for the treatment of cancer and other disorders associated with mitochondrial function, including diabetes, autoimmune diseases, inflammatory diseases, cardiovascular diseases and neurodegenerative diseases and their preparation. The present invention is also directed to the pharmaceutical compositions and treatment methods, prodrugs based on those compounds and the use thereof.

2 Claims, No Drawings

(56) References Cited

OTHER PUBLICATIONS

Gatza et al., Manipulating the bioenergetics of alloreactive T cells causes their selective apoptosis and arrests graft-versus-host disease. Sci Transl Med. Jan. 26, 2011;3(67):67ra8. 16 pages.
Glick et al., Anaplerotic metabolism of alloreactive T cells provides a metabolic approach to treat graft-versus-host disease. J Pharmacol Exp Ther. Nov. 2014;351(2):298-307.
Hu et al., Heterogeneity of tumor-induced gene expression changes in the human metabolic network. Nat Biotechnol. Jun. 2013;31(6):522-9.
Kumar et al., The Nature of Myeloid-Derived Suppressor Cells in the Tumor Microenvironment. Trends Immunol. Mar. 2016;37(3):208-220.
Kuntz et al., Targeting mitochondrial oxidative phosphorylation eradicates therapy-resistant chronic myeloid leukemia stem cells. Nat Med. Oct. 2017;23(10):1234-1240.
Lee et al., MYC and MCL1 Cooperatively Promote Chemotherapy-Resistant Breast Cancer Stem Cells via Regulation of Mitochondrial Oxidative Phosphorylation. Cell Metab. Oct. 3, 2017;26(4):633-647.e7.
Lissanu Deribe et al., Mutations in the SWI/SNF complex induce a targetable dependence on oxidative phosphorylation in lung cancer. Nat Med. Jul. 2018;24(7):1047-1057.
Matsuzaki et al., Selective inhibition of deactivated mitochondrial complex I by biguanides. Biochemistry. Mar. 24, 2015;54(11):2011-21.
Molina et al., An inhibitor of oxidative phosphorylation exploits cancer vulnerability. Nat Med. Jul. 2018;24(7):1036-1046.
Pubchem, SID 384135687, Available date: May 15, 2019 [retrieved on Feb. 9, 2023] Retrieved from the internet <URL: https://pubchem. Ncbi.nlm.nih.gov/substance/384135687> entire document. 5 pages.
Roesch et al., Overcoming intrinsic multidrug resistance in melanoma by blocking the mitochondrial respiratory chain of slow-cycling JARID1B(high) cells. Cancer Cell. Jun. 10, 2013;23(6):811-25.
Salmond. mTOR Regulation of Glycolytic Metabolism in T Cells. Front Cell Dev Biol. Sep. 25, 2018;6:122. 9 pages.
Sancho et al., Hallmarks of cancer stem cell metabolism. Br J Cancer. Jun. 14, 2016;114(12):1305-12.
Shi et al., Gboxin is an oxidative phosphorylation inhibitor that targets glioblastoma. Nature. Mar. 2019;567(7748):341-346.
Sriskanthadevan et al., AML cells have low spare reserve capacity in their respiratory chain that renders them susceptible to oxidative metabolic stress. Blood. Mar. 26, 2015;125(13):2120-30.
Sullivan et al., Supporting Aspartate Biosynthesis Is an Essential Function of Respiration in Proliferating Cells. Cell. Jul. 30, 2015;162(3):552-63.
Vats et al., Oxidative metabolism and PGC-1beta attenuate macrophage-mediated inflammation. Cell Metab. Jul. 2006;4(1):13-24.
Vazquez et al., PGC1α expression defines a subset of human melanoma tumors with increased mitochondrial capacity and resistance to oxidative stress. Cancer Cell. Mar. 18, 2013;23(3):287-301.
Viale et al., Oncogene ablation-resistant pancreatic cancer cells depend on mitochondrial function. Nature. Oct. 30, 2014;514(7524):628-32.
Wahl et al., Characterization of the metabolic phenotype of chronically activated lymphocytes. Lupus. Nov. 2010; 19(13):1492-501.
Wheaton et al., Metformin inhibits mitochondrial complex I of cancer cells to reduce tumorigenesis. Elife. May 13, 2014;3:e02242. 18 pages.
Zhang et al., Metabolic reprogramming toward oxidative phosphorylation identifies a therapeutic target for mantle cell lymphoma. Sci Transl Med. May 8, 2019;11(491):eaau1167. 17 pages.

* cited by examiner

MITOCHONDRIAL TARGETING COMPOUNDS FOR THE TREATMENT OF ASSOCIATED DISEASES

CROSS-REFERENCE TO RELATED APPLICATION

The present application claims priority to U.S. Provisional Patent Application No 63/029,979 filed May 26, 2020, which is hereby incorporated by reference in its entirety.

STATEMENT REGARDING FEDERALLY SPONSORED RESEARCH

This invention was made with government support under Grant No. CA188252 awarded by the National Institutes of Health. The government has certain rights in the invention.

FIELD OF THE INVENTION

The present invention is directed to the use and preparation of a series of mitochondrial targeted compounds inhibiting oxidative phosphorylation for the treatment of cancer and disorders associated with mitochondrial function. More specifically, the present invention is directed to a series of compounds for the treatment of cancers such as brain cancer, pancreatic cancer, ovarian cancer, renal cancer, breast cancer, prostate cancer, lung cancer, leukemia and lymphoma, as well as other disorders, such as diabetes, autoimmune diseases, inflammatory diseases, cardiovascular diseases and neurodegenerative diseases. The present invention is also directed to the pharmaceutical compositions and treatment methods based on these compounds.

BACKGROUND OF THE INVENTION

Metabolic reprogramming is an emerging hallmark of cancer and draws extensive attention in the field of drug discovery and pathological studies. Ever since the discovery of Warburg effect, researchers have been focusing on the glycolysis pathways, the most effective way to generate energy for cancer cells. However, recent studies highlight that tumors rely on oxidative phosphorylation (OXPHOS) for bioenergetics[1-3] and, more importantly, biomass production[4, 5], which is essential for enhanced tumor growth.

Consisting of over 90 proteins, OXPHOS complexes form one of the most important machinery in the mitochondria, linking the TCA cycle to the production of ATP. It is comprised of five complexes (Complex I to V). The complexes I-IV, also called the electron transport chain (ETC), transfer electrons from donors generated by the TCA cycle or fatty acid oxidation to oxygen. In the meantime, the energy released from the oxidation of NADH and $FADH_2$ is used to pump protons across the inner membrane of the mitochondrion. This causes protons to build up in the intermembrane space and generates an electrochemical gradient across the membrane. The energy stored in this electrochemical gradient is then used by ATP synthase (complex V) to produce ATP. OXPHOS defect not only causes reduction in ATP production but also decreases the production of aspartate[4], a limiting metabolite for cell proliferation.

OXPHOS is required for cancer cells to strive. Subpopulations of tumor cells are dependent on OXPHOS including, for example, glycolysis-deficient cells[6] and SWI SNF complex mutated cells in lung cancer[7]. In addition, exacerbated OXPHOS dependency is frequently characterized by cancer stem cells[8 9], as well as KRAS ablation-resistant cells in pancreatic cancers[10]. Importantly, OXPHOS inhibition is promising in overcoming resistance against chemotherapy[11, 12 13] or tyrosine kinase inhibitors[14]. Thus, inhibition of OXPHOS might be a promising therapeutic strategy to treat various cancers.

Most OXPHOS inhibitors, including biguanides, oligomycin, and other toxins have been known for decades. As the most widely prescribed drug to treat patients with type II diabetes, metformin's mechanism of action remains partly unknown despite its use for over 60 years. Metformin and other biguanides are reported to exert their function as OXPHOS complex I inhibitors, leading to reduce tumorigenesis[15-18]. However, due to the inadequate potency in cancer cells, the usage of biguanides is largely limited. For other OXPHOS inhibitors, the unspecificity and poor drug-like properties blocked their potential usage in cancer treatment. Gboxin, an OXPHOS inhibitor, was reported to show specific inhibition of mouse and human glioblastoma cells through the depletion of the activity of FOF1ATP synthase[19]. However, it is still unclear that if this compound can cross blood-brain barrier hindering its path toward clinical trial. Other therapeutic compounds such as ME344, lonidamine and carboxyamidotriazoles are also claimed as OXPHOS inhibitors, however, all of them possess other primary drug targets and are considered as non-specific OXPHOS inhibitors. Recently, a potent and specific OXPHOS inhibitor, IACS-010759 (IACS) was reported and is currently being evaluated in phase I clinical trials. IACS targets OXPHOS complex I and shows significant efficacy in brain cancer and acute myeloid leukemia (AML) mouse xenografts[20]. Phase I trial of IACS indicated that it is well tolerated with preliminary evidence of antitumor activity. Loss of ENO1 or mutations in SMARCA4, which result in high dependency on OXPHOS, are used as predictive biomarkers of sensitivity to OXPHOS inhibition. In addition, the clinical usage of IACS in ibrutinib-resistant MCL will be evaluated. Overall, the discovery and development of OXPHOS inhibitors is a largely unexplored but promising field in cancer treatment.

Tumor progression is profoundly influenced by the interaction of cancer cells with their surrounding microenvironment, especially the infiltrating immune cells. The differentiation and functions of effector CD8+ T cells, Th1, Th2, and Th17 CD4+ T cells rely on the engagement of aerobic glycolysis[21], and antitumor M1 macrophages[22] also rely on glycolysis. Inhibition of OXPHOS leads to the upregulation of lactate secretion, leading to upregulation of glycolysis. It might potentially lead to the activation of cytotoxic T cells and M1 macrophages, resulting in improved antitumor engagement of immune cells. On the other hand, immunosuppressive M2 macrophages and other protumor cells, including regulatory T cells and myeloid-derived suppressor cells[21-23], depend on various mitochondrial functions including OXPHOS. Thus, in addition to direct targeting of tumor cells, inhibition of OXPHOS might indirectly boost anti-tumor effect through the modulation of tumor microenvironments.

Autoimmune and inflammatory diseases are diverse conditions caused by inappropriate and prolonged activation of immune cells with associated ongoing production of inflammatory mediators that cause tissue damage. Immune cell activation and differentiation occurs concurrently with metabolic reprogramming. This ensures activated cells to generate the energy and substrates necessary to perform their specified functions. It's reported that alternatively activated M2 macrophages and Tregs rely on oxidative phosphorylation to provide their energy[24, 25]. In a mouse model of bone marrow allotransplant, proliferating bone marrow cells reconstituting the immune system of a lethally irradiated syngeneic host underwent a dramatically different metabolic process than pathogenic cells, with healthy cells relying more on glycolysis than oxidative phosphorylation[26]. OXPHOS inhibitors have demonstrated promise as a metabolic therapy for graft-versus-host disease (GVHD)[26, 27]. Similar to pathogenic T cells in GVHD, and in contrast with the lymphocytes activated under normal conditions or in the case of solid organ transplant, CD4 T cells in systemic lupus erythematosus (SLE) meet their energetic needs mostly through oxidative phosphorylation[28]. Targeting metabolic pathways through inhibition of OXPHOS could lead to selective regulation of immune system to fight various diseases.

Disclosed herein are new compounds selectively inhibiting complex I of the mitochondrial electron transport chain to disrupt OXPHOS. The hit compound is selected from a phenotypical screening of a library of 24,000 compounds. These compounds show profound anti-tumor effect as a single agent and have synergistic effect with radiation and select FDA-approved drugs as well as drugs under clinical trials. Therefore, OXPHOS selective drugs can be used as single agent and in combination to treat various cancers as well as other diseases related to OXPHOS and immune modulation.

SUMMARY OF THE INVENTION

Disclosed herein is a series of novel compounds as mitochondrial modulators that can be used as treatment of diseases associated with mitochondrial functions, including, but not limited to, cancer, inflammatory disease and diabetes.

Accordingly, in one aspect, the present invention features a series of compounds of Formula 1.

Formula 1

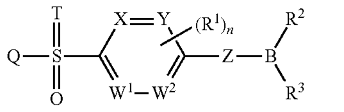

Such that Q is

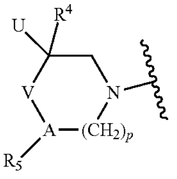

or

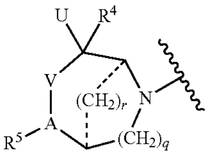

or

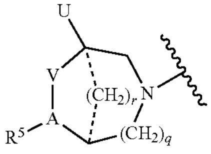

or

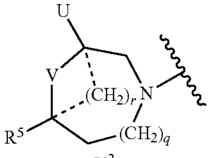

or

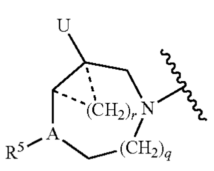

or

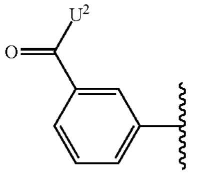

Such that n=0-4;

p=0-2;

q=0 or 1;

r=1 or 2;

A is CH, or when V is $CR^6R^7$ and p is 2 or q is 1, may also be $NR^8$, O or S;

T is =O or =$NR^6$;

U is $U^1$—$U^2$,

B is N or $CR^8$

Wherein $U^1$ is a bond, C=O or $SO_2$;

$U^2$ is $R^9$, $OR^{10}$, $NHR^{11}$, $NR^{11}R^{12}$, $NR^{11}$-(4-6-ring azacycloalkyl), 1-piperazinyl, 1-homopiperazinyl, "C"$_{7-10}$ N-linked-1,x'-diaza-(spiro/fused/bridged)bicycloalkyl, where x' is 4 or greater, wherein up to four carbon atoms of $U^2$ may be independently substituted with $R^{13}$, and each of the remaining N atom may be substituted with $R^{14}$;

V is $CR^6R^7$, O, S or $NR^8$.

$W^1$ and $W^2$ are independently selected from CH and N, or the two may be taken together as S or $NR^8$;

X and Y are independently selected from CH and N

Z is selected from a direct bond, —N($R^{16}$)—, —N($R^{16}$)C(O)—, —O—, —C(O)—, —C(S)—, —S(O)$_t$— (where t is 0, 1 or 2), —S(O)(N($R^{16}$))— and P(O);

$R^1$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^2$ and $R^3$ are independently hydrogen, $C_1$-$C_8$ alkyl, $C_3$-$C_8$ carbocyclyl, $C_3$-$C_8$ heterocyclyl, or aryl; or $R^2$ and $R^3$, together with the nitrogen to which they are joined form $C_3$-$C_8$ heterocyclyl, which for the 6 and 7 membered rings may include an extra heteroatom chosen from O, S, SO, $SO_2$ and $NR^8$, and wherein up to four carbon of $R^2$ and $R^3$ may be independently substituted with $R^{13}$;

$R^4$ is selected from hydrogen, cyano, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, carboxy, amino, acylamino, aryloxy, heteroaryloxy and $C_1$-$C_4$ alkoxy;

$R^5$ is selected from hydrogen, halogen, cyano, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^6$ and $R^7$ are independently hydrogen or lower $C_{1-4}$ alkyl, or, if $R^4$, is not H, halogen, or OH or lower $C_{1-4}$ alkoxy, or $R^6$ and $R^7$ taken together may be oxo or lower $C_{1-4}$ alkylidene;

$R_8$ is selected from hydrogen, cyano, $C_1$-$C_4$ alkyl, $C_3$-$C_8$ cycloalkyl, $C_3$-$C_8$ heterocycloalkyl, aryl, heteroaryl, aralkyl, alkoxycarbonyl, carbamoyl, acyl and sulfonyl.

$R^9$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{10}$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{11}$ and $R^{12}$ are independently hydrogen, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, arylalkyl or heteroarylalkyl; or $R^{11}$ and $R^{12}$, together with the nitrogen to which they are joined form $C_3$-$C_{10}$ heterocyclyl, which for the 6 and 7 membered rings may include an extra heteroatom chosen from O, S, SO, $SO_2$ and $NR^8$, and wherein up to four carbon of $R^{11}$ and $R^{12}$ may be independently substituted with $R^{13}$;

$R^{13}$ is selected from hydrogen, halogen, cyano, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^{14}$ is H, lower $C_{1-4}$ alkyl, C(=O)-lower $C_{1-4}$ alkyl, C(=O)-lower $C_{1-4}$ alkoxy, $S(=O)_2$-lower $C_{1-4}$ alkyl, 5-tetrazyl, 5-oxo-1,24-oxadiazol-3-yl, isoxazol-5-yl, 1,2,4-oxadiazol-5-yl, 1,2,4-oxadiazol-3-yl, phenyl, 2/3/4-pyridinyl, 2/4/5-pyrimidyl, pyrazinyl, 3/4-pyridazinyl, wherein any of the aromatic groups may be substituted with one $R^{15}$.

$R^{15}$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, $R^{16}$ is selected from hydrogen, $C_1$-$C_8$ alkyl, $C_3$-$C_8$ carbocyclyl, $C_3$-$C_8$ heterocyclyl, aryl, heteroaryl, arylalkyl and heteroarylalkyl.

In one embodiment, the invention features compounds of Formula 1-1.

Formula 1-1

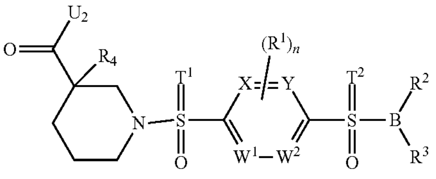

Such that n=0-4;

$T^1$ and $T^2$ are independently =O or =$NR^6$;

$U^2$ is $R^9$, $OR^{10}$, $NHR^{11}$, $NR^{11}R^{12}$, $NR^{11}$-(4-6-ring azacycloalkyl), 1-piperazinyl, 1-homopiperazinyl, "C"$_{7-10}$ N-linked-1,x'-diaza-(spiro/fused/bridged)bicycloalkyl, where x' is 4 or greater, wherein up to four carbon atoms of $U^2$ may be independently substituted with $R^{13}$, and each of the remaining N atom may be substituted with $R^{14}$;

$W^1$ and $W^2$ are independently selected from CH and N, or the two may be taken together as S or $NR^8$;

X and Y are independently selected from CH and N;

B is N or $CR^8$;

$R^1$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^2$ and $R^3$ are independently hydrogen, $C_1$-$C_8$ alkyl, $C_3$-$C_8$ carbocyclyl, $C_3$-$C_8$ heterocyclyl, or aryl; or $R^2$ and $R^3$, together with the nitrogen to which they are joined form $C_3$-$C_8$ heterocyclyl, which for the 6 and 7 membered rings may include an extra heteroatom chosen from O, S, SO, $SO_2$ and $NR^8$, and wherein up to four carbon of $R^2$ and $R^3$ may be independently substituted with $R^{13}$;

$R^4$ is selected from hydrogen, cyano, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, carboxy, amino, acylamino, aryloxy, heteroaryloxy and $C_1$-$C_4$ alkoxy;

$R^6$ is hydrogen or lower $C_{1-4}$ alkyl or OH or lower $C_{1-4}$ alkoxy;

$R_8$ is selected from hydrogen, cyano, $C_1$-$C_4$ alkyl, $C_3$-$C_8$ cycloalkyl, $C_3$-$C_8$ heterocycloalkyl, aryl, heteroaryl, aralkyl, alkoxycarbonyl, carbamoyl, acyl and sulfonyl.

$R^9$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{10}$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{11}$ and $R^{12}$ are independently hydrogen, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, arylalkyl or heteroarylalkyl; or $R^{11}$ and $R^{12}$, together with the nitrogen to which they are joined form $C_3$-$C_{10}$ heterocyclyl, which for the 6 and 7 membered rings may include an extra heteroatom chosen from O, S, SO, $SO_2$ and $NR^8$, and wherein up to four carbon of $R^{11}$ and $R^{12}$ may be independently substituted with $R^{13}$;

$R^{13}$ is selected from hydrogen, halogen, cyano, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^{14}$ is H, lower $C_{1-4}$ alkyl, C(=O)-lower $C_{1-4}$ alkyl, C(=O)-lower $C_{1-4}$ alkoxy, $S(=O)_2$-lower $C_{1-4}$ alkyl, 5-tetrazyl, 5-oxo-1,24-oxadiazol-3-yl, isoxazol-5-yl, 1,2,4-oxadiazol-5-yl, 1,2,4-oxadiazol-3-yl, phenyl, 2/3/4-pyridinyl, 2/4/5-pyrimidyl, pyrazinyl, 3/4-pyridazinyl, wherein any of the aromatic groups may be substituted with one $R^{15}$.

$R^{15}$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy.

In a further embodiment, the invention features compounds of Formula 1-1-1.

Formula 1-1-1

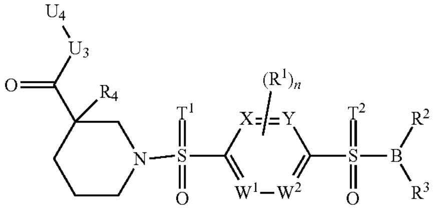

Such that n=0-4;

$T^1$ and $T^2$ are independently =O or =$NR^6$;

$U^3$ is selected from the following groups:
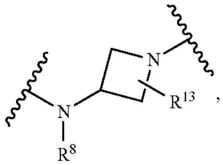, 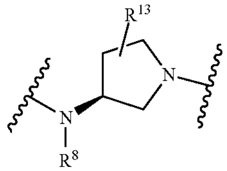, 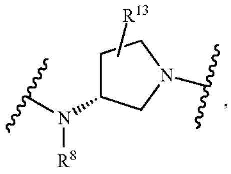, 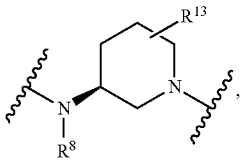, 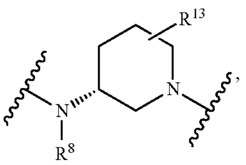, 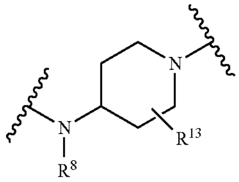, 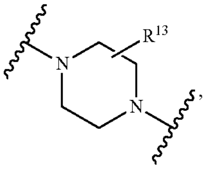, 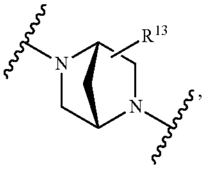, 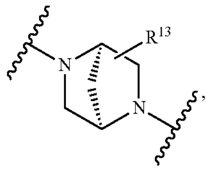, 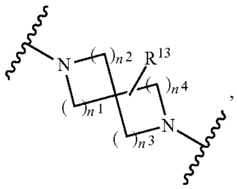, 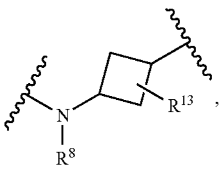, 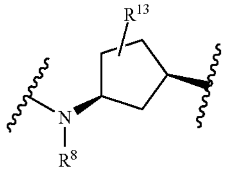, 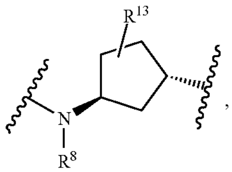, 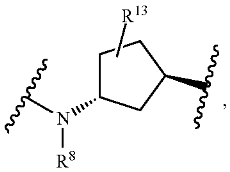, 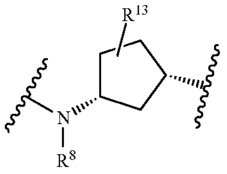, 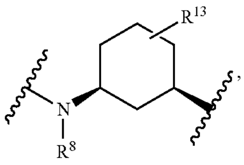, 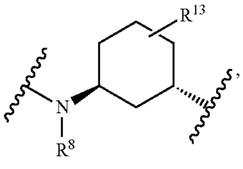, 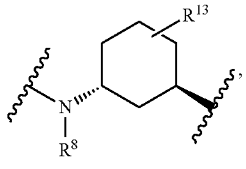,
-continued
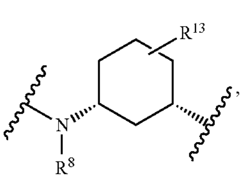, 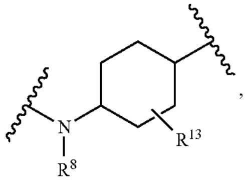, 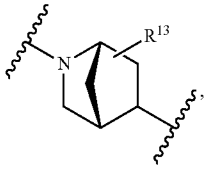, 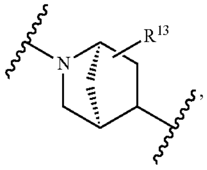, 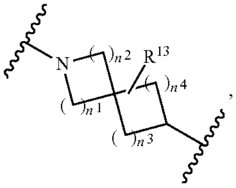, 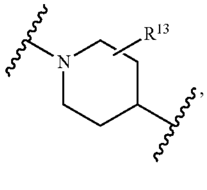, 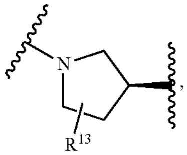, 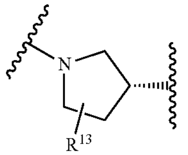 and
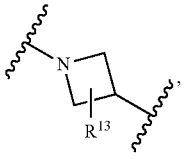,
wherein either side of the can be attached to the carbonyl of the core structure, and the other nitrogen attached to $U^4$, wherein $n^1$, $n^2$, $n^3$ and $n^4$ are independently 0, 1, 2 or 3;
Wherein $U^4$ is selected from the following groups:
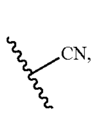 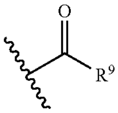, 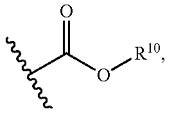
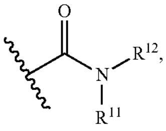 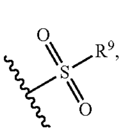 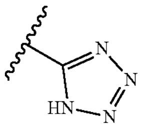,
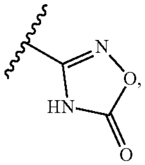 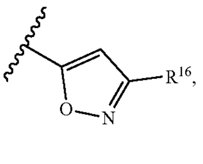
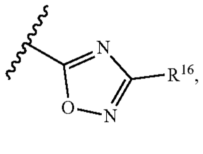 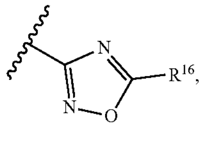

-continued

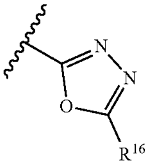, 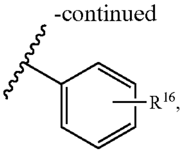 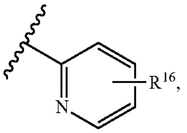

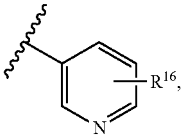 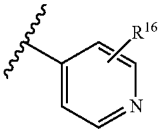,

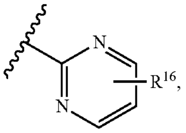 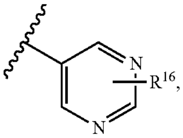

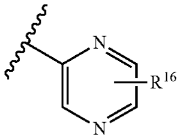 and 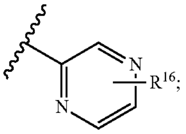

$W^1$ and $W^2$ are independently selected from CH and N, or the two may be taken together as S or $NR^8$;

X and Y are independently selected from CH and N;

B is N or $CR^8$;

$R^1$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^2$ and $R^3$ are independently hydrogen, $C_1$-$C_8$ alkyl, $C_3$-$C_8$ carbocyclyl, $C_3$-$C_8$ heterocyclyl, or aryl; or $R^2$ and $R^3$, together with the nitrogen to which they are joined form $C_3$-$C_8$ heterocyclyl, which for the 6 and 7 membered rings may include an extra heteroatom chosen from O, S, SO, $SO_2$ and $NR^8$, and wherein up to four carbon of $R^2$ and $R^3$ may be independently substituted with $R^{13}$.

$R^4$ is selected from hydrogen, cyano, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, carboxy, amino, acylamino, aryloxy, heteroaryloxy and $C_1$-$C_4$ alkoxy;

$R^6$ is hydrogen or lower $C_{1-4}$ alkyl or OH or lower $C_{1-4}$ alkoxy;

$R_8$ is selected from hydrogen, cyano, $C_1$-$C_4$ alkyl, $C_3$-$C_8$ cycloalkyl, $C_3$-$C_8$ heterocycloalkyl, aryl, heteroaryl, aralkyl, alkoxycarbonyl, carbamoyl, acyl and sulfonyl.

$R^9$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{10}$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{11}$ and $R^{12}$ are independently hydrogen, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, arylalkyl or heteroarylalkyl; or $R^{11}$ and $R^{12}$, together with the nitrogen to which they are joined form $C_3$-$C_{10}$ heterocyclyl, which for the 6 and 7 membered rings may include an extra heteroatom chosen from O, S, SO, $SO_2$ and $NR^8$, and wherein up to four carbon of $R^{11}$ and $R^{12}$ may be independently substituted with $R^{13}$;

$R^{13}$ is selected from hydrogen, halogen, cyano, $C_1$-$C_4$ alkyl, $C_1$-$C_4$ heteroalkyl, $C_1$-$C_4$ haloalkyl, aryl, heteroaryl, hydroxy, $C_1$-$C_4$ alkoxy, carboxy and amino;

$R^{16}$ is selected from hydrogen, halogen, cyano, nitro, $C_1$-$C_4$ alkyl, $C_1$-$C_4$ heteroalkyl, $C_1$-$C_4$haloalkyl, hydroxy, carboxy, amino and $C_1$-$C_4$ alkoxy.

In another further embodiment, the invention features compounds of Formula 1-1-2.

Formula 1-1-2

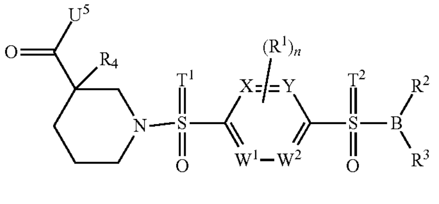

Such that n=0-4;

$T^1$ and $T^2$ are independently =O or =$NR^6$;

$U^5$ is selected from the following groups:

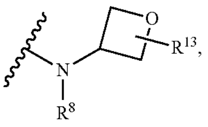 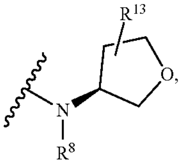

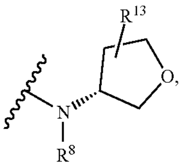 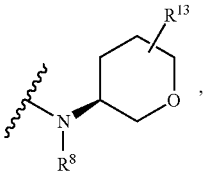

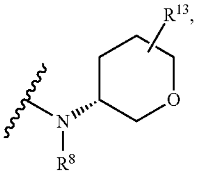 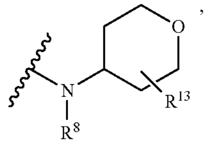

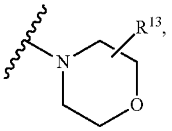 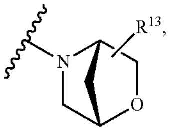 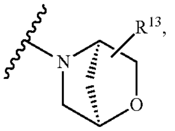

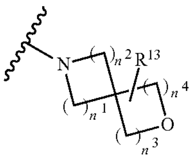 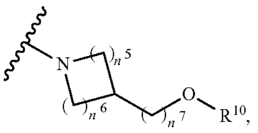

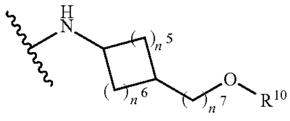 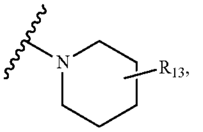

-continued

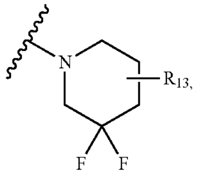
,
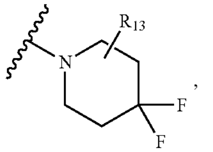
,
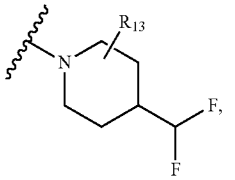
,
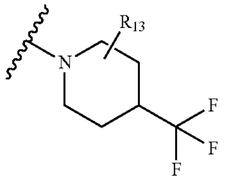

wherein $n^1$, $n^2$, $n^3$, $n^4$ and $n^7$ are independently 0, 1, 2 or 3, $n^5$ and $n^6$ are independently 1, 2 or 3;

- $W^1$ and $W^2$ are independently selected from CH and N, or the two may be taken together as S or $NR^8$;
- X and Y are independently selected from CH and N;
- B is N or $CR^8$;
- $R^1$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;
- $R^2$ and $R^3$ are independently hydrogen, $C_1$-$C_8$ alkyl, $C_3$-$C_8$ carbocyclyl, $C_3$-$C_8$ heterocyclyl, or aryl; or $R^2$ and $R^3$, together with the nitrogen to which they are joined form $C_3$-$C_8$ heterocyclyl, which for the 6 and 7 membered rings may include an extra heteroatom chosen from O, S, SO, $SO_2$ and $NR^8$, and wherein up to four carbon of $R^2$ and $R^3$ may be independently substituted with $R^{13}$;
- $R^4$ is selected from hydrogen, cyano, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, carboxy, amino, acylamino, aryloxy, heteroaryloxy and $C_1$-$C_4$ alkoxy;
- $R^6$ is hydrogen or lower $C_{1-4}$ alkyl or OH or lower $C_{1-4}$ alkoxy;
- $R_8$ is selected from hydrogen, cyano, $C_1$-$C_4$ alkyl, $C_3$-$C_8$ cycloalkyl, $C_3$-$C_8$ heterocycloalkyl, aryl, heteroaryl, aralkyl, alkoxycarbonyl, carbamoyl, acyl and sulfonyl.
- $R^{10}$ is selected from hydrogen, $C_1$-$C_4$ alkyl, $C_3$-$C_8$ cycloalkyl, $C_3$-$C_8$ heterocycloalkyl, aryl, heteroaryl and aralkyl;
- $R^{13}$ is selected from hydrogen, halogen, cyano, $C_1$-$C_4$ alkyl, $C_1$-$C_4$ heteroalkyl, $C_1$-$C_4$ haloalkyl, aryl, heteroaryl, hydroxy, $C_1$-$C_4$ alkoxy, carboxy and amino.

In another embodiment, the invention features compounds of Formula 1-2.

Formula 1-2

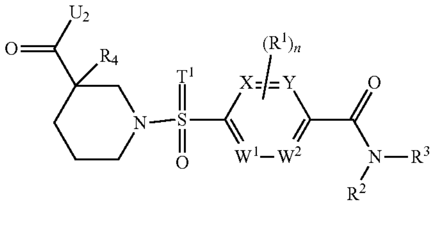

Such that n=0-4;

T is =O or =$NR^6$;

- $U^2$ is $R^9$, $OR^{10}$, $NHR^{11}$, $NR^{11}R^{12}$, $NR^{11}$-(4-6-ring azacycloalkyl), 1-piperazinyl, 1-homopiperazinyl, "C"$_{7-10}$ N-linked-1,x'-diaza-(spiro/fused/bridged)bicycloalkyl, where x' is 4 or greater, wherein up to four carbon atoms of $U^2$ may be independently substituted with $R^{13}$, and each of the remaining N atom may be substituted with $R^{14}$;
- $W^1$ and $W^2$ are independently selected from CH and N, or the two may be taken together as S or $NR^8$;
- X and Y are independently selected from CH and N;
- $R^1$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;
- $R^2$ and $R^3$ are independently hydrogen, $C_1$-$C_8$ alkyl, $C_3$-$C_8$ carbocyclyl, $C_3$-$C_8$ heterocyclyl, or aryl; or $R^2$ and $R^3$, together with the nitrogen to which they are joined form $C_3$-$C_8$ heterocyclyl, which for the 6 and 7 membered rings may include an extra heteroatom chosen from O, S, SO, $SO_2$ and $NR^8$, and wherein up to four carbon of $R^2$ and $R^3$ may be independently substituted with $R^{13}$;
- $R^4$ is selected from hydrogen, cyano, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, carboxy, amino, acylamino, aryloxy, heteroaryloxy and $C_1$-$C_4$ alkoxy;
- $R^6$ is hydrogen or lower $C_{1-4}$ alkyl or OH or lower $C_{1-4}$ alkoxy;
- $R_8$ is selected from hydrogen, cyano, $C_1$-$C_4$ alkyl, $C_3$-$C_8$ cycloalkyl, $C_3$-$C_8$ heterocycloalkyl, aryl, heteroaryl, aralkyl, alkoxycarbonyl, carbamoyl, acyl and sulfonyl.
- $R^9$ is selected from hydrogen, $C_1$-$C_4$ alkyl, $C_3$-$C_8$ cycloalkyl, $C_3$-$C_8$ heterocycloalkyl, aryl, heteroaryl and aralkyl;
- $R^{10}$ is selected from hydrogen, $C_1$-$C_4$ alkyl, $C_3$-$C_8$ cycloalkyl, $C_3$-$C_8$ heterocycloalkyl, aryl, heteroaryl and aralkyl;
- $R^{11}$ and $R^{12}$ are independently hydrogen, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, arylalkyl or heteroarylalkyl; or $R^{11}$ and $R^{12}$, together with the nitrogen to which they are joined form $C_3$-$C_{10}$ heterocyclyl, which for the 6 and 7 membered rings may include an extra heteroatom chosen from O, S, SO, $SO_2$ and $NR^8$, and wherein up to four carbon of $R^{11}$ and $R^{12}$ may be independently substituted with $R^{13}$;
- $R^{13}$ is selected from hydrogen, halogen, cyano, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;
- $R^{14}$ is H, lower $C_{1-4}$ alkyl, C(=O)-lower $C_{1-4}$ alkyl, C(=O)-lower $C_{1-4}$ alkoxy, $S(=O)_2$-lower $C_{1-4}$ alkyl, 5-tetrazyl, 5-oxo-1,24-oxadiazol-3-yl, isoxazol-5-yl, 1,2,4-oxadiazol-5-yl, 1,2,4-oxadiazol-3-yl, phenyl, 2/3/4-pyridinyl, 2/4/5-pyrimidyl, pyrazinyl, 3/4-pyridazinyl, wherein any of the aromatic groups may be substituted with one $R^{15}$.
- $R^{15}$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy.

In another embodiment, the invention features compounds of Formula 1-3.

Formula 1-3

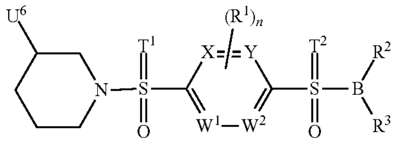

Such that n=0-4;

$T^1$ and $T^2$ are independently =O or =$NR^6$;

Wherein $U^6$ is selected from the following groups:

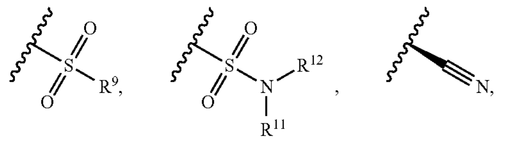

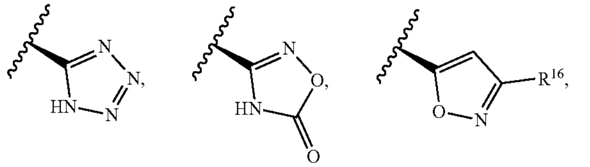

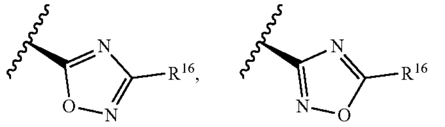

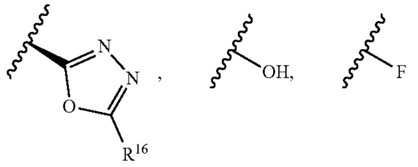

and

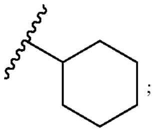

;

$W^1$ and $W^2$ are independently selected from CH and N, or the two may be taken together as S or $NR^8$;

X and Y are independently selected from CH and N;

B is N or $CR^8$;

$R^1$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^2$ and $R^3$ are independently hydrogen, $C_1$-$C_8$ alkyl, $C_3$-$C_8$ carbocyclyl, $C_3$-$C_8$ heterocyclyl, or aryl; or $R^2$ and $R^3$, together with the nitrogen to which they are joined form $C_3$-$C_8$ heterocyclyl, which for the 6 and 7 membered rings may include an extra heteroatom chosen from O, S, SO, $SO_2$ and $NR^8$, and wherein up to four carbon of $R^2$ and $R^3$ may be independently substituted with $R^{13}$;

$R^4$ is selected from hydrogen, cyano, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, carboxy, amino, acylamino, aryloxy, heteroaryloxy and $C_1$-$C_4$ alkoxy;

$R^6$ is hydrogen or lower $C_{1-4}$ alkyl or OH or lower $C_{1-4}$ alkoxy;

$R_8$ is selected from hydrogen, cyano, $C_1$-$C_4$ alkyl, $C_3$-$C_8$ cycloalkyl, $C_3$-$C_8$ heterocycloalkyl, aryl, heteroaryl, aralkyl, alkoxycarbonyl, carbamoyl, acyl and sulfonyl.

$R^9$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{11}$ and $R^{12}$ are independently hydrogen, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, arylalkyl or heteroarylalkyl; or $R^{11}$ and $R^{12}$, together with the nitrogen to which they are joined form $C_3$-$C_{10}$ heterocyclyl, which for the 6 and 7 membered rings may include an extra heteroatom chosen from O, S, SO, $SO_2$ and $NR^8$, and wherein up to four carbon of $R^{11}$ and $R^{12}$ may be independently substituted with $R^{13}$;

$R^{13}$ is selected from hydrogen, halogen, cyano, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^{16}$ is selected from hydrogen, halogen, cyano, nitro, $C_1$-$C_4$ alkyl, $C_1$-$C_4$ heteroalkyl, $C_1$-$C_4$haloalkyl, hydroxy, carboxy, amino and $C_1$-$C_4$ alkoxy.

In another embodiment of the invention, there is provided a compound selected from the compounds as shown in Table 1.

The invention provides the stereochemical mixtures or pure forms for all compounds of invention.

The invention also provides all pharmaceutically acceptable salts, esters, amides, tautomers, geometric isomers, solvates thereof, as well as pharmaceutical composition comprising an effective amount of a compound of the invention and a pharmaceutically acceptable carrier. The composition may further comprise an effective amount of one or more other agents for treating cancer or a disorder associated with mitochondrial function.

The invention further provides prodrugs of all compounds of invention. The term "prodrug" used herein refers to a pharmacologically inactive derivative of a parent "drug" molecule which requires biotransformation within the target physiological system to release, or to convert the prodrug into the active drug. Prodrugs can address the problems associated with solubility, stability, cell permeability or bioavailability. Prodrugs usually comprise an active drug molecule and a chemical masking group. Prodrugs can be readily prepared from the parent compounds with well-known methods.

Furthermore, the invention provides a packaged product comprising a container; an effective amount of a compound of invention.

The invention also provides methods of preparing the compounds of invention.

Definitions

Certain terms employed in the specification, examples, and appended claims are further described here in the present invention. These definitions should be read in light of the entire invention and as would be understood by a person skilled in the art.

"Cycloalkyl" refers to a saturated hydrocarbon ring that is not aromatic. Cycloalkyl rings are monocyclic, or are fused, spiro, or bridged bicyclic or polycyclic ring systems. Monocyclic cycloalkyl rings contain from about 3 to about 12 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6- or 7-membered rings. Cycloalkyl rings may be unsubstituted or substituted with from 1 to 4 substituents on the ring. Cycloalkyl may be substituted with halogen, cyano, nitro, alkyl, heteroalkyl, haloalkyl, cycloalkyl, heterocycloalkyl, aryl, heteroaryl, keto, hydroxy, carboxy, amino, acylamino, aryloxy, heteroaryloxy, alkoxy, arylalkyl, heteroarylalkyl or any combination thereof. Preferred cycloalkyl rings include cyclopropyl, cyclopentyl, cyclohexyl, cycloheptyl, cyclooctyl and cyclononyl rings.

"Heterocycloalkyl" is a saturated or unsaturated ring containing carbon atoms and from 1 to 4 (preferably 1 to 3) heteroatoms in the ring. Heterocycloalkyl rings are monocyclic, or are fused, spiro, or bridged bicyclic or polycyclic ring systems. Monocyclic heterocycloalkyl rings contain from about 3 to about 9 member atoms (including both carbons and heteroatoms), preferably from 5 to 7 member atoms, in the ring. Bicyclic heterocycloalkyl rings may be fused, spiro, or bridged ring systems. Preferred bicyclic heterocycloalkyl rings comprise 5-, 6- or 7-membered rings fused to 5-, 6- or 7-membered rings. Heterocycloalkyl rings may be unsubstituted (i.e., contain hydrogen) or substituted (on either carbons or heteroatoms or both) with from 1 to 4 substituents selected from halogen, cyano, nitro, alkyl, heteroalkyl, haloalkyl, cycloalkyl, heterocycloalkyl, aryl, heteroaryl, keto, hydroxy, carboxy, amino, acylamino, aryloxy, heteroaryloxy, alkoxy, arylalkyl, heteroarylalkyl or any combination thereof.

"Aryl" refers to aromatic monocyclic or multicyclic groups containing from 3 to 16 carbon atoms. Aryl may be unsubstituted or substituted with from 1 to 4 substituents. Preferred substituted aryls are mono-, di, or tri-substituted. Aryls may be substituted with halogen, cyano, nitro, alkyl, heteroalkyl, haloalkyl, cycloalkyl, heterocycloalkyl, aryl, heteroaryl, keto, hydroxy, carboxy, amino, acylamino, aryloxy, heteroaryloxy, alkoxy, arylalkyl, heteroarylalkyl or any combination thereof.

"Heteroaryl" refers to a monocyclic or multicyclic aromatic ring system, of about 5 to about 15 members where one or more of the atoms in the ring system is a heteroatom, that is, an element other than carbon, including but not limited to nitrogen, oxygen or sulfur. The heteroaryl group may be optionally fused to a benzene ring. Heteroaryl may be unsubstituted or substituted with from 1 to 4 substituents. Preferred substituted heteroaryls are mono-, di, or tri-substituted. Heteroaryls may be substituted with halogen, cyano, nitro, alkyl, heteroalkyl, haloalkyl, cycloalkyl, heterocycloalkyl, aryl, heteroaryl, keto, hydroxy, carboxy, amino, acylamino, aryloxy, heteroaryloxy, alkoxy, arylalkyl, heteroarylalkyl or any combination thereof.

"Halo" or "halogen" is fluoro, chloro, bromo or iodo.

"Alkyl" means a saturated hydrocarbon radical having 1 to 15 carbon atoms, preferably 1 to 10 carbon atoms, more preferably 1 to 5 carbon atoms, most preferably 1 to 3 carbon atoms, that may be branched or unbranched. Non-limiting example of alkyl radicals include methyl, ethyl, n-propyl, isopropyl, n-butyl, isobutyl, sec-butyl, tert-butyl, pentyl, hexyl, heptyl, octyl and the like, wherein methyl, ethyl, n-propyl and isopropyl represent specifically preferred examples.

"Heteroalkyl" is a saturated or unsaturated chain carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bounds and/or one or more carbon-carbon triple bounds. Preferred unsaturated heteroalkyl have one or two carbon-carbon double bounds or one carbon-carbon triple bound, more preferably one double bound. Heteroalkyl chains may be unsubstituted or substituted with from 1 to 4 substituents. Preferred substituted heteroalkyl are mono-, di, or tri-substituted. Heteroalkyl may be substituted with halogen, cyano, nitro, alkyl, heteroalkyl, haloalkyl, cycloalkyl, heterocycloalkyl, aryl, heteroaryl, keto, hydroxy, carboxy, amino, acylamino, aryloxy, heteroaryloxy, alkoxy, arylalkyl, heteroarylalkyl or any combination thereof.

"Alkoxy" means an oxygen radical having a hydrocarbon chain substituent, where the hydrocarbon chain is an alkyl or alkenyl (i.e., —O-alkyl or —O-alkenyl). Examples of alkoxy include methoxy, ethoxy, n-propoxy, isopropoxy, n-butoxy, isobutoxy, sec-butoxy, tert-butoxy, allyloxy and the like.

"Arylalkyl" alone or in combination, refers to an alkyl radical in which one hydrogen atom is replaced by an aryl radical, for example, benzyl and the like.

"Heteroarylalkyl" refers to an alkyl radical in which one hydrogen atom is replaced by a heteroaryl radical.

"Independently" groups are groups present in the same structure that need not all represent the same substitution.

"Pharmacological composition" refers to a mixture of one or more of the compounds described herein or pharmaceutically acceptable salts thereof, with other chemical components, such as pharmaceutically acceptable carriers and/or excipients. The purpose of a pharmacological composition is to facilitate administration of a compound to an organism.

"Pharmaceutically acceptable salts" is a cationic salt formed at any acidic (e.g., carboxylic acid) group, or an anionic salt formed at any basic (e.g., amino) group.

"Solvate" is a physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

"Prodrug" refers to a pharmacologically inactive derivative of a parent "drug" molecule which requires biotransformation within the target physiological system to release, or to convert the prodrug into the active drug. Prodrugs can address the problems associated with solubility, stability, cell permeability or bioavailability. Prodrugs usually comprise an active drug molecule and a chemical masking group. Prodrugs can be readily prepared from the parent compounds with well-known methods.

DETAILED DESCRIPTION OF THE INVENTION

Disclosed herein is a series of novel compounds as mitochondrial modulators that can be used as treatment of diseases associated with mitochondrial functions, including, but not limited to, cancer, inflammatory disease and diabetes.

Accordingly, in one aspect, the present invention features a series of compounds of Formula 1.

Formula 1

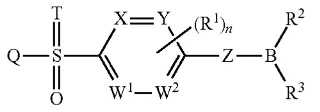

Such that Q is

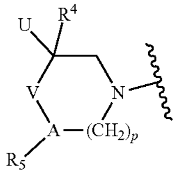 or 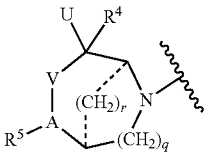 or 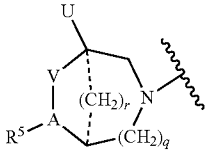 or 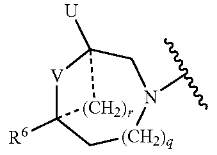 or 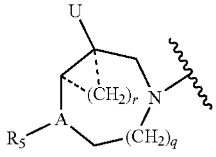 or 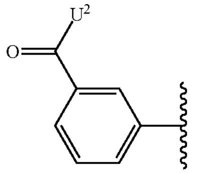

Such that n=0-4;

p=0-2;

q=0 or 1;

r=1 or 2;

A is CH, or when V is $CR^6R^7$ and p is 2 or q is 1, may also be $NR^8$, O or S;

T is =O or $=NR^6$;

U is $U^1$—$U^2$,

Wherein $U^1$ is a bond, C=O or $SO_2$;

$U^2$ is $R^9$, $OR^{10}$, $NHR^{11}$, $NR^{11}R^{12}$, $NR^{11}$-(4-6-ring azacycloalkyl), 1-piperazinyl, 1-homopiperazinyl, "C"$_{7\text{-}10}$ N-linked-1,x'-diaza-(spiro/fused/bridged)bicycloalkyl, where x' is 4 or greater, wherein up to four carbon atoms of $U^2$ may be independently substituted with $R^{13}$, and each of the remaining N atom may be substituted with $R^{14}$;

V is $CR^6R^7$, O, S or $NR^8$.

$W^1$ and $W^2$ are independently selected from CH and N, or the two may be taken together as S or $NR^8$;

X and Y are independently selected from CH and N

Z is selected from a direct bond, —$N(R^{16})$—, —$N(R^{16})C(O)$—, —O—, —C(O)—, —C(S)—, —$S(O)_t$— (where t is 0, 1 or 2) and —$S(O)(N(R^{16}))$—;

B is N or $CR^8$;

$R^1$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^2$ and $R^3$ are independently hydrogen, $C_1$-$C_8$ alkyl, $C_3$-$C_8$ carbocyclyl, $C_3$-$C_8$ heterocyclyl, or aryl; or $R^2$ and $R^3$, together with the nitrogen to which they are joined form $C_3$-$C_8$ heterocyclyl, which for the 6 and 7 membered rings may include an extra heteroatom chosen from O, S, SO, $SO_2$ and $NR^8$, and wherein up to four carbon of $R^2$ and $R^3$ may be independently substituted with $R^{13}$;

$R^4$ is selected from hydrogen, cyano, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, carboxy, amino, acylamino, aryloxy, heteroaryloxy and $C_1$-$C_4$ alkoxy;

$R^5$ is selected from hydrogen, halogen, cyano, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^6$ and $R^7$ are independently hydrogen or lower $C_{1\text{-}4}$ alkyl, or, if $R^4$, is not H, halogen, or OH or lower $C_{1\text{-}4}$ alkoxy, or $R^6$ and $R^7$ taken together may be oxo or lower $C_{1\text{-}4}$ alkylidene;

$R_8$ is selected from hydrogen, cyano, $C_1$-$C_4$ alkyl, $C_3$-$C_8$ cycloalkyl, $C_3$-$C_8$ heterocycloalkyl, aryl, heteroaryl, aralkyl, alkoxycarbonyl, carbamoyl, acyl and sulfonyl.

$R^9$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{10}$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{11}$ and $R^{12}$ are independently hydrogen, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, arylalkyl or heteroarylalkyl; or $R^{11}$ and $R^{12}$, together with the nitrogen to which they are joined form $C_3$-$C_{10}$ heterocyclyl, which for the 6 and 7 membered rings may include an extra heteroatom chosen from O, S, SO, $SO_2$ and $NR^8$, and wherein up to four carbon of $R^{11}$ and $R^{12}$ may be independently substituted with $R^{13}$;

$R^{13}$ is selected from hydrogen, halogen, cyano, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^{14}$ is H, lower $C_{1\text{-}4}$ alkyl, C(=O)-lower $C_{1\text{-}4}$ alkyl, C(=O)-lower $C_{1\text{-}4}$ alkoxy, $S(=O)_2$-lower $C_{1\text{-}4}$ alkyl, 5-tetrazyl, 5-oxo-1,24-oxadiazol-3-yl, isoxazol-5-yl, 1,2,4-oxadiazol-5-yl, 1,2,4-oxadiazol-3-yl, phenyl, 2/3/4-pyridinyl, 2/4/5-pyrimidyl, pyrazinyl, 3/4-pyridazinyl, wherein any of the aromatic groups may be substituted with one $R^{15}$.

$R^{15}$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, $R^{16}$ is selected from hydrogen, $C_1$-$C_8$ alkyl, $C_3$-$C_8$ carbocyclyl, $C_3$-$C_8$ heterocyclyl, aryl, heteroaryl, arylalkyl and heteroarylalkyl.

In one embodiment, the invention features compounds of Formula 1-1.

Formula 1-1

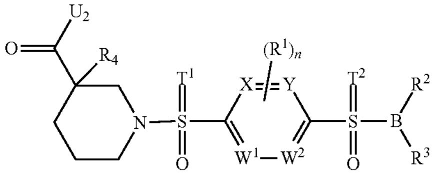

Such that n=0-4;

$T^1$ and $T^2$ are independently =O or $=NR^6$;

$U^2$ is $R^9$, $OR^{10}$, $NHR^{11}$, $NR^{11}R^{12}$, $NR^{11}$-(4-6-ring azacycloalkyl), 1-piperazinyl, 1-homopiperazinyl, "C"$_{7-10}$ N-linked-1,x'-diaza-(spiro/fused/bridged)bicycloalkyl, where x' is 4 or greater, wherein up to four carbon atoms of $U^2$ may be independently substituted with $R^{13}$, and each of the remaining N atom may be substituted with $R^{14}$;

$W^1$ and $W^2$ are independently selected from CH and N, or the two may be taken together as S or $NR^8$;

X and Y are independently selected from CH and N;

B is N or $CR^8$;

$R^1$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^2$ and $R^3$ are independently hydrogen, $C_1$-$C_8$ alkyl, $C_3$-$C_8$ carbocyclyl, $C_3$-$C_8$ heterocyclyl, or aryl; or $R^2$ and $R^3$, together with the nitrogen to which they are joined form $C_3$-$C_8$ heterocyclyl, which for the 6 and 7 membered rings may include an extra heteroatom chosen from O, S, SO, $SO_2$ and $NR^8$, and wherein up to four carbon of $R^2$ and $R^3$ may be independently substituted with $R^{13}$;

$R^4$ is selected from hydrogen, cyano, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, carboxy, amino, acylamino, aryloxy, heteroaryloxy and $C_1$-$C_4$ alkoxy;

$R^6$ is hydrogen or lower $C_{1-4}$ alkyl or OH or lower $C_{1-4}$ alkoxy;

$R_8$ is selected from hydrogen, cyano, $C_1$-$C_4$ alkyl, $C_3$-$C_8$ cycloalkyl, $C_3$-$C_8$ heterocycloalkyl, aryl, heteroaryl, aralkyl, alkoxycarbonyl, carbamoyl, acyl and sulfonyl.

$R^9$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{10}$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{11}$ and $R^{12}$ are independently hydrogen, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, arylalkyl or heteroarylalkyl; or $R^{11}$ and $R^{12}$, together with the nitrogen to which they are joined form $C_3$-$C_{10}$ heterocyclyl, which for the 6 and 7 membered rings may include an extra heteroatom chosen from O, S, SO, $SO_2$ and $NR^8$, and wherein up to four carbon of $R^{11}$ and $R^{12}$ may be independently substituted with $R^{13}$.

$R^{13}$ is selected from hydrogen, halogen, cyano, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^{14}$ is H, lower $C_{1-4}$ alkyl, C(=O)-lower $C_{1-4}$ alkyl, C(=O)-lower $C_{1-4}$ alkoxy, $S(=O)_2$-lower $C_{1-4}$ alkyl, 5-tetrazyl, 5-oxo-1,24-oxadiazol-3-yl, isoxazol-5-yl, 1,2,4-oxadiazol-5-yl, 1,2,4-oxadiazol-3-yl, phenyl, 2/3/4-pyridinyl, 2/4/5-pyrimidyl, pyrazinyl, 3/4-pyridazinyl, wherein any of the aromatic groups may be substituted with one $R^{15}$.

$R^{15}$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy.

In a further embodiment, the invention features compounds of Formula 1-1-1.

Formula 1-1-1

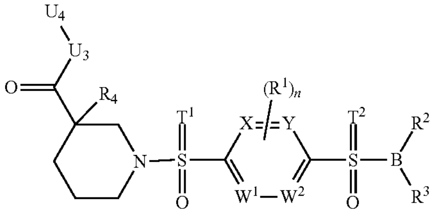

Such that n=0-4;

$T^1$ and $T^2$ are independently =O or $=NR^6$;

$U^3$ is selected from the following groups:

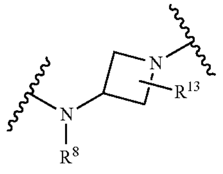
,
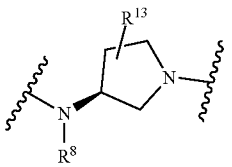
,
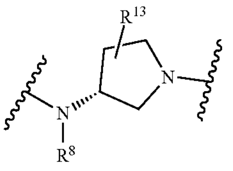
,
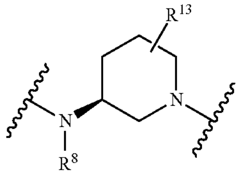
,
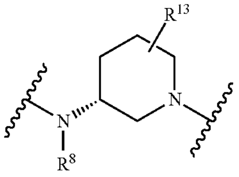
,
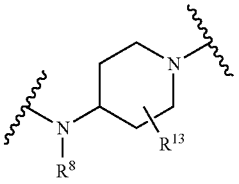
,
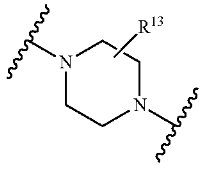
,
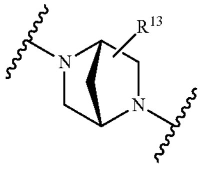
, -continued

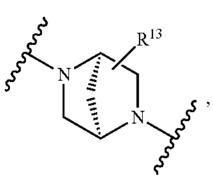 ,
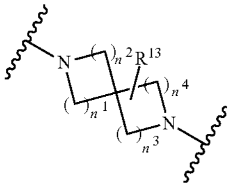 ,
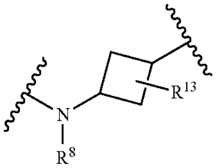 ,
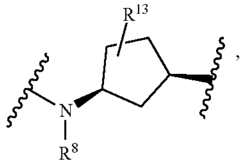 ,
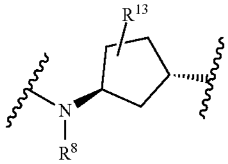
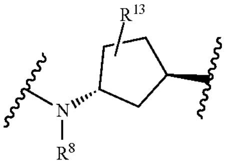 ,
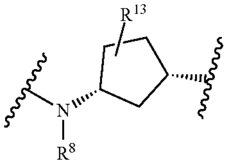
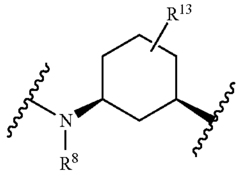 ,
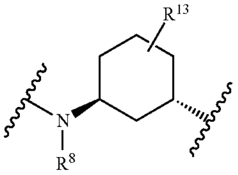 ,
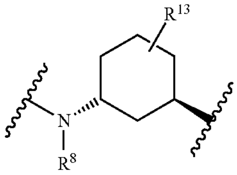
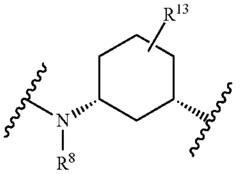 ,
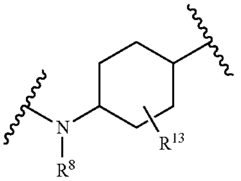 ,
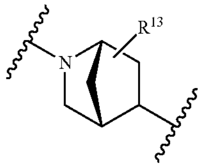 ,
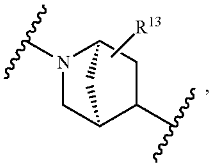 ,
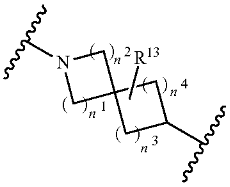 ,
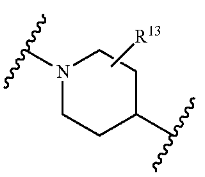 ,
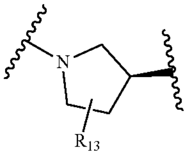 ,
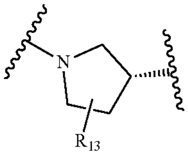
and -continued

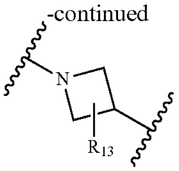 , wherein either side of the can be attached to the carbonyl of the core structure, and the other nitrogen attached to $U^4$, wherein $n^1$, $n^2$, $n^3$ and $n^4$ are independently 0, 1, 2 or 3;

Wherein $U^4$ is selected from the following groups:

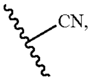
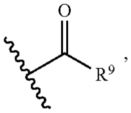 ,
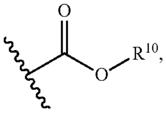
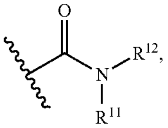
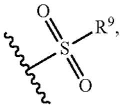
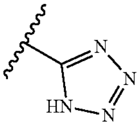 ,
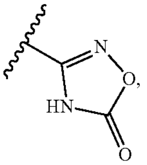
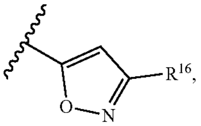
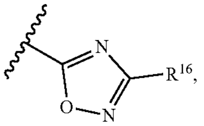
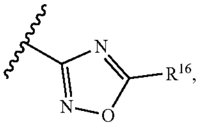
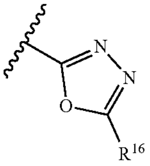 ,
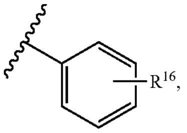
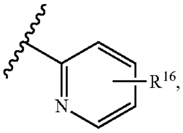
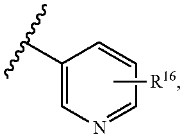
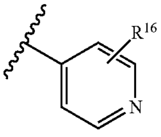 ,
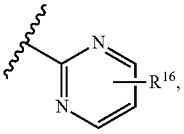
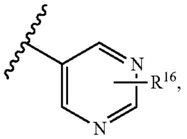
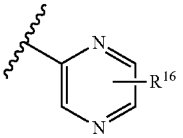
and
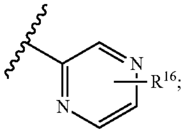

$W^1$ and $W^2$ are independently selected from CH and N, or the two may be taken together as S or $NR^8$;

X and Y are independently selected from CH and N;

B is N or $CR^8$;

$R^1$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^2$ and $R^3$ are independently hydrogen, $C_1$-$C_8$ alkyl, $C_3$-$C_8$ carbocyclyl, $C_3$-$C_8$ heterocyclyl, or aryl; or $R^2$ and $R^3$, together with the nitrogen to which they are joined form $C_3$-$C_8$ heterocyclyl, which for the 6 and 7 membered rings may include an extra heteroatom chosen from O, S, SO, $SO_2$ and $NR^8$, and wherein up to four carbon of $R^2$ and $R^3$ may be independently substituted with $R^{13}$;

$R^4$ is selected from hydrogen, cyano, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, carboxy, amino, acylamino, aryloxy, heteroaryloxy and $C_1$-$C_4$ alkoxy;

$R^6$ is hydrogen or lower $C_{1-4}$ alkyl or OH or lower $C_{1-4}$ alkoxy;

$R_8$ is selected from hydrogen, cyano, $C_1$-$C_4$ alkyl, $C_3$-$C_8$ cycloalkyl, $C_3$-$C_8$ heterocycloalkyl, aryl, heteroaryl, aralkyl, alkoxycarbonyl, carbamoyl, acyl and sulfonyl.

$R^9$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{10}$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{11}$ and $R^{12}$ are independently hydrogen, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, arylalkyl or heteroarylalkyl; or $R^{11}$ and $R^{12}$, together with the nitrogen to which they are joined form $C_3$-$C_{10}$ heterocyclyl, which for the 6 and 7 membered rings may include an extra heteroatom chosen from O, S, SO, $SO_2$ and $NR^8$, and wherein up to four carbon of $R^{11}$ and $R^{12}$ may be independently substituted with $R^{13}$;

$R^{13}$ is selected from hydrogen, halogen, cyano, $C_1$-$C_4$ alkyl, $C_1$-$C_4$ heteroalkyl, $C_1$-$C_4$ haloalkyl, aryl, heteroaryl, hydroxy, $C_1$-$C_4$ alkoxy, carboxy and amino;

$R^{16}$ is selected from hydrogen, halogen, cyano, nitro, $C_1$-$C_4$ alkyl, $C_1$-$C_4$ heteroalkyl, $C_1$-$C_4$haloalkyl, hydroxy, carboxy, amino and $C_1$-$C_4$ alkoxy.

In another further embodiment, the invention features compounds of Formula 1-1-2.

Formula 1-1-2

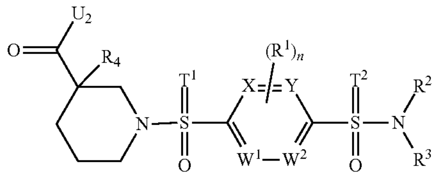

Such that n=0-4;

$T^1$ and $T^2$ are independently =O or =$NR^6$;

$U^5$ is selected from the following groups:

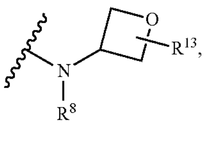

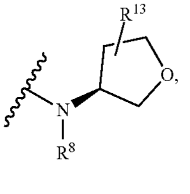

-continued

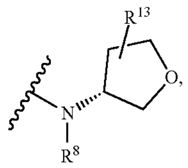

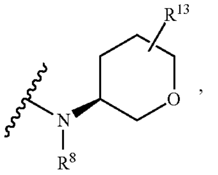

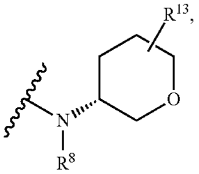

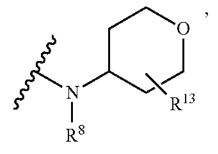

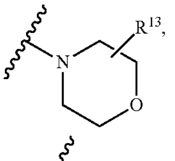

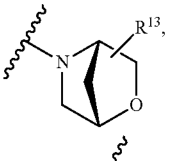

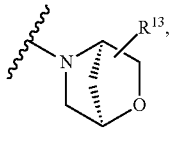

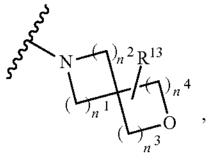

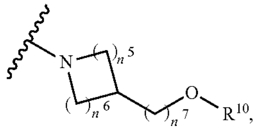

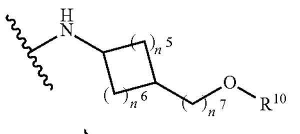

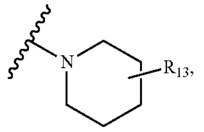

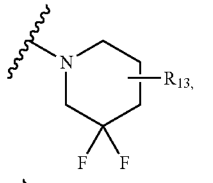

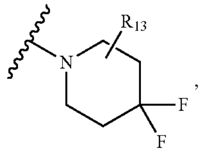

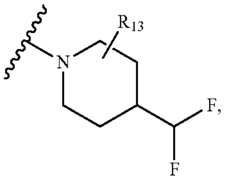

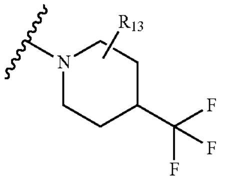

wherein $n^1$, $n^2$, $n^3$, $n^4$ and $n^7$ are independently 0, 1, 2 or 3, $n^5$ and $n^6$ are independently 1, 2 or 3;

$W^1$ and $W^2$ are independently selected from CH and N, or the two may be taken together as S or $NR^8$;

X and Y are independently selected from CH and N;

B is N or $CR^8$;

$R^1$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^2$ and $R^3$ are independently hydrogen, $C_1$-$C_8$ alkyl, $C_3$-$C_8$ carbocyclyl, $C_3$-$C_8$ heterocyclyl, or aryl; or $R^2$ and $R^3$, together with the nitrogen to which they are joined form $C_3$-$C_8$ heterocyclyl, which for the 6 and 7 membered rings may include an extra heteroatom chosen from O, S, SO, $SO_2$ and $NR^8$, and wherein up to four carbon of $R^2$ and $R^3$ may be independently substituted with $R^{13}$;

$R^4$ is selected from hydrogen, cyano, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, carboxy, amino, acylamino, aryloxy, heteroaryloxy and $C_1$-$C_4$ alkoxy;

$R^6$ is hydrogen or lower $C_{1-4}$ alkyl or OH or lower $C_{1-4}$ alkoxy;

$R_8$ is selected from hydrogen, cyano, $C_1$-$C_4$ alkyl, $C_3$-$C_8$ cycloalkyl, $C_3$-$C_8$ heterocycloalkyl, aryl, heteroaryl, aralkyl, alkoxycarbonyl, carbamoyl, acyl and sulfonyl.

$R^{10}$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{13}$ is selected from hydrogen, halogen, cyano, $C_1$-$C_4$ alkyl, $C_1$-$C_4$ heteroalkyl, $C_1$-$C_4$ haloalkyl, aryl, heteroaryl, hydroxy, $C_1$-$C_4$ alkoxy, carboxy and amino.

In another embodiment, the invention features compounds of Formula 1-2.

Formula 1-2

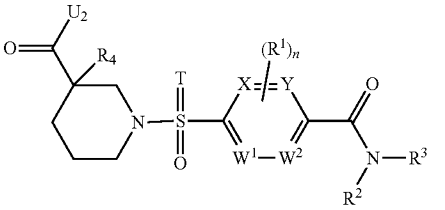

Such that n=0-4;

T is =O or =$NR^6$;

$U^2$ is $R^9$, $OR^{10}$, $NHR^{11}$, $NR^{11}R^{12}$, $NR^{11}$-(4-6-ring azacycloalkyl), 1-piperazinyl, 1-homopiperazinyl, "C"$_{7-10}$ N-linked-1,x'-diaza-(spiro/fused/bridged)bicycloalkyl, where x' is 4 or greater, wherein up to four carbon atoms of $U^2$ may be independently substituted with $R^{13}$, and each of the remaining N atom may be substituted with $R^{14}$;

$W^1$ and $W^2$ are independently selected from CH and N, or the two may be taken together as S or $NR^8$;

X and Y are independently selected from CH and N;

$R^1$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^2$ and $R^3$ are independently hydrogen, $C_1$-$C_8$ alkyl, $C_3$-$C_8$ carbocyclyl, $C_3$-$C_8$ heterocyclyl, or aryl; or $R^2$ and $R^3$, together with the nitrogen to which they are joined form $C_3$-$C_8$ heterocyclyl, which for the 6 and 7 membered rings may include an extra heteroatom chosen from O, S, SO, $SO_2$ and $NR^8$, and wherein up to four carbon of $R^2$ and $R^3$ may be independently substituted with $R^{13}$;

$R^4$ is selected from hydrogen, cyano, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, carboxy, amino, acylamino, aryloxy, heteroaryloxy and $C_1$-$C_4$ alkoxy;

$R^6$ is hydrogen or lower $C_{1-4}$ alkyl or OH or lower $C_{1-4}$ alkoxy;

$R_8$ is selected from hydrogen, cyano, $C_1$-$C_4$ alkyl, $C_3$-$C_8$ cycloalkyl, $C_3$-$C_8$ heterocycloalkyl, aryl, heteroaryl, aralkyl, alkoxycarbonyl, carbamoyl, acyl and sulfonyl.

$R^9$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{10}$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{11}$ and $R^{12}$ are independently hydrogen, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, arylalkyl or heteroarylalkyl; or $R^{11}$ and $R^{12}$, together with the nitrogen to which they are joined form $C_3$-$C_{10}$ heterocyclyl, which for the 6 and 7 membered rings may include an extra heteroatom chosen from O, S, SO, $SO_2$ and $NR^8$, and wherein up to four carbon of $R^{11}$ and $R^{12}$ may be independently substituted with $R^{13}$;

$R^{13}$ is selected from hydrogen, halogen, cyano, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^{14}$ is H, lower $C_{1-4}$ alkyl, C(=O)-lower $C_{1-4}$ alkyl, C(=O)-lower $C_{1-4}$ alkoxy, $S(=O)_2$-lower $C_{1-4}$ alkyl, 5-tetrazyl, 5-oxo-1,24-oxadiazol-3-yl, isoxazol-5-yl, 1,2,4-oxadiazol-5-yl, 1,2,4-oxadiazol-3-yl, phenyl, 2/3/4-pyridinyl, 2/4/5-pyrimidyl, pyrazinyl, 3/4-pyridazinyl, wherein any of the aromatic groups may be substituted with one $R^{15}$.

$R^{15}$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy.

In another embodiment, the invention features compounds of Formula 1-3.

Formula 1-3

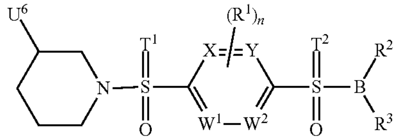

Such that n=0-4;

$T^1$ and $T^2$ are independently =O or =$NR^6$;

Wherein $U^6$ is selected from the following groups:

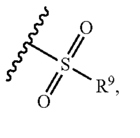
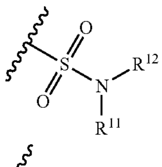
,
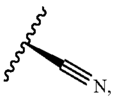

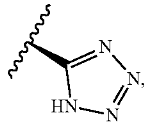
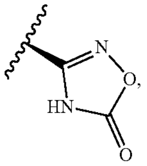
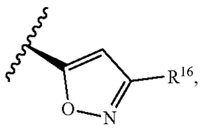

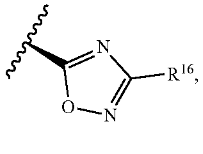
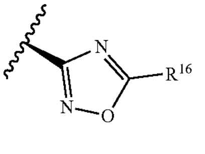

-continued

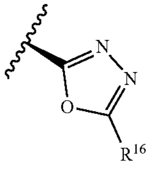 , 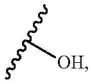 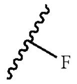 and

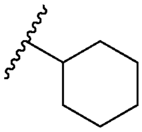 ;

$W^1$ and $W^2$ are independently selected from CH and N, or the two may be taken together as S or $NR^8$;

X and Y are independently selected from CH and N;

B is N or $CR^8$;

$R^1$ is selected from hydrogen, halogen, cyano, nitro, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^2$ and $R^3$ are independently hydrogen, $C_1$-$C_8$ alkyl, $C_3$-$C_8$ carbocyclyl, $C_3$-$C_8$ heterocyclyl, or aryl; or $R^2$ and $R^3$, together with the nitrogen to which they are joined form $C_3$-$C_8$ heterocyclyl, which for the 6 and 7 membered rings may include an extra heteroatom chosen from O, S, SO, $SO_2$ and $NR^8$, and wherein up to four carbon of $R^2$ and $R^3$ may be independently substituted with $R^{13}$;

$R^4$ is selected from hydrogen, cyano, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, carboxy, amino, acylamino, aryloxy, heteroaryloxy and $C_1$-$C_4$ alkoxy;

$R^6$ is hydrogen or lower $C_{1-4}$ alkyl or OH or lower $C_{1-4}$ alkoxy;

$R_8$ is selected from hydrogen, cyano, $C_1$-$C_4$ alkyl, $C_3$-$C_8$ cycloalkyl, $C_3$-$C_8$ heterocycloalkyl, aryl, heteroaryl, aralkyl, alkoxycarbonyl, carbamoyl, acyl and sulfonyl.

$R^9$ is selected from hydrogen, $C_1$-$C_4$ alkyl, $C_3$-$C_8$ cycloalkyl, $C_3$-$C_8$ heterocycloalkyl, aryl, heteroaryl and aralkyl;

$R^{11}$ and $R^{12}$ are independently hydrogen, $C_1$-$C_4$ alkyl, $C_1$-$C_4$ heteroalkyl, $C_1$-$C_4$haloalkyl, $C_3$-$C_8$ cycloalkyl, $C_3$-$C_8$ heterocycloalkyl, aryl, heteroaryl, arylalkyl or heteroarylalkyl; or $R^{11}$ and $R^{12}$, together with the nitrogen to which they are joined form $C_3$-$C_{10}$ heterocyclyl, which for the 6 and 7 membered rings may include an extra heteroatom chosen from O, S, SO, $SO_2$ and $NR^8$, and wherein up to four carbon of $R^{11}$ and $R^{12}$ may be independently substituted with $R^{13}$;

$R^{13}$ is selected from hydrogen, halogen, cyano, $C_1$-$C_4$ alkyl, $C_1$-$C_4$ heteroalkyl, $C_1$-$C_4$ haloalkyl, $C_3$-$C_8$ cycloalkyl, $C_3$-$C_8$ heterocycloalkyl, aryl, heteroaryl, keto, hydroxy, carboxy, amino, acylamino, aryloxy, heteroaryloxy, $C_1$-$C_4$ alkoxy, arylalkyl, and heteroarylalkyl;

$R^{16}$ is selected from hydrogen, halogen, cyano, nitro, $C_1$-$C_4$ alkyl, $C_1$-$C_4$ heteroalkyl, $C_1$-$C_4$haloalkyl, hydroxy, carboxy, amino and $C_1$-$C_4$ alkoxy.

In another embodiment of the invention, there is provided a compound selected from the compounds as shown in Table 1:

TABLE 1

| Code | Structure | IUPAC name | M.W. | cLogP |
|---|---|---|---|---|
| DX2-201 | 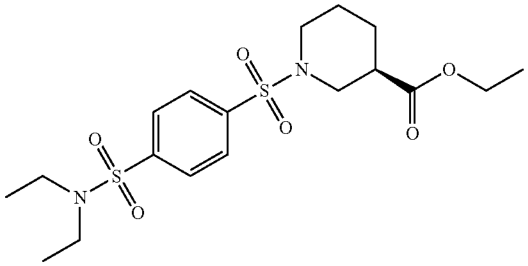 [SMILES: CCOC(=O)[C@@H]1CCCN(S(=O)(=O)c2ccc(S(=O)(=O)N(CC)CC)cc2)C1] | ethyl (R)-1-((4-(N,N-diethylsulfamoyl)phenyl)sulfonyl) piperidine-3-carboxylate | 432.55 | 2.99 |
| DX2-202 | 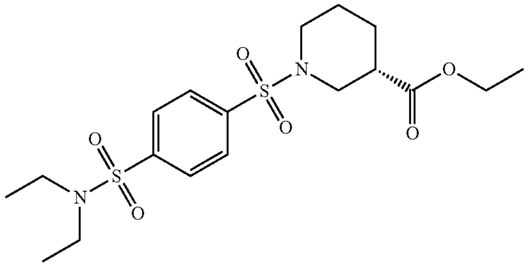 [SMILES: CCOC(=O)[C@H]1CCCN(S(=O)(=O)c2ccc(S(=O)(=O)N(CC)CC)cc2)C1] | ethyl (S)-1-((4-(N,N-diethylsulfamoyl)phenyl)sulfonyl) piperidine-3-carboxylate | 432.55 | 2.99 |

TABLE 1-continued

| Code | Structure | IUPAC name | M.W. | cLogP |
|---|---|---|---|---|
| DX2-208 | 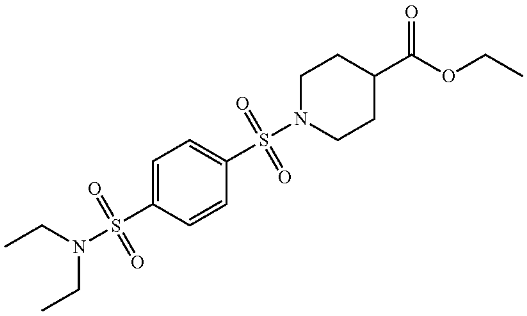 [SMILES: CCOC(=O)C1CCN(S(=O)(=O)c2ccc(S(=O)(=O)N(CC)CC)cc2)CC1] | ethyl 1-((4-(N,N-diethylsulfamoyl)phenyl)sulfonyl) piperidine-4-carboxylate | 432.55 | 2.17 |
| DX2-209 | 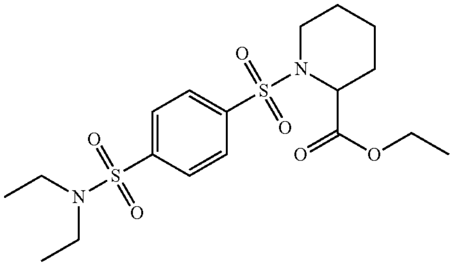 [SMILES: CCOC(=O)C1CCCCN1S(=O)(=O)c1ccc(S(=O)(=O)N(CC)CC)cc1] | ethyl 1-((4-(N,N-diethylsulfamoyl)phenyl)sulfonyl) piperidine-2-carboxylate | 432.55 | 3.30 |
| DX2-217 | 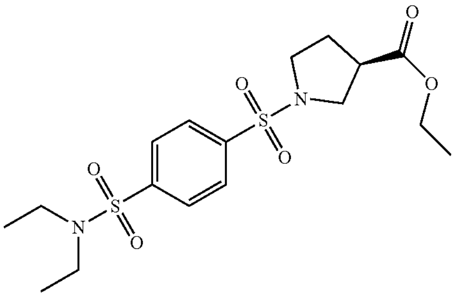 [SMILES: CCOC(=O)[C@@H]1CCN(S(=O)(=O)c2ccc(S(=O)(=O)N(CC)CC)cc2)C1] | ethyl (R)-1-((4-(N,N-diethylsulfamoyl)phenyl)sulfonyl) pyrrolidine-3-carboxylate | 418.53 | 2.43 |
| DX2-218 | 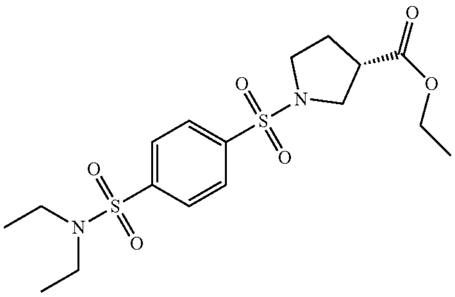 [SMILES: CCOC(=O)[C@H]1CCN(S(=O)(=O)c2ccc(S(=O)(=O)N(CC)CC)cc2)C1] | ethyl (S)-1-((4-(N,N-diethylsulfamoyl)phenyl)sulfonyl) pyrrolidine-3-carboxylate | 418.53 | 2.43 |
| DX2-219 | 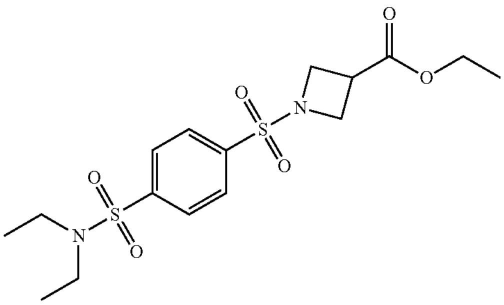 [SMILES: CCOC(=O)C1CN(S(=O)(=O)c2ccc(S(=O)(=O)N(CC)CC)cc2)C1] | ethyl 1-((4-(N,N-diethylsulfamoyl)phenyl)sulfonyl) azetidine-3-carboxylate | 404.50 | 2.68 |

TABLE 1-continued

| Code | Structure | IUPAC name | M.W. | cLogP |
|---|---|---|---|---|
| DX2-221 | 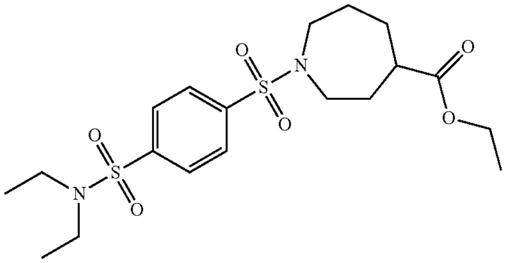 [SMILES: CCOC(=O)C1CCCN(S(=O)(=O)c2ccc(S(=O)(=O)N(CC)CC)cc2)CC1] | ethyl 1-((4-(N,N-diethylsulfamoyl)phenyl)sulfonyl) azepane-4-carboxylate | 446.58 | 2.73 |
| DX2-225 | 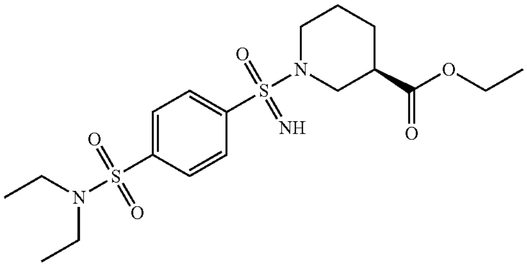 [SMILES: CCOC(=O)[C@@H]1CCCN(S(=N)(=O)c2ccc(S(=O)(=O)N(CC)CC)cc2)C1] | ethyl (3R)-1-(4-(N,N-diethylsulfamoyl)phenyl-sulfonimidoyl) piperidine-3-carboxylate | 431.57 | 3.25 |
| DX2-226 | 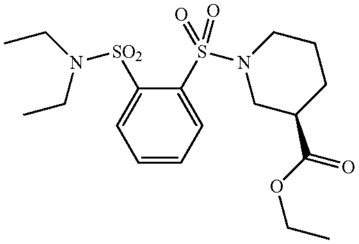 [SMILES: CCOC(=O)[C@@H]1CCCN(S(=O)(=O)c2ccccc2S(=O)(=O)N(CC)CC)C1] | ethyl (R)-1-((2-(N,N-diethylsulfamoyl)phenyl)sulfonyl) piperidine-3-carboxylate | 432.55 | 2.99 |
| DX2-229 | 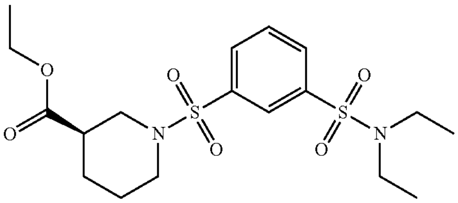 [SMILES: CCOC(=O)[C@@H]1CCCN(S(=O)(=O)c2cccc(S(=O)(=O)N(CC)CC)c2)C1] | ethyl (R)-1-((3-(N,N-diethylsulfamoyl)phenyl)sulfonyl) piperidine-3-carboxylate | 432.55 | 2.99 |
| DX2-230 | 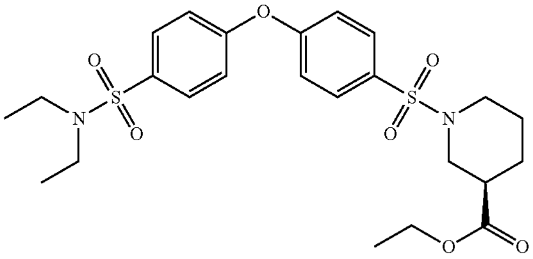 [SMILES: CCOC(=O)[C@@H]1CCCN(S(=O)(=O)c2ccc(Oc3ccc(S(=O)(=O)N(CC)CC)cc3)cc2)C1] | ethyl (R)-1-((4-(4-(N,N-diethylsulfamoyl)phenoxy)phenyl) sulfonyl)piperidine-3-carboxylate | 524.65 | 5.08 |
| DX2-235 | 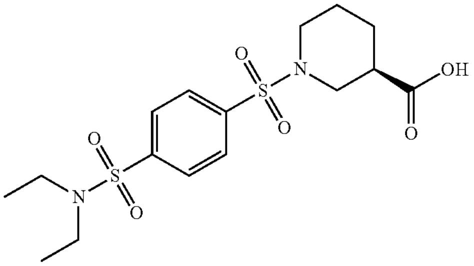 [SMILES: CCN(CC)S(=O)(=O)c1ccc(S(=O)(=O)N2CCC[C@@H](C(=O)O)C2)cc1] | (R)-1-((4-(N,N-diethylsulfamoyl)phenyl)sulfonyl) piperidine-3-carboxylic acid | 404.50 | 1.99 |

TABLE 1-continued

| Code | Structure | IUPAC name | M.W. | cLogP |
|---|---|---|---|---|
| DX2-237 | 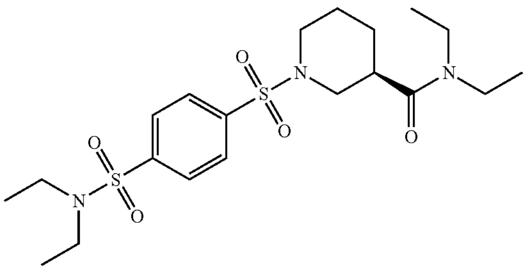 [SMILES: CCN(CC)C(=O)[C@@H]1CCCN(S(=O)(=O)c2ccc(S(=O)(=O)N(CC)CC)cc2)C1] | (R)-1-((4-(N,N-diethylsulfamoyl)phenyl)sulfonyl)-N,N-diethylpiperidine-3-carboxamide | 459.62 | 2.93 |
| DX2-238 | 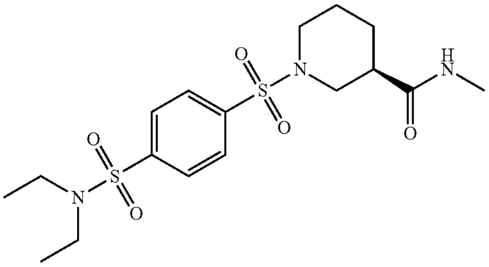 [SMILES: CCN(CC)S(=O)(=O)c1ccc(S(=O)(=O)N2CCC[C@@H](C(=O)NC)C2)cc1] | (R)-1-((4-(N,N-diethylsulfamoyl)phenyl)sulfonyl)-N-methylpiperidine-3-carboxamide | 417.54 | 1.49 |
| DX2-241 | 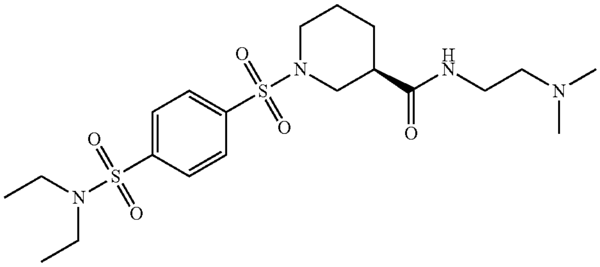 [SMILES: CCN(CC)S(=O)(=O)c1ccc(S(=O)(=O)N2CCC[C@@H](C(=O)NCCN(C)C)C2)cc1] | (R)-1-((4-(N,N-diethylsulfamoyl)phenyl)sulfonyl)-N-(2-(dimethylamino)ethyl)piperidine-3-carboxamide | 474.64 | 2.13 |
| DX2-242 | 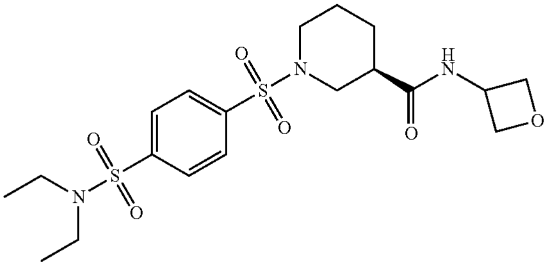 [SMILES: CCN(CC)S(=O)(=O)c1ccc(S(=O)(=O)N2CCC[C@@H](C(=O)NC3COC3)C2)cc1] | (R)-1-((4-(N,N-diethylsulfamoyl)phenyl)sulfonyl)-N-(oxetan-3-yl)piperidine-3-carboxamide | 459.58 | 2.05 |
| DX2-244 | 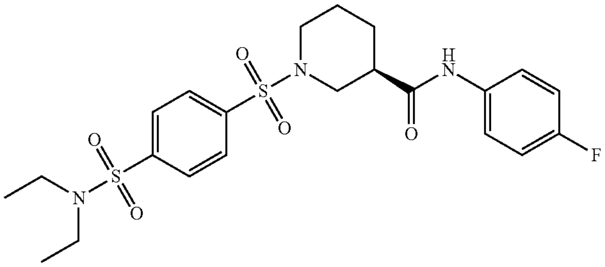 [SMILES: CCN(CC)S(=O)(=O)c1ccc(S(=O)(=O)N2CCC[C@@H](C(=O)Nc3ccc(F)cc3)C2)cc1] | (R)-1-((4-(N,N-diethylsulfamoyl)phenyl)sulfonyl)-N-(4-fluorophenyl)piperidine-3-carboxamide | 497.60 | 3.85 |

TABLE 1-continued

| Code | Structure | IUPAC name | M.W. | cLogP |
| --- | --- | --- | --- | --- |
| DX2-245 | 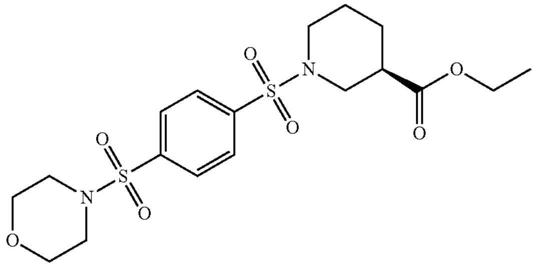 [SMILES: CCOC(=O)[C@@H]1CCCN(S(=O)(=O)c2ccc(S(=O)(=O)N3CCOCC3)cc2)C1] | ethyl (R)-1-((4-(morpholinosulfonyl)phenyl) sulfonyl)piperidine-3-carboxylate | 446.54 | 1.87 |
| DX2-246 | 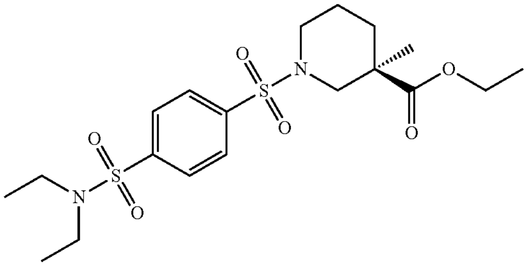 [SMILES: CCOC(=O)[C@]1(C)CCCN(S(=O)(=O)c2ccc(S(=O)(=O)N(CC)CC)cc2)C1] | ethyl (R)-1-((4-(N,N-diethylsulfamoyl)phenyl)sulfonyl)-3-methylpiperidine-3-carboxylate | 446.58 | 3.50 |
| DX2-248 | 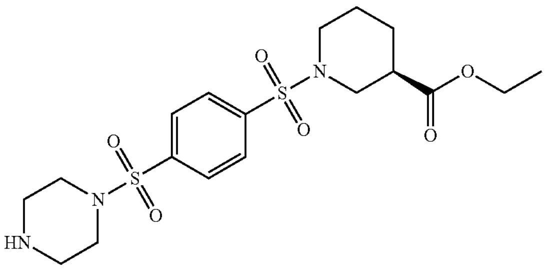 [SMILES: CCOC(=O)[C@@H]1CCCN(S(=O)(=O)c2ccc(S(=O)(=O)N3CCNCC3)cc2)C1] | ethyl (R)-1-((4-(piperazin-1-ylsulfonyl)phenyl)sulfonyl) piperidine-3-carboxylate | 445.55 | 1.86 |
| DX2-249 | 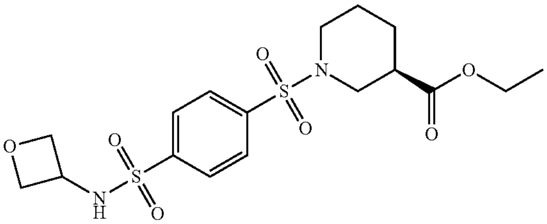 [SMILES: CCOC(=O)[C@@H]1CCCN(S(=O)(=O)c2ccc(S(=O)(=O)NC3COC3)cc2)C1] | ethyl (R)-1-((4-(N-(oxetan-3-yl)sulfamoyl)phenyl)sulfonyl) piperidine-3-carboxylate | 432.51 | 2.18 |
| DX2-258 | 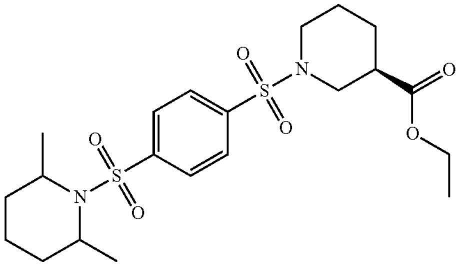 [SMILES: CCOC(=O)[C@@H]1CCCN(S(=O)(=O)c2ccc(S(=O)(=O)N3C(C)CCCC3C)cc2)C1] | ethyl (3R)-1-((4-((2,6-dimethylpiperidin-1-yl)sulfonyl)phenyl)sulfonyl) piperidine-3-carboxylate | 472.62 | 4.16 |
| DX2-259 | 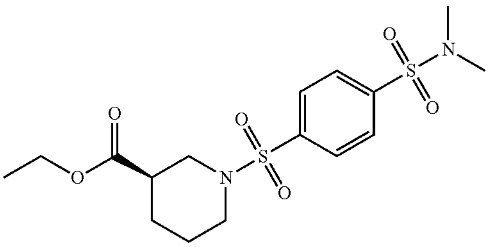 [SMILES: CCOC(=O)[C@@H]1CCCN(S(=O)(=O)c2ccc(S(=O)(=O)N(C)C)cc2)C1] | ethyl (R)-1-((4-(N,N-dimethylsulfamoyl)phenyl) sulfonyl)piperidine-3-carboxylate | 404.50 | 1.93 |

TABLE 1-continued

| Code | Structure | IUPAC name | M.W. | cLogP |
|---|---|---|---|---|
| DX2-260 | 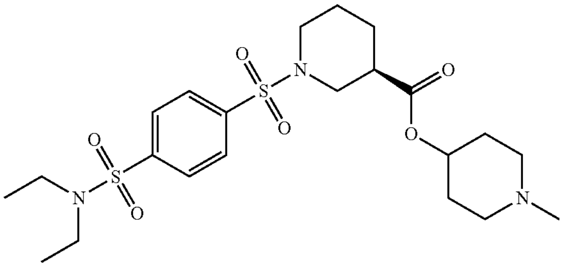 [SMILES: CCN(CC)S(=O)(=O)c1ccc(S(=O)(=O)N2CCC[C@@H](C(=O)OC3CCN(C)CC3)C2)cc1] | 1-methylpiperidin-4-yl (R)-1-((4-(N,N-diethylsulfamoyl)phenyl)sulfonyl) piperidine-3-carboxylate | 501.66 | 2.34 |
| DX2-261 | 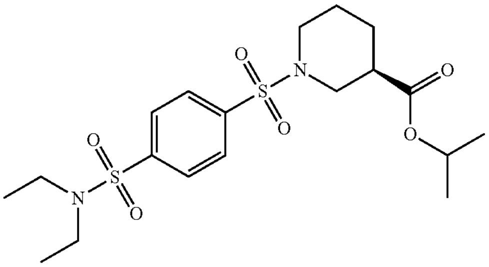 [SMILES: CCN(CC)S(=O)(=O)c1ccc(S(=O)(=O)N2CCC[C@@H](C(=O)OC(C)C)C2)cc1] | isopropyl (R)-1-((4-(N,N-diethylsulfamoyl)phenyl)sulfonyl) piperidine-3-carboxylate | 446.58 | 3.29 |
| DX2-262 | 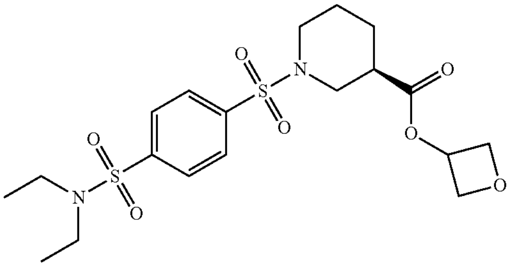 [SMILES: CCN(CC)S(=O)(=O)c1ccc(S(=O)(=O)N2CCC[C@@H](C(=O)OC3COC3)C2)cc1] | oxetan-3-yl (R)-1-((4-(N,N-diethylsulfamoyl)phenyl)sulfonyl) piperidine-3-carboxylate | 460.56 | 2.44 |
| DX2-263 | 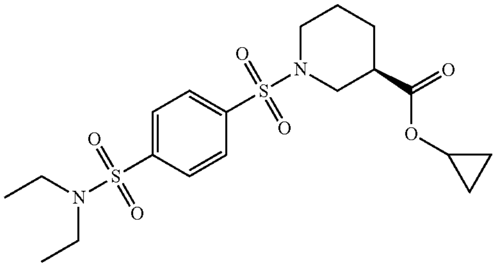 [SMILES: CCN(CC)S(=O)(=O)c1ccc(S(=O)(=O)N2CCC[C@@H](C(=O)OC3CC3)C2)cc1] | cyclopropyl (R)-1-((4-(N,N-diethylsulfamoyl)phenyl)sulfonyl) piperidine-3-carboxylate | 444.57 | 3.04 |
| DX2-264 | 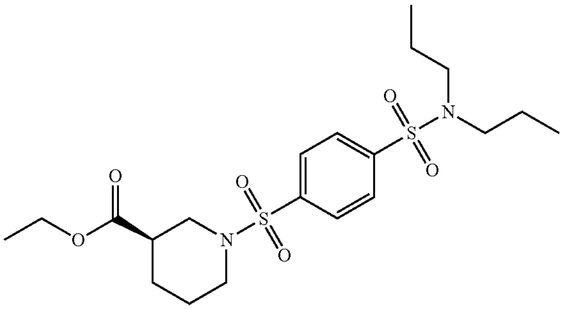 [SMILES: CCCN(CCC)S(=O)(=O)c1ccc(S(=O)(=O)N2CCC[C@@H](C(=O)OCC)C2)cc1] | ethyl (R)-1-((4-(N,N-dipropylsulfamoyl)phenyl)sulfonyl) piperidine-3-carboxylate | 460.61 | 4.04 |

TABLE 1-continued

| Code | Structure | IUPAC name | M.W. | cLogP |
|---|---|---|---|---|
| DX2-265 | 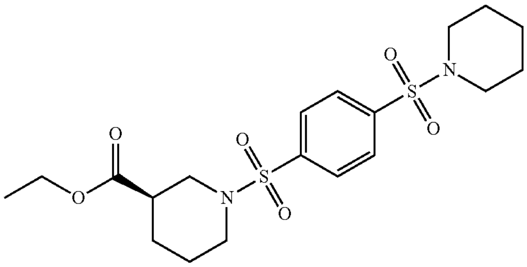 [SMILES: CCOC(=O)[C@@H]1CCCN(S(=O)(=O)c2ccc(S(=O)(=O)N3CCCCC3)cc2)C1] | ethyl (R)-1-((4-(piperidin-1-ylsulfonyl)phenyl)sulfonyl) piperidine-3-carboxylate | 444.57 | 3.12 |
| DX2-266 | 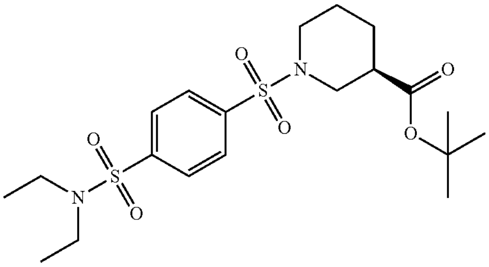 [SMILES: CCN(CC)S(=O)(=O)c1ccc(S(=O)(=O)N2CCC[C@@H](C(=O)OC(C)(C)C)C2)cc1] | tert-butyl (R)-1-((4-(N,N-diethylsulfamoyl)phenyl)sulfonyl) piperidine-3-carboxylate | 460.61 | 3.69 |
| DX2-275 | 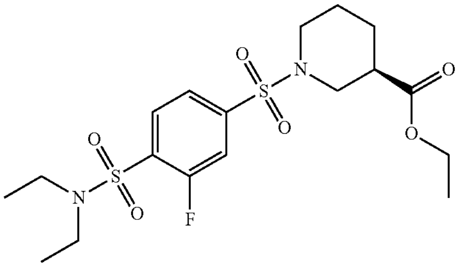 [SMILES: CCOC(=O)[C@@H]1CCCN(S(=O)(=O)c2ccc(S(=O)(=O)N(CC)CC)c(F)c2)C1] | ethyl (R)-1-((4-(N,N-diethylsulfamoyl)-3-fluorophenyl)sulfonyl)piperidine-3-carboxylate | 450.55 | 3.13 |
| DX2-276 | 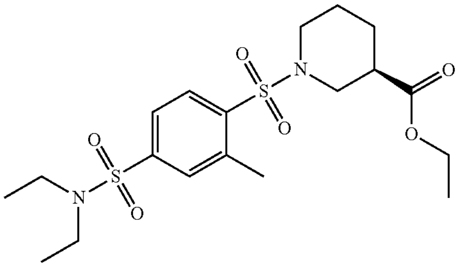 [SMILES: CCOC(=O)[C@@H]1CCCN(S(=O)(=O)c2ccc(S(=O)(=O)N(CC)CC)cc2C)C1] | ethyl (R)-1-((4-(N,N-diethylsulfamoyl)-2-methylphenyl)sulfonyl)piperidine-3-carboxylate | 446.58 | 3.48 |
| DX2-280 | 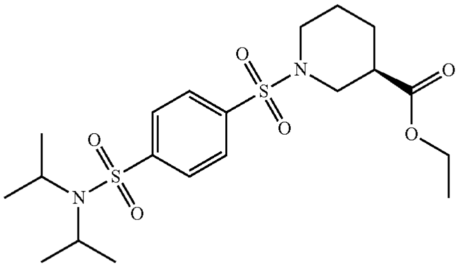 [SMILES: CCOC(=O)[C@@H]1CCCN(S(=O)(=O)c2ccc(S(=O)(=O)N(C(C)C)C(C)C)cc2)C1] | ethyl (R)-1-((4-(N,N-diisopropylsulfamoyl)phenyl) sulfonyl)piperidine-3-carboxylate | 460.61 | 3.60 |

TABLE 1-continued

| Code | Structure | IUPAC name | M.W. | cLogP |
|---|---|---|---|---|
| DX2-282 | 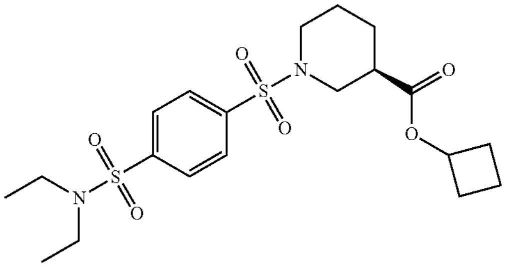 [SMILES: CCN(CC)S(=O)(=O)c1ccc(S(=O)(=O)N2CCC[C@@H](C(=O)OC3CCC3)C2)cc1] | cyclobutyl (R)-1-((4-(N,N-diethylsulfamoyl)phenyl)sulfonyl) piperidine-3-carboxylate | 458.59 | 3.37 |
| DX2-291 | 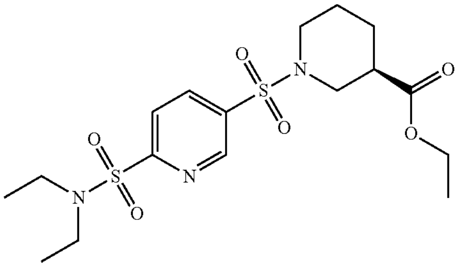 [SMILES: CCOC(=O)[C@@H]1CCCN(S(=O)(=O)c2ccc(S(=O)(=O)N(CC)CC)nc2)C1] | ethyl (R)-1-((6-(N,N-diethylsulfamoyl)pyridin-3-yl)sulfonyl)piperidine-3-carboxylate | 433.54 | 1.79 |
| DX2-293 | 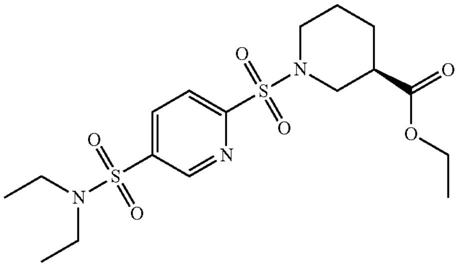 [SMILES: CCOC(=O)[C@@H]1CCCN(S(=O)(=O)c2ccc(S(=O)(=O)N(CC)CC)cn2)C1] | ethyl (R)-1-((5-(N,N-diethylsulfamoyl)pyridin-2-yl)sulfonyl)piperidine-3-carboxylate | 433.54 | 1.79 |
| DX2-295 | 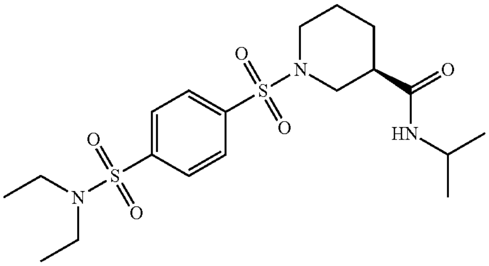 [SMILES: CCN(CC)S(=O)(=O)c1ccc(S(=O)(=O)N2CCC[C@@H](C(=O)NC(C)C)C2)cc1] | (R)-1-((4-(N,N-diethylsulfamoyl)phenyl)sulfonyl)-N-isopropylpiperidine-3-carboxamide | 445.60 | 2.32 |
| DX2-296 | 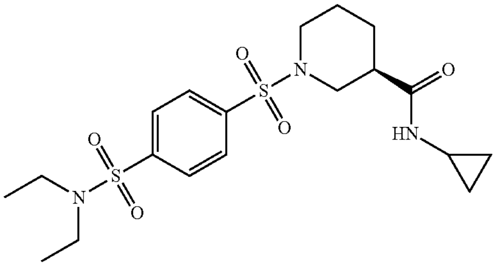 [SMILES: CCN(CC)S(=O)(=O)c1ccc(S(=O)(=O)N2CCC[C@@H](C(=O)NC3CC3)C2)cc1] | (R)-N-cyclopropyl-1-((4-(N,N-diethylsulfamoyl)phenyl)sulfonyl) piperidine-3-carboxamide | 443.58 | 2.07 |

TABLE 1-continued

| Code | Structure | IUPAC name | M.W. | cLogP |
|---|---|---|---|---|
| DX2-297 | 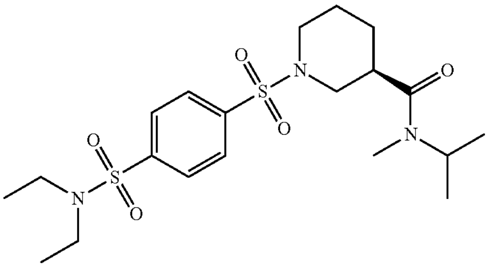 [SMILES: CCN(CC)S(=O)(=O)c1ccc(S(=O)(=O)N2CCC[C@@H](C(=O)N(C)C(C)C)C2)cc1] | (R)-1-((4-(N,N-diethylsulfamoyl)phenyl)sulfonyl)-N-isopropyl-N-methylpiperidine-3-carboxamide | 459.62 | 2.71 |
| DX2-300 | 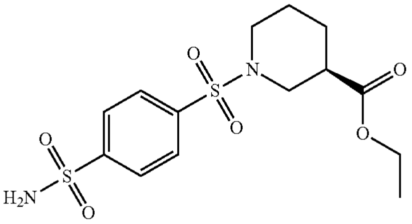 [SMILES: CCOC(=O)[C@@H]1CCCN(S(=O)(=O)c2ccc(S(N)(=O)=O)cc2)C1] | ethyl (R)-1-((4-sulfamoylphenyl)sulfonyl) piperidine-3-carboxylate | 376.44 | 1.34 |
| DX3-3 | 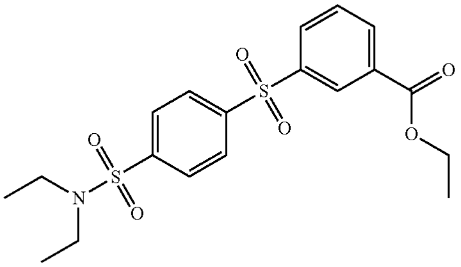 [SMILES: CCOC(=O)c1cccc(S(=O)(=O)c2ccc(S(=O)(=O)N(CC)CC)cc2)c1] | ethyl 3-((4-(N,N-diethylsulfamoyl)phenyl)sulfonyl) benzoate | 425.51 | 3.49 |
| DX3-13 | 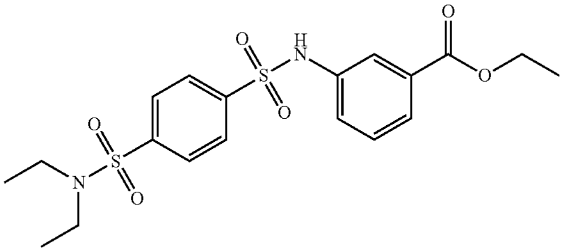 [SMILES: CCOC(=O)c1cccc(NS(=O)(=O)c2ccc(S(=O)(=O)N(CC)CC)cc2)c1] | ethyl 3-((4-(N,N-diethylsulfamoyl)phenyl) sulfonamido)benzoate | 440.563 | 4.00 |
| DX3-14B-P1 | 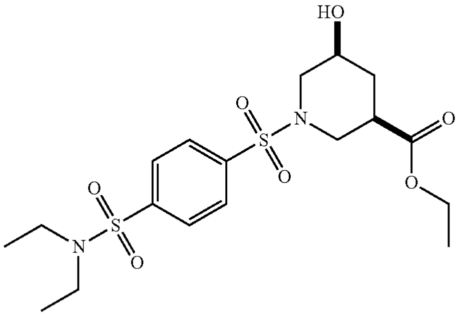 [SMILES: CCOC(=O)[C@@H]1C[C@H](O)CN(S(=O)(=O)c2ccc(S(=O)(=O)N(CC)CC)cc2)C1] | (cis)-ethyl 1-((4-(N,N-diethylsulfamoyl)phenyl)sulfonyl)-5-hydroxypiperidine-3-carboxylate | 448.55 | 2.37 |

TABLE 1-continued

| Code | Structure | IUPAC name | M.W. | cLogP |
|---|---|---|---|---|
| DX3-14B-P2 | 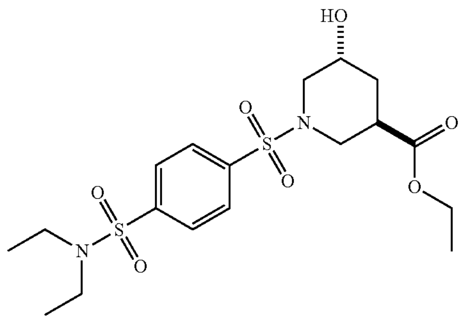 [SMILES: CCOC(=O)[C@@H]1C[C@@H](O)CN(S(=O)(=O)c2ccc(S(=O)(=O)N(CC)CC)cc2)C1] | (trans)-ethyl 1-((4-(N,N-diethylsulfamoyl)phenyl)sulfonyl)-5-hydroxypiperidine-3-carboxylate | 448.55 | 2.37 |
| DX3-30 | 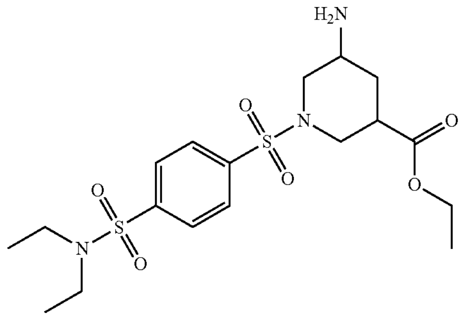 [SMILES: CCOC(=O)C1CC(N)CN(S(=O)(=O)c2ccc(S(=O)(=O)N(CC)CC)cc2)C1] | ethyl 5-amino-1-((4-(N,N-diethylsulfamoyl)phenyl)sulfonyl) piperidine-3-carboxylate | 447.57 | 2.43 |
| DX3-35B | 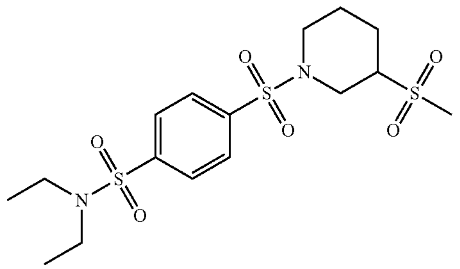 [SMILES: CCN(CC)S(=O)(=O)c1ccc(S(=O)(=O)N2CCCC(S(C)(=O)=O)C2)cc1] | N,N-diethyl-4-((3-(methylsulfonyl)piperidin-1-yl)sulfonyl)benzenesulfonamide | 438.57 | 1.16 |
| DX3-37 | 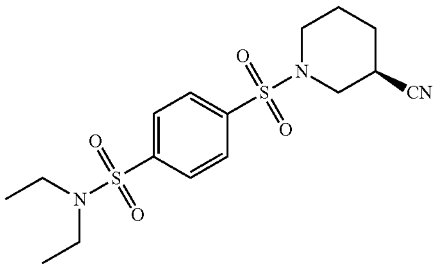 [SMILES: CCN(CC)S(=O)(=O)c1ccc(S(=O)(=O)N2CCC[C@@H](C#N)C2)cc1] | (R)-4-((3-cyanopiperidin-1-yl)sulfony))-N,N-diethylbenzenesulfonamide | 385.50 | 1.88 |
| DX3-38 | 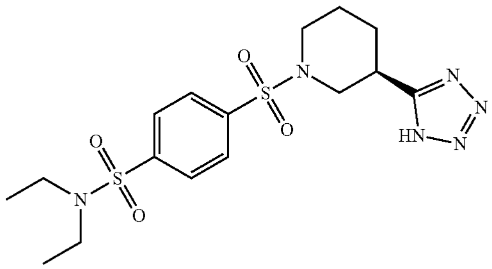 [SMILES: CCN(CC)S(=O)(=O)c1ccc(S(=O)(=O)N2CCC[C@@H](c3nnn[nH]3)C2)cc1] | (R)-4-((3-(1H-tetrazol-5-yl)piperidin-1-yl)sulfonyl)-N,N-diethylbenzenesulfonamide | 428.53 | 1.51 |

TABLE 1-continued

| Code | Structure | IUPAC name | M.W. | cLogP |
|---|---|---|---|---|
| DX3-39 | 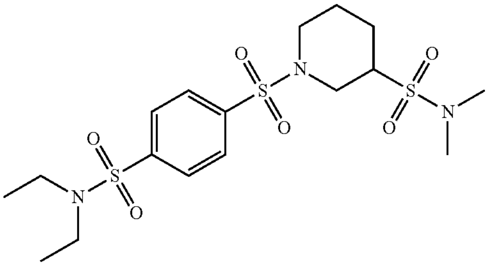 [SMILES: CCN(CC)S(=O)(=O)c1ccc(S(=O)(=O)N2CCCC(S(=O)(=O)N(C)C)C2)cc1] | 1-((4-(N,N-diethylsulfamoyl)phenyl)sulfonyl)-N,N-dimethylpiperidine-3-sulfonamide | 467.61 | 2.02 |
| DX3-39B | 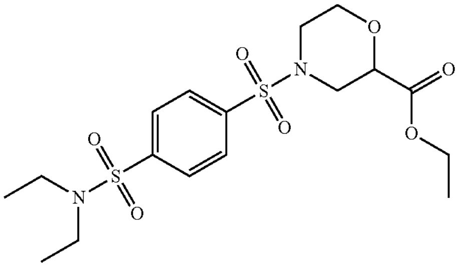 [SMILES: CCOC(=O)C1CN(S(=O)(=O)c2ccc(S(=O)(=O)N(CC)CC)cc2)CCO1] | ethyl 4-((4-(N,N-diethylsulfamoyl)phenyl)sulfonyl) morpholine-2-carboxylate | 434.52 | 2.07 |
| DX3-43 | 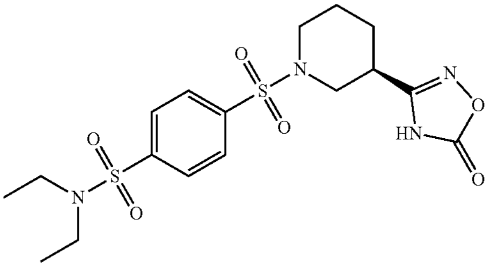 [SMILES: CCN(CC)S(=O)(=O)c1ccc(S(=O)(=O)N2CCC[C@@H](c3noc(=O)[nH]3)C2)cc1] | (R)-N,N-diethyl-4-((3-(5-oxo-4,5-dihydro-1,2,4-oxadiazol-3-yl)piperidin-1-yl)sulfonyl)benzenesulfonamide | 444.52 | 1.25 |
| DX3-43B | 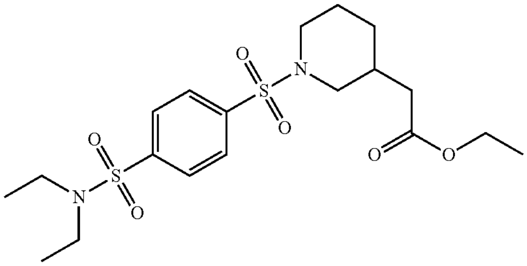 [SMILES: CCOC(=O)CC1CCCN(S(=O)(=O)c2ccc(S(=O)(=O)N(CC)CC)cc2)C1] | ethyl 2-(1-((4-(N,N-diethylsulfamoyl)phenyl)sulfonyl) piperidin-3-yl)acetate | 446.58 | 2.79 |
| DX3-44B | 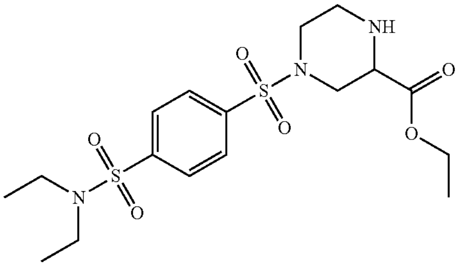 [SMILES: CCOC(=O)C1CN(S(=O)(=O)c2ccc(S(=O)(=O)N(CC)CC)cc2)CCN1] | ethyl 4-((4-(N,N-diethylsulfamoyl)phenyl)sulfonyl) piperazine-2-carboxylate | 433.54 | 2.06 |

TABLE 1-continued

| Code | Structure | IUPAC name | M.W. | cLogP |
|---|---|---|---|---|
| DX3-45 | 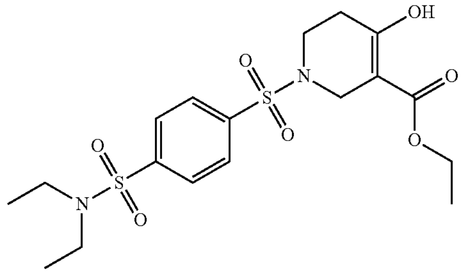 [SMILES: CCOC(=O)C1=C(O)CCN(S(=O)(=O)c2ccc(S(=O)(=O)N(CC)CC)cc2)C1] | ethyl 1-((4-(N,N-diethylsulfamoyl)phenyl)sulfonyl)-4-hydroxy-1,2,5,6-tetrahydropyridine-3-carboxylate | 446.53 | 2.03 |
| DX3-46 | 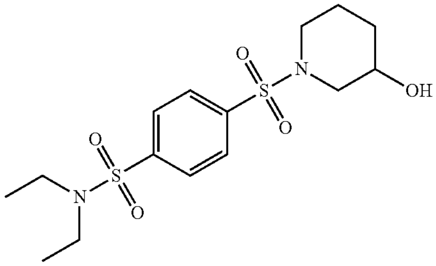 [SMILES: CCN(CC)S(=O)(=O)c1ccc(S(=O)(=O)N2CCCC(O)C2)cc1] | N,N-diethyl-4-((3-hydroxypiperidin-1-yl)sulfonyl)benzenesulfonamide | 376.49 | 1.55 |
| DX3-47 | 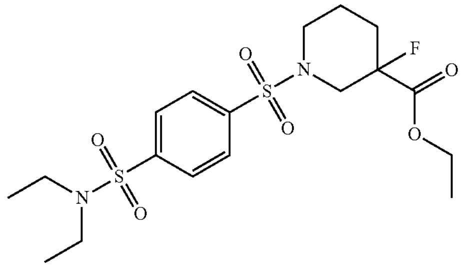 [SMILES: CCOC(=O)C1(F)CCCN(S(=O)(=O)c2ccc(S(=O)(=O)N(CC)CC)cc2)C1] | ethyl 1-((4-(N,N-diethylsulfamoyl)phenyl)sulfonyl)-3-fluoropiperidine-3-carboxylate | 450.54 | 3.23 |
| DX3-48B | 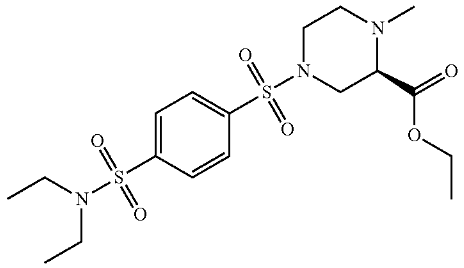 [SMILES: CCOC(=O)[C@H]1CN(S(=O)(=O)c2ccc(S(=O)(=O)N(CC)CC)cc2)CCN1C] | ethyl (R)-4-((4-(N,N-diethylsulfamoyl)phenyl)sulfonyl)-1-methylpiperazine-2-carboxylate | 447.57 | 2.66 |
| DX3-49B | 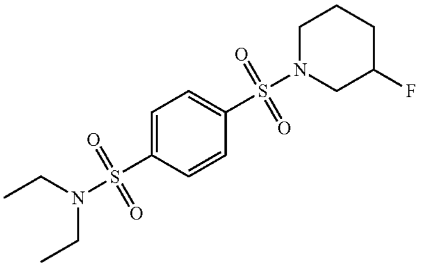 [SMILES: CCN(CC)S(=O)(=O)c1ccc(S(=O)(=O)N2CCCC(F)C2)cc1] | N,N-diethyl-4-((3-fluoropiperidin-1-yl)sulfonyl)benzenesulfonamide | 378.48 | 2.63 |

TABLE 1-continued

| Code | Structure | IUPAC name | M.W. | cLogP |
|---|---|---|---|---|
| DX3-50 | 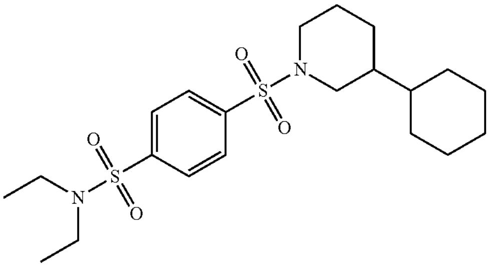 [SMILES: CCN(CC)S(=O)(=O)c1ccc(S(=O)(=O)N2CCCC(C3CCCCC3)C2)cc1] | 4-((3-cyclohexylpiperidin-1-yl)sulfonyl)-N,N-diethylbenzenesulfonamide | 442.63 | 5.33 |
| DX3-52B | 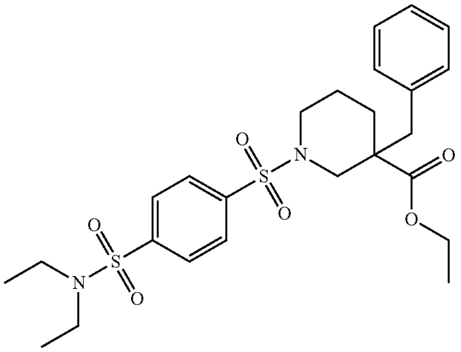 [SMILES: CCOC(=O)C1(Cc2ccccc2)CCCN(S(=O)(=O)c2ccc(S(=O)(=O)N(CC)CC)cc2)C1] | ethyl 3-benzyl-1-((4-(N,N-diethylsulfamoyl)phenyl)sulfonyl) piperidine-3-carboxylate | 522.68 | 5.07 |
| DX3-69B-P1 | 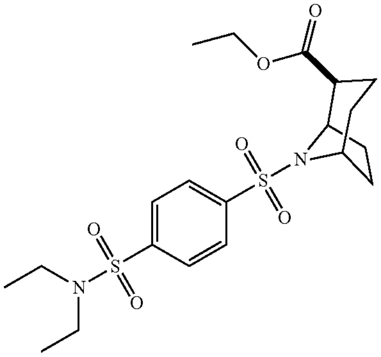 [SMILES: CCOC(=O)[C@H]1CCC2CCC1N2S(=O)(=O)c1ccc(S(=O)(=O)N(CC)CC)cc1] | (trans)-ethyl-8-((4-(N,N-diethylsulfamoyl)phenyl)sulfonyl)-8-azabicyclo[3.2.1]octane-2-carboxylate | 458.59 | 3.30 |
| DX3-69B-P2 | 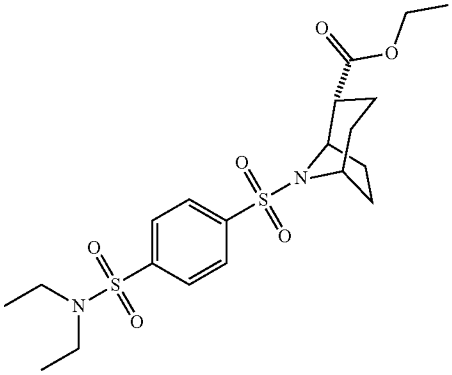 [SMILES: CCOC(=O)[C@@H]1CCC2CCC1N2S(=O)(=O)c1ccc(S(=O)(=O)N(CC)CC)cc1] | (cis)-ethyl-8-((4-(N,N-diethylsulfamoyl)phenyl)sulfonyl)-8-azabicyclo[3.2.1]octane-2-carboxylate | 458.59 | 3.30 |

TABLE 1-continued

| Code | Structure | IUPAC name | M.W. | cLogP |
|---|---|---|---|---|
| DX3-78 | 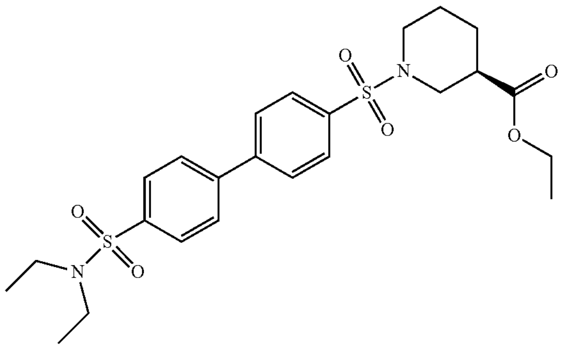 [SMILES: CCOC(=O)[C@@H]1CCCN(S(=O)(=O)c2ccc(-c3ccc(S(=O)(=O)N(CC)CC)cc3)cc2)C1] | ethyl (R)-1-((4'-(N,N-diethylsulfamoyl)-[1,1'-biphenyl]-4-yl)sulfonyl)piperidine-3-carboxylate | 508.65 | 4.87 |
| DX3-78B | 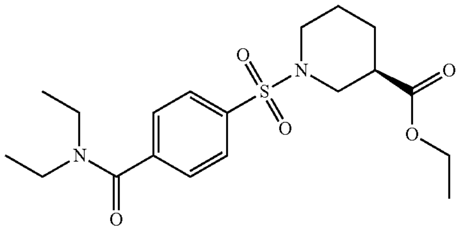 [SMILES: CCOC(=O)[C@@H]1CCCN(S(=O)(=O)c2ccc(C(=O)N(CC)CC)cc2)C1] | ethyl (R)-1-((4-(diethylcarbamoyl)phenyl)sulfonyl) piperidine-3-carboxylate | 396.50 | 2.39 |
| DX3-79 | 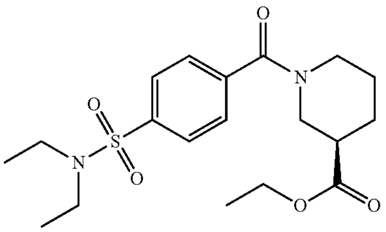 [SMILES: CCOC(=O)[C@@H]1CCCN(C(=O)c2ccc(S(=O)(=O)N(CC)CC)cc2)C1] | ethyl (R)-1-(4-(N,N-diethylsulfamoyl)benzoyl) piperidine-3-carboxylate | 396.50 | 2.56 |
| DX3-84 | 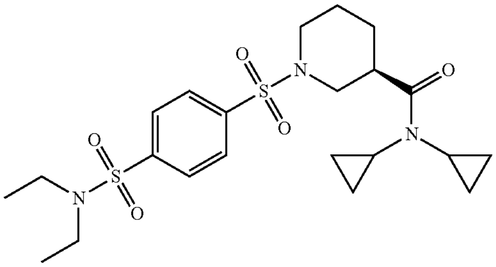 [SMILES: CCN(CC)S(=O)(=O)c1ccc(S(=O)(=O)N2CCC[C@@H](C(=O)N(C3CC3)C3CC3)C2)cc1] | (R)-N,N-dicyclopropyl-1-((4-(N,N-diethylsulfamoyl)phenyl)sulfonyl) piperidine-3-carboxamide | 483.64 | 3.10 |
| DX3-86B | 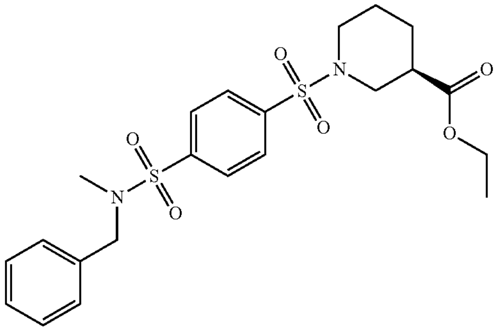 [SMILES: CCOC(=O)[C@@H]1CCCN(S(=O)(=O)c2ccc(S(=O)(=O)N(C)Cc3ccccc3)cc2)C1] | ethyl (R)-1-((4-(N-benzyl-N-methylsulfamoyl)phenyl)sulfonyl) piperidine-3-carboxylate | 480.59 | 3.70 |

TABLE 1-continued

| Code | Structure | IUPAC name | M.W. | cLogP |
|---|---|---|---|---|
| DX3-90 | 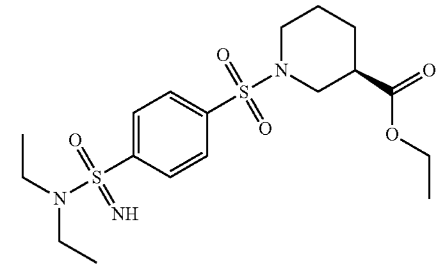 [SMILES: CCOC(=O)[C@@H]1CCCN(S(=O)(=O)c2ccc(S(=N)(=O)N(CC)CC)cc2)C1] | ethyl (3R)-1-((4-(N,N-diethylsulfamidimidoyl)phenyl)sulfonyl)piperidine-3-carboxylate | 431.57 | 2.64 |
| DX3-99B | 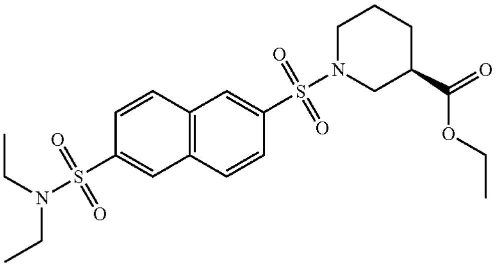 [SMILES: CCOC(=O)[C@@H]1CCCN(S(=O)(=O)c2ccc3cc(S(=O)(=O)N(CC)CC)ccc3c2)C1] | ethyl (R)-1-((6-(N,N-diethylsulfamoyl)naphthalen-2-yl)sulfonyl)piperidine-3-carboxylate | 482.61 | 4.16 |
| DX3-100 | 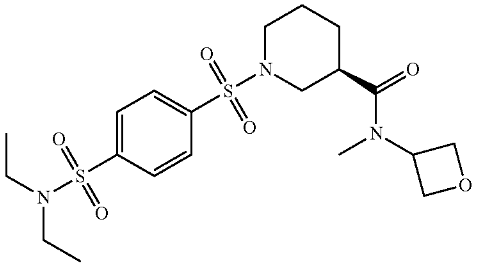 [SMILES: CCN(CC)S(=O)(=O)c1ccc(S(=O)(=O)N2CCC[C@@H](C(=O)N(C)C3COC3)C2)cc1] | (R)-1-((4-(N,N-diethylsulfamoyl)phenyl)sulfonyl)-N-methyl-N-(oxetan-3-yl)piperidine-3-carboxamide | 473.60 | 2.66 |
| DX3-100B | 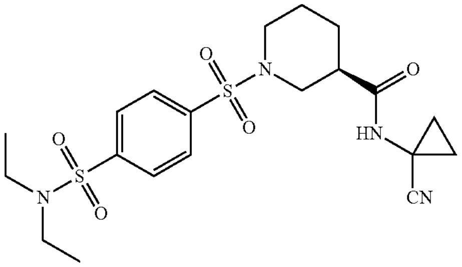 [SMILES: CCN(CC)S(=O)(=O)c1ccc(S(=O)(=O)N2CCC[C@@H](C(=O)NC3(C#N)CC3)C2)cc1] | (R)-N-(1-cyanocyclopropyl)-1-((4-(N,N-diethylsulfamoyl)phenyl)sulfonyl)piperidine-3-carboxamide | 468.59 | 1.43 |
| DX3-101-P1 | 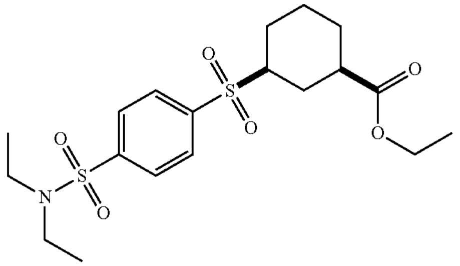 | (cis)-ethyl 3-((4-(N,N-diethylsulfamoyl)phenyl)sulfonyl)cyclohexane-1-carboxylate | 431.56 | 3.12 |

TABLE 1-continued

| Code | Structure | IUPAC name | M.W. | cLogP |
|---|---|---|---|---|
| DX3-101-P2 | 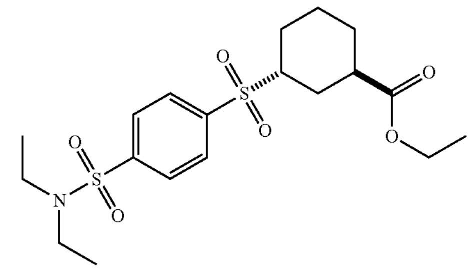 | (trans)-ethyl 3-((4-(N,N-diethylsulfamoyl)phenyl)sulfonyl) cyclohexane-1-carboxylate | 431.56 | 3.12 |
| DX3-102B | 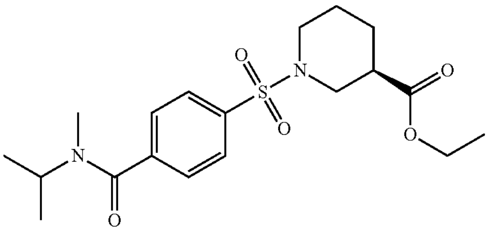 [SMILES: CCOC(=O)[C@@H]1CCCN(S(=O)(=O)c2ccc(C(=O)N(C)C(C)C)cc2)C1] | ethyl (R)-1-((4-(isopropyl(methyl)carbamoyl) phenyl)sulfonyl)piperidine-3-carboxylate | 396.50 | 2.17 |
| DX3-103 | 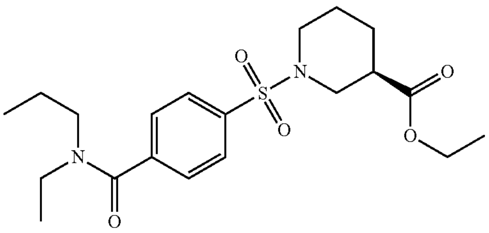 [SMILES: CCCN(CC)C(=O)c1ccc(S(=O)(=O)N2CCC[C@@H](C(=O)OCC)C2)cc1] | ethyl (R)-1-((4-(ethyl(propyl)carbamoyl)phenyl) sulfonyl)piperidine-3-carboxylate | 410.53 | 2.92 |
| DX3-104 | 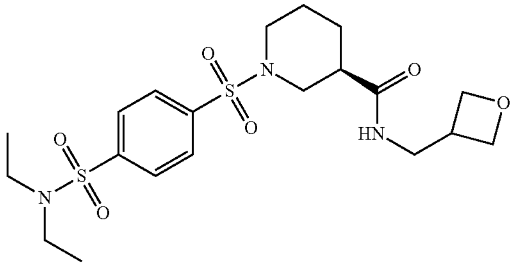 [SMILES: CCN(CC)S(=O)(=O)c1ccc(S(=O)(=O)N2CCC[C@@H](C(=O)NCC3COC3)C2)cc1] | (R)-1-((4-(N,N-diethylsulfamoyl)phenyl)sulfonyl)-N-(oxetan-3-ylmethyl)piperidine-3-carboxamide | 473.60 | 0.62 |
| DX3-104B | 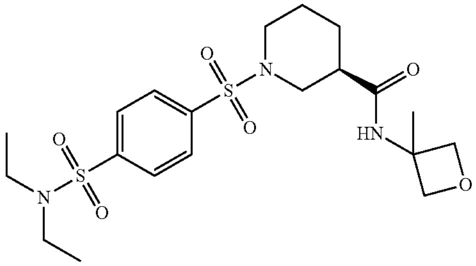 [SMILES: CCN(CC)S(=O)(=O)c1ccc(S(=O)(=O)N2CCC[C@@H](C(=O)NC3(C)COC3)C2)cc1] | (R)-1-((4-(N,N-diethylsulfamoyl)phenyl)sulfonyl)-N-(3-methyloxetan-3-yl)piperidine-3-carboxamide | 473.60 | 2.57 |
| DX3-105 | 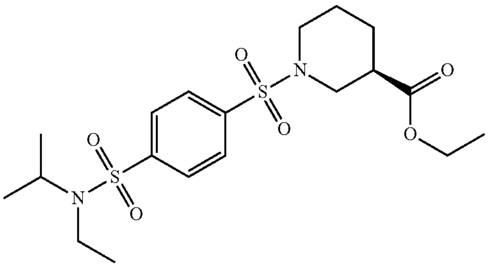 [SMILES: CCOC(=O)[C@@H]1CCCN(S(=O)(=O)c2ccc(S(=O)(=O)N(CC)C(C)C)cc2)C1] | ethyl (R)-1-((4-(N-ethyl-N-isopropylsulfamoyl)phenyl)sulfonyl) piperidine-3-carboxylate | 446.58 | 3.29 |

TABLE 1-continued

| Code | Structure | IUPAC name | M.W. | cLogP |
|---|---|---|---|---|
| DX3-106B | 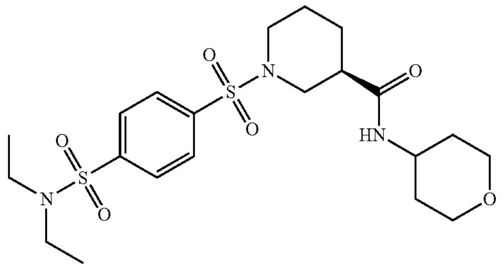 [SMILES: CCN(CC)S(=O)(=O)c1ccc(S(=O)(=O)N2CCC[C@@H](C(=O)NC3CCOCC3)C2)cc1] | (R)-1-((4-(N,N-diethylsulfamoyl)phenyl)sulfonyl)-N-(tetrahydro-2H-pyran-4-yl)piperidine-3-carboxamide | 487.63 | 1.12 |
| DX3-107 | 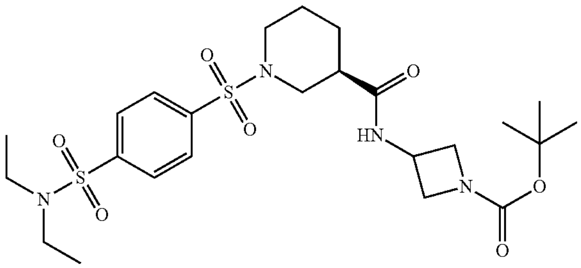 [SMILES: CCN(CC)S(=O)(=O)c1ccc(S(=O)(=O)N2CCC[C@@H](C(=O)NC3CN(C(=O)OC(C)(C)C)C3)C2)cc1] | tert-butyl (R)-3-(1-((4-(N,N-diethylsulfamoyl)phenyl)sulfonyl) piperidine-3-carboxamido)azetidine-1-carboxylate | 558.71 | 4.06 |
| DX3-107B | 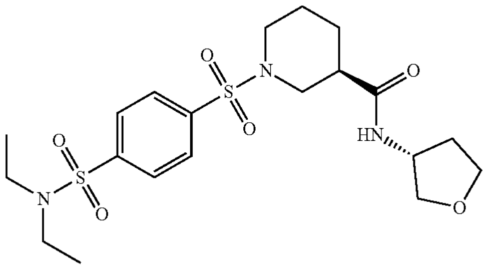 [SMILES: CCN(CC)S(=O)(=O)c1ccc(S(=O)(=O)N2CCC[C@@H](C(=O)N[C@@H]3CCOC3)C2)cc1] | (R)-1-((4-(N,N-diethylsulfamoyl)phenyl)sulfonyl)-N-((R)-tetrahydrofuran-3-yl)piperidine-3-carboxamide | 473.60 | 1.71 |
| DX3-108 | 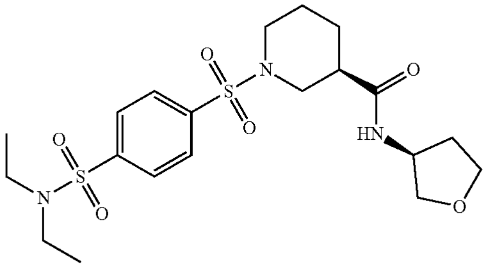 [SMILES: CCN(CC)S(=O)(=O)c1ccc(S(=O)(=O)N2CCC[C@@H](C(=O)N[C@H]3CCOC3)C2)cc1] | (R)-1-((4-(N,N-diethylsulfamoyl)phenyl)sulfonyl)-N-((S)-tetrahydrofuran-3-yl)piperidine-3-carboxamide | 473.60 | 1.71 |
| DX3-110 | 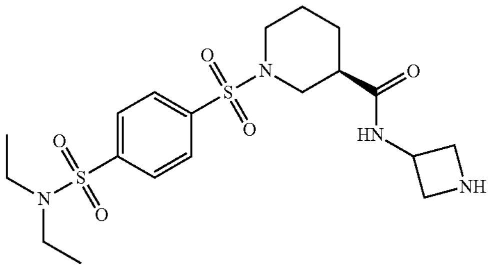 [SMILES: CCN(CC)S(=O)(=O)c1ccc(S(=O)(=O)N2CCC[C@@H](C(=O)NC3CNC3)C2)cc1] | (R)-N-(azetidin-3-yl)-1-((4-(N,N-diethylsulfamoyl)phenyl)sulfonyl) piperidine-3-carboxamide | 458.59 | 2.04 |

TABLE 1-continued

| Code | Structure | IUPAC name | M.W. | cLogP |
|---|---|---|---|---|
| DX3-112B | 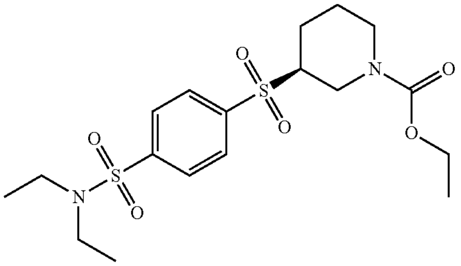 [SMILES: CCOC(=O)N1CCC[C@H](S(=O)(=O)c2ccc(S(=O)(=O)N(CC)CC)cc2)C1] | ethyl (S)-3-((4-(N,N-diethylsulfamoyl)phenyl)sulfonyl) piperidine-1-carboxylate | 432.55 | 2.76 |
| DX3-114 | 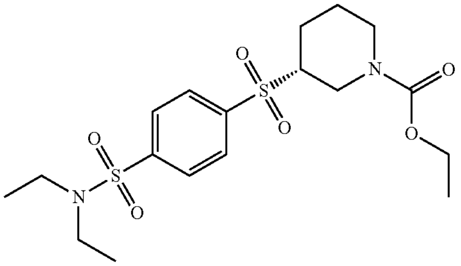 [SMILES: CCOC(=O)N1CCC[C@@H](S(=O)(=O)c2ccc(S(=O)(=O)N(CC)CC)cc2)C1] | ethyl (R)-3-((4-(N,N-diethylsulfamoyl)phenyl)sulfonyl) piperidine-1-carboxylate | 432.55 | 2.76 |
| DX3-115 | 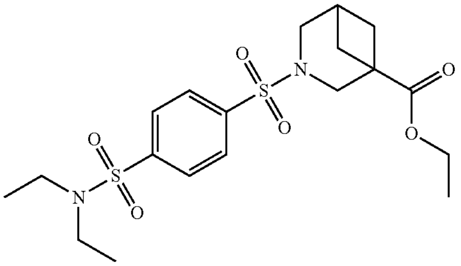 [SMILES: CCOC(=O)C12CC(CN(S(=O)(=O)c3ccc(S(=O)(=O)N(CC)CC)cc3)C1)C2] | ethyl 3-((4-(N,N-diethylsulfamoyl)phenyl)sulfonyl)-3-azabicyclo[3.1.1]heptane-1-carboxylate | 444.56 | 2.74 |
| DX3-115B | 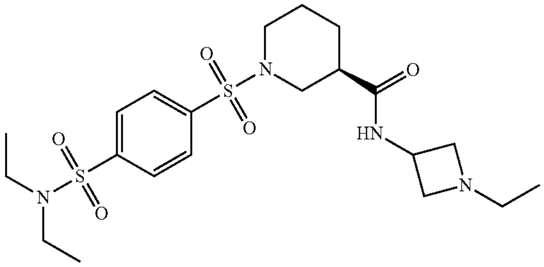 [SMILES: CCN1CC(NC(=O)[C@@H]2CCCN(S(=O)(=O)c3ccc(S(=O)(=O)N(CC)CC)cc3)C2)C1] | (R)-1-((4-(N,N-diethylsulfamoyl)phenyl)sulfonyl)-N-(1-ethylazetidin-3-yl)piperidine-3-carboxamide | 486.65 | 3.21 |
| DX3-116 | 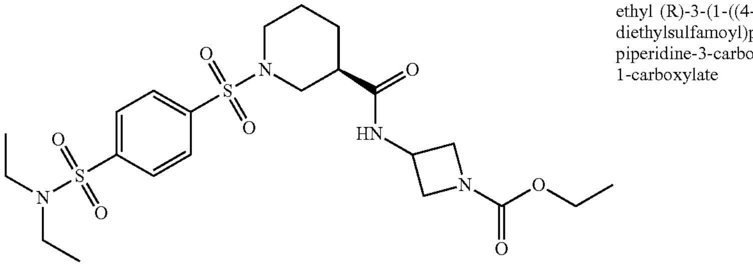 | ethyl (R)-3-(1-((4-(N,N-diethylsulfamoyl)phenyl)sulfonyl) piperidine-3-carboxamido)azetidine-1-carboxylate | 530.66 | 3.35 |

TABLE 1-continued

| Code | Structure | IUPAC name | M.W. | cLogP |
|---|---|---|---|---|
| DX3-116B | 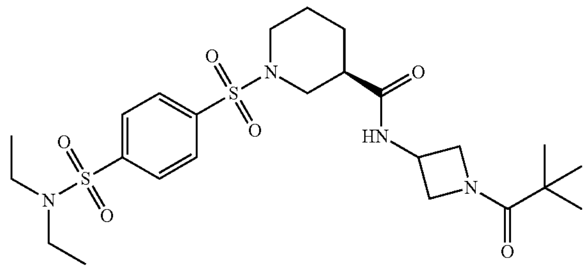 [SMILES: CCN(CC)S(=O)(=O)c1ccc(S(=O)(=O)N2CCC[C@@H](C(=O)NC3CN(C(=O)C(C)(C)C)C3)C2)cc1] | (R)-1-((4-(N,N-diethylsulfamoyl)phenyl)sulfonyl)-N-(1-pivaloylazetidin-3-yl)piperidine-3-carboxamide | 542.71 | 3.17 |
| DX3-117 | 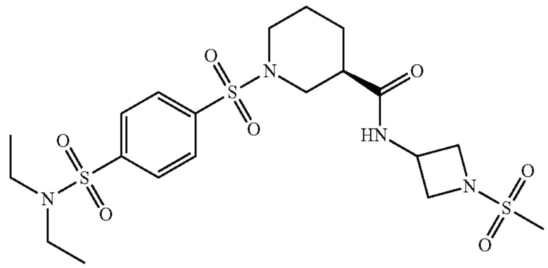 [SMILES: CCN(CC)S(=O)(=O)c1ccc(S(=O)(=O)N2CCC[C@@H](C(=O)NC3CN(S(C)(=O)=O)C3)C2)cc1] | (R)-1-((4-(N,N-diethylsulfamoyl)phenyl)sulfonyl)-N-(1-(methylsulfonyl)azetidin-3-yl)piperidine-3-carboxamide | 536.68 | 2.25 |
| DX3-117B | 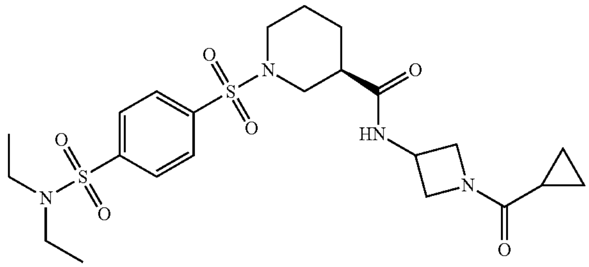 [SMILES: CCN(CC)S(=O)(=O)c1ccc(S(=O)(=O)N2CCC[C@@H](C(=O)NC3CN(C(=O)C4CC4)C3)C2)cc1] | (R)-N-(1-(cyclopropanecarbonyl)azetidin-3-yl)-1-((4-(N,N-diethylsulfamoyl)phenyl)sulfonyl) piperidine-3-carboxamide | 526.67 | 2.51 |
| DX3-118 | 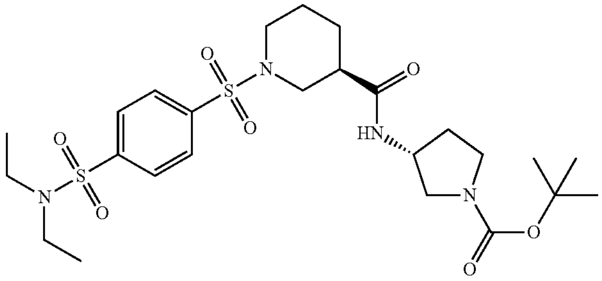 [SMILES: CCN(CC)S(=O)(=O)c1ccc(S(=O)(=O)N2CCC[C@@H](C(=O)N[C@@H]3CCN(C(=O)OC(C)(C)C)C3)C2)cc1] | tert-butyl (R)-3-((R)-1-((4-(N,N-diethylsulfamoyl)phenyl)sulfonyl) piperidine-3-carboxamido)pyrrolidine-1-carboxylate | 572.74 | 3.54 |
| DX3-118B | 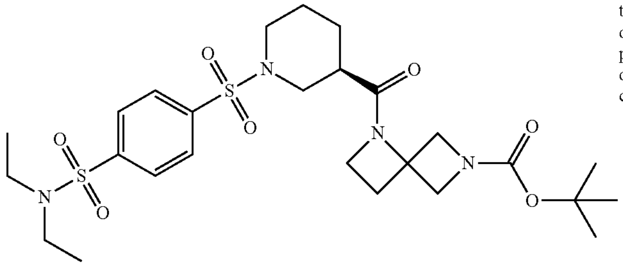 [SMILES: CCN(CC)S(=O)(=O)c1ccc(S(=O)(=O)N2CCC[C@@H](C(=O)N3CCC34CN(C(=O)OC(C)(C)C)C4)C2)cc1] | tert-butyl (R)-1-(1-((4-(N,N-diethylsulfamoyl)phenyl)sulfonyl) piperidine-3-carbonyl)-1,6-diazaspiro[3.3]heptane-6-carboxylate | 584.75 | 3.68 |

TABLE 1-continued

| Code | Structure | IUPAC name | M.W. | cLogP |
|---|---|---|---|---|
| DX3-119 | 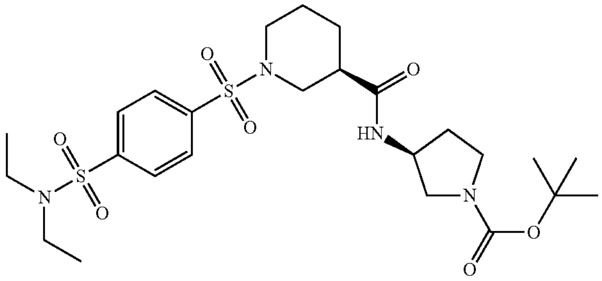 [SMILES: CCN(CC)S(=O)(=O)c1ccc(S(=O)(=O)N2CCC[C@@H](C(=O)N[C@H]3CCN(C(=O)OC(C)(C)C)C3)C2)cc1] | tert-butyl (S)-3-((R)-1-((4-(N,N-diethylsulfamoyl)phenyl)sulfonyl) piperidine-3-carboxamido)pyrrolidine-1-carboxylate | 572.74 | 3.54 |
| DX3-120 | 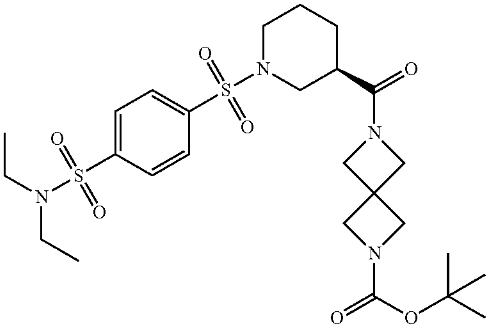 [SMILES: CCN(CC)S(=O)(=O)c1ccc(S(=O)(=O)N2CCC[C@@H](C(=O)N3CC4(CN(C(=O)OC(C)(C)C)C4)C3)C2)cc1] | tert-butyl (R)-6-(1-((4-(N,N-diethylsulfamoyl)phenyl)sulfonyl) piperidine-3-carbonyl)-2,6-diazaspiro[3.3]heptane-2-carboxylate | 584.75 | 3.82 |
| DX3-121 | 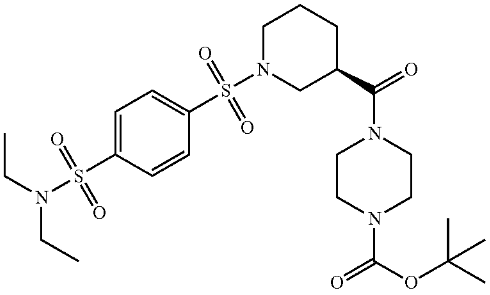 [SMILES: CCN(CC)S(=O)(=O)c1ccc(S(=O)(=O)N2CCC[C@@H](C(=O)N3CCN(C(=O)OC(C)(C)C)CC3)C2)cc1] | tert-butyl (R)-4-(1-((4-(N,N-diethylsulfamoyl)phenyl)sulfonyl) piperidine-3-carbonyl)piperazine-1-carboxylate | 572.74 | 3.93 |
| DX3-121B | 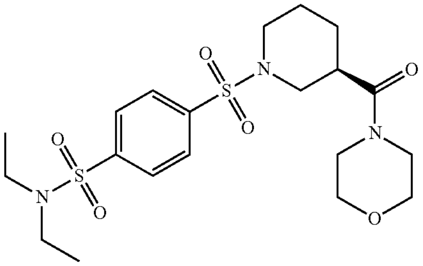 [SMILES: CCN(CC)S(=O)(=O)c1ccc(S(=O)(=O)N2CCC[C@@H](C(=O)N3CCOCC3)C2)cc1] | (R)-N,N-diethyl-4-((3-(morpholine-4-carbonyl)piperidin-1-yl)sulfonyl)benzenesulfonamide | 473.60 | 1.96 |
| DX3-122 | 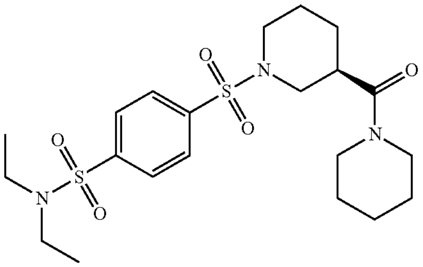 [SMILES: CCN(CC)S(=O)(=O)c1ccc(S(=O)(=O)N2CCC[C@@H](C(=O)N3CCCCC3)C2)cc1] | (R)-N,N-diethyl-4-((3-(piperidine-1-carbonyl)piperidin-1-yl)sulfonyl)benzenesulfonamide | 471.63 | 2.75 |

TABLE 1-continued

| Code | Structure | IUPAC name | M.W. | cLogP |
|---|---|---|---|---|
| DX3-122B | 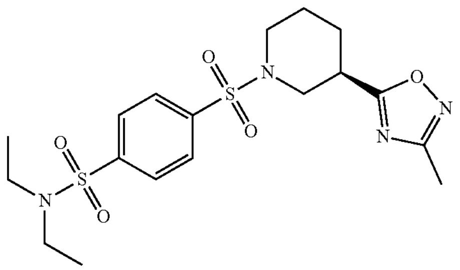 | (R)-N,N-diethyl-4-((3-(3-methyl-1,2,4-oxadiazol-5-yl)piperidin-1-yl)sulfonyl)benzenesulfonamide | 442.55 | 1.73 |
| DX3-123 | 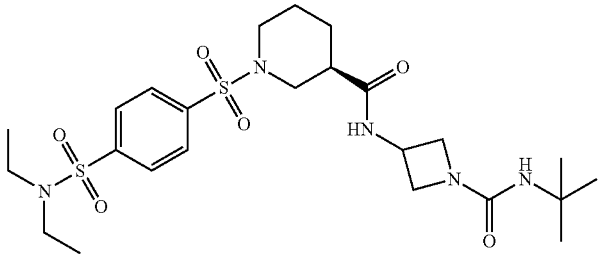 [SMILES: CCN(CC)S(=O)(=O)c1ccc(S(=O)(=O)N2CCC[C@@H](C(=O)NC3CN(C(=O)NC(C)(C)C)C3)C2)cc1] | (R)-N-(1-(tert butylcarbamoyl)azetidin-3-yl)-1-((4-(N,N-diethylsulfamoyl)phenyl)sulfonyl)piperidine-3-carboxamide | 557.73 | 3.36 |
| DX3-123B | 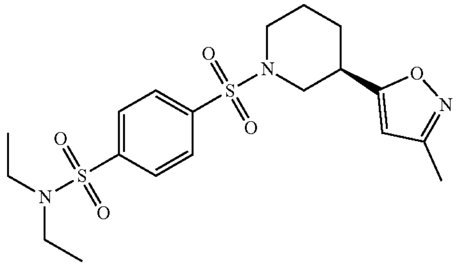 [SMILES: CCN(CC)S(=O)(=O)c1ccc(S(=O)(=O)N2CCC[C@@H](c3cc(C)no3)C2)cc1] | (R)-N,N-diethyl-4-((3-(3-methylisoxazol-5-yl)piperidin-1-yl)sulfonyl)benzenesulfonamide | 441.56 | 2.36 |
| DX3-124 | 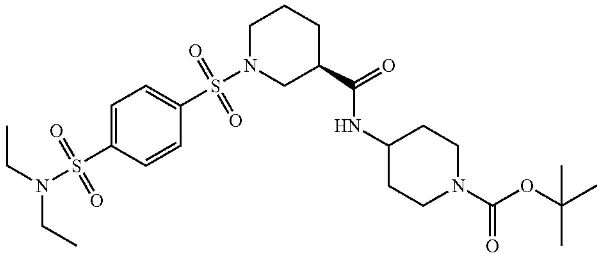 [SMILES: CCN(CC)S(=O)(=O)c1ccc(S(=O)(=O)N2CCC[C@@H](C(=O)NC3CCN(C(=O)OC(C)(C)C)CC3)C2)cc1] | tert-butyl (R)-4-(1-((4-(N,N-diethylsulfamoyl)phenyl)sulfonyl)piperidine-3-carboxamido)piperidine-1-carboxylate | 586.76 | 3.03 |
| DX3-125 | 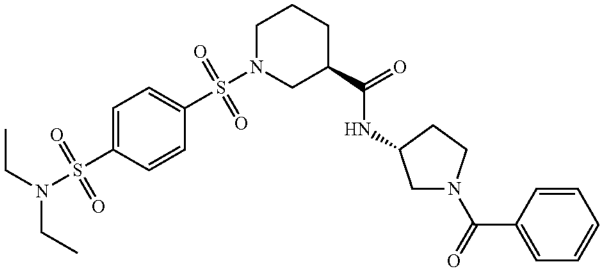 [SMILES: CCN(CC)S(=O)(=O)c1ccc(S(=O)(=O)N2CCC[C@@H](C(=O)N[C@@H]3CCN(C(=O)c4ccccc4)C3)C2)cc1] | (R)-N-((R)-1-benzoylpyrrolidin-3-yl)-1-((4-(N,N-diethylsulfamoyl)phenyl)sulfonyl)piperidine-3-carboxamide | 576.73 | 2.68 |

TABLE 1-continued

| Code | Structure | IUPAC name | M.W. | cLogP |
|---|---|---|---|---|
| DX3-125B | 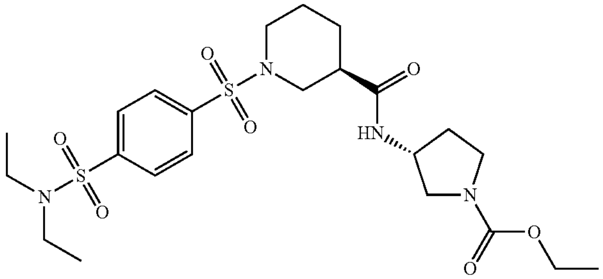 [SMILES: CCOC(=O)N1CC[C@@H](NC(=O)[C@@H]2CCCN(S(=O)(=O)c3ccc(S(=O)(=O)N(CC)CC)cc3)C2)C1] | ethyl (R)-3-((R)-1-((4-(N,N-diethylsulfamoyl)phenyl)sulfonyl) piperidine-3-carboxamido)pyrrolidine-1-carboxylate | 544.68 | 2.84 |
| DX3-126B | 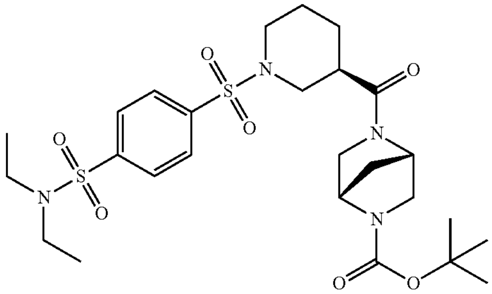 [SMILES: CCN(CC)S(=O)(=O)c1ccc(S(=O)(=O)N2CCC[C@@H](C(=O)N3C[C@@H]4C[C@H]3CN4C(=O)OC(C)(C)C)C2)cc1] | tert-butyl (1S,4S)-5-((R)-1-((4-(N,N-diethylsulfamoyl)phenyl)sulfonyl) piperidine-3-carbonyl)-2,5-diazabicyclo[2.2.1]heptane-2-carboxylate | 584.75 | 4.24 |
| DX3-127 | 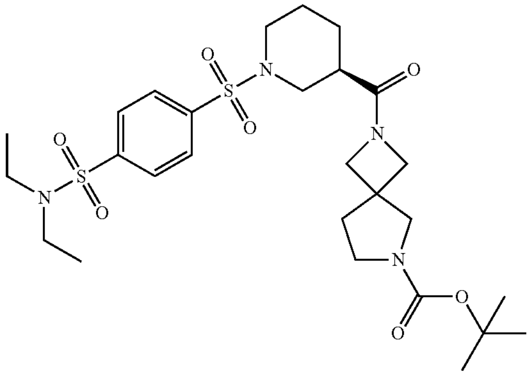 [SMILES: CCN(CC)S(=O)(=O)c1ccc(S(=O)(=O)N2CCC[C@@H](C(=O)N3CC4(CCN(C(=O)OC(C)(C)C)C4)C3)C2)cc1] | tert-butyl (R)-2-(1-((4-(N,N-diethylsulfamoyl)phenyl)sulfonyl) piperidine-3-carbonyl)-2,6-diazaspiro[3.4]octane-6-carboxylate | 598.77 | 3.55 |
| DX3-127B | 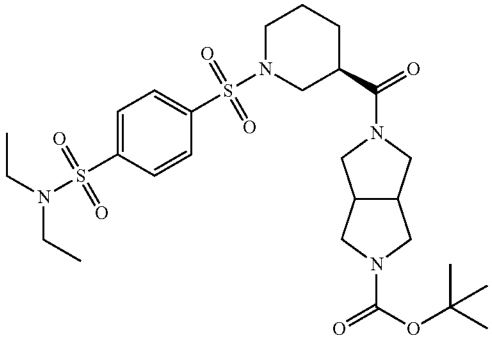 [SMILES: CCN(CC)S(=O)(=O)c1ccc(S(=O)(=O)N2CCC[C@@H](C(=O)N3CC4CN(C(=O)OC(C)(C)C)CC4C3)C2)cc1] | tert-butyl 5-((R)-1-((4-(N,N-diethylsulfamoyl)phenyl)sulfonyl) piperidine-3-carbonyl)hexahydropyrrolo[3,4-c]pyrrole-2(1H)-carboxylate | 598.77 | 3.55 |
| DX3-128 | 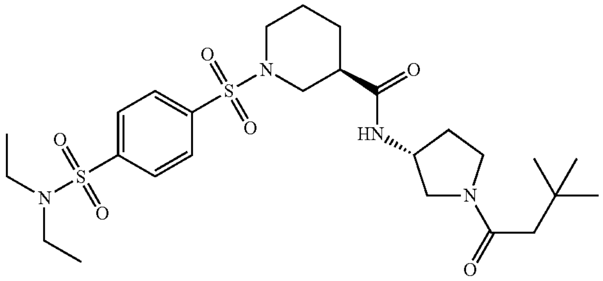 | (R)-1-((4-(N,N-diethylsulfamoyl)phenyl)sulfonyl)-N-((R)-1-(3,3-dimethylbutanoyl)pyrrolidin-3-yl)piperidine-3-carboxamide | 570.76 | 2.89 |

TABLE 1-continued

| Code | Structure | IUPAC name | M.W. | cLogP |
|---|---|---|---|---|
| DX3-128B | 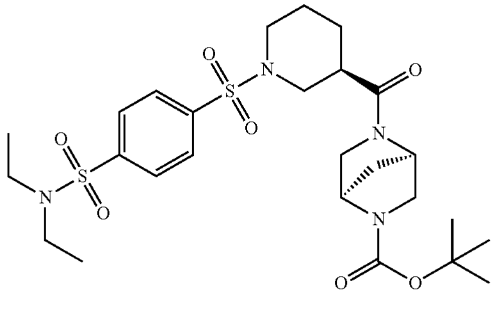 [SMILES: CCN(CC)S(=O)(=O)c1ccc(S(=O)(=O)N2CCC[C@@H](C(=O)N3C[C@H]4C[C@@H]3CN4C(=O)OC(C)(C)C)C2)cc1] | tert-butyl (1R,4R)-5-((R)-1-((4-(N,N-diethylsulfamoyl)phenyl)sulfonyl) piperidine-3-carbonyl)-2,5-diazabicyclo[2.2.1]heptane-2-carboxylate | 584.75 | 4.24 |
| DX3-130 | 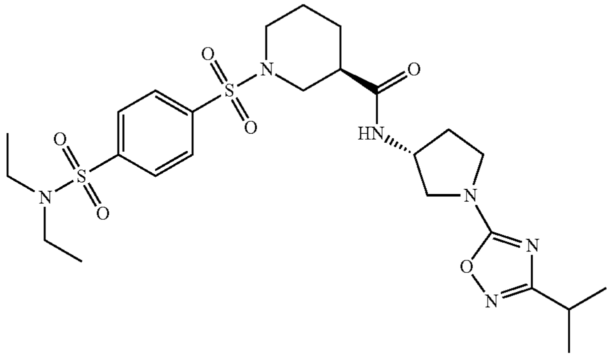 [SMILES: CCN(CC)S(=O)(=O)c1ccc(S(=O)(=O)N2CCC[C@@H](C(=O)N[C@@H]3CCN(c4nc(C(C)C)no4)C3)C2)cc1] | (R)-1-((4-(N,N-diethylsulfamoyl)phenyl)sulfonyl)-N-((R)-1-(3-isopropyl-1,2,4-oxadiazol-5-yl)pyrrolidin-3-yl)piperidine-3-carboxamide | 582.74 | 2.87 |
| DX3-132B | 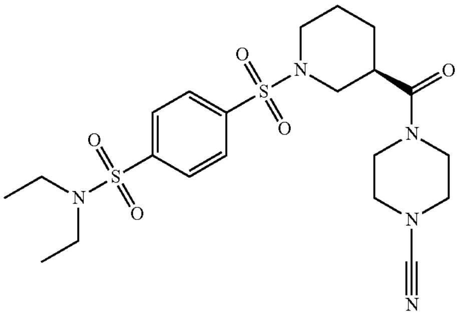 [SMILES: CCN(CC)S(=O)(=O)c1ccc(S(=O)(=O)N2CCC[C@@H](C(=O)N3CCN(C#N)CC3)C2)cc1] | (R)-4-((3-(4-cyanopiperazine-1-carbonyl)piperidin-1-yl)sulfonyl)-N,N-diethylbenzenesulfonamide | 497.63 | 1.93 |
| DX3-134 | 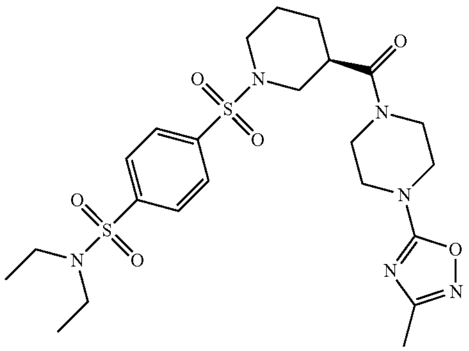 [SMILES: CCN(CC)S(=O)(=O)c1ccc(S(=O)(=O)N2CCC[C@@H](C(=O)N3CCN(c4nc(C)no4)CC3)C2)cc1] | (R)-N,N-diethyl-4-((3-(4-(3-methyl-1,2,4-oxadiazol-5-yl)piperazine-1-carbonyl)piperidin-1-yl)sulfonyl)benzenesulfonamide | 554.68 | 2.30 |

TABLE 1-continued

| Code | Structure | IUPAC name | M.W. | cLogP |
|---|---|---|---|---|
| DX3-134B | 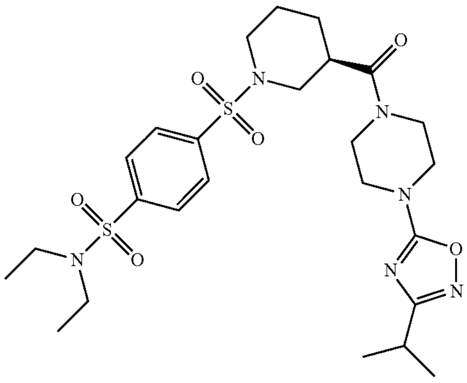 [SMILES: CCN(CC)S(=O)(=O)c1ccc(S(=O)(=O)N2CCC[C@@H](C(=O)N3CCN(c4nc(C(C)C)no4)CC3)C2)cc1] | (R)-N,N-diethyl-4-((3-(4-(3-isopropyl-1,2,4-oxadiazol-5-yl)piperazine-1-carbonyl)piperidin-1-yl)sulfonyl)benzenesulfonamide | 582.74 | 3.23 |
| DX3-139B | 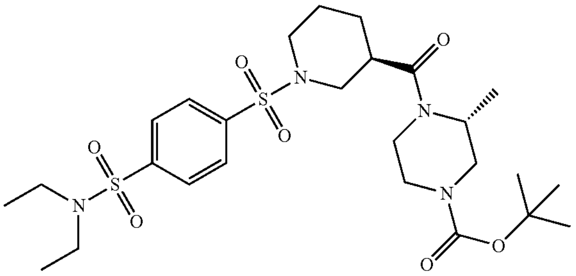 [SMILES: CCN(CC)S(=O)(=O)c1ccc(S(=O)(=O)N2CCC[C@@H](C(=O)N3CCN(C(=O)OC(C)(C)C)C[C@H]3C)C2)cc1] | tert-butyl (R)-4-((R)-1-((4-(N,N-diethylsulfamoyl)phenyl)sulfonyl) piperidine-3-carbonyl)-3-methylpiperazine-1-carboxylate | 586.76 | 4.45 |
| DX3-140 | 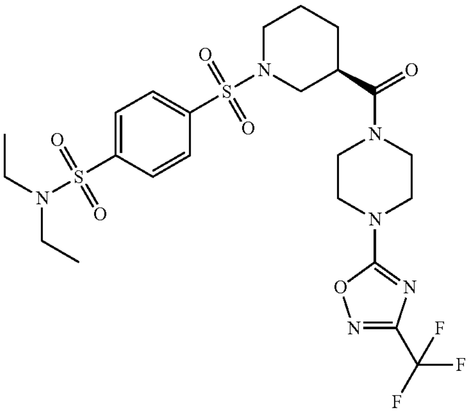 [SMILES: CCN(CC)S(=O)(=O)c1ccc(S(=O)(=O)N2CCC[C@@H](C(=O)N3CCN(c4nc(C(F)(F)F)no4)CC3)C2)cc1] | (R)-N,N-diethyl-4-((3-(4-(3-(trifluoromethyl)-1,2,4-oxadiazol-5-yl)piperazine-1-carbonyl)piperidin-1-yl)sulfonyl)benzenesulfonamide | 608.65 | 2.94 |
| DX3-141 | 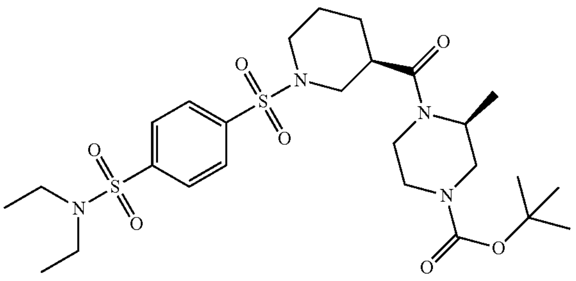 [SMILES: CCN(CC)S(=O)(=O)c1ccc(S(=O)(=O)N2CCC[C@@H](C(=O)N3CCN(C(=O)OC(C)(C)C)C[C@@H]3C)C2)cc1] | tert-butyl (S)-4-((R)-1-((4-(N,N-diethylsulfamoyl)phenyl)sulfonyl) piperidine-3-carbonyl)-3-methylpiperazine-1-carboxylate | 586.76 | 4.45 |

TABLE 1-continued

| Code | Structure | IUPAC name | M.W. | cLogP |
|---|---|---|---|---|
| DX3-141B | 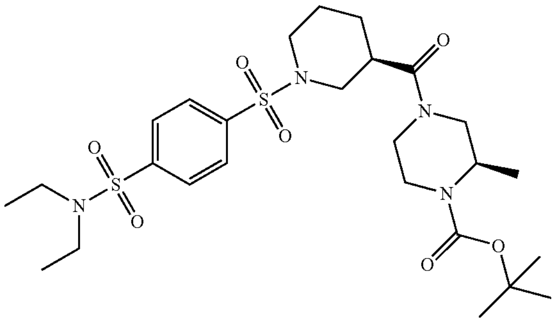 [SMILES: CCN(CC)S(=O)(=O)c1ccc(S(=O)(=O)N2CCC[C@@H](C(=O)N3CCN(C(=O)OC(C)(C)C)[C@H](C)C3)C2)cc1] | tert-butyl (R)-4-((R)-1-((4-(N,N-diethylsulfamoyl)phenyl)sulfonyl) piperidine-3-carbonyl)-2-methylpiperazine-1-carboxylate | 586.76 | 4.45 |
| DX3-142 | 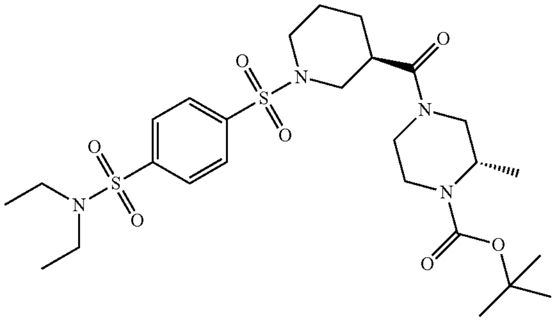 [SMILES: CCN(CC)S(=O)(=O)c1ccc(S(=O)(=O)N2CCC[C@@H](C(=O)N3CCN(C(=O)OC(C)(C)C)[C@@H](C)C3)C2)cc1] | tert-butyl (S)-4-((R)-1-((4-(N,N-diethylsulfamoyl)phenyl)sulfonyl) piperidine-3-carbonyl)-2-methylpiperazine-1-carboxylate | 586.76 | 4.45 |
| DX3-142B | 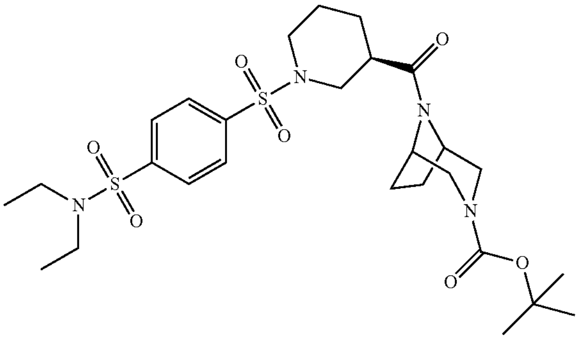 [SMILES: CCN(CC)S(=O)(=O)c1ccc(S(=O)(=O)N2CCC[C@@H](C(=O)N3C4CCC3CN(C(=O)OC(C)(C)C)C4)C2)cc1] | tert-butyl 8-((R)-1-((4-(N,N-diethylsulfamoyl)phenyl)sulfonyl) piperidine-3-carbonyl)-3,8-diazabicyclo[3.2.1]octane-3-carboxylate | 598.77 | 4.24 |
| DX3-146 | 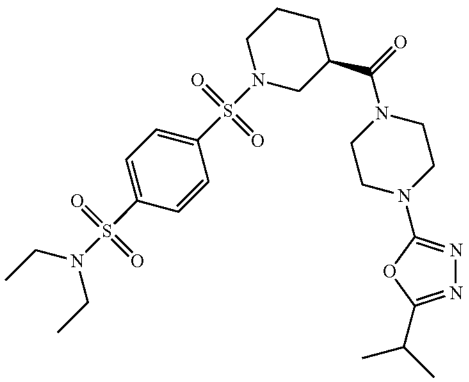 [SMILES: CCN(CC)S(=O)(=O)c1ccc(S(=O)(=O)N2CCC[C@@H](C(=O)N3CCN(c4nnc(C(C)C)o4)CC3)C2)cc1] | (R)-N,N-diethyl-4-((3-(4-(5-isopropyl-1,3,4-oxadiazol-2-yl)piperazine-1-carbonyl)piperidin-1-yl)sulfonyl)benzenesulfonamide | 582.74 | 2.42 |

TABLE 1-continued

| Code | Structure | IUPAC name | M.W. | cLogP |
|---|---|---|---|---|
| DX3-149 | 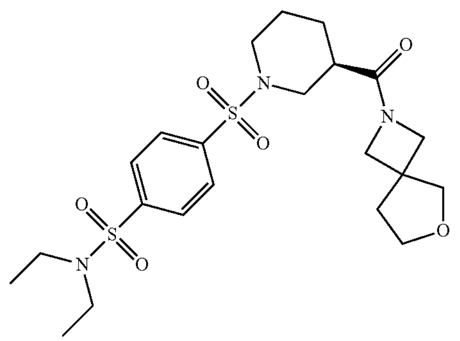 [SMILES: CCN(CC)S(=O)(=O)c1ccc(S(=O)(=O)N2CCC[C@@H](C(=O)N3CC4(CCOC4)C3)C2)cc1] | (R)-4-((3-(6-oxa-2-azaspiro[3.4]octane-2-carbonyl)piperidin-1-yl)sulfonyl)-N,N-diethylbenzenesulfonamide | 499.64 | 1.73 |
| DX3-149B | 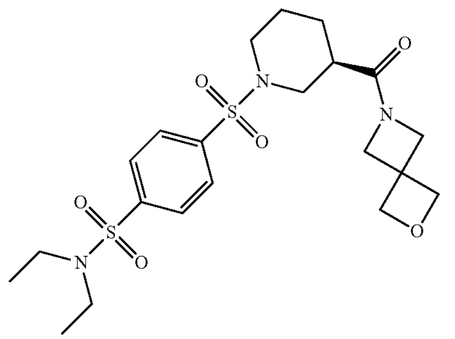 [SMILES: CCN(CC)S(=O)(=O)c1ccc(S(=O)(=O)N2CCC[C@@H](C(=O)N3CC4(COC4)C3)C2)cc1] | (R)-4-((3-(2-oxa-6-azaspiro[3.3]heptane-6-carbonyl)piperidin-1-yl)sulfonyl)-N,N-diethylbenzenesulfonamide | 485.61 | 1.84 |
| DX3-162B | 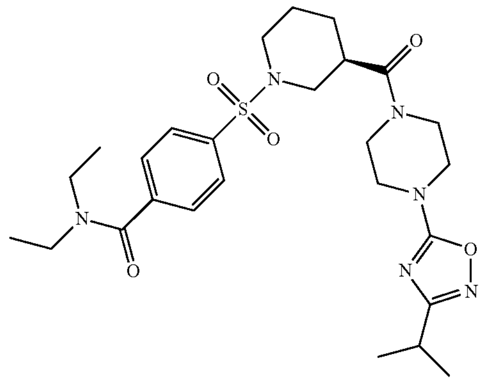 [SMILES: CCN(CC)C(=O)c1ccc(S(=O)(=O)N2CCC[C@@H](C(=O)N3CCN(c4nc(C(C)C)no4)CC3)C2)cc1] | (R)-N,N-diethyl-4-((3-(4-(3-isopropyl-1,2,4-oxadiazol-5-yl)piperazine-1-carbonyl)piperidin-1-yl)sulfonyl)benzamide | 546.69 | 2.64 |
| DX3-164B | 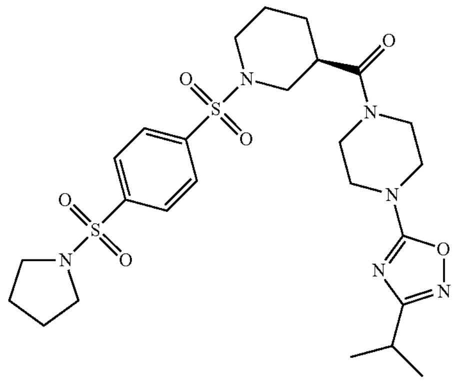 [SMILES: CC(C)c1noc(N2CCN(C(=O)[C@@H]3CCCN(S(=O)(=O)c4ccc(S(=O)(=O)N5CCCC5)cc4)C3)CC2)n1] | (R)-(4-(3-isopropyl-1,2,4-oxadiazol-5-yl)piperazin-1-yl)(1-((4-(pyrrolidin-1-ylsulfonyl)phenyl)sulfonyl)piperidin-3-yl)methanone | 580.72 | 2.81 |

TABLE 1-continued

| Code | Structure | IUPAC name | M.W. | cLogP |
|---|---|---|---|---|
| DX3-165B | 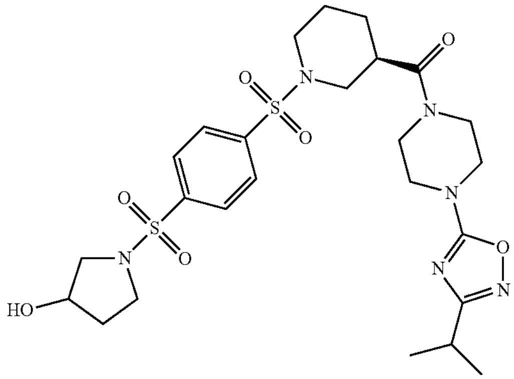 [SMILES: CC(C)c1noc(N2CCN(C(=O)[C@@H]3CCCN(S(=O)(=O)c4ccc(S(=O)(=O)N5CCC(O)C5)cc4)C3)CC2)n1] | ((3R)-1-((4-((3-hydroxypyrrolidin-1-yl)sulfonyl)phenyl)sulfonyl) piperidin-3-yl)(4-(3-isopropyl-1,2,4-oxadiazol-5-yl)piperazin-1-yl)methanone | 596.72 | 1.58 |
| DX3-166B | 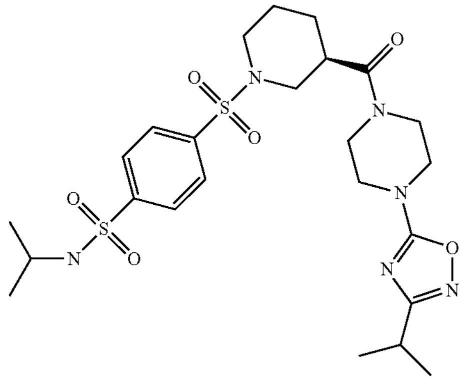 [SMILES: CC(C)NS(=O)(=O)c1ccc(S(=O)(=O)N2CCC[C@@H](C(=O)N3CCN(c4nc(C(C)C)no4)CC3)C2)cc1] | (R)-N-isopropyl-4-((3-(4-(3-isopropyl-1,2,4-oxadiazol-5-yl)piperazine-1-carbonyl)piperidin-1-yl)sulfonyl)benzenesulfonamide | 568.71 | 3.14 |
| DX3-167 | 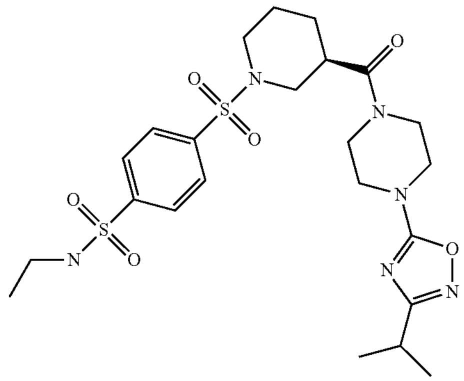 [SMILES: CCNS(=O)(=O)c1ccc(S(=O)(=O)N2CCC[C@@H](C(=O)N3CCN(c4nc(C(C)C)no4)CC3)C2)cc1] | (R)-N-ethyl-4-((3-(4-(3-isopropyl-1,2,4-oxadiazol-5-yl)piperazine-1-carbonyl)piperidin-1-yl)sulfonyl)benzenesulfonamide | 554.68 | 2.83 |
| DX3-167B | 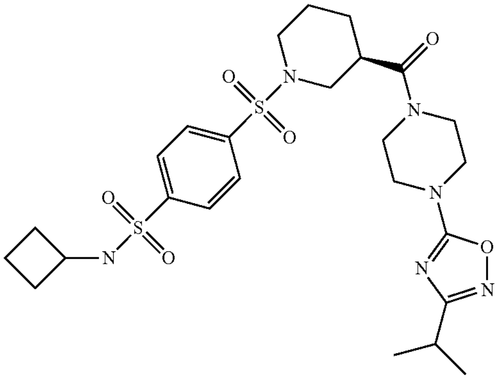 [SMILES: CC(C)c1noc(N2CCN(C(=O)[C@@H]3CCCN(S(=O)(=O)c4ccc(S(=O)(=O)NC5CCC5)cc4)C3)CC2)n1] | (R)-N-cyclobutyl-4-((3-(4-(3-isopropyl-1,2,4-oxadiazol-5-yl)piperazine-1-carbonyl)piperidin-1-yl)sulfonyl)benzenesulfonamide | 580.72 | 3.21 |

TABLE 1-continued

| Code | Structure | IUPAC name | M.W. | cLogP |
|---|---|---|---|---|
| DX3-175 | 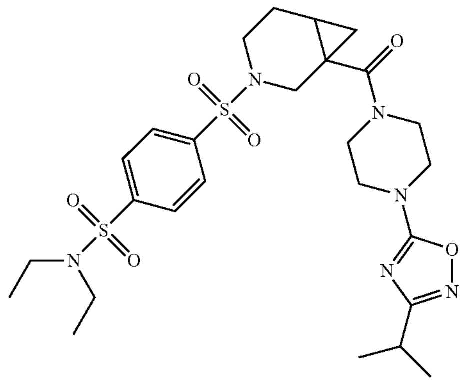 [SMILES: CCN(CC)S(=O)(=O)c1ccc(S(=O)(=O)N2CCC3CC3(C(=O)N3CCN(c4nc(C(C)C)no4)CC3)C2)cc1] | N,N-diethyl-4-((1-(4-(3-isopropyl-1,2,4-oxadiazol-5-yl)piperazine-1-carbonyl)-3-azabicyclo[4.1.0]heptan-3-yl)sulfonyl)benzenesulfonamide | 594.75 | 2.99 |
| DX3-176 | 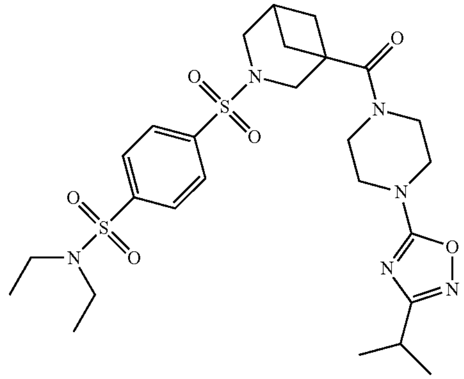 [SMILES: CCN(CC)S(=O)(=O)c1ccc(S(=O)(=O)N2CC3CC(C(=O)N4CCN(c5nc(C(C)C)no5)CC4)(C3)C2)cc1] | N,N-diethyl-4-((1-(4-(3-isopropyl-1,2,4-oxadiazol-5-yl)piperazine-1-carbonyl)-3-azabicyclo[3.1.1]heptan-3-yl)sulfonyl)benzenesulfonamide | 594.75 | 2.99 |
| DX3-177B | 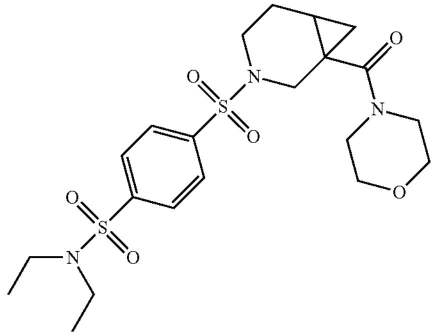 [SMILES: CCN(CC)S(=O)(=O)c1ccc(S(=O)(=O)N2CCC3CC3(C(=O)N3CCOCC3)C2)cc1] | N,N-diethyl-4-((1-(4-(morpholine-4-carbonyl)-3-azabicyclo[4.1.0]heptan-3-yl)sulfonyl)benzenesulfonamide | 485.61 | 1.71 |
| DX3-178 | 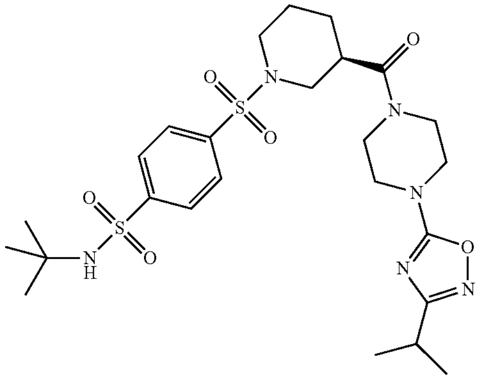 [SMILES: CC(C)c1noc(N2CCN(C(=O)[C@@H]3CCCN(S(=O)(=O)c4ccc(S(=O)(=O)NC(C)(C)C)cc4)C3)CC2)n1] | (R)-N-(tert-butyl)-4-((3-(4-(3-isopropyl-1,2,4-oxadiazol-5-yl)piperazine-1-carbonyl)piperidin-1-yl)sulfonyl)benzenesulfonamide | 582.74 | 3.54 |

TABLE 1-continued

| Code | Structure | IUPAC name | M.W. | cLogP |
|---|---|---|---|---|
| DX3-178B | 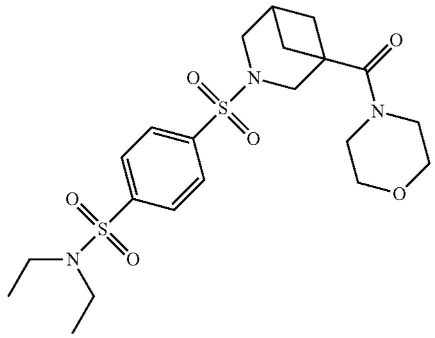 [SMILES: CCN(CC)S(=O)(=O)c1ccc(S(=O)(=O)N2CC3CC(C(=O)N4CCOCC4)(C3)C2)cc1] | N,N-diethyl-4-((1-(morpholine-4-carbonyl)-3-azabicyclo[3.1.1]heptan-3-yl)sulfonyl)benzenesulfonamide | 485.61 | 1.71 |
| DX3-179B | 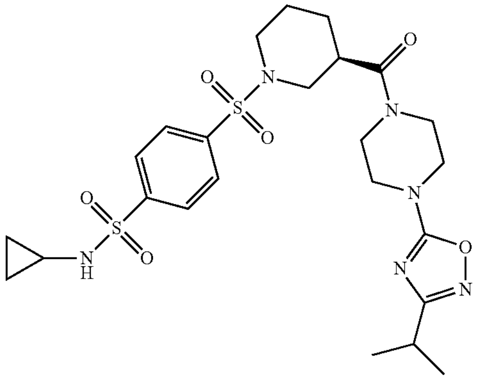 [SMILES: CC(C)c1noc(N2CCN(C(=O)[C@@H]3CCCN(S(=O)(=O)c4ccc(S(=O)(=O)NC5CC5)cc4)C3)CC2)n1] | (R)-N-cyclopropyl-4-((3-(4-(3-isopropyl-1,2,4-oxadiazol-5-yl)piperazine-1-carbonyl)piperidin-1-yl)sulfonyl)benzenesulfonamide | 566.69 | 2.88 |
| DX3-184 | 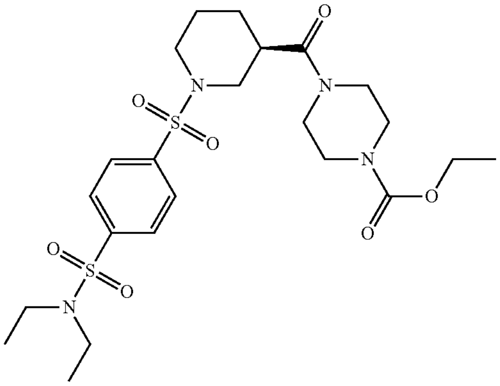 [SMILES: CCOC(=O)N1CCN(C(=O)[C@@H]2CCCN(S(=O)(=O)c3ccc(S(=O)(=O)N(CC)CC)cc3)C2)CC1] | ethyl (R)-4-(1-((4-(N,N-diethylsulfamoyl)phenyl)sulfonyl) piperidine-3-carbonyl)piperazine-1-carboxylate | 544.68 | 3.22 |
| DX3-184B | 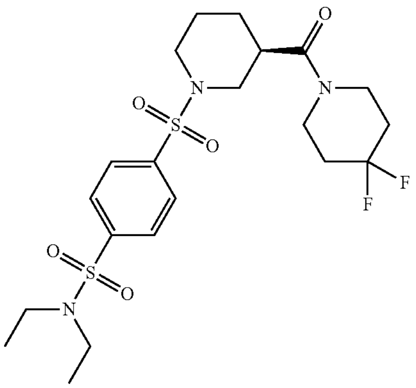 [SMILES: CCN(CC)S(=O)(=O)c1ccc(S(=O)(=O)N2CCC[C@@H](C(=O)N3CCC(F)(F)CC3)C2)cc1] | (R)-4-((3-(4,4-difluoropiperidine-1-carbonyl)piperidin-1-yl)sulfonyl)-N,N-diethylbenzenesulfonamide | 507.61 | 2.14 |

TABLE 1-continued

| Code | Structure | IUPAC name | M.W. | cLogP |
|---|---|---|---|---|
| DX3-185 | 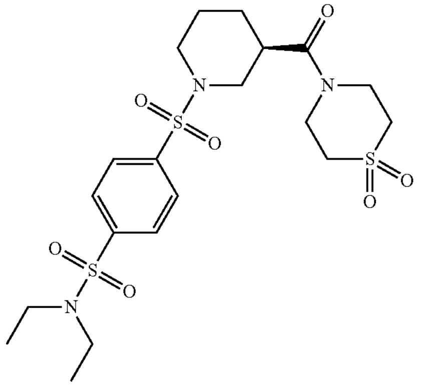 [SMILES: CCN(CC)S(=O)(=O)c1ccc(S(=O)(=O)N2CCC[C@@H](C(=O)N3CCS(=O)(=O)CC3)C2)cc1] | (R)-4-((3-(1,1-dioxidothiomorpholine-4-carbonyl)piperidin-1-yl)sulfonyl)-N,N-diethylbenzenesulfonamide | 521.66 | 0.99 |
| DX3-185B | 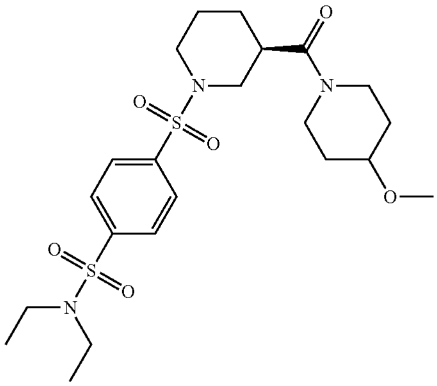 [SMILES: CCN(CC)S(=O)(=O)c1ccc(S(=O)(=O)N2CCC[C@@H](C(=O)N3CCC(OC)CC3)C2)cc1] | (R)-N,N-diethyl-4-((3-(4-methoxypiperidine-1-carbonyl)piperidin-1-yl)sulfonyl)benzenesulfonamide | 501.66 | 1.38 |
| DX3-186 | 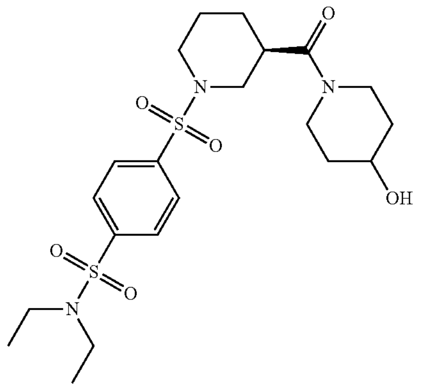 [SMILES: CCN(CC)S(=O)(=O)c1ccc(S(=O)(=O)N2CCC[C@@H](C(=O)N3CCC(O)CC3)C2)cc1] | (R)-N,N-diethyl-4-((3-(4-hydroxypiperidine-1-carbonyl)piperidin-1-yl)sulfonyl)benzenesulfonamide | 487.63 | 0.66 |
| DX3-186B | 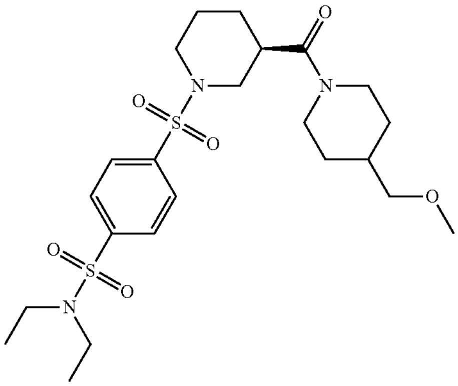 [SMILES: CCN(CC)S(=O)(=O)c1ccc(S(=O)(=O)N2CCC[C@@H](C(=O)N3CCC(COC)CC3)C2)cc1] | (R)-N,N-diethyl-4-((3-(4-(methoxymethyl)piperidine-1-carbonyl)piperidin-1-yl)sulfonyl)benzenesulfonamide | 515.68 | 2.00 |

TABLE 1-continued

| Code | Structure | IUPAC name | M.W. | cLogP |
|---|---|---|---|---|
| DX3-187B | 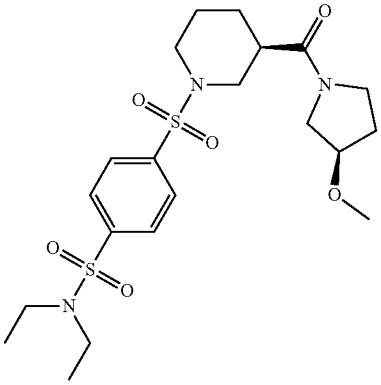 [SMILES: CCN(CC)S(=O)(=O)c1ccc(S(=O)(=O)N2CCC[C@@H](C(=O)N3CC[C@@H](OC)C3)C2)cc1] | N,N-diethyl-4-(((R)-3-((R)-3-methoxypyrrolidine-1-carbonyl)piperidin-1-yl)sulfonyl)benzenesulfonamide | 487.63 | 2.07 |
| DX3-188 | 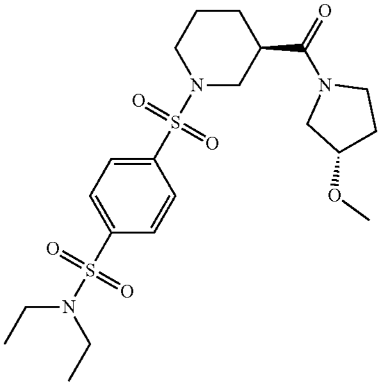 [SMILES: CCN(CC)S(=O)(=O)c1ccc(S(=O)(=O)N2CCC[C@@H](C(=O)N3CC[C@H](OC)C3)C2)cc1] | N,N-diethyl-4-(((R)-3-((S)-3-methoxypyrrolidine-1-carbonyl)piperidin-1-yl)sulfonyl)benzenesulfonamide | 487.63 | 2.07 |
| DX3-188B | 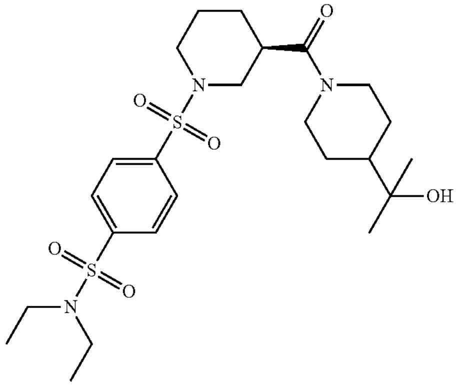 [SMILES: CCN(CC)S(=O)(=O)c1ccc(S(=O)(=O)N2CCC[C@@H](C(=O)N3CCC(C(C)(C)O)CC3)C2)cc1] | (R)-N,N-diethyl-4-((3-(4-(2-hydroxypropan-2-yl)piperidine-1-carbonyl)piperidin-1-yl)sulfonyl)benzenesulfonamide | 529.71 | 1.99 |
| DX3-192 | 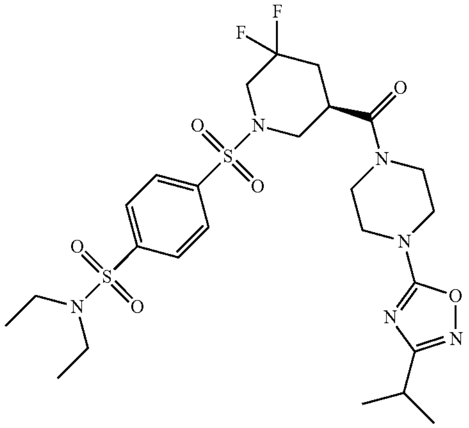 [SMILES: CCN(CC)S(=O)(=O)c1ccc(S(=O)(=O)N2C[C@H](C(=O)N3CCN(c4nc(C(C)C)no4)CC3)CC(F)(F)C2)cc1] | (R)-4-((3,3-difluoro-5-(4-(3-isopropyl-1,2,4-oxadiazol-5-yl)piperazine-1-carbonyl)piperidin-1-yl)sulfony))-N,N-diethylbenzenesulfonamide | 618.72 | 3.52 |

TABLE 1-continued

| Code | Structure | IUPAC name | M.W. | cLogP |
|---|---|---|---|---|
| DX3-193 | 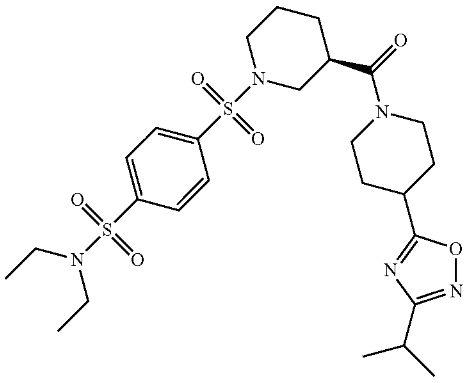 [SMILES: CCN(CC)S(=O)(=O)c1ccc(S(=O)(=O)N2CCC[C@@H](C(=O)N3CCC(c4nc(C(C)C)no4)CC3)C2)cc1] | (R)-N,N-diethyl-4-((3-(4-(3-isopropyl-1,2,4-oxadiazol-5-yl)piperidine-1-carbonyl)piperidin-1-yl)sulfonyl)benzenesulfonamide | 581.75 | 2.48 |
| DX3-193B | 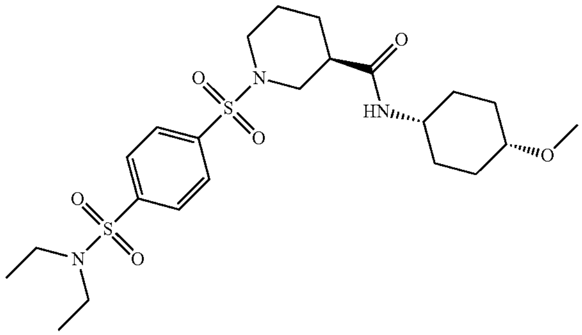 [SMILES: CCN(CC)S(=O)(=O)c1ccc(S(=O)(=O)N2CCC[C@@H](C(=O)N[C@H]3CC[C@@H](OC)CC3)C2)cc1] | (R)-1-((4-(N,N-diethylsulfamoyl)phenyl)sulfonyl)-N-((1s,4S)-4-methoxycyclohexyl)piperidine-3-carboxamide | 515.68 | 2.15 |
| DX3-194 | 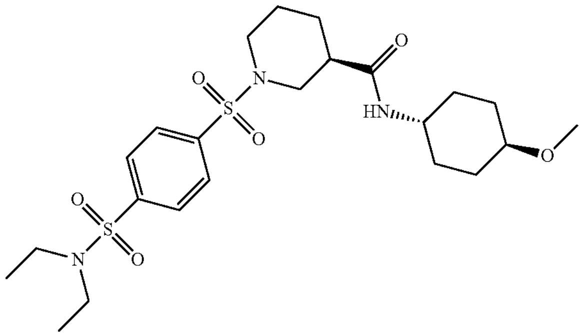 [SMILES: CCN(CC)S(=O)(=O)c1ccc(S(=O)(=O)N2CCC[C@@H](C(=O)N[C@H]3CC[C@H](OC)CC3)C2)cc1] | (R)-1-((4-(N,N-diethylsulfamoyl)phenyl)sulfonyl)-N-((1r,4R)-4-methoxycyclohexyl)piperidine-3-carboxamide | 515.68 | 2.15 |
| DX3-194B | 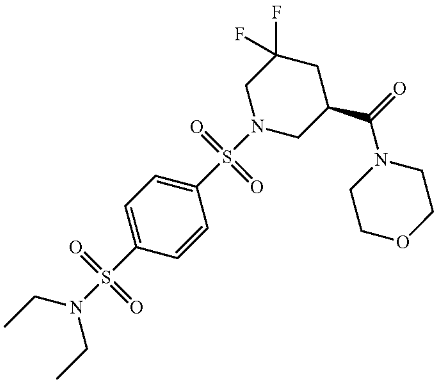 [SMILES: CCN(CC)S(=O)(=O)c1ccc(S(=O)(=O)N2C[C@H](C(=O)N3CCOCC3)CC(F)(F)C2)cc1] | (R)-4-((3,3-difluoro-5-(morpholine-4-carbonyl)piperidin-1-yl)sulfonyl)-N,N-diethylbenzenesulfonamide | 509.58 | 2.24 |

TABLE 1-continued

| Code | Structure | IUPAC name | M.W. | cLogP |
|---|---|---|---|---|
| DX3-195B | 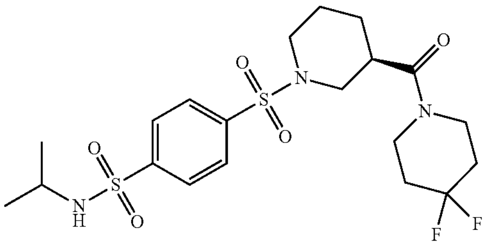 [SMILES: CC(C)NS(=O)(=O)c1ccc(S(=O)(=O)N2CCC[C@@H](C(=O)N3CCC(F)(F)CC3)C2)cc1] | (R)-4-((3-(4,4-difluoropiperidine-1-carbonyl)piperidin-1-yl)sulfonyl)-N-isopropylbenzenesulfonamide | 493.58 | 2.04 |
| DX3-198 | 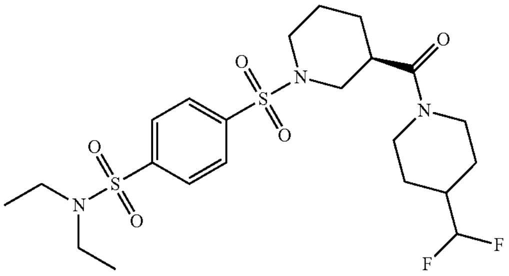 [SMILES: CCN(CC)S(=O)(=O)c1ccc(S(=O)(=O)N2CCC[C@@H](C(=O)N3CCC(C(F)F)CC3)C2)cc1] | (R)-4-(3-(4-(difluoromethyl)piperidine-1-carbonyl)piperidin-1-yl)sulfonyl)-N,N-diethylbenzenesulfonamide | 521.64 | 2.41 |
| DX3-198B | 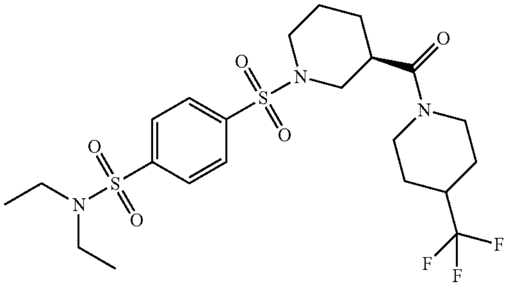 [SMILES: CCN(CC)S(=O)(=O)c1ccc(S(=O)(=O)N2CCC[C@@H](C(=O)N3CCC(C(F)(F)F)CC3)C2)cc1] | (R)-N,N-diethyl-4-((3-(4-(trifluoromethyl)piperidine-1-carbonyl)piperidin-1-yl)sulfonyl)benzenesulfonamide | 539.63 | 2.84 |
| DX3-201B | 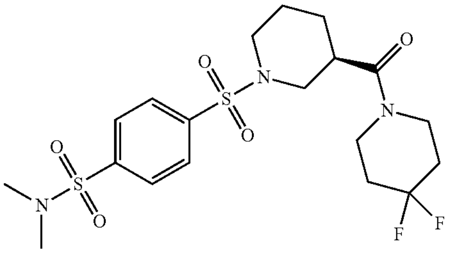 [SMILES: CN(C)S(=O)(=O)c1ccc(S(=O)(=O)N2CCC[C@@H](C(=O)N3CCC(F)(F)CC3)C2)cc1] | (R)-4-((3-(4,4-difluoropiperidine-1-carbonyl)piperidin-1-yl)sulfonyl)-N,N-dimethylbenzenesulfonamide | 479.56 | 1.08 |
| DX3-202B | 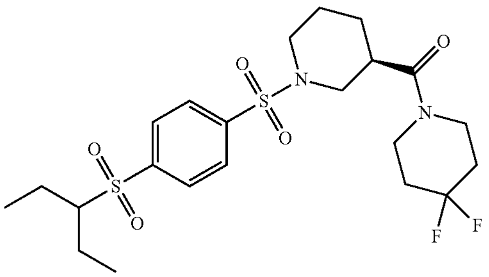 [SMILES: CCC(CC)S(=O)(=O)c1ccc(S(=O)(=O)N2CCC[C@@H](C(=O)N3CCC(F)(F)CC3)C2)cc1] | (R)-(4,4-difluoropiperidin-1-yl)(1-((4-(pentan-3-ylsulfonyl)phenyl)sulfonyl)piperidin-3-yl)methanone | 506.62 | 2.36 |

TABLE 1-continued

| Code | Structure | IUPAC name | M.W. | cLogP |
|---|---|---|---|---|
| DX3-203 | 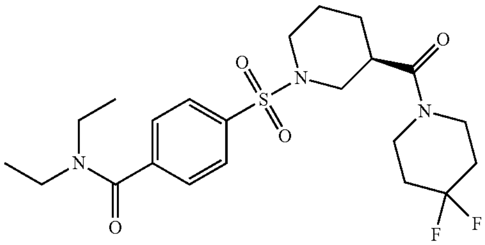 [SMILES: CCN(CC)C(=O)c1ccc(S(=O)(=O)N2CCC[C@@H](C(=O)N3CCC(F)(F)CC3)C2)cc1] | (R)-4-((3-(4,4-difluoropiperidine-1-carbonyl)piperidin-1-yl)sulfonyl)-N,N-diethylbenzamide | 471.56 | 1.54 |
| DX3-205 | 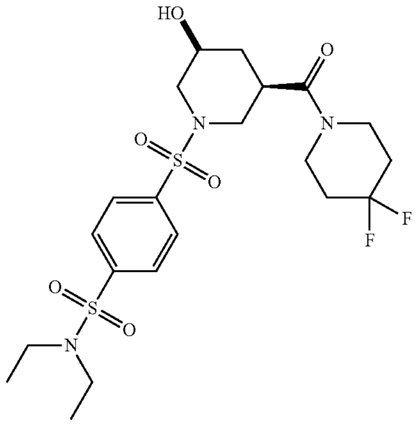 [SMILES: CCN(CC)S(=O)(=O)c1ccc(S(=O)(=O)N2C[C@@H](O)C[C@@H](C(=O)N3CCC(F)(F)CC3)C2)cc1] | 4-(((3R,5S)-3-(4,4-difluoropiperidine-1-carbonyl)-5-hydroxypiperidin-1-yl)sulfonyl)-N,N-diethylbenzenesulfonamide | 507.61 | 1.95 |
| DX3-206 | 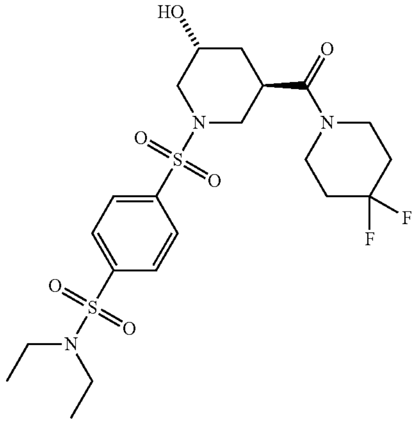 [SMILES: CCN(CC)S(=O)(=O)c1ccc(S(=O)(=O)N2C[C@H](O)C[C@@H](C(=O)N3CCC(F)(F)CC3)C2)cc1] | 4-(((3R,5R)-3-(4,4-difluoropiperidine-1-carbonyl)-5-hydroxypiperidin-1-yl)sulfonyl)-N,N-diethylbenzenesulfonamide | 507.61 | 1.95 |
| DX3-207 | 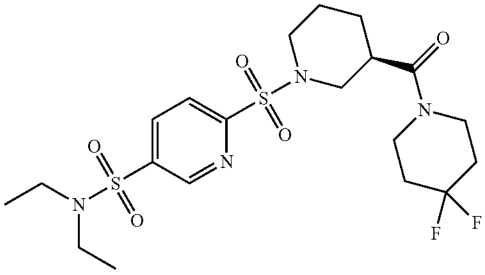 [SMILES: CCN(CC)S(=O)(=O)c1ccc(S(=O)(=O)N2CCC[C@@H](C(=O)N3CCC(F)(F)CC3)C2)nc1] | (R)-6-((3-(4,4-difluoropiperidine-1-carbonyl)piperidin-1-yl)sulfonyl)-N,N-diethylpyridine-3-sulfonamide | 508.60 | 0.94 |

TABLE 1-continued

| Code | Structure | IUPAC name | M.W. | cLogP |
|---|---|---|---|---|
| DX3-208 | 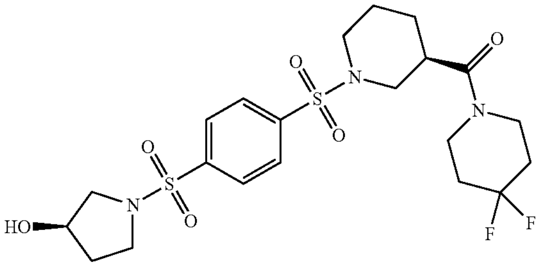 [SMILES: O=C([C@@H]1CCCN(S(=O)(=O)c2ccc(S(=O)(=O)N3CC[C@@H](O)C3)cc2)C1)N1CCC(F)(F)CC1] | (4,4-difluoropiperidin-1-yl)((R)-1-((4-(((R)-3-hydroxypyrrolidin-1-yl)sulfonyl)phenyl)sulfonyl) piperidin-3-yl)methanone | 521.59 | 0.48 |
| DX3-209 | 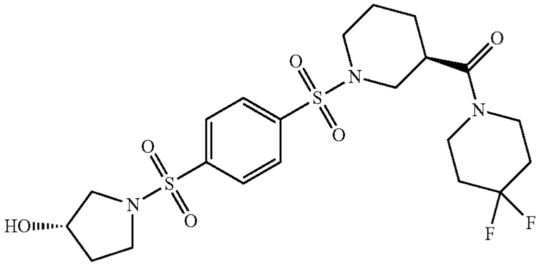 [SMILES: O=C([C@@H]1CCCN(S(=O)(=O)c2ccc(S(=O)(=O)N3CC[C@H](O)C3)cc2)C1)N1CCC(F)(F)CC1] | (4,4-difluoropiperidin-1-yl)((R)-1-((4-(((S)-3-hydroxypyrrolidin-1-yl)sulfonyl)phenyl)sulfonyl) piperidin-3-yl)methanone | 521.59 | 0.48 |
| DX3-209B | 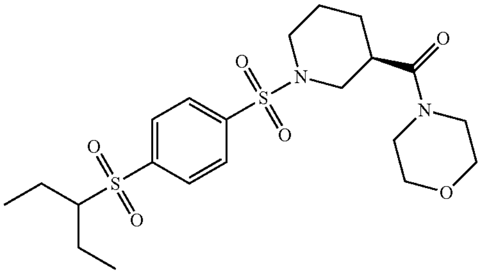 [SMILES: CCC(CC)S(=O)(=O)c1ccc(S(=O)(=O)N2CCC[C@@H](C(=O)N3CCOCC3)C2)cc1] | (R)-morpholino(1-((4-(pentan-3-ylsulfonyl)phenyl)sulfonyl) piperidin-3-yl)methanone | 472.62 | 2.18 |
| DX3-210 | 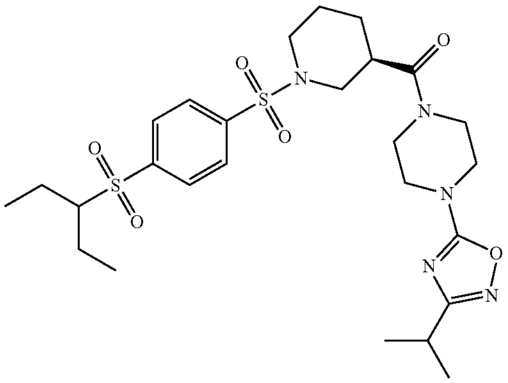 [SMILES: CCC(CC)S(=O)(=O)c1ccc(S(=O)(=O)N2CCC[C@@H](C(=O)N3CCN(c4nc(C(C)C)no4)CC3)C2)cc1] | (R)-(4-(3-isopropyl-1,2,4-oxadiazol-5-yl)piperazin-1-yl)(1-((4-(pentan-3-ylsulfonyl)phenyl)sulfonyl) piperidin-3-yl)methanone | 581.75 | 3.46 |
| DX3-213B | 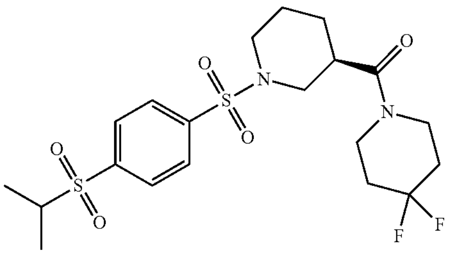 [SMILES: CC(C)S(=O)(=O)c1ccc(S(=O)(=O)N2CCC[C@@H](C(=O)N3CCC(F)(F)CC3)C2)cc1] | (R)-(4,4-difluoropiperidin-1-yl)(1-((4-(isopropylsulfonyl)phenyl)sulfonyl) piperidin-3-yl)methanone | 478.57 | 1.30 |

TABLE 1-continued

| Code | Structure | IUPAC name | M.W. | cLogP |
|---|---|---|---|---|
| DX3-214 | 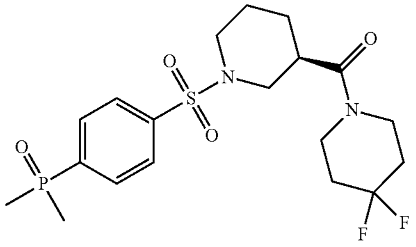 [SMILES: CP(C)(=O)c1ccc(S(=O)(=O)N2CCC[C@@H](C(=O)N3CCC(F)(F)CC3)C2)cc1] | (R)-(4,4-difluoropiperidin-1-yl)(1-((4-(dimethylphosphoryl)phenyl) sulfonyl)piperidin-3-yl)methanone | 448.47 | −0.75 |
| DX3-215 | 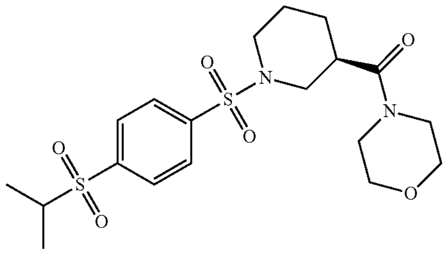 [SMILES: CC(C)S(=O)(=O)c1ccc(S(=O)(=O)N2CCC[C@@H](C(=O)N3CCOCC3)C2)cc1] | (R)-(1-((4-(isopropylsulfonyl)phenyl)sulfonyl) piperidin-3-yl)(morpholino)methanone | 444.56 | 1.12 |
| DX3-216 | 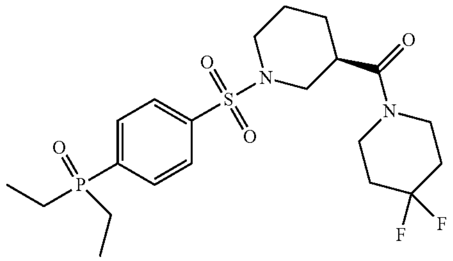 [SMILES: CCP(=O)(CC)c1ccc(S(=O)(=O)N2CCC[C@@H](C(=O)N3CCC(F)(F)CC3)C2)cc1] | (R)-(1-((4-(diethylphosphoryl)phenyl)sulfonyl) piperidin-3-yl)(4,4-difluoropiperidin-1-yl)methanone | 476.52 | 0.15 |
| DX3-218 | 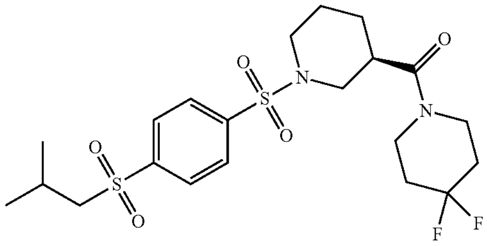 [SMILES: CC(C)CS(=O)(=O)c1ccc(S(=O)(=O)N2CCC[C@@H](C(=O)N3CCC(F)(F)CC3)C2)cc1] | (R)-(4,4-difluoropiperidin-1-yl)(1-((4-(isobutylsulfonyl)phenyl)sulfonyl) piperidin-3-yl)methanone | 492.60 | 1.92 |
| DX3-219B | 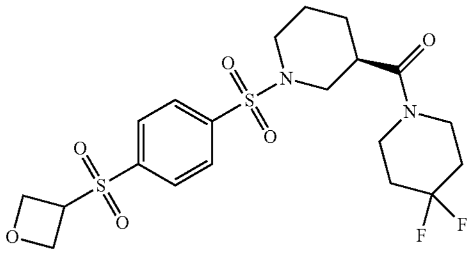 [SMILES: O=C([C@@H]1CCCN(S(=O)(=O)c2ccc(S(=O)(=O)C3COC3)cc2)C1)N1CCC(F)(F)CC1] | (R)-(4,4-difluoropiperidin-1-yl)(1-((4-(oxetan-3-ylsulfonyl)phenyl)sulfonyl) piperidin-3-yl)methanone | 492.55 | 0.78 |
| DX3-220B | 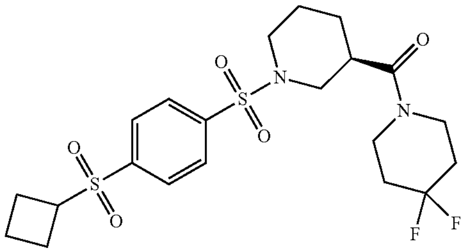 [SMILES: O=C([C@@H]1CCCN(S(=O)(=O)c2ccc(S(=O)(=O)C3CCC3)cc2)C1)N1CCC(F)(F)CC1] | (R)-(1-((4-(cyclobutylsulfonyl)phenyl) sulfonyl)piperidin-3-yl)(4,4-difluoropiperidin-1-yl)methanone | 490.58 | 1.38 |

TABLE 1-continued

| Code | Structure | IUPAC name | M.W. | cLogP |
|---|---|---|---|---|
| DX3-221 | 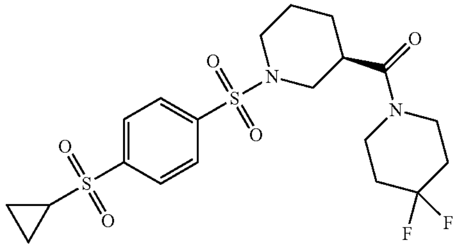 [SMILES: O=C([C@@H]1CCCN(S(=O)(=O)c2ccc(S(=O)(=O)C3CC3)cc2)C1)N1CCC(F)(F)CC1] | (R)-(1-((4-(cyclopropylsulfonyl)phenyl)sulfonyl)piperidin-3-yl)(4,4-difluoropiperidin-1-yl)methanone | 476.55 | 1.05 |
| DX3-221B | 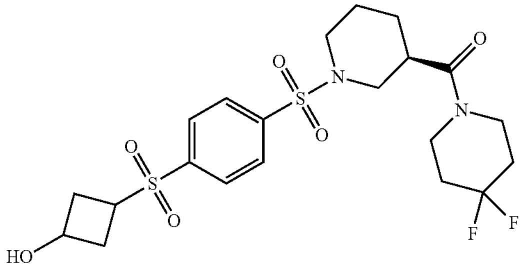 [SMILES: O=C([C@@H]1CCCN(S(=O)(=O)c2ccc(S(=O)(=O)C3CC(O)C3)cc2)C1)N1CCC(F)(F)CC1] | (R)-(4,4-difluoropiperidin-1-yl)(1-((4-((3-hydroxyazetidin-1-yl)sulfonyl)phenyl)sulfonyl)piperidin-3-yl)methanone | 507.6 | 0.78 |
| DX3-224 | 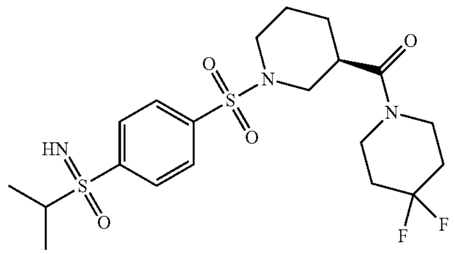 [SMILES: CC(C)S(=N)(=O)c1ccc(S(=O)(=O)N2CCC[C@@H](C(=O)N3CCC(F)(F)CC3)C2)cc1] | (4-(((R)-3-(4,4-difluoropiperidine-1-carbonyl)piperidin-1-yl)sulfonyl)phenyl)(imino)(isopropyl)-l6-sulfanone | 477.6 | 1.04 |
| DX3-226 | 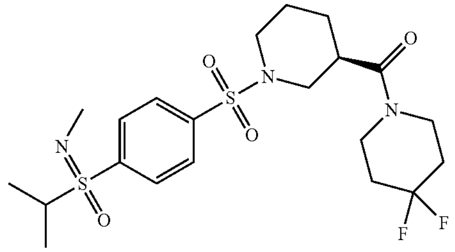 [SMILES: CN=S(=O)(c1ccc(S(=O)(=O)N2CCC[C@@H](C(=O)N3CCC(F)(F)CC3)C2)cc1)C(C)C] | (4-(((R)-3-(4,4-difluoropiperidine-1-carbonyl)piperidin-1-yl)sulfonyl)phenyl)(isopropyl)(methylimino)-l6-sulfanone | 491.6 | 1.80 |
| DX3-226 | 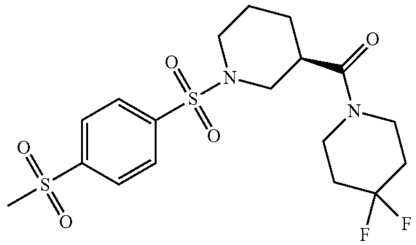 [SMILES: CS(=O)(=O)c1ccc(S(=O)(=O)N2CCC[C@@H](C(=O)N3CCC(F)(F)CC3)C2)cc1] | (R)-(4,4-difluoropiperidin-1-yl)(1-((4-(methylsulfonyl)phenyl)sulfonyl)piperidin-3-yl)methanone | 450.5 | 0.47 |
| DX3-226 | 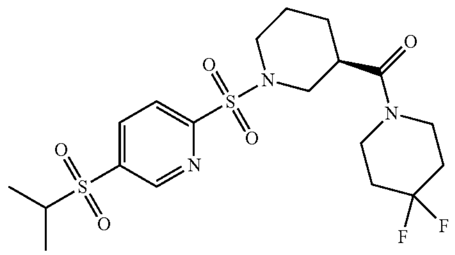 [SMILES: CC(C)S(=O)(=O)c1ccc(S(=O)(=O)N2CCC[C@@H](C(=O)N3CCC(F)(F)CC3)C2)nc1] | (R)-(4,4-difluoropiperidin-1-yl)(1-((5-(isopropylsulfonyl)pyridin-2-yl)sulfonyl)piperidin-3-yl)methanone | 479.6 | 0.39 |

The invention provides the stereochemical mixtures or pure forms for all compounds of invention.

The invention also provides all pharmaceutically acceptable salts, esters, amides, tautomers, geometric isomers, solvates thereof, as well as pharmaceutical composition comprising an effective amount of a compound of the invention and a pharmaceutically acceptable carrier. The composition may further comprise an effective amount of one or more other agents for treating cancer or a disorder associated with mitochondrial function.

The invention further provides prodrugs of all compounds of invention. The term "prodrug" used herein refers to a pharmacologically inactive derivative of a parent "drug" molecule which requires biotransformation within the target physiological system to release, or to convert the prodrug into the active drug. Prodrugs can address the problems associated with solubility, stability, cell permeability or bioavailability. Prodrugs usually comprise an active drug molecule and a chemical masking group. Prodrugs can be readily prepared from the parent compounds with well-known methods.

Furthermore, the invention provides a packaged product comprising a container; an effective amount of a compound of invention.

The invention also provides methods of preparing the compounds of invention.

The following schemes can be used to practice the present invention. Additional structural groups, including but not limited to those defined elsewhere in the specification and not shown in the compounds described in the schemes can be incorporated to give various compound disclosed herein, or intermediate compounds which can, after further manipulation using techniques known in the art, be converted to compounds of the present invention.

One route for preparation of compounds of the present invention is depicted in Scheme 1.

Scheme 1

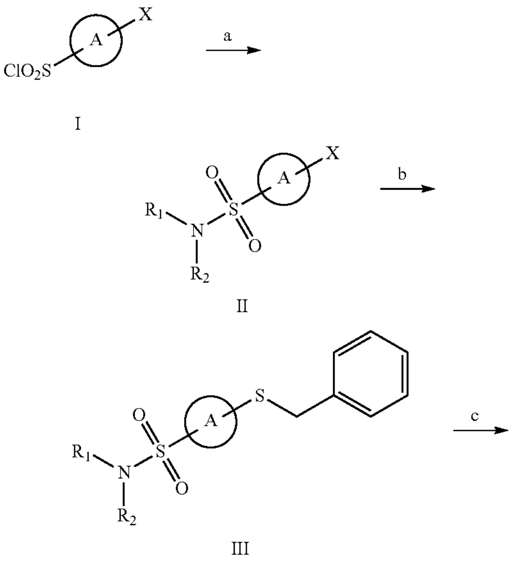

I
II
III

-continued

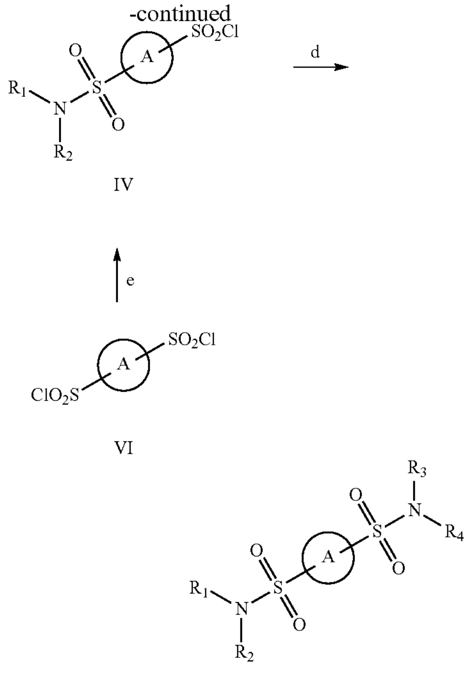

IV
VI
V

X = Cl, Br, I

Reagents and conditions: a) $NHR_1R_2$, $Et_3N$, DCM, rt; b) benzyl mercaptan, $Pd_2(dba)_3$, XantPhos, DIEA, dioxane, reflux, or benzyl mercaptan, $Cs_2CO_3$, DMF, heat; c) 1,3-dichloro-5,5-dimethylimidazolidine-2,4-dione, $CH_3CN$, $CH_3COOH$, $H_2O$, 0° C.; d) $NHR_3R_4$, $Et_3N$, DCM, rt; e) $NHR_1R_2$, $Et_3N$, DCM, rt.

The typical synthesis of the compounds of the invention starts from a condensation reaction between halogen substituted sulfonyl chloride (I) and the appropriate amine to give sulfonamide intermediate II. A Palladium catalyzed coupling or $S_NAr$ replacement reaction, depending on the electronic nature of the core structure A, between II and benzyl mercaptan furnish intermediate III, which is then subjected to an oxidative chlorination to give sulfonyl chloride IV. A second condensation reaction between IV and an amine give rise to the final product V. For part of the compounds of the invention, the mono-substituted sulfonyl chloride IV can be obtained directly from the reaction of a commercially available disulfonyl chloride VI and the appropriate amine.

In cases when the starting material I is not readily available, it was synthesized following Scheme 2.

Scheme 2

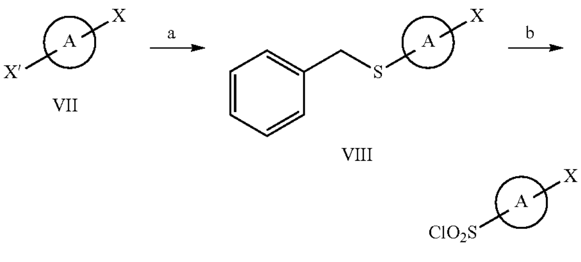

VII
VIII
I

X or X′ = Cl, Br, or I

Reagents and conditions: a) benzyl mercaptan, $Cs_2CO_3$, DMF, heat; b) 1,3-dichloro-5,5-dimethylimidazolidine-2,4-dione, $CH_3CN$, $CH_3COOH$, $H_2O$, 0° C.

Starting from a di-halogenated compound VII, the selective Palladium catalyzed coupling or $S_NAr$ replacement reaction, depending on the electronic nature of the core structure A, give rise to intermediate VIII, which was converted to I with a similar oxidative chlorination approach.

For compounds with diverse piperidine-3-carboxylate or piperidine-3-carboxamide structures, exemplified by Formula III, when $R_1$ is —OR or $NR_1R_2$, the synthesis is further following the method depicted in Scheme 3 based on Scheme 1.

Scheme 3

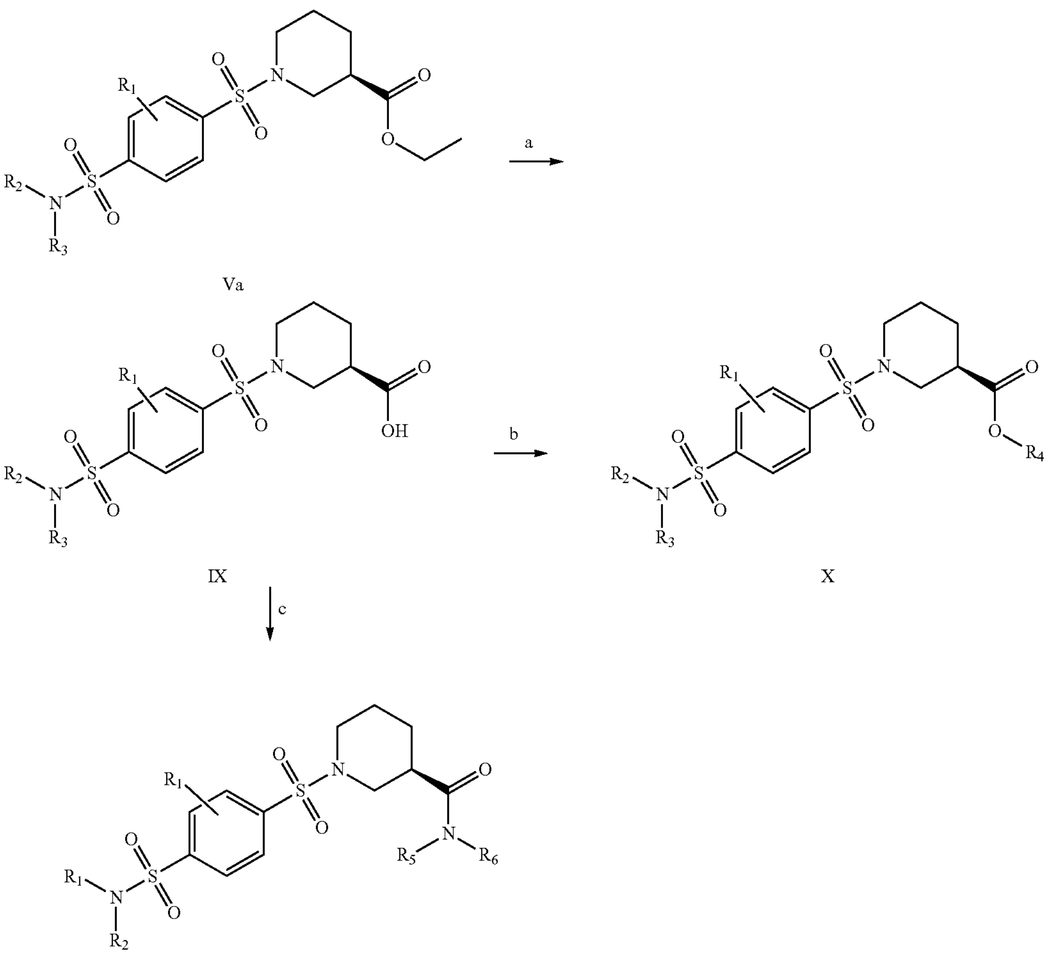

Va

IX

X

XI

Reagents and conditions: a) LiOH, THF, $H_2O$, rt; b) alcohols, EDCI, DMAP, DCM, rt; c) $NHR_5R_6$, HATU, DIEA, DMF.

Starting from compound Va with an ethyl piperidine-3-carboxylate structure, the corresponding carboxylic acid IX is obtained through a basic hydrolysis. With either EDCI/DMAP or HATU/DIEA coupling reagent/base combination, the corresponding esters X or amides XI is obtained respectively.

EXAMPLES

The following examples are illustrative, but not limiting, of the compounds, compositions, and methods of present invention. Other suitable modifications and adaptations of the variety of conditions and parameters normally encountered in clinical therapy and which are obvious to those skilled in the art are within the spirit and scope of the invention.

In case the preparative examples are obtained as a mixture of enantiomers, the pure enantiomer can be obtained by methods known to those skilled in the art, such as e.g. chiral chromatography or crystallization.

Example I

Chemistry

General Experimental Methods

All commercial reagents and anhydrous solvents were purchased and used without purification, unless specified. Column chromatography was performed on a Biotage Isolera flash chromatography system on Biotage normal phase silica gel columns. Preparative-HPLC purification was performed by Shimadzu Semi-Prep LC system. Analytical thin layer chromatography was performed on Merck pre-coated plates (silica gel 60 $F_{254}$). NMR spectra were recorded on a Bruker Ultrashield 300 MHz or Bruker Ascend 400 MHz spectrometer using deuterated $CDCl_3$ or $CD_3OD$ as solvents. Chemical shifts for proton magnetic resonance spectra ($^1H$ NMR) are quoted in parts per million (ppm) referenced to the appropriate solvent peak or 0.0 ppm for tetramethylsilane (TMS). The following abbreviations are used to describe the peak-splitting patterns when appropriate: br, broad; s, singlet; d, doublet; t, triplet; q, quartet; m, multiplet; and dd, doublet of doublets. Coupling constants, J, are reported in hertz (Hz). Mass spectra were recorded on a Shimadzu LCMS-2020 system using the electro spray ionization (ESI) ion source. HPLC was used to determine the purity of biologically tested compounds using Shimadzu LC-2030C 3D system on Kinetex XB-C18 column (2.6 μm, 4.6×75 mm) under the following gradient elution conditions: acetonitrile/water (10-95%) or methanol/water (10-95%), both with 0.1% formic acid as the additive, over 15 minutes at a 0.80 mL/min flow rate at room temperature. The purity was established by integration of the areas of major peaks detected at 254 nm, and all final products have >95% purity.

Scheme 4

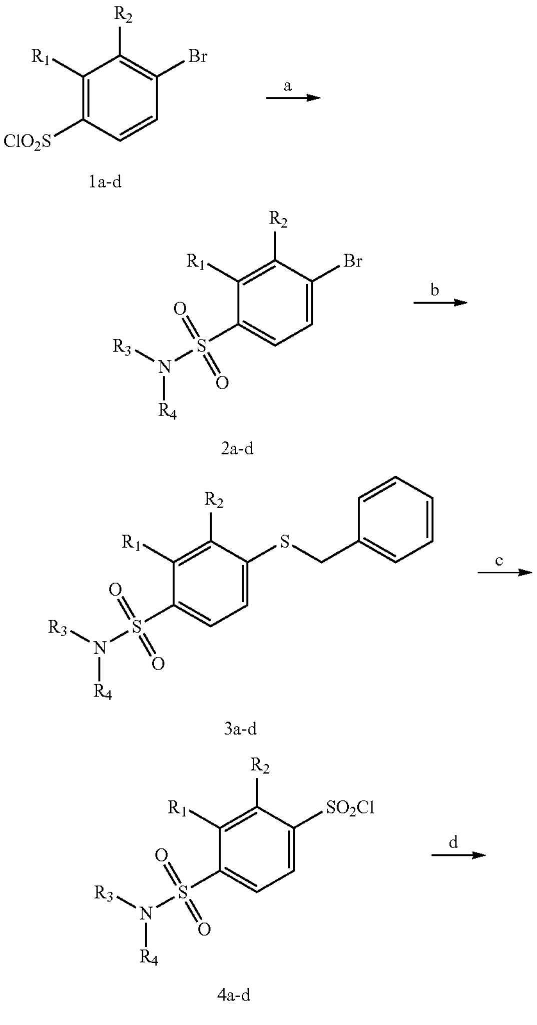

1a-d 2a-d 3a-d 4a-d

-continued

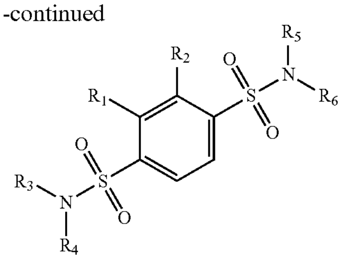

Reagents and conditions: a) $NHR_3R_4$, $Et_3N$, DCM, rt; b) benzyl mercaptan, $Pd_2(dba)_3$, XantPhos, DIEA, dioxane, reflux; c) 1,3-dichloro-5,5-dimethylimidazolidine-2,4-dione, $CH_3CN$, $CH_3COOH$, $H_2O$, 0° C.; d) $NHR_5R_6$, $Et_3N$, DCM, rt, or pyridine, rt, or $Cs_2CO_3$, $CH_3CN$, 60° C.

4-Bromo-N,N-diethylbenzenesulfonamide (2a)

To a solution of diethylamine (730 mg, 10.0 mmol) and triethylamine (2.02 g, 20.0 mmol) was added 4-bromobenzenesulfonyl chloride (1a, 2.56 g, 10.0 mmol) portionwise. The mixture was stirred at room temperature overnight. The mixture was concentrated and purified with flash chromatography (10% EtOAc in hexane) to give 2a as a colorless oil. (2.44 g, 83%). $^1H$ NMR (300 MHz, $CDCl_3$) δ 7.73-7.62 (m, 4H), 3.26 (q, J=7.1 Hz, 4H), 1.15 (t, J=7.1 Hz, 6H). LC-MS (ESI) m/z 291.9, 293.9 $[M+H]^+$.

4-(Benzylthio)-N,N-diethylbenzenesulfonamide (3a)

A solution of 2a, DIEA in dioxane was degassed and flushed with argon for three times. Then $Pd_2(dba)_3$, XantPhos, and benzyl mercaptan was added subsequently. Then it was degassed and flushed with argon for three times again before it was heated at reflux overnight. The mixture was cooled and the needle-like crystals generated was filtered off. The filtrate was concentrated and purified with flash chromatography (20% EtOAc in hexane) to give 3a as a yellow solid (520 mg, 91%). $^1H$ NMR (300 MHz, $CDCl_3$) δ 7.68 (d, J=8.1 Hz, 2H), 7.43-7.22 (m, 7H), 4.22 (s, 2H), 3.23 (q, J=7.2 Hz, 4H), 1.13 (t, J=7.2 Hz, 6H). LC-MS (ESI) m/z 336.0 $[M+H]^+$.

4-(N,N-Diethylsulfamoyl)benzenesulfonyl chloride (4a)

To an ice-cooled solution of 3a (100 mg, 0.30 mmol) in a mixture of $CH_3CN$ (2.5 mL), HOAc (0.16 mL) and $H_2O$ (0.1 mL) was added 1,3-dichloro-5,5-dimethylimidazolidine-2,4-dione (117 mg, 0.60 mmol) portionwise. The mixture was kept stirring at 0-5° C. for 2 h and concentrated. The residue obtained was taken up by DCM, washed with 5% $NaHCO_3$ solution at 0° C., dried over $Na_2SO_4$, filtered and concentrated to give 4a as a white solid (94 mg, 100% crude) and used in the next step without further purification. $^1H$ NMR (300 MHz, $CDCl_3$) δ 8.22-8.04 (m, 4H), 3.32 (q, J=7.2 Hz, 4H), 1.19 (t, J=7.1 Hz, 6H).

Ethyl (R)-1-((4-(N,N-diethylsulfamoyl)phenyl)sulfonyl)piperidine-3-carboxylate (DX2-201)

To a solution of ethyl (R)-piperidine-3-carboxylate (1.97 g, 12.53 mmol) and triethylamine (2.11 g, 20.88 mmol) in DCM (50 mL) was added 4a (3.25 g, 10.44 mmol). The mixture was stirred at room temperature for 3 h. The mixture was concentrated and purified with flash chromatography (20% EtOAc in hexane) to give 2a (4.12 g, 91%) as a white solid. $^1$H NMR (300 MHz, $CDCl_3$) δ 7.99 (d, J=8.2 Hz, 2H), 7.90 (d, J=8.3 Hz, 2H), 4.16 (q, J=7.1 Hz, 2H), 3.86 (d, J=7.8 Hz, 1H), 3.64 (d, J=11.6 Hz, 1H), 3.30 (q, J=7.2 Hz, 4H), 2.72-2.54 (m, 2H), 2.50-2.38 (m, 1H), 2.03 (d, J=13.6 Hz, 1H), 1.91-1.76 (m, 2H), 1.72-1.60 (m, 1H), 1.44 (q, J=10.2 Hz, 1H), 1.28 (t, J=7.1 Hz, 3H), 1.17 (t, J=7.2 Hz, 6H). LC-MS (ESI) m/z 433.0 $[M+H]^+$.

Ethyl (S)-1-((4-(N,N-diethylsulfamoyl)phenyl)sulfonyl)piperidine-3-carboxylate (DX2-202)

Using a similar procedure as described for DX2-201 with 4a (47 mg, 0.15 mmol) and ethyl (S)-piperidine-3-carboxylate (26 mg, 0.17 mmol), white solid (44 mg, 68%). $^1$H NMR (300 MHz, $CDCl_3$) δ 7.99 (d, J=8.2 Hz, 2H), 7.90 (d, J=8.4 Hz, 2H), 4.16 (q, J=7.1 Hz, 2H), 3.86 (d, J=7.9 Hz, 1H), 3.64 (d, J=11.6 Hz, 1H), 3.30 (q, J=7.1 Hz, 4H), 2.69-2.56 (m, 2H), 2.44 (td, J=11.3, 3.1 Hz, 1H), 2.03 (d, J=13.6 Hz, 1H), 1.91-1.78 (m, 1H), 1.69 (t, J=12.0 Hz, 1H), 1.44 (d, J=10.6 Hz, 1H), 1.28 (t, J=7.1 Hz, 3H), 1.17 (t, J=7.1 Hz, 6H). LC-MS (ESI) m/z 433.2 $[M+H]^+$.

Ethyl 1-((4-(N,N-diethylsulfamoyl)phenyl)sulfonyl)piperidine-4-carboxylate (DX2-208)

Using a similar procedure as described for DX2-201 with 4a (47 mg, 0.15 mmol) and ethyl piperidine-4-carboxylate (26 mg, 0.17 mmol), white solid (40 mg, 62%). $^1$H NMR (300 MHz, $CDCl_3$) δ 7.99 (d, J=8.4 Hz, 2H), 7.89 (d, J=8.4 Hz, 2H), 4.14 (q, J=7.1 Hz, 2H), 3.72-3.61 (m, 2H), 3.30 (q, J=7.1 Hz, 4H), 2.64-2.52 (m, 2H), 2.37-2.25 (m, 1H), 2.06-1.97 (m, 2H), 1.91-1.77 (m, 2H), 1.24 (t, J=7.1 Hz, 3H), 1.17 (t, J=7.1 Hz, 6H). LC-MS (ESI) m/z 433.0 $[M+H]^+$.

Ethyl 1-((4-(N,N-diethylsulfamoyl)phenyl)sulfonyl)piperidine-2-carboxylate (DX2-209)

Using a similar procedure as described for DX2-201 with 4a (47 mg, 0.15 mmol) and ethyl piperidine-2-carboxylate (26 mg, 0.17 mmol), white solid (26 mg, 40%). $^1$H NMR (300 MHz, $CDCl_3$) δ 7.93 (s, 4H), 4.76 (d, J=5.7 Hz, 1H), 4.12-3.93 (m, 2H), 3.82 (d, J=13.4 Hz, 1H), 3.33-3.17 (m, 5H), 2.20 (d, J=13.7 Hz, 1H), 1.87-1.65 (m, 3H), 1.60-1.42 (m, 1H), 1.40-1.23 (m, 1H), 1.20-1.12 (m, 9H). LC-MS (ESI) m/z 433.0 $[M+H]^+$.

Ethyl (R)-1-((4-(N,N-diethylsulfamoyl)phenyl)sulfonyl)pyrrolidine-3-carboxylate (DX2-217)

Using a similar procedure as described for DX2-201 with 4a (40 mg, 0.13 mmol) and ethyl (R)-pyrrolidine-3-carboxylate (23 mg, 0.13 mmol), white solid (32 mg, 59%). $^1$H NMR (400 MHz, $CDCl_3$) δ 8.04-7.94 (m, 4H), 4.09 (q, J=7.2 Hz, 2H), 3.66-3.56 (m, 1H), 3.49 (ddd, J=10.3, 6.4, 1.0 Hz, 1H), 3.45-3.33 (m, 2H), 3.37-3.26 (m, 4H), 3.01 (p, J=7.2 Hz, 1H), 2.21-2.03 (m, 2H), 1.23 (t, J=7.1 Hz, 3H), 1.18 (t, J=7.1 Hz, 6H). LC-MS (ESI) m/z 419.0 $[M+H]^+$.

Ethyl (S)-1-((4-(N,N-diethylsulfamoyl)phenyl)sulfonyl)pyrrolidine-3-carboxylate (DX2-218)

Using a similar procedure as described for DX2-201 with 4a (40 mg, 0.13 mmol) and ethyl (S)-pyrrolidine-3-carboxylate (23 mg, 0.13 mmol), white solid (32 mg, 59%). $^1$H NMR (300 MHz, $CDCl_3$) δ 7.98 (s, 4H), 4.08 (q, J=7.1 Hz, 2H), 3.65-3.56 (m, 1H), 3.51-3.44 (m, 1H), 3.42-3.25 (m, 6H), 3.05-2.95 (m, 1H), 2.16-2.06 (m, 2H), 1.25-1.14 (m, 9H). LC-MS (ESI) m/z 419.0 $[M+H]^+$.

Ethyl 1-((4-(N,N-diethylsulfamoyl)phenyl)sulfonyl)azetidine-3-carboxylate (DX2-219)

Using a similar procedure as described for DX2-201 with 4a (40 mg, 0.13 mmol) and ethyl azetidine-3-carboxylate (22 mg, 0.13 mmol), white solid (28 mg, 53%). $^1$H NMR (300 MHz, $CDCl_3$) δ 8.01 (q, J=8.5 Hz, 4H), 4.15-4.04 (m, 4H), 4.01-3.94 (m, 2H), 3.31 (q, J=7.2 Hz, 5H), 1.20 (dt, J=11.5, 7.1 Hz, 9H). LC-MS (ESI) m/z 405.0 $[M+H]^+$.

Ethyl 1-((4-(N,N-diethylsulfamoyl)phenyl)sulfonyl)azepane-4-carboxylate (DX2-221)

Using a similar procedure as described for DX2-201 with 4a (40 mg, 0.13 mmol) and ethyl azepane-4-carboxylate (22 mg, 0.13 mmol), white solid (30 mg, 52%). $^1$H NMR (300 MHz, $CDCl_3$) δ 8.00-7.88 (m, 4H), 4.14 (q, J=7.1 Hz, 2H), 3.54-3.43 (m, 1H), 3.38 (q, J=5.0, 4.3 Hz, 2H), 3.29 (q, J=7.1 Hz, 4H), 3.15 (dd, J=13.2, 8.8 Hz, 1H), 2.59 (s, 1H), 2.18-2.03 (m, 2H), 1.95 (dd, J=14.2, 8.0 Hz, 2H), 1.82-1.71 (m, 2H), 1.27 (t, J=7.1 Hz, 3H), 1.17 (t, J=7.1 Hz, 6H). LC-MS (ESI) m/z 447.0 $[M+H]^+$.

Ethyl (R)-1-((4-(N,N-diethylsulfamoyl)phenyl)sulfonyl)-3-methylpiperidine-3-carboxylate (DX2-246)

Using a similar procedure as described for DX2-201 with 4a (40 mg, 0.13 mmol) and ethyl (R)-3-methylpiperidine-3-carboxylate (24 mg, 0.14 mmol), white solid (17 mg, 29%). $^1$H NMR (300 MHz, $CDCl_3$) δ 8.01-7.96 (m, 2H), 7.92-7.87 (m, 2H), 4.20 (ddq, J=10.6, 7.1, 3.5 Hz, 2H), 3.64 (d, J=11.6 Hz, 1H), 3.30 (q, J=7.2 Hz, 4H), 3.25-3.16 (m, 1H), 2.78 (dd, J=13.0, 7.4 Hz, 1H), 2.61 (d, J=11.5 Hz, 1H), 2.07-1.95 (m, 1H), 1.81-1.68 (m, 2H), 1.30 (t, J=7.1 Hz, 4H), 1.23 (s, 3H), 1.17 (t, J=7.2 Hz, 6H). LC-MS (ESI) m/z 447.1 $[M+H]^+$.

Ethyl 3-((4-(N,N-diethylsulfamoyl)phenyl)sulfonamido)benzoate (DX3-13)

To a solution of ethyl 3-aminobenzoate (12 mg, 0.07 mmol) in pyridine (1 mL) was added 4a (20 mg, 0.07 mmol). The mixture was stirred at room temperature for 3 h. The mixture was then concentrated and purified with flash chromatography (40% EtOAc in hexane) to give DX3-13 as a white solid (17 mg, 58%). $^1$H NMR (300 MHz, $CDCl_3$) δ 7.89 (s, 4H), 7.87-7.83 (m, 1H), 7.70 (td, J=1.8, 0.7 Hz, 1H), 7.46-7.36 (m, 2H), 6.97 (s, 1H), 4.39 (q, J=7.1 Hz, 2H), 3.25 (q, J=7.2 Hz, 4H), 1.40 (t, J=7.1 Hz, 3H), 1.11 (t, J=7.1 Hz, 6H). LC-MS (ESI) m/z 439.2 $[M-H]^-$.

(cis)-Ethyl 1-((4-(N,N-diethylsulfamoyl)phenyl)sulfonyl)-5-hydroxypiperidine-3-carboxylate (DX3-14B-P1) and (trans)-ethyl 1-((4-(N,N-diethylsulfamoyl)phenyl)sulfonyl)-5-hydroxypiperidine-3-carboxylate (DX3-14B-P2)

Using a similar procedure as described for DX2-201 with 4a (62 mg, 0.20 mmol) and ethyl 5-hydroxypiperidine-3-carboxylate (38 mg, 0.22 mmol), and purified with flash chromatography (50% EtOAc in hexane) to give DX3-14B-P1 as a white solid (18 mg, 20%) and DX3-14B-P2 as a white solid (8 mg, 9%). DX3-14B-P1 $^1$H NMR (400 MHz, $CDCl_3$) δ 7.99 (d, J=8.6 Hz, 2H), 7.92 (d, J=8.7 Hz, 2H), 4.17 (q, J=7.1 Hz, 2H), 3.89 (tt, J=8.9, 4.3 Hz, 1H), 3.82-3.74 (m, 1H), 3.71 (dd, J=11.4, 4.3 Hz, 1H), 3.30 (q, J=7.2 Hz, 4H), 2.79-2.64 (m, 2H), 2.42 (dd, J=11.3, 8.7 Hz, 1H), 2.32-2.21 (m, 1H), 1.58-1.45 (m, 1H), 1.28 (t, J=7.1 Hz, 3H), 1.17 (t, J=7.1 Hz, 6H). LC-MS (ESI) m/z 449.2 $[M+H]^+$. DX3-14B-P2 $^1H$ NMR (400 MHz, $CDCl_3$) δ 7.99 (d, J=8.7 Hz, 2H), 7.93 (d, J=8.7 Hz, 2H), 4.22-4.14 (m, 2H), 4.13 (tt, J=4.8, 2.1 Hz, 1H), 3.81 (dd, J=12.0, 4.0 Hz, 1H), 3.54 (dd, J=12.0, 4.2 Hz, 1H), 3.31 (q, J=7.2 Hz, 4H), 3.02 (tt, J=10.6, 4.1 Hz, 1H), 2.81 (ddd, J=12.0, 6.0, 3.6 Hz, 2H), 2.08 (dd, J=13.9, 4.5 Hz, 1H), 1.71 (ddd, J=13.9, 11.0, 3.0 Hz, 1H), 1.29 (t, J=7.1 Hz, 3H), 1.18 (t, J=7.1 Hz, 6H). LC-MS (ESI) m/z 449.0 $[M+H]^+$.

N,N-Diethyl-4-((3-(methylsulfonyl)piperidin-1-yl)sulfonyl)benzenesulfonamide (DX3-35B)

Using a similar procedure as described for DX2-201 with 4a (47 mg, 0.15 mmol) and 3-(methylsulfonyl)piperidine (30 mg, 0.15 mmol), white solid (53 mg, 80%). $^1H$ NMR (400 MHz, $CDCl_3$) δ 8.01 (d, J=8.7 Hz, 2H), 7.92 (d, J=8.7 Hz, 2H), 4.25 (ddd, J=11.8, 3.9, 1.9 Hz, 1H), 3.86 (d, J=12.2 Hz, 1H), 3.32 (q, J=7.2 Hz, 4H), 3.20 (tt, J=11.4, 3.9 Hz, 1H), 2.94 (s, 3H), 2.63 (t, J=11.4 Hz, 1H), 2.37 (td, J=11.9, 2.8 Hz, 1H), 2.29 (d, J=13.1 Hz, 1H), 2.00 (dt, J=13.5, 3.4 Hz, 1H), 1.76 (qt, J=12.7, 3.9 Hz, 1H), 1.65 (td, J=12.4, 3.8 Hz, 1H), 1.19 (t, J=7.2 Hz, 6H). LC-MS (ESI) m/z 439.0 $[M+H]^+$.

(R)-4-((3-Cyanopiperidin-1-yl)sulfonyl)-N,N-diethylbenzenesulfonamide (DX3-37)

Using a similar procedure as described for DX2-201 with 4a (221 mg, 0.71 mmol) and (R)-piperidine-3-carbonitrile (78 mg, 0.71 mmol), white solid (223 mg, 81%). $^1H$ NMR (300 MHz, $CDCl_3$) δ 8.00 (d, J=8.6 Hz, 2H), 7.91 (d, J=8.5 Hz, 2H), 3.59 (dd, J=11.9, 3.6 Hz, 1H), 3.40-3.25 (q, J=7.1 Hz, 5H), 3.04 (dd, J=11.8, 8.2 Hz, 1H), 2.94-2.79 (m, 2H), 2.05-1.86 (m, 2H), 1.81-1.66 (m, 2H), 1.17 (t, J=7.1 Hz, 6H). LC-MS (ESI) m/z 386.1 $[M+H]^+$.

1-((4-(N,N-Diethylsulfamoyl)phenyl)sulfonyl)-N,N-dimethylpiperidine-3-sulfonamide (DX3-39)

Using a similar procedure as described for DX2-201 with 4a (40 mg, 0.13 mmol) and N,N-dimethylpiperidine-3-sulfonamide (32 mg, 0.14 mmol), white solid (50 mg, 82%). $^1H$ NMR (300 MHz, $CDCl_3$) δ 8.03 (d, J=8.6 Hz, 2H), 7.92 (d, J=8.5 Hz, 2H), 4.20 (d, J=11.8 Hz, 1H), 3.88 (d, J=12.0 Hz, 1H), 3.33 (q, J=7.1 Hz, 4H), 3.30-3.23 (m, 1H), 2.97 (s, 6H), 2.57 (t, J=11.4 Hz, 1H), 2.38-2.26 (m, 1H), 2.23-2.12 (m, 1H), 2.03-1.89 (m, 1H), 1.84-1.64 (m, 2H), 1.21 (t, J=7.1 Hz, 6H). LC-MS (ESI) m/z 468.3 $[M+H]^+$.

Ethyl 4-((4-(N,N-diethylsulfamoyl)phenyl)sulfonyl)morpholine-2-carboxylate (DX3-39B)

Using a similar procedure as described for DX2-201 with 4a (40 mg, 0.13 mmol) and ethyl morpholine-2-carboxylate (22 mg, 0.14 mmol), white solid (27 mg, 48%). $^1H$ NMR (300 MHz, $CDCl_3$) δ 8.01 (d, J=8.7 Hz, 2H), 7.90 (d, J=8.6 Hz, 2H), 4.32-4.21 (m, 3H), 4.11 (dt, J=11.8, 3.2 Hz, 1H), 3.85-3.70 (m, 2H), 3.48 (d, J=12.0 Hz, 1H), 3.31 (q, J=7.1 Hz, 4H), 2.74-2.61 (m, 2H), 1.33 (t, J=7.1 Hz, 3H), 1.18 (t, J=7.1 Hz, 6H). LC-MS (ESI) m/z 435.0 $[M+H]^+$.

Ethyl 2-(1-((4-(N,N-diethylsulfamoyl)phenyl)sulfonyl)piperidin-3-yl)acetate (DX3-43B)

Using a similar procedure as described for DX2-201 with 4a (40 mg, 0.13 mmol) and ethyl 2-(piperidin-3-yl)acetate (29 mg, 0.14 mmol), white solid (30 mg, 52%). $^1H$ NMR (300 MHz, $CDCl_3$) δ 7.98 (d, J=8.6 Hz, 2H), 7.89 (d, J=8.5 Hz, 2H), 4.16 (q, J=7.1 Hz, 2H), 3.67-3.49 (m, 2H), 3.30 (q, J=7.1 Hz, 4H), 2.59-2.47 (m, 1H), 2.37-2.09 (m, 4H), 1.84-1.63 (m, 4H), 1.28 (t, J=7.1 Hz, 3H), 1.16 (t, J=7.1 Hz, 6H). LC-MS (ESI) m/z 447.2 $[M+H]^+$.

Ethyl 1-((4-(N,N-diethylsulfamoyl)phenyl)sulfonyl)-4-hydroxy-1,2,5,6-tetrahydropyridine-3-carboxylate (DX3-45)

Using a similar procedure as described for DX2-201 with 4a (150 mg, 0.48 mmol) and ethyl 4-oxopiperidine-3-carboxylate (120 mg, 0.58 mmol), white solid (135 mg, 63%). $^1H$ NMR (400 MHz, $CDCl_3$) δ 12.06 (s, 1H), 8.03-7.93 (m, 4H), 4.27 (q, J=7.1 Hz, 2H), 3.85 (t, J=1.7 Hz, 2H), 3.37 (t, J=6.0 Hz, 2H), 3.31 (q, J=7.2 Hz, 4H), 2.49 (tt, J=6.0, 1.6 Hz, 2H), 1.34 (t, J=7.1 Hz, 3H), 1.18 (t, J=7.2 Hz, 6H). LC-MS (ESI) m/z 475.1 $[M+CH_3CN+H]^+$.

N,N-Diethyl-4-((3-hydroxypiperidin-1-yl)sulfonyl)benzenesulfonamide (DX3-46)

Using a similar procedure as described for DX2-201 with 4a (40 mg, 0.13 mmol) and ethyl piperidin-3-ol (16 mg, 0.16 mmol), white solid (30 mg, 61%). $^1H$ NMR (400 MHz, $CDCl_3$) δ 8.02-7.97 (m, 2H), 7.91 (d, J=8.6 Hz, 2H), 3.90 (s, 1H), 3.41 (dd, J=11.5, 3.6 Hz, 1H), 3.31 (q, J=7.2 Hz, 4H), 3.21 (dt, J=11.0, 5.1 Hz, 1H), 2.86 (ddd, J=11.8, 8.4, 3.4 Hz, 1H), 2.77 (dd, J=11.5, 7.3 Hz, 1H), 1.94-1.78 (m, 3H), 1.66 (dq, J=12.8, 4.3 Hz, 1H), 1.45 (dtd, J=12.6, 8.3, 3.7 Hz, 1H), 1.18 (t, J=7.1 Hz, 6H). LC-MS (ESI) m/z 377.0 $[M+H]^+$.

Ethyl 1-((4-(N,N-diethylsulfamoyl)phenyl)sulfonyl)-3-fluoropiperidine-3-carboxylate (DX3-47)

Using a similar procedure as described for DX2-201 with 4a (45 mg, 0.15 mmol) and ethyl 3-fluoropiperidine-3-carboxylate (28 mg, 0.16 mmol), white solid (41 mg, 60%). $^1H$ NMR (400 MHz, $CDCl_3$) δ 8.01-7.92 (m, 4H), 4.33-4.24 (m, 2H), 4.00 (ddt, J=13.5, 9.8, 1.9 Hz, 1H), 3.77 (d, J=12.5 Hz, 1H), 3.31 (q, J=7.1 Hz, 4H), 3.14 (dd, J=30.6, 13.4 Hz, 1H), 2.79-2.70 (m, 1H), 2.05 (d, J=11.7 Hz, 1H), 1.92-1.77 (m, 2H), 1.70 (dt, J=12.3, 3.3 Hz, 1H), 1.34 (t, J=7.1 Hz, 3H), 1.17 (t, J=7.1 Hz, 6H). LC-MS (ESI) m/z 451.1 $[M+H]^+$.

N,N-Diethyl-4-((3-fluoropiperidin-1-yl)sulfonyl)benzenesulfonamide (DX3-49B)

Using a similar procedure as described for DX2-201 with 4a (40 mg, 0.13 mmol) and 3-fluoropiperidine (22 mg, 0.16 mmol), white solid (30 mg, 61%). $^1H$ NMR (400 MHz, $CDCl_3$) δ 7.99 (d, J=8.7 Hz, 2H), 7.93 (d, J=8.8 Hz, 2H), 4.80-4.61 (m, 1H), 3.40-3.34 (m, 1H), 3.34-3.22 (m, 5H), 3.14 (dq, J=9.9, 5.2, 4.5 Hz, 2H), 1.94-1.72 (m, 3H), 1.68-1.59 (m, 1H), 1.17 (t, J=7.2 Hz, 6H). LC-MS (ESI) m/z 420.1 $[M+CH_3CN+H]^+$.

4-((3-Cyclohexylpiperidin-1-yl)sulfonyl)-N,N-diethylbenzenesulfonamide (DX3-50)

Using a similar procedure as described for DX2-201 with 4a (40 mg, 0.13 mmol) and 3-cyclohexylpiperidine (26 mg, 0.16 mmol), white solid (20 mg, 34%). $^1$H NMR (400 MHz, $CDCl_3$) δ 8.01-7.96 (m, 2H), 7.89 (d, J=8.6 Hz, 2H), 3.76-3.66 (m, 2H), 3.31 (q, J=7.1 Hz, 4H), 2.31 (td, J=11.6, 2.8 Hz, 1H), 2.11 (t, J=11.0 Hz, 1H), 1.83-1.59 (m, 8H), 1.42 (dtt, J=10.4, 6.9, 3.4 Hz, 1H), 1.17 (t, J=7.1 Hz, 10H), 1.04-0.88 (m, 3H). LC-MS (ESI) m/z 484.3 [M+$CH_3CN$+H]$^+$.

Ethyl 3-benzyl-1-((4-(N,N-diethylsulfamoyl)phenyl) sulfonyl)piperidine-3-carboxylate (DX3-52B)

Using a similar procedure as described for DX2-201 with 4a (40 mg, 0.13 mmol) and ethyl 3-benzylpiperidine-3-carboxylate (38 mg, 0.16 mmol), white solid (40 mg, 59%). $^1$H NMR (400 MHz, $CDCl_3$) δ 7.99 (d, J=8.7 Hz, 2H), 7.90 (d, J=8.5 Hz, 2H), 7.34-7.21 (m, 3H), 7.14-7.07 (m, 2H), 4.12 (qd, J=7.1, 3.2 Hz, 2H), 3.61 (d, J=11.6 Hz, 1H), 3.31 (q, J=7.2 Hz, 4H), 3.22-3.13 (m, 1H), 3.04 (d, J=13.4 Hz, 1H), 2.78 (d, J=13.1 Hz, 3H), 1.95 (dt, J=12.9, 5.3 Hz, 1H), 1.79 (qt, J=9.0, 4.4 Hz, 2H), 1.43 (ddd, J=13.4, 8.7, 4.7 Hz, 1H), 1.22 (t, J=7.2 Hz, 3H), 1.18 (t, J=7.2 Hz, 6H). LC-MS (ESI) m/z 523.2 [M+H]$^+$.

(trans)-Ethyl-8-((4-(N,N-diethylsulfamoyl)phenyl) sulfonyl)-8-azabicyclo[3.2.1]octane-2-carboxylate (DX3-69B-P1) and (cis)-ethyl-8-((4-(N,N-diethylsulfamoyl)phenyl)sulfonyl)-8-azabicyclo[3.2.1]octane-2-carboxylate (DX3-69B-P2)

Using a similar procedure as described for DX2-201 with 4a (34 mg, 0.11 mmol) and ethyl-8-azabicyclo[3.2.1]octane-2-carboxylate (38 mg, 0.16 mmol), and purified with preparative-HPLC to give the two diastereoisomers. DX3-69B-P1 (20 mg, 40%). $^1$H NMR (400 MHz, $CDCl_3$) δ 7.99 (d, J=8.1 Hz, 2H), 7.93 (d, J=8.7 Hz, 2H), 4.71 (dd, J=7.2, 2.8 Hz, 1H), 4.33-4.23 (m, 1H), 4.19-4.04 (m, 1H), 4.01-3.88 (m, 1H), 3.28 (q, J=7.1 Hz, 4H), 2.52 (dd, J=6.4, 2.9 Hz, 1H), 2.11-1.97 (m, 2H), 1.88-1.58 (m, 5H), 1.48 (ddd, J=13.0, 6.3, 3.4 Hz, 1H), 1.23 (t, J=7.1 Hz, 3H), 1.15 (t, J=7.0 Hz, 6H). LC-MS (ESI) m/z 459.1 [M+H]$^+$. DX3-69B-P2 (27 mg, 53%). $^1$H NMR (400 MHz, $CDCl_3$) δ 8.02 (d, J=8.5 Hz, 2H), 7.94 (d, J=8.4 Hz, 2H), 4.51 (dd, J=6.0, 2.8 Hz, 1H), 4.27 (d, J=3.1 Hz, 1H), 4.15 (q, J=7.1 Hz, 2H), 3.29 (q, J=7.2 Hz, 4H), 2.83 (ddd, J=12.2, 5.2, 2.8 Hz, 1H), 1.98-1.51 (m, 8H), 1.27 (t, J=7.1 Hz, 3H), 1.14 (t, J=7.1 Hz, 6H). LC-MS (ESI) m/z 459.1 [M+H]$^+$.

Ethyl 3-((4-(N,N-diethylsulfamoyl)phenyl)sulfonyl)-3-azabicyclo[3.1.1]heptane-1-carboxylate (DX3-115)

Using a similar procedure as described for DX2-201 with 4a (20 mg, 0.064 mmol) and ethyl 3-azabicyclo[3.1.1]heptane-1-carboxylate hydrochloride (11 mg, 0.064 mmol), white solid (21 mg, 75%). $^1$H NMR (300 MHz, $CDCl_3$) δ 7.99 (s, 4H), 4.15 (q, J=7.1 Hz, 2H), 3.68 (s, 2H), 3.52 (d, J=2.5 Hz, 2H), 3.31 (q, J=7.2 Hz, 4H), 2.50-2.35 (m, 3H), 1.42 (dd, J=7.0, 2.7 Hz, 2H), 1.28 (t, J=7.1 Hz, 3H), 1.16 (t, J=7.1 Hz, 6H). LC-MS (ESI) m/z 445.1 [M+H]$^+$.

Ethyl (R)-1-((4-bromophenyl)sulfonyl)piperidine-3-carboxylate (2b)

Using a similar procedure as described for 2a with 4-bromobenzenesulfonyl chloride (1a, 1.50 g, 5.86 mmol) and ethyl (R)-piperidine-3-carboxylate (0.92 g, 5.86 mmol), white solid (2.16 g, 98%). $^1$H NMR (300 MHz, $CDCl_3$) δ 7.67 (q, J=8.6 Hz, 4H), 4.16 (q, J=7.2 Hz, 2H), 3.85 (d, J=11.0 Hz, 1H), 3.63 (d, J=11.8 Hz, 1H), 2.68-2.49 (m, 2H), 2.38 (td, J=11.3, 3.2 Hz, 1H), 2.02 (d, J=12.6 Hz, 1H), 1.88-1.77 (m, 1H), 1.77-1.61 (m, 1H), 1.50-1.34 (m, 1H), 1.28 (t, J=7.1 Hz, 3H).

Ethyl (R)-1-((4-(benzylthio)phenyl)sulfonyl)piperidine-3-carboxylate (3b)

Using a similar procedure as described for 4a with 2b (1.20 g, 3.19 mmol) and benzyl mercaptan (0.40 g, 3.19 mmol), white solid (1.17 g, 87%). $^1$H NMR (300 MHz, $CDCl_3$) δ 7.63 (d, J=8.5 Hz, 2H), 7.43-7.26 (m, 7H), 4.24 (s, 2H), 4.15 (q, J=7.1 Hz, 2H), 3.84 (d, J=11.3 Hz, 1H), 3.61 (d, J=11.2 Hz, 1H), 2.69-2.56 (m, 1H), 2.50 (t, J=10.8 Hz, 1H), 2.34 (td, J=11.2, 3.0 Hz, 1H), 2.00 (d, J=13.8 Hz, 1H), 1.87-1.75 (m, 1H), 1.73-1.57 (m, 1H), 1.47-1.34 (m, 1H), 1.28 (t, J=7.1 Hz, 3H).

Ethyl (R)-1-((4-(chlorosulfonyl)phenyl)sulfonyl) piperidine-3-carboxylate (4b)

Using a similar procedure as described for 4a with 3b (600 mg, 1.43 mmol), white solid (520 mg, 92%). $^1$H NMR (300 MHz, $CDCl_3$) δ 8.23 (d, J=8.5 Hz, 2H), 8.03 (d, J=8.5 Hz, 2H), 4.16 (q, J=7.1 Hz, 2H), 3.86 (t, J=8.7 Hz, 1H), 3.67 (d, J=11.7 Hz, 1H), 2.73-2.57 (m, 2H), 2.50 (td, J=11.3, 3.1 Hz, 1H), 2.10-1.98 (m, 1H), 1.92-1.80 (m, 1H), 1.77-1.60 (m, 1H), 1.47 (s, 1H), 1.28 (t, J=7.1 Hz, 3H).

Ethyl (R)-1-((4-(morpholinosulfonyl)phenyl)sulfonyl)piperidine-3-carboxylate (DX2-245)

Using a similar procedure as described for DX2-201 with 4b (40 mg, 0.10 mmol) and morpholine (11 mg, 0.12 mmol), white solid (36 mg, 81%). $^1$H NMR (300 MHz, $CDCl_3$) δ 8.02-7.89 (m, 4H), 4.17 (q, J=7.1 Hz, 2H), 3.88 (d, J=7.4 Hz, 1H), 3.82-3.74 (m, 4H), 3.66 (d, J=11.7 Hz, 1H), 3.08 (dd, J=5.8, 3.6 Hz, 4H), 2.65 (d, J=8.8 Hz, 2H), 2.53-2.40 (m, 1H), 2.04 (d, J=10.1 Hz, 2H), 1.92-1.59 (m, 2H), 1.48 (s, 1H), 1.28 (t, J=7.1 Hz, 3H). LC-MS (ESI) m/z 447.0 [M+H]$^+$.

Ethyl (R)-1-((4-(piperazin-1-ylsulfonyl)phenyl) sulfonyl)piperidine-3-carboxylate (DX2-248)

Using a similar procedure as described for DX2-201 with 4b (40 mg, 0.10 mmol) and piperazine (11 mg, 0.12 mmol), white solid (4 mg, 9%). $^1$H NMR (400 MHz, $CDCl_3$) δ 8.00-7.90 (m, 4H), 4.17 (q, J=7.1 Hz, 2H), 3.88 (d, J=8.1 Hz, 1H), 3.70-3.62 (m, 1H), 3.17 (t, J=4.9 Hz, 4H), 3.05 (t, J=5.0 Hz, 4H), 2.70-2.63 (m, 2H), 2.48 (td, J=11.3, 3.2 Hz, 1H), 2.07-2.00 (m, 1H), 1.85 (dt, J=13.7, 3.8 Hz, 1H), 1.74-1.63 (m, 1H), 1.54-1.42 (m, 1H), 1.29 (t, J=7.1 Hz, 3H). LC-MS (ESI) m/z 446.0 [M+H]$^+$.

Ethyl (R)-1-((4-(N-(oxetan-3-yl)sulfamoyl)phenyl) sulfonyl)piperidine-3-carboxylate (DX2-249)

Using a similar procedure as described for DX2-201 with 4b (40 mg, 0.10 mmol) and oxetan-3-amine hydrochloride (13 mg, 0.12 mmol), white solid (25 mg, 58%). $^1$H NMR (400 MHz, $CDCl_3$) δ 8.03 (d, J=8.5 Hz, 2H), 7.94 (d, J=8.5 Hz, 2H), 5.48 (d, J=9.0 Hz, 1H), 4.80 (t, J=7.1 Hz, 2H), 4.66-4.53 (m, 1H), 4.49-4.41 (m, 2H), 4.17 (q, J=7.1 Hz, 2H), 3.87 (d, J=8.0 Hz, 1H), 3.66 (d, J=11.6 Hz, 1H), 2.64 (dd, J=9.2, 4.5 Hz, 2H), 2.45 (td, J=11.3, 3.1 Hz, 1H), 2.05

(dd, J=13.0, 4.3 Hz, 1H), 1.85 (dt, J=13.5, 3.8 Hz, 1H), 1.70 (td, J=10.7, 10.1, 5.1 Hz, 1H), 1.52-1.38 (m, 1H), 1.29 (t, J=7.1 Hz, 3H). LC-MS (ESI) m/z 433.0 $[M+H]^+$.

Ethyl (3R)-1-((4-((2,6-dimethylpiperidin-1-yl)sulfonyl)phenyl)sulfonyl)piperidine-3-carboxylate (DX2-258)

To a solution of 4b (20 mg, 0.05 mmol) and 2,6-dimethylpiperidine (7 mg, 0.06 mmol) in $CH_3CN$ was added $Cs_2CO_3$ (32 mg, 0.10 mmol). The mixture was heated at 60° C. for 1 h and diluted with EtOAc, washed with water, brine, dried over anhydrous $Na_2SO_4$, filtered and purified with flash chromatography (20% EtOAc in hexane) to give DX2-258 as a white solid (13 mg, 52%). $^1$H NMR (300 MHz, $CDCl_3$) δ 8.00 (d, J=8.2 Hz, 2H), 7.89 (t, J=7.2 Hz, 2H), 4.26-4.04 (m, 4H), 3.91-3.80 (m, 1H), 3.71-3.57 (m, 1H), 2.68-2.56 (m, 2H), 2.43 (td, J=11.6, 2.2 Hz, 1H), 2.09-1.97 (m, 1H), 1.89-1.60 (m, 7H), 1.56-1.45 (m, 2H), 1.39 (d, J=7.1 Hz, 3H), 1.28 (t, J=6.6 Hz, 6H). LC-MS (ESI) m/z 473.1 $[M+H]^+$.

Ethyl (R)-1-((4-(N,N-dimethylsulfamoyl)phenyl)sulfonyl)piperidine-3-carboxylate (DX2-259)

Using a similar procedure as described for DX2-201 with 4b (40 mg, 0.10 mmol) and dimethylamine (5.4 mg, 0.12 mmol), white solid (16 mg, 40%). $^1$H NMR (300 MHz, $CDCl_3$) δ 7.96 (s, 4H), 4.17 (q, J=7.2 Hz, 2H), 3.88 (d, J=7.4 Hz, 1H), 3.67 (d, J=11.9 Hz, 1H), 2.79 (s, 6H), 2.64 (d, J=8.4 Hz, 2H), 2.46 (td, J=11.6, 3.3 Hz, 1H), 2.06 (s, 2H), 1.90-1.80 (m, 1H), 1.77-1.62 (m, 1H), 1.54-1.40 (m, 1H), 1.28 (t, J=7.1 Hz, 3H). LC-MS (ESI) m/z 405.0 $[M+H]^+$.

Ethyl (R)-1-((4-(N,N-dipropylsulfamoyl)phenyl)sulfonyl)piperidine-3-carboxylate (DX2-264)

Using a similar procedure as described for DX2-201 with 4b (40 mg, 0.10 mmol) and dipropylamine (12 mg, 0.12 mmol), white solid (20 mg, 43%). $^1$H NMR (400 MHz, $CDCl_3$) δ 7.99 (d, J=8.6 Hz, 2H), 7.91 (d, J=8.5 Hz, 2H), 4.17 (q, J=7.1 Hz, 2H), 3.87 (d, J=7.4 Hz, 1H), 3.65 (d, J=11.7 Hz, 1H), 3.20-3.11 (m, 4H), 2.68-2.59 (m, 2H), 2.45 (td, J=11.4, 3.1 Hz, 1H), 2.08-2.00 (m, 1H), 1.84 (dt, J=13.7, 3.7 Hz, 1H), 1.71 (dq, J=11.2, 3.6, 3.2 Hz, 1H), 1.64-1.53 (m, 4H), 1.46 (dd, J=12.6, 9.0 Hz, 1H), 1.29 (t, J=7.1 Hz, 3H), 0.90 (t, J=7.4 Hz, 6H). LC-MS (ESI) m/z 461.0 $[M+H]^+$.

Ethyl (R)-1-((4-(piperidin-1-ylsulfonyl)phenyl)sulfonyl)piperidine-3-carboxylate (DX2-265)

Using a similar procedure as described for DX2-201 with 4b (40 mg, 0.10 mmol) and piperidine (10 mg, 0.12 mmol), white solid (20 mg, 45%). $^1$H NMR (400 MHz, $CDCl_3$) δ 7.94 (s, 4H), 4.17 (q, J=7.1 Hz, 2H), 3.88 (d, J=8.0 Hz, 1H), 3.67 (d, J=11.7 Hz, 1H), 3.15-3.03 (m, 4H), 2.71-2.60 (m, 2H), 2.48 (td, J=11.4, 3.1 Hz, 1H), 2.04 (dd, J=12.8, 3.9 Hz, 1H), 1.85 (dt, J=13.7, 3.8 Hz, 1H), 1.69 (hept, J=7.6, 6.8 Hz, 5H), 1.50 (q, J=6.3, 5.8 Hz, 3H), 1.29 (t, J=7.1 Hz, 3H). LC-MS (ESI) m/z 445.0 $[M+H]^+$.

Ethyl (R)-1-((4-(N,N-diisopropylsulfamoyl)phenyl)sulfonyl)piperidine-3-carboxylate (DX2-280)

Using a similar procedure as described for DX2-258 with 4b (60 mg, 0.15 mmol) and diisopropylamine (11 mg, 0.30 mmol) and purified with flash chromatography (20% EtOAc in hexane), white solid (11 mg, 16%). $^1$H NMR (300 MHz, $CDCl_3$) δ 8.04 (d, J=8.2 Hz, 2H), 7.89 (d, J=8.4 Hz, 2H), 4.16 (q, J=7.2 Hz, 2H), 3.93-3.81 (m, 1H), 3.77 (p, J=6.8 Hz, 2H), 3.63 (d, J=11.6 Hz, 1H), 2.62 (d, J=8.8 Hz, 2H), 2.52-2.35 (m, 1H), 2.10-1.96 (m, 1H), 1.91-1.75 (m, 1H), 1.73-1.57 (m, 1H), 1.57-1.38 (m, 1H), 1.35-1.21 (m, 15H). LC-MS (ESI) m/z 461.1 $[M+H]^+$.

Ethyl (R)-1-((4-sulfamoylphenyl)sulfonyl)piperidine-3-carboxylate (DX2-300)

4b (40 mg, 0.10 mmol) was dissolved in $NH_3$ in dioxane solution (1 mL, 4M) and stirred at room temperature for 3 h. The mixture was concentrated and purified with flash chromatography (10% MeOH in DCM) to give DX-300 as a white solid (30 mg, 80%). $^1$H NMR (300 MHz, DMSO) (8.26 (d, J=8.5 Hz, 2H), 8.16 (d, J=8.6 Hz, 2H), 4.27 (q, J=7.1 Hz, 2H), 3.56-3.45 (m, 1H), 2.99-2.70 (m, 4H), 2.04-1.86 (m, 2H), 1.78-1.55 (m, 2H), 1.38 (t, J=7.1 Hz, 3H). LC-MS (ESI) m/z 377.0 $[M+H]^+$.

Ethyl (R)-1-((4-(N-benzyl-N-methylsulfamoyl)phenyl)sulfonyl)piperidine-3-carboxylate (DX3-86B)

Using a similar procedure as described for DX2-201 with 4b (20 mg, 0.05 mmol) and N-methyl-1-phenylmethanamine (6 mg, 0.05 mmol), white solid (13 mg, 54%). $^1$H NMR (300 MHz, $CDCl_3$) δ 8.05-7.92 (m, 4H), 7.42-7.30 (m, 5H), 4.24 (s, 2H), 4.17 (q, J=7.1 Hz, 2H), 3.88 (t, J=8.7 Hz, 1H), 3.68 (d, J=11.6 Hz, 1H), 2.70 (s, 3H), 2.65 (dd, J=8.8, 2.2 Hz, 2H), 2.47 (td, J=11.3, 3.1 Hz, 1H), 2.12-2.00 (m, 1H), 1.86 (dt, J=13.3, 3.7 Hz, 1H), 1.78-1.63 (m, 1H), 1.53-1.38 (m, 1H), 1.29 (t, J=7.1 Hz, 3H). LC-MS (ESI) m/z 481.0 $[M+H]^+$.

Ethyl (R)-1-((4-(N-ethyl-N-isopropylsulfamoyl)phenyl)sulfonyl)piperidine-3-carboxylate (DX3-105)

Using a similar procedure as described for DX2-201 with 4b (20 mg, 0.05 mmol) and N-ethylpropan-2-amine (4.4 mg, 0.05 mmol), white solid (11 mg, 50%). $^1$H NMR (300 MHz, $CDCl_3$) δ 8.01 (d, J=8.5 Hz, 2H), 7.90 (d, J=8.5 Hz, 2H), 4.14 (dq, J=11.8, 6.9 Hz, 3H), 3.86 (d, J=7.9 Hz, 1H), 3.64 (d, J=11.6 Hz, 1H), 3.25 (q, J=7.1 Hz, 2H), 2.69-2.55 (m, 2H), 2.43 (td, J=11.3, 3.1 Hz, 1H), 2.09-1.97 (m, 1H), 1.84 (dt, J=13.3, 3.9 Hz, 1H), 1.75-1.61 (m, 1H), 1.51-1.36 (m, 1H), 1.29 (td, J=7.1, 6.2 Hz, 6H), 1.11 (d, J=6.8 Hz, 6H). LC-MS (ESI) m/z 447.1 $[M+H]^+$.

4-Bromo-N,N-diethyl-2-fluorobenzenesulfonamide (2c)

Using a similar procedure as described for 2a with 1c (1.00 g, 3.65 mmol) and diethylamine (320 mg, 4.38 mmol), white solid (861 mg, 76%). $^1$H NMR (400 MHz, $CDCl_3$) δ 7.84-7.75 (m, 1H), 7.46-7.36 (m, 2H), 3.36 (q, J=7.1 Hz, 4H), 1.17 (t, J=7.2 Hz, 6H).

4-(Benzylthio)-N,N-diethyl-2-fluorobenzenesulfonamide (3c)

Using a similar procedure as described for 3a with 2c (861 mg, 2.78 mmol) and benzyl mercaptan (344 mg, 2.78 mmol), yellow solid (950 mg, 97%). $^1$H NMR (400 MHz, $CDCl_3$) δ 7.76 (dd, J=8.3, 7.5 Hz, 1H), 7.41-7.29 (m, 5H), 7.10 (dd, J=8.3, 1.8 Hz, 1H), 7.05 (dd, J=10.8, 1.8 Hz, 1H), 4.22 (s, 2H), 3.34 (q, J=7.1 Hz, 4H), 1.15 (t, J=7.2 Hz, 6H).

4-(N,N-Diethylsulfamoyl)-3-fluorobenzenesulfonyl chloride (4c)

Using a similar procedure as described for 4a with 3c (500 mg, 1.42 mmol), yellow solid (403 mg, 86). $^1$H NMR (400 MHz, $CDCl_3$) δ 8.21 (dd, J=8.3, 6.6 Hz, 1H), 7.98-7.93 (m, 1H), 7.88 (dd, J=8.6, 1.8 Hz, 1H), 3.46-3.38 (m, 4H), 1.20 (t, J=7.1 Hz, 6H).

Ethyl (R)-1-((4-(N,N-diethylsulfamoyl)-3-fluorophenyl)sulfonyl)piperidine-3-carboxylate (DX2-275)

Using a similar procedure as described for DX2-201 with 4c (60 mg, 0.18 mmol) and ethyl (R)-piperidine-3-carboxylate (31 mg, 0.20 mmol), white solid (60 mg, 74%). $^1$H NMR (300 MHz, $CDCl_3$) δ 8.15-8.05 (m, 1H), 7.62 (dd, J=15.2, 8.6 Hz, 2H), 4.17 (q, J=7.1 Hz, 2H), 3.85 (d, J=8.5 Hz, 1H), 3.63 (dd, J=12.8, 5.4 Hz, 1H), 3.40 (q, J=7.1 Hz, 4H), 2.67 (q, J=9.6 Hz, 2H), 2.50 (t, J=9.8 Hz, 1H), 2.11-1.98 (m, 1H), 1.93-1.80 (m, 1H), 1.75-1.59 (m, 1H), 1.57-1.39 (m, 1H), 1.29 (t, J=7.1 Hz, 3H), 1.18 (t, J=7.2 Hz, 6H). LC-MS (ESI) m/z 451.0 [M+H]$^+$.

4-Bromo-N,N-diethyl-3-methylbenzenesulfonamide (2d)

Using a similar procedure as described for 2a with 1d (1.00 g, 3.70 mmol) and diethylamine (324 mg, 4.44 mmol), white solid (950 mg, 84%). $^1$H NMR (400 MHz, $CDCl_3$) δ 7.68-7.62 (m, 2H), 7.50-7.43 (m, 1H), 3.23 (q, J=7.2 Hz, 4H), 2.45 (s, 3H), 1.13 (t, J=7.2 Hz, 6H).

4-(Benzylthio)-N,N-diethyl-3-methylbenzenesulfonamide (3d)

Using a similar procedure as described for 3a with 2d (950 mg, 3.10 mmol) and benzyl mercaptan (384 mg, 3.10 mmol), yellow solid (900 mg, 83%). $^1$H NMR (400 MHz, $CDCl_3$) δ 7.61-7.53 (m, 2H), 7.41-7.26 (m, 6H), 4.21 (s, 2H), 3.24 (q, J=7.1 Hz, 4H), 2.37 (s, 3H), 1.15 (t, J=7.2 Hz, 6H).

4-(N,N-Diethylsulfamoyl)-2-methylbenzenesulfonyl Chloride (4d)

Using a similar procedure as described for 4a with 3d (500 mg, 1.43 mmol), yellow solid (mg, %). $^1$H NMR (400 MHz, $CDCl_3$) δ 7.97 (d, J=8.2 Hz, 1H), 7.65 (s, 1H), 7.61 (d, J=8.1 Hz, 1H), 3.22 (q, J=7.2 Hz, 4H), 2.61 (s, 3H), 1.14 (t, J=7.1 Hz, 6H).

Ethyl (R)-1-((4-(N,N-diethylsulfamoyl)-2-methylphenyl)sulfonyl)piperidine-3-carboxylate (DX2-276)

Using a similar procedure as described for DX2-201 with 4d (60 mg, 0.18 mmol) and ethyl (R)-piperidine-3-carboxylate (31 mg, 0.20 mmol), white solid (41 mg, 51%). $^1$H NMR (300 MHz, $CDCl_3$) δ 8.04 (d, J=8.1 Hz, 1H), 7.79-7.70 (m, 2H), 4.21-4.03 (m, 2H), 3.81 (ddt, J=12.5, 4.0, 1.5 Hz, 1H), 3.62 (d, J=12.5 Hz, 1H), 3.29 (q, J=7.1 Hz, 4H), 2.95 (dd, J=12.5, 10.0 Hz, 1H), 2.86-2.75 (m, 1H), 2.68 (s, 3H), 2.60 (ddd, J=10.2, 6.2, 4.0 Hz, 1H), 2.12-2.02 (m, 1H), 1.88-1.80 (m, 1H), 1.73-1.54 (m, 2H), 1.25 (t, J=7.1 Hz, 3H), 1.17 (t, J=7.1 Hz, 6H). LC-MS (ESI) m/z 447.1 [M+H]$^+$.

Scheme 5

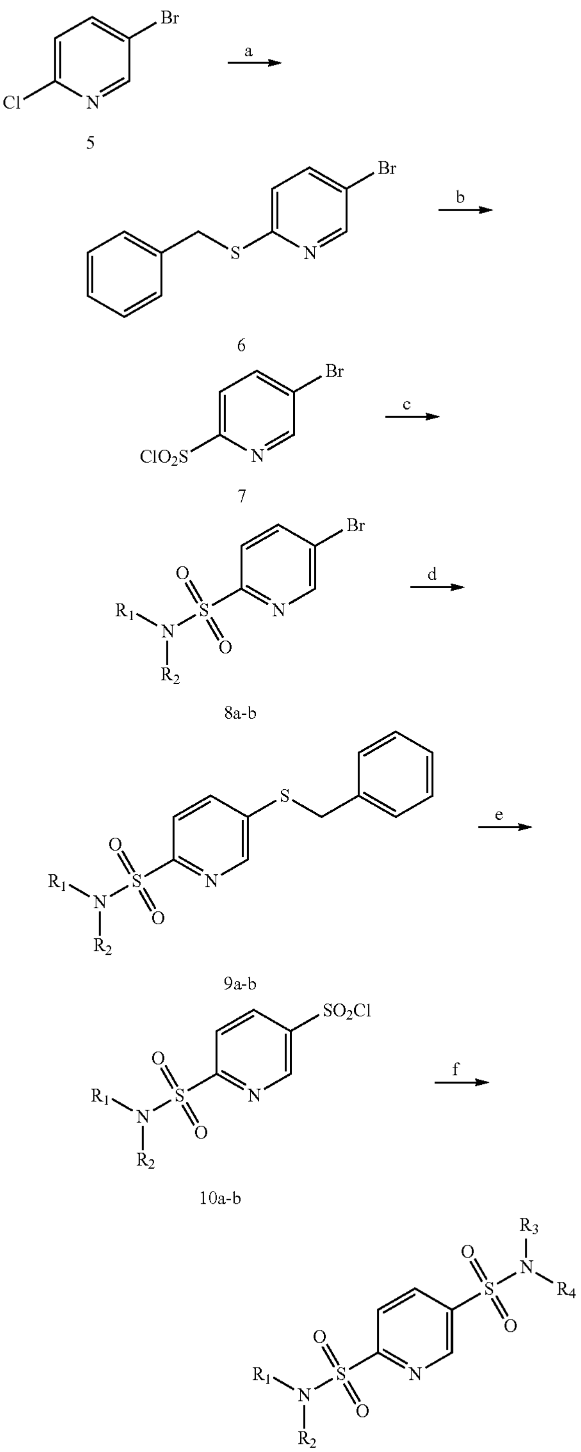

Reagents and conditions: a) benzyl mercaptan, $Cs_2CO_3$, DMF, rt; b) 1,3-dichloro-5,5-dimethylimidazolidine-2,4-dione, $CH_3CN$, $CH_3COOH$, $H_2O$, 0° C.; c) $NHR_1R_2$, $Et_3N$, DCM, rt; d) benzyl mercaptan, $Pd_2(dba)_3$, XantPhose, DIEA, dioxane, reflux; e) 1,3-dichloro-5,5-dimethylimidazolidine-2,4-dione, $CH_3CN$, $CH_3COOH$, $H_2O$, 0° C.;
f) $NHR_3R_4$, $Et_3N$, DCM, rt;

2-(Benzylthio)-5-bromopyridine (6)

To a solution of 5 (2.00 g, 10.42 mmol) and benzyl mercaptan (1.30 g, 10.42 mmol) in DMF (40 mL) was added $Cs_2CO_3$ (6.80 g, 20.84 mmol). The mixture was stirred at room temperature for 3 h, then diluted with EtOAc, washed with water, brine, dried over anhydrous $Na_2SO_4$, filtered and purified with flash chromatography to give 6 as a colorless oil (1.96 g, 67%). $^1$H NMR (300 MHz, $CDCl_3$) δ 8.57-8.49 (m, 1H), 7.59 (dd, J=8.6, 2.4 Hz, 1H), 7.42 (d, J=7.4 Hz, 2H), 7.37-7.22 (m, 3H), 7.08 (d, J=8.5 Hz, 1H), 4.43 (s, 2H). LC-MS (ESI) m/z 279.8, 281.7 $[M+H]^+$.

5-Bromopyridine-2-sulfonyl Chloride (7)

Using a similar procedure as described for 4a with 6 (1.86 g, 6.64 mmol), white solid (1.61 g, 94%). $^1$H NMR (300 MHz, $CDCl_3$) δ 8.92-8.86 (m, 1H), 8.21 (dd, J=9.0, 1.6 Hz, 1H), 8.02 (d, J=8.4 Hz, 1H).

5-Bromo-N,N-diethylpyridine-2-sulfonamide (8a)

Using a similar procedure as described for DX2-201 with 7 (800 mg, 3.11 mmol) and diethylamine (250 mg, 3.42 mmol), white solid (422 mg, 74%). $^1$H NMR (300 MHz, $CDCl_3$) δ 8.74 (d, J=2.2 Hz, 1H), 8.03 (dd, J=8.3, 2.3 Hz, 1H), 7.87 (d, J=8.3 Hz, 1H), 3.41 (q, J=7.2 Hz, 4H), 1.18 (t, J=7.1 Hz, 6H).

5-(Benzylthio)-N,N-diethylpyridine-2-sulfonamide (9a)

Using a similar procedure as described for 3a with 8a (280 mg, 0.95 mmol) and benzyl mercaptan (119 mg, 0.95 mmol), white solid (287 mg, 90%). $^1$H NMR (400 MHz, $CDCl_3$) δ 8.52 (dd, J=2.4, 0.8 Hz, 1H), 7.83-7.78 (m, 1H), 7.67 (dd, J=8.2, 2.3 Hz, 1H), 7.36-7.29 (m, 5H), 4.22 (s, 2H), 3.39 (q, J=7.1 Hz, 4H), 1.15 (t, J=7.2 Hz, 6H). LC-MS (ESI) m/z 337.0 $[M+H]^+$.

6-(N,N-Diethylsulfamoyl)pyridine-3-sulfonyl Chloride (10a)

Using a similar procedure as described for 4a with 9a (80 mg, 0.24 mmol), white solid (75 mg, 75%). $^1$H NMR (300 MHz, $CDCl_3$) δ 9.27 (d, J=2.4 Hz, 1H), 8.51 (dd, J=8.4, 2.3 Hz, 1H), 8.22 (d, J=8.3 Hz, 1H), 3.47 (q, J=7.2 Hz, 4H), 1.22 (t, J=7.2 Hz, 6H).

Ethyl (R)-1-((6-(N,N-diethylsulfamoyl)pyridin-3-yl)sulfonyl)piperidine-3-carboxylate (DX2-291)

Using a similar procedure as described for DX2-201 with 10a (72 mg, 0.23 mmol) and ethyl (R)-piperidine-3-carboxylate (40 mg, 0.25 mmol), white solid (40 mg, 40%). $^1$H NMR (300 MHz, $CDCl_3$) δ 9.02 (d, J=1.7 Hz, 1H), 8.28-8.21 (m, 1H), 8.13 (d, J=8.2 Hz, 1H), 4.17 (q, J=7.1 Hz, 2H), 3.87 (d, J=9.8 Hz, 1H), 3.71-3.61 (m, 1H), 3.45 (q, J=7.1 Hz, 4H), 2.69 (q, J=10.1 Hz, 2H), 2.58-2.47 (m, 1H), 2.11-2.00 (m, 1H), 1.92-1.80 (m, 1H), 1.75-1.59 (m, 1H), 1.56-1.42 (m, 1H), 1.28 (t, J=7.1 Hz, 3H), 1.20 (t, J=7.1 Hz, 6H). LC-MS (ESI) m/z 434.0 $[M+H]^+$.

Ethyl (R)-1-((5-bromopyridin-2-yl)sulfonyl)piperidine-3-carboxylate (8b)

Using a similar procedure as described for DX2-201 with 7 (660 mg, 2.57 mmol) and ethyl (R)-piperidine-3-carboxylate (444 mg, 2.82 mmol), white solid (120 mg, 12%). $^1$H NMR (300 MHz, $CDCl_3$) δ 8.74 (d, J=2.3 Hz, 1H), 8.04 (dd, J=8.3, 2.3 Hz, 1H), 7.83 (d, J=8.3 Hz, 1H), 4.11 (dt, J=7.2, 4.5 Hz, 2H), 4.00 (dd, J=12.3, 4.0 Hz, 1H), 3.77 (d, J=12.5 Hz, 1H), 3.56-3.44 (m, 1H), 3.00-2.89 (m, 1H), 2.81 (dd, J=11.6, 3.0 Hz, 1H), 2.60 (tt, J=10.6, 3.9 Hz, 1H), 1.86-1.73 (m, 1H), 1.70-1.58 (m, 2H), 1.34-1.16 (m, 3H). LC-MS (ESI) m/z 376.9, 378.9 $[M+H]^+$.

Ethyl (R)-1-((5-(benzylthio)pyridin-2-yl)sulfonyl)piperidine-3-carboxylate (9b)

Using a similar procedure as described for 3a with 8b (120 mg, 0.32 mmol) and benzyl mercaptan (39 mg, 0.32 mmol), white solid (81 mg, 60%). $^1$H NMR (300 MHz, $CDCl_3$) δ 8.53 (d, J=2.3 Hz, 1H), 7.78 (d, J=8.2 Hz, 1H), 7.69 (dd, J=8.2, 2.3 Hz, 1H), 7.41-7.30 (m, 5H), 4.14 (qd, J=7.1, 2.2 Hz, 2H), 4.00 (d, J=10.5 Hz, 1H), 3.78 (d, J=12.6 Hz, 1H), 2.93-2.82 (m, 1H), 2.74 (td, J=11.7, 3.0 Hz, 1H), 2.67-2.54 (m, 1H), 2.06 (s, 1H), 1.80 (dt, J=12.5, 3.6 Hz, 1H), 1.70-1.57 (m, 1H), 1.57-1.41 (m, 1H), 1.34-1.22 (m, 3H). LC-MS (ESI) m/z 421.1 $[M+H]^+$.

Ethyl (R)-1-((5-(chlorosulfonyl)pyridin-2-yl)sulfonyl)piperidine-3-carboxylate (10b)

Using a similar procedure as described for 4a with 9b (50 mg, 0.12 mmol), white solid (44 mg, 92%). $^1$H NMR (300 MHz, $CDCl_3$) δ 9.30 (d, J=2.3 Hz, 1H), 8.54 (dd, J=8.4, 2.3 Hz, 1H), 8.21 (d, J=8.4 Hz, 1H), 4.16 (q, J=7.1 Hz, 2H), 4.06 (d, J=11.0 Hz, 1H), 3.85 (d, J=12.3 Hz, 1H), 3.17-3.06 (m, 1H), 2.98 (t, J=11.5 Hz, 1H), 2.72-2.61 (m, 1H), 2.14-2.04 (m, 1H), 1.93-1.82 (m, 1H), 1.74-1.56 (m, 2H), 1.28 (t, J=7.1 Hz, 3H).

Ethyl (R)-1-((5-(N,N-diethylsulfamoyl)pyridin-2-yl)sulfonyl)piperidine-3-carboxylate (DX2-293)

Using a similar procedure as described for DX2-201 with 10b (44 mg, 0.12 mmol) and diethylamine (10 mg, 0.13 mmol), white solid (24 mg, 46%). $^1$H NMR (300 MHz, $CDCl_3$) δ 9.08 (d, J=2.1 Hz, 1H), 8.31 (dd, J=8.2, 2.3 Hz, 1H), 8.08 (d, J=8.2 Hz, 1H), 4.16 (q, J=7.1 Hz, 2H), 4.04 (dd, J=9.4, 6.2 Hz, 1H), 3.83 (dt, J=12.1, 3.9 Hz, 1H), 3.32 (q, J=7.1 Hz, 4H), 3.10-2.99 (m, 1H), 2.88 (t, J=11.7 Hz, 1H), 2.71-2.58 (m, 1H), 2.14-2.03 (m, 1H), 1.91-1.79 (m, 1H), 1.71-1.49 (m, 3H), 1.28 (t, J=7.1 Hz, 3H), 1.20 (t, J=7.1 Hz, 6H). LC-MS (ESI) m/z 434.0 $[M+H]^+$.

Scheme 6

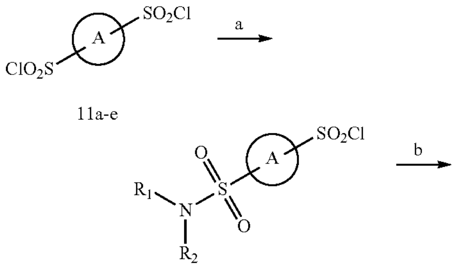

11a-e 12a-e

-continued

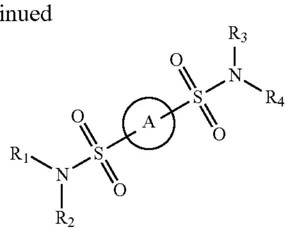

Reagents and conditions: a) $NHR_1R_2$, $Et_3N$, DCM, rt; b) $NHR_3R_4$, $Et_3N$, DCM, rt.

2-(N,N-Diethylsulfamoyl)benzenesulfonyl Chloride (12a)

To a solution of diethylamine (21 mg, 0.29 mmol) and triethylamine (88 mg, 0.84 mmol) in DCM (2 mL) was added benzene-1,2-disulfonyl dichloride (11a, 80 mg, 0.29 mmol) at 0° C. The mixture was stirred at room temperature overnight. The mixture was concentrated and purified with flash chromatography (30% EtOAc in hexane) to give 12a as a white solid (15 mg, 17%). $^1$H NMR (300 MHz, $CDCl_3$) δ 8.40 (dd, J=7.7, 1.6 Hz, 1H), 8.17 (dd, J=7.6, 1.7 Hz, 1H), 7.94-7.75 (m, 2H), 3.46 (q, J=7.3 Hz, 4H), 1.19 (t, J=6.9 Hz, 6H).

Ethyl (R)-1-((2-(N,N-diethylsulfamoyl)phenyl)sulfonyl)piperidine-3-carboxylate (DX2-226)

Using a similar procedure as described for DX2-201 with 12a (15 mg, 0.048 mmol) and ethyl (R)-piperidine-3-carboxylate (8.3 mg, 0.053 mmol), white solid (5 mg, 24%). $^1$H NMR (300 MHz, $CDCl_3$) δ 8.05 (d, J=8.2 Hz, 2H), 7.97 (d, J=8.3 Hz, 2H), 4.17 (qd, J=7.1, 3.0 Hz, 2H), 3.69 (s, 1H), 3.45 (s, 1H), 3.36-3.22 (m, 4H), 2.72-2.55 (m, 2H), 2.40 (t, J=12.5 Hz, 1H), 2.04-1.41 (m, 4H), 1.28 (t, J=7.1 Hz, 3H), 1.16 (t, J=7.0 Hz, 6H). LC-MS (ESI) m/z 433.1 [M+H]$^+$.

3-(N,N-Diethylsulfamoyl)benzenesulfonyl Chloride (12b)

Using a similar procedure as described for 12a with benzene-1,3-disulfonyl dichloride (11b, 275 mg, 1.00 mmol) and diethylamine (73 mg, 1.00 mmol), white solid (97 mg, 31%). $^1$H NMR (300 MHz, $CDCl_3$) δ 8.47 (d, J=1.9 Hz, 1H), 8.21 (ddt, J=13.0, 7.9, 1.5 Hz, 2H), 7.82 (t, J=7.9 Hz, 1H), 3.32 (q, J=7.2 Hz, 4H), 1.19 (t, J=7.1 Hz, 6H).

Ethyl (R)-1-((3-(N,N-diethylsulfamoyl)phenyl)sulfonyl)piperidine-3-carboxylate (DX2-229)

Using a similar procedure as described for DX2-201 with 12b (47 mg, 0.15 mmol) and ethyl (R)-piperidine-3-carboxylate (27 mg, 0.18 mmol), white solid (22 mg, 34%). $^1$H NMR (300 MHz, $CDCl_3$) δ 8.20 (d, J=1.8 Hz, 1H), 8.05 (dd, J=7.9, 1.6 Hz, 1H), 7.96 (d, J=8.0 Hz, 1H), 7.71 (t, J=7.8 Hz, 1H), 4.16 (q, J=7.1 Hz, 2H), 3.83 (d, J=7.5 Hz, 1H), 3.63 (d, J=11.7 Hz, 1H), 3.29 (q, J=7.1 Hz, 4H), 2.70-2.56 (m, 2H), 2.46 (td, J=11.2, 3.2 Hz, 1H), 2.00 (d, J=13.6 Hz, 1H), 1.84 (dt, J=13.3, 3.9 Hz, 1H), 1.75-1.57 (m, 1H), 1.44 (q, J=15.3, 13.1 Hz, 1H), 1.28 (t, J=7.1 Hz, 3H), 1.16 (t, J=7.1 Hz, 6H). LC-MS (ESI) m/z 433.0 [M+H]$^+$.

4-(4-(N,N-Diethylsulfamoyl)phenoxy)benzenesulfonyl Chloride (12c)

Using a similar procedure as described for 12a with 4,4'-oxydibenzenesulfonyl chloride (11c, 200 mg, 0.54 mmol) and diethylamine (40 mg, 0.54 mmol), white solid (72 mg, 33%). $^1$H NMR (300 MHz, $CDCl_3$) δ 8.06 (d, J=9.0 Hz, 2H), 7.90 (d, J=8.7 Hz, 2H), 7.20 (dd, J=8.8, 6.7 Hz, 4H), 3.30 (q, J=7.1 Hz, 4H), 1.18 (t, J=7.1 Hz, 6H).

Ethyl (R)-1-((4-(4-(N,N-diethylsulfamoyl)phenoxy)phenyl)sulfonyl)piperidine-3-carboxylate (DX2-230)

Using a similar procedure as described for DX2-201 with 12c (14 mg, 0.039 mmol) and ethyl (R)-piperidine-3-carboxylate (7 mg, 0.042 mmol), white solid (5 mg, 25%). $^1$H NMR (300 MHz, $CDCl_3$) δ 7.83 (dd, J=20.6, 8.3 Hz, 4H), 7.15 (d, J=8.3 Hz, 4H), 4.16 (q, J=7.1 Hz, 2H), 3.88 (d, J=11.3 Hz, 1H), 3.67 (d, J=11.2 Hz, 1H), 3.29 (q, J=7.2 Hz, 4H), 2.60 (dt, J=33.2, 10.8 Hz, 2H), 2.39 (t, J=11.1 Hz, 1H), 2.03 (d, J=13.2 Hz, 1H), 1.91-1.78 (m, 1H), 1.69 (d, J=12.4 Hz, 1H), 1.51-1.34 (m, 1H), 1.28 (t, J=7.1 Hz, 3H), 1.18 (t, J=7.2 Hz, 6H). LC-MS (ESI) m/z 525.1 [M+H]$^+$.

4'-(N,N-Diethylsulfamoyl)-[1,1'-biphenyl]-4-sulfonyl Chloride (12d)

Using a similar procedure as described for 12a with [1,1'-biphenyl]-4,4'-disulfonyl dichloride (11d, 200 mg, 0.57 mmol) and diethylamine (42 mg, 0.57 mmol), white solid (47 mg, 21%). $^1$H NMR (300 MHz, $CDCl_3$) δ 8.21-8.11 (m, 2H), 7.99-7.93 (m, 2H), 7.85 (d, J=8.7 Hz, 2H), 7.76 (d, J=8.0 Hz, 2H), 3.31 (q, J=7.1 Hz, 4H), 1.18 (t, J=7.1 Hz, 6H).

Ethyl (R)-1-((4'-(N,N-diethylsulfamoyl)-[1,1'-biphenyl]-4-yl)sulfonyl)piperidine-3-carboxylate (DX3-78)

Using a similar procedure as described for DX2-201 with 12d (45 mg, 0.12 mmol) and ethyl (R)-piperidine-3-carboxylate (18 mg, 0.12 mmol), white solid (39 mg, 64%). $^1$H NMR (300 MHz, $CDCl_3$) δ 7.92 (dd, J=16.5, 8.5 Hz, 4H), 7.76 (t, J=8.6 Hz, 4H), 4.16 (q, J=7.1 Hz, 2H), 3.92 (d, J=10.9 Hz, 1H), 3.70 (d, J=11.7 Hz, 1H), 3.31 (q, J=7.1 Hz, 4H), 2.72-2.53 (m, 2H), 2.42 (td, J=11.3, 3.1 Hz, 1H), 2.09-1.98 (m, 1H), 1.85 (dt, J=13.6, 3.6 Hz, 1H), 1.78-1.65 (m, 1H), 1.48-1.36 (m, 1H), 1.28 (t, J=7.1 Hz, 3H), 1.19 (t, J=7.1 Hz, 6H). LC-MS (ESI) m/z 509.1 [M+H]$^+$.

6-(N,N-Diethylsulfamoyl)naphthalene-2-sulfonyl Chloride (12e)

Using a similar procedure as described for 12a with naphthalene-2,6-disulfonyl dichloride (11e, 200 mg, 0.62 mmol) and diethylamine (36 mg, 0.49 mmol), white solid (42 mg, 19%). $^1$H NMR (400 MHz, $CDCl_3$) δ 8.68 (s, 1H), 8.52 (s, 1H), 8.28-8.13 (m, 3H), 8.02 (dd, J=8.6, 1.8 Hz, 1H), 3.36 (q, J=7.1 Hz, 4H), 1.19 (td, J=7.2, 1.0 Hz, 6H).

Ethyl (R)-1-((6-(N,N-diethylsulfamoyl)naphthalen-2-yl)sulfonyl)piperidine-3-carboxylate (DX3-99B)

Using a similar procedure as described for DX2-201 with 12e (21 mg, 0.058 mmol) and ethyl (R)-piperidine-3-carboxylate (18 mg, 0.12 mmol), white solid (4 mg, 14%). $^1$H NMR (300 MHz, $CDCl_3$) δ 8.47 (s, 1H), 8.41 (s, 1H), 8.12 (dd, J=8.6, 1.9 Hz, 2H), 7.92 (ddd, J=15.0, 8.6, 1.8 Hz, 2H), 4.15 (q, J=7.1 Hz, 2H), 3.95 (d, J=8.2 Hz, 1H), 3.74 (d, J=11.6 Hz, 1H), 3.35 (q, J=7.1 Hz, 4H), 2.72-2.58 (m, 2H), 2.47 (td, J=11.4, 3.2 Hz, 1H), 2.01 (d, J=13.4 Hz, 1H), 1.89-1.78 (m, 1H), 1.78-1.61 (m, 1H), 1.49-1.33 (m, 2H), 1.27 (t, J=7.1 Hz, 3H), 1.18 (t, J=7.2 Hz, 6H). LC-MS (ESI) m/z 483.0 [M+H]$^+$.

Scheme 7

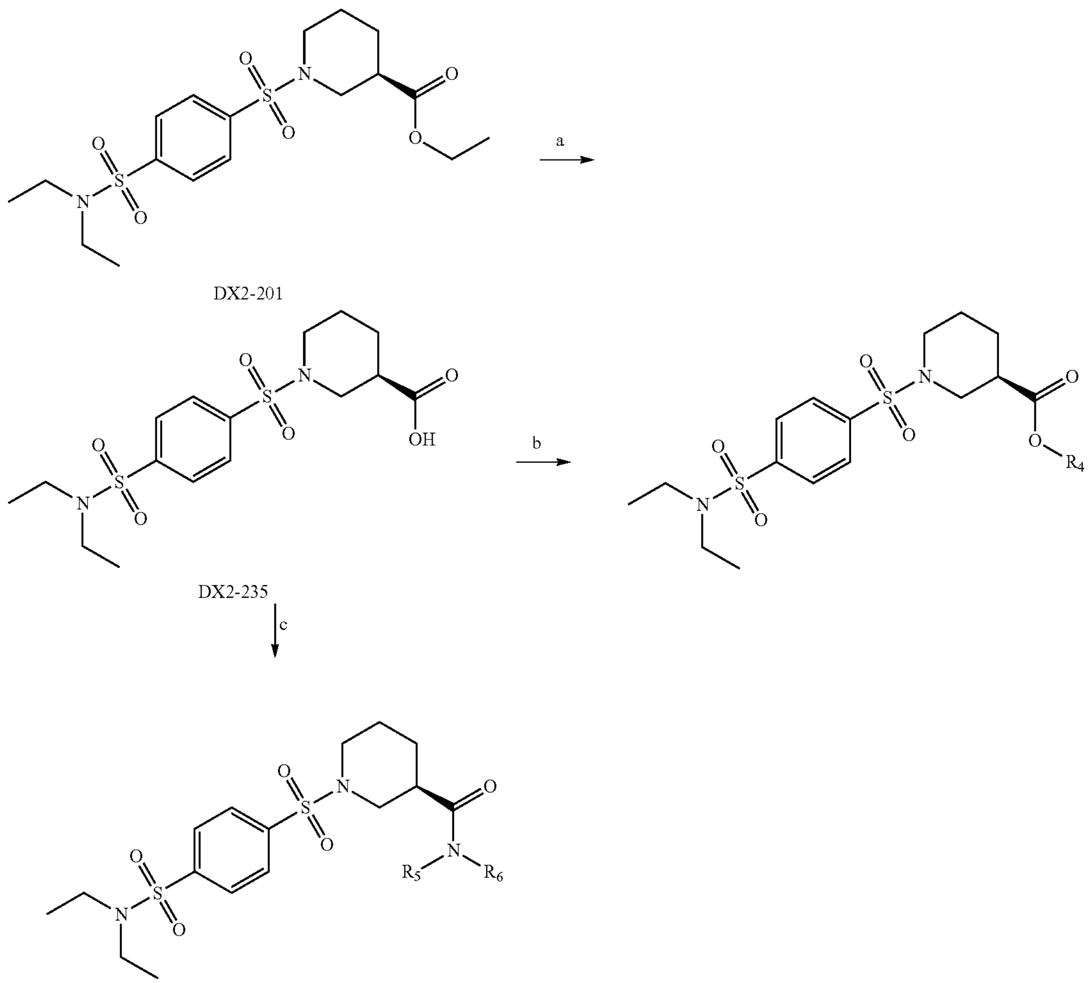

DX2-201

DX2-235

Reagents and conditions: a) LiOH, THF, $H_2O$, rt; b) alcohols, EDCl, DMAP, DCM, rt; c) $NHR_5R_6$, HATU, DIEA, DMF.

(R)-1-((4-(N,N-Diethylsulfamoyl)phenyl)sulfonyl) piperidine-3-carboxylic Acid (DX2-235)

To a solution of DX2-201 (230 mg, 0.53 mmol) in THF (1 mL) and $H_2O$ (1 mL) was added LiOH·$H_2O$ (186 mg, 2.66 mmol) at 0° C. and stirred at room temperature for 5 h. The mixture was then diluted with $H_2O$, and the pH was adjusted to 3 by 1N HCl solution. It was extracted with EtOAc, and the organic layer was washed with brine, dried over anhydrous $Na_2SO_4$, filtered and concentrated to give DX2-235 as a white solid (187 mg, 87%). $^1H$ NMR (300 MHz, MeOD) δ 8.07 (d, J=8.1 Hz, 2H), 7.99 (d, J=7.9 Hz, 2H), 3.82-3.70 (m, 1H), 3.60-3.48 (m, 1H), 3.36-3.24 (m, 4H), 2.69 (t, J=10.7 Hz, 1H), 2.65-2.47 (m, 2H), 2.05-1.91 (m, 1H), 1.89-1.76 (m, 1H), 1.71-1.57 (m, 1H), 1.56-1.38 (m, 1H), 1.15 (t, J=7.1 Hz, 6H). LC-MS (ESI) m/z 405.0 $[M+H]^+$.

(R)-1-((4-(N,N-Diethylsulfamoyl)phenyl)sulfonyl)-N,N-diethylpiperidine-3-carboxamide (DX2-237)

To a solution of DX2-235 (30 mg, 0.074 mmol) and HATU (42 mg, 0.11 mmol) in DCM (1 mL) was added diethylamine (65 mg, 0.089 mmol) and DIEA (29 mg, 0.22 mmol). The mixture was stirred at room temperature overnight. The mixture was then diluted with EtOAc, washed with brine, dried over anhydrous $Na_2SO_4$, filtered and concentrated. The residue was purified with flash chromatography (10% MeOH in DCM) to give DX2-237 as a white solid (21 mg, 62%). $^1H$ NMR (300 MHz, $CDCl_3$) δ 7.97 (d, J=8.3 Hz, 2H), 7.89 (d, J=8.3 Hz, 2H), 3.87 (d, J=11.9 Hz, 2H), 3.43-3.23 (m, 8H), 2.84-2.73 (m, 1H), 2.58 (t, J=11.3 Hz, 1H), 2.34-2.22 (m, 1H), 1.91-1.66 (m, 3H), 1.56-1.46 (m, 1H), 1.30-1.06 (m, 12H). LC-MS (ESI) m/z 460.1 $[M+H]^+$.

(R)-1-((4-(N,N-Diethylsulfamoyl)phenyl)sulfonyl)-N-methylpiperidine-3-carboxamide (DX2-238)

Using a similar procedure as described for DX2-237 with DX2-235 (30 mg, 0.074 mmol) and methylamine (2.3 mg, 0.074 mmol), white solid (26 mg, 84%). $^1H$ NMR (300 MHz, $CDCl_3$) δ 7.99 (d, J=8.3 Hz, 2H), 7.88 (d, J=8.4 Hz, 2H), 5.79 (s, 1H), 3.72 (d, J=11.5 Hz, 1H), 3.61 (d, J=11.6 Hz, 1H), 3.30 (q, J=7.1 Hz, 4H), 2.84 (d, J=4.6 Hz, 3H), 2.76-2.66 (m, 1H), 2.57-2.37 (m, 2H), 1.89-1.78 (m, 2H), 1.76-1.59 (m, 2H), 1.18 (t, J=7.1 Hz, 6H). LC-MS (ESI) m/z 418.1 $[M+H]^+$.

(R)-1-((4-(N,N-Diethylsulfamoyl)phenyl)sulfonyl)-N-(2-(dimethylamino)ethyl)piperidine-3-carboxamide (DX2-241)

Using a similar procedure as described for DX2-237 with DX2-235 (30 mg, 0.074 mmol) and N,N-dimethylethane-1,2-diamine (7 mg, 0.074 mmol) in DMF (1 mL), white solid (27 mg, 77%). $^1$H NMR (300 MHz, $CDCl_3$) δ 8.03-7.90 (m, 4H), 3.88-3.64 (m, 2H), 3.61-3.37 (m, 3H), 3.30 (q, J=7.1 Hz, 4H), 3.08 (s, 2H), 2.79 (s, 6H), 2.67-2.48 (m, 2H), 1.96-1.84 (m, 2H), 1.76-1.48 (m, 3H), 1.18 (t, J=7.1 Hz, 6H). LC-MS (ESI) m/z 475.1 $[M+H]^+$.

(R)-1-((4-(N,N-Diethylsulfamoyl)phenyl)sulfonyl)-N-(oxetan-3-yl)piperidine-3-carboxamide (DX2-242)

Using a similar procedure as described for DX2-237 with DX2-235 (30 mg, 0.074 mmol) and oxetan-3-amine (5.4 mg, 0.074 mmol) in DMF (1 mL), white solid (24 mg, 71%). $^1$H NMR (300 MHz, $CDCl_3$) δ 7.99 (d, J=8.4 Hz, 2H), 7.89 (d, J=8.5 Hz, 2H), 6.56 (d, J=7.2 Hz, 1H), 5.09-4.87 (m, 3H), 4.54 (q, J=6.5 Hz, 2H), 3.73-3.48 (m, 1H), 3.31 (q, J=7.2 Hz, 4H), 2.84-2.70 (m, 1H), 2.56 (d, J=23.6 Hz, 2H), 1.90-1.57 (m, 4H), 1.18 (t, J=7.2 Hz, 6H). LC-MS (ESI) m/z 460.1 $[M+H]^+$.

(R)-1-((4-(N,N-Diethylsulfamoyl)phenyl)sulfonyl)-N-(4-fluorophenyl)piperidine-3-carboxamide (DX2-244)

Using a similar procedure as described for DX2-237 with DX2-235 (30 mg, 0.074 mmol) and 4-fluoroaniline (8.2 mg, 0.074 mmol) in DMF (1 mL), white solid (32 mg, 86%). $^1$H NMR (300 MHz, $CDCl_3$) δ 8.01 (d, J=8.5 Hz, 2H), 7.91 (d, J=8.4 Hz, 2H), 7.75 (s, 1H), 7.53 (dd, J=9.0, 4.8 Hz, 2H), 7.04 (t, J=8.7 Hz, 2H), 3.70 (dd, J=10.2, 2.9 Hz, 1H), 3.60-3.50 (m, 1H), 3.31 (q, J=7.1 Hz, 4H), 2.98-2.87 (m, 1H), 2.77-2.59 (m, 2H), 2.00-1.72 (m, 4H), 1.19 (t, J=7.1 Hz, 6H). LC-MS (ESI) m/z 498.1 $[M+H]^+$.

(R)-1-((4-(N,N-Diethylsulfamoyl)phenyl)sulfonyl)-N-isopropylpiperidine-3-carboxamide (DX2-295)

Using a similar procedure as described for DX2-237 with DX2-235 (30 mg, 0.074 mmol) and propan-2-amine (5.2 mg, 0.079 mmol) in DMF (1 mL), white solid (29 mg, 88%). $^1$H NMR (300 MHz, $CDCl_3$) δ 7.99 (d, J=8.0 Hz, 2H), 7.89 (d, J=7.9 Hz, 2H), 5.61 (s, 1H), 4.18-4.05 (m, 1H), 3.74-3.56 (m, 2H), 3.31 (q, J=7.3 Hz, 4H), 2.80-2.67 (m, 1H), 2.60-2.47 (m, 1H), 2.42-2.32 (m, 1H), 1.89-1.77 (m, 2H), 1.75-1.62 (m, 2H), 1.18 (t, J=6.9 Hz, 12H). LC-MS (ESI) m/z 446.0 $[M+H]^+$.

(R)—N-Cyclopropyl-1-((4-(N,N-diethylsulfamoyl)phenyl)sulfonyl)piperidine-3-carboxamide (DX2-296)

Using a similar procedure as described for DX2-237 with DX2-235 (30 mg, 0.074 mmol) and cyclopropanamine (5.0 mg, 0.089 mmol) in DMF (1 mL), white solid (17 mg, 52%). $^1$H NMR (300 MHz, $CDCl_3$) δ 7.99 (d, J=8.3 Hz, 2H), 7.88 (d, J=8.2 Hz, 2H), 5.86 (s, 1H), 3.73-3.53 (m, 2H), 3.31 (q, J=7.2 Hz, 4H), 2.79-2.63 (m, 2H), 2.58-2.47 (m, 1H), 2.37 (d, J=11.2 Hz, 1H), 1.90-1.76 (m, 2H), 1.74-1.60 (m, 2H), 1.18 (t, J=7.2 Hz, 6H), 0.81 (d, J=6.7 Hz, 2H), 0.53 (t, J=5.6 Hz, 2H). LC-MS (ESI) m/z 444.1 $[M+H]^+$.

(R)-1-((4-(N,N-Diethylsulfamoyl)phenyl)sulfonyl)-N-isopropyl-N-methylpiperidine-3-carboxamide (DX2-297)

Using a similar procedure as described for DX2-237 with DX2-235 (30 mg, 0.074 mmol) and N-methylpropan-2-amine (6.5 mg, 0.089 mmol) in DMF (1 mL), white solid (25 mg, 74%). $^1$H NMR (400 MHz, $CDCl_3$) δ 8.01-7.95 (m, 2H), 7.89 (d, J=8.7 Hz, 2H), 3.86 (d, J=11.5 Hz, 2H), 3.31 (q, J=7.1 Hz, 5H), 2.66-2.57 (m, 1H), 2.57-2.44 (m, 2H), 2.29 (td, J=12.0, 2.8 Hz, 1H), 1.85 (dd, J=12.6, 5.7 Hz, 2H), 1.73 (dtd, J=17.9, 8.9, 4.8 Hz, 1H), 1.46 (ddd, J=12.2, 10.3, 3.8 Hz, 1H), 1.19 (t, J=7.1 Hz, 6H), 1.06-0.94 (m, 2H), 0.94-0.81 (m, 4H), 0.63 (s, 2H). LC-MS (ESI) m/z 460.1 $[M+H]^+$.

(R)—N,N-dicyclopropyl-1-((4-(N,N-diethylsulfamoyl)phenyl)sulfonyl)piperidine-3-carboxamide (DX3-84)

Using a similar procedure as described for DX2-237 with DX2-235 (30 mg, 0.074 mmol) and dicyclopropylamine (10 mg, 0.074 mmol) in DMF (1 mL), white solid (25 mg, 74%). $^1$H NMR (400 MHz, $CDCl_3$) δ 8.01-7.95 (m, 2H), 7.89 (d, J=8.7 Hz, 2H), 3.86 (d, J=11.5 Hz, 2H), 3.31 (q, J=7.1 Hz, 5H), 2.66-2.57 (m, 1H), 2.57-2.44 (m, 2H), 2.29 (td, J=12.0, 2.8 Hz, 1H), 1.85 (dd, J=12.6, 5.7 Hz, 2H), 1.73 (dtd, J=17.9, 8.9, 4.8 Hz, 1H), 1.46 (ddd, J=12.2, 10.3, 3.8 Hz, 1H), 1.19 (t, J=7.1 Hz, 6H), 1.06-0.94 (m, 2H), 0.94-0.81 (m, 4H), 0.63 (s, 2H). LC-MS (ESI) m/z 484.1 $[M+H]^+$.

(R)-1-((4-(N,N-diethylsulfamoyl)phenyl)sulfonyl)-N-methyl-N-(oxetan-3-yl)piperidine-3-carboxamide (DX3-100)

Using a similar procedure as described for DX2-237 with DX2-235 (30 mg, 0.074 mmol) and N-methyloxetan-3-amine (6.5 mg, 0.074 mmol) in DMF (1 mL), white solid (30 mg, 86%). $^1$H NMR (300 MHz, $CDCl_3$) δ 8.01-7.94 (m, 2H), 7.92-7.85 (m, 2H), 5.41 (p, J=7.1 Hz, 1H), 4.89-4.79 (m, 2H), 4.66 (q, J=7.0 Hz, 2H), 3.88 (d, J=11.4 Hz, 2H), 3.30 (q, J=7.2 Hz, 4H), 3.21 (s, 3H), 2.53 (q, J=11.1 Hz, 1H), 2.28 (td, J=12.0, 3.0 Hz, 1H), 1.87 (q, J=12.5, 10.7 Hz, 2H), 1.80-1.60 (m, 2H), 1.45 (td, J=12.5, 4.0 Hz, 1H), 1.18 (t, J=7.1 Hz, 6H). LC-MS (ESI) m/z 474.1 $[M+H]^+$.

(R)—N-(1-Cyanocyclopropyl)-1-((4-(N,N-diethylsulfamoyl)phenyl)sulfonyl)piperidine-3-carboxamide (DX3-100B)

Using a similar procedure as described for DX2-237 with DX2-235 (30 mg, 0.074 mmol) and 1-aminocyclopropane-1-carbonitrile hydrochloride (8.8 mg, 0.074 mmol) in DMF (1 mL), white solid (30 mg, 86%). $^1$H NMR (300 MHz, $CDCl_3$) δ 8.01 (d, J=8.4 Hz, 2H), 7.92-7.86 (m, 2H), 6.60 (s, 1H), 3.59 (dd, J=12.1, 3.7 Hz, 1H), 3.50 (d, J=11.5 Hz, 1H), 3.31 (q, J=7.2 Hz, 4H), 2.82 (dd, J=12.0, 9.0 Hz, 1H), 2.73-2.61 (m, 1H), 2.48 (s, 1H), 1.89-1.77 (m, 2H), 1.77-1.65 (m, 2H), 1.59 (dd, J=8.0, 5.3 Hz, 3H), 1.31-1.23 (m, 3H), 1.19 (t, J=7.1 Hz, 6H). LC-MS (ESI) m/z 469.1 $[M+H]^+$.

(R)-1-((4-(N,N-Diethylsulfamoyl)phenyl)sulfonyl)-N-(oxetan-3-ylmethyl)piperidine-3-carboxamide (DX3-104)

Using a similar procedure as described for DX2-237 with DX2-235 (20 mg, 0.05 mmol) and oxetan-3-ylmethanamine (4.4 mg, 0.05 mmol) in DMF (1 mL), white solid (19 mg, 80%). $^1$H NMR (300 MHz, $CDCl_3$) δ 7.99 (d, J=8.7 Hz, 2H), 7.89 (d, J=8.7 Hz, 2H), 6.10 (t, J=6.5 Hz, 1H), 4.83 (ddd, J=7.7, 6.3, 2.3 Hz, 2H), 4.42 (td, J=6.1, 2.3 Hz, 2H), 3.59 (td, J=6.4, 6.0, 2.6 Hz, 3H), 3.50 (d, J=11.3 Hz, 1H), 3.31 (q, J=7.2 Hz, 4H), 3.19 (p, J=6.4 Hz, 1H), 2.84 (dd, J=11.9, 9.1 Hz, 1H), 2.63 (d, J=10.6 Hz, 1H), 2.48 (dt, J=9.1, 4.8 Hz, 1H), 1.89-1.65 (m, 4H), 1.18 (t, J=7.1 Hz, 6H). LC-MS (ESI) m/z 474.1 $[M+H]^+$.

(R)-1-((4-(N,N-Diethylsulfamoyl)phenyl)sulfonyl)-N-(3-methyloxetan-3-yl)piperidine-3-carboxamide (DX3-104B)

Using a similar procedure as described for DX2-237 with DX2-235 (20 mg, 0.05 mmol) and 3-methyloxetan-3-amine (4.4 mg, 0.05 mmol) in DMF (1 mL), white solid (22 mg, 93%). $^1$H NMR (300 MHz, $CDCl_3$) δ 8.00 (d, J=8.6 Hz, 2H), 7.89 (d, J=8.7 Hz, 2H), 6.22 (s, 1H), 4.74 (dd, J=6.5, 2.9 Hz, 2H), 4.50 (d, J=6.5 Hz, 2H), 3.62 (dd, J=11.9, 3.8 Hz, 1H), 3.51 (d, J=11.3 Hz, 1H), 3.31 (q, J=7.2 Hz, 4H), 2.82 (dd, J=11.7, 9.3 Hz, 1H), 2.65 (t, J=9.9 Hz, 1H), 2.46 (s, 1H), 1.89-1.68 (m, 4H), 1.66 (s, 3H), 1.18 (t, J=7.2 Hz, 6H). LC-MS (ESI) m/z 474.0 $[M+H]^+$.

(R)-1-((4-(N,N-Diethylsulfamoyl)phenyl)sulfonyl)-N-(tetrahydro-2H-pyran-4-yl)piperidine-3-carboxamide (DX3-106B)

Using a similar procedure as described for DX2-237 with DX2-235 (20 mg, 0.05 mmol) and tetrahydro-2H-pyran-4-amine (6.9 mg, 0.05 mmol) in DMF (1 mL), white solid (21 mg, 86%). $^1$H NMR (300 MHz, $CDCl_3$) δ 7.99 (d, J=8.7 Hz, 2H), 7.89 (d, J=8.7 Hz, 2H), 5.70 (d, J=8.0 Hz, 1H), 3.98 (dt, J=11.2, 3.5 Hz, 3H), 3.66 (d, J=11.0 Hz, 1H), 3.61-3.42 (m, 3H), 3.31 (q, J=7.2 Hz, 4H), 2.84-2.73 (m, 1H), 2.60 (d, J=10.3 Hz, 1H), 2.49-2.36 (m, 1H), 1.97-1.63 (m, 6H), 1.51 (ddd, J=12.9, 6.5, 4.4 Hz, 2H), 1.18 (t, J=7.1 Hz, 6H). LC-MS (ESI) m/z 488.2 $[M+H]^+$.

tert-Butyl (R)-3-(1-((4-(N,N-diethylsulfamoyl)phenyl)sulfonyl)piperidine-3-carboxamido)azetidine-1-carboxylate (DX3-107)

Using a similar procedure as described for DX2-237 with DX2-235 (40 mg, 0.10 mmol) and tert-butyl 3-aminoazetidine-1-carboxylate (17.2 mg, 0.10 mmol) in DMF (2 mL), white solid (54 mg, 96%). $^1$H NMR (300 MHz, $CDCl_3$) δ 7.99 (d, J=8.7 Hz, 2H), 7.89 (d, J=8.7 Hz, 2H), 6.40 (d, J=7.1 Hz, 1H), 4.69-4.54 (m, 1H), 4.27 (td, J=8.5, 7.9, 4.4 Hz, 2H), 3.77 (dt, J=9.3, 5.8 Hz, 2H), 3.67 (d, J=10.4 Hz, 1H), 3.57 (d, J=11.7 Hz, 1H), 3.31 (q, J=7.1 Hz, 4H), 2.83-2.69 (m, 1H), 2.65-2.42 (m, 2H), 1.84 (d, J=12.1 Hz, 2H), 1.68 (t, J=9.2 Hz, 2H), 1.46 (s, 9H), 1.18 (t, J=7.1 Hz, 6H). LC-MS (ESI) m/z 559.2 $[M+H]^+$.

(R)-1-((4-(N,N-Diethylsulfamoyl)phenyl)sulfonyl)-N—((R)-tetrahydrofuran-3-yl)piperidine-3-carboxamide (DX3-107B)

Using a similar procedure as described for DX2-237 with DX2-235 (20 mg, 0.05 mmol) and (R)-tetrahydrofuran-3-amine hydrochloride (6.2 mg, 0.05 mmol) in DMF (1 mL), white solid (15 mg, 63%). $^1$H NMR (300 MHz, $CDCl_3$) δ 7.99 (d, J=8.5 Hz, 2H), 7.89 (d, J=8.6 Hz, 2H), 6.01 (d, J=7.4 Hz, 1H), 4.50 (dt, J=7.6, 5.8 Hz, 1H), 3.96 (q, J=7.6 Hz, 1H), 3.83 (qd, J=9.1, 5.5 Hz, 2H), 3.73-3.54 (m, 3H), 3.31 (q, J=7.1 Hz, 4H), 2.74 (dd, J=11.8, 9.6 Hz, 1H), 2.55 (t, J=10.3 Hz, 1H), 2.44 (dd, J=10.0, 6.2 Hz, 1H), 2.37-2.20 (m, 1H), 1.91-1.63 (m, 5H), 1.18 (t, J=7.1 Hz, 6H). LC-MS (ESI) m/z 474.1 $[M+H]^+$.

(R)-1-((4-(N,N-Diethylsulfamoyl)phenyl)sulfonyl)-N—((S)-tetrahydrofuran-3-yl)piperidine-3-carboxamide (DX3-108)

Using a similar procedure as described for DX2-237 with DX2-235 (20 mg, 0.05 mmol) and (S)-tetrahydrofuran-3-amine hydrochloride (6.2 mg, 0.05 mmol) in DMF (1 mL), white solid (23 mg, 98%). $^1$H NMR (300 MHz, $CDCl_3$) δ 8.03-7.95 (m, 2H), 7.89 (d, J=8.7 Hz, 2H), 6.01 (d, J=7.4 Hz, 1H), 4.57-4.45 (m, 1H), 3.99 (q, J=7.9, 7.5 Hz, 1H), 3.83 (ddd, J=9.6, 5.5, 2.4 Hz, 2H), 3.66 (dd, J=9.6, 2.8 Hz, 2H), 3.57 (d, J=11.7 Hz, 1H), 3.31 (q, J=7.2 Hz, 4H), 2.84-2.71 (m, 1H), 2.57 (t, J=10.0 Hz, 1H), 2.43 (s, 1H), 2.37-2.23 (m, 1H), 1.90-1.63 (m, 5H), 1.18 (t, J=7.1 Hz, 6H). LC-MS (ESI) m/z 474.0 $[M+H]^+$.

tert-Butyl (R)-3-((R)-1-((4-(N,N-diethylsulfamoyl)phenyl)sulfonyl)piperidine-3-carboxamido)pyrrolidine-1-carboxylate (DX3-118)

Using a similar procedure as described for DX2-237 with DX2-235 (20 mg, 0.05 mmol) and tert-butyl (R)-3-aminopyrrolidine-1-carboxylate (9.3 mg, 0.05 mmol) in DMF (1 mL), white solid (19 mg, 66%). $^1$H NMR (300 MHz, $CDCl_3$) δ 7.99 (d, J=8.8 Hz, 2H), 7.89 (d, J=8.6 Hz, 2H), 5.98 (s, 1H), 4.44 (q, J=5.8 Hz, 1H), 3.65 (dd, J=11.6, 5.3 Hz, 2H), 3.60-3.52 (m, 1H), 3.52-3.40 (m, 2H), 3.31 (q, J=7.2 Hz, 4H), 3.24-3.13 (m, 1H), 2.81-2.70 (m, 1H), 2.67-2.53 (m, 1H), 2.49-2.39 (m, 1H), 2.16 (dq, J=13.4, 6.9 Hz, 1H), 1.91-1.75 (m, 3H), 1.75-1.62 (m, 2H), 1.50 (s, 9H), 1.18 (t, J=7.1 Hz, 6H). LC-MS (ESI) m/z 595.3 $[M+Na]^+$.

tert-Butyl (R)-1-(1-((4-(N,N-diethylsulfamoyl)phenyl)sulfonyl)piperidine-3-carbonyl)-1,6-diazaspiro[3.3]heptane-6-carboxylate (DX3-118B)

Using a similar procedure as described for DX2-237 with DX2-235 (20 mg, 0.05 mmol) and tert-butyl 1,6-diazaspiro[3.3]heptane-6-carboxylate hemioxylate (12 mg, 0.05 mmol) in DMF (1 mL), white solid (22 mg, 76%). $^1$H NMR (300 MHz, $CDCl_3$) δ 7.98 (d, J=8.5 Hz, 2H), 7.88 (d, J=8.6 Hz, 2H), 4.64 (t, J=9.5 Hz, 2H), 4.22-3.99 (m, 2H), 3.97-3.78 (m, 4H), 3.30 (q, J=7.1 Hz, 4H), 2.60-2.35 (m, 4H), 2.25 (t, J=11.5 Hz, 1H), 1.85 (d, J=12.5 Hz, 2H), 1.75-1.60 (m, 2H), 1.44 (s, 9H), 1.19 (t, J=7.2 Hz, 6H). LC-MS (ESI) m/z 607.2 $[M+Na]^+$.

tert-Butyl (S)-3-((R)-1-((4-(N,N-diethylsulfamoyl)phenyl)sulfonyl)piperidine-3-carboxamido)pyrrolidine-1-carboxylate (DX3-119)

Using a similar procedure as described for DX2-237 with DX2-235 (20 mg, 0.05 mmol) and tert-butyl (S)-3-aminopyrrolidine-1-carboxylate (9.3 mg, 0.05 mmol) in DMF (1 mL), white solid (18 mg, 62%). $^1$H NMR (300 MHz, $CDCl_3$) δ 7.99 (d, J=8.3 Hz, 2H), 7.88 (d, J=8.1 Hz, 2H), 6.03 (d, J=7.2 Hz, 1H), 4.45 (s, 1H), 3.71-3.40 (m, 5H), 3.31 (q, J=7.1 Hz, 4H), 3.17 (s, 1H), 2.87-2.75 (m, 1H), 2.68-2.54 (m, 1H), 2.52-2.39 (m, 1H), 2.19 (dq, J=12.8, 6.9, 6.2 Hz, 1H), 1.95-1.66 (m, 5H), 1.49 (s, 9H), 1.18 (t, J=7.1 Hz, 6H). LC-MS (ESI) m/z 595.1 [M+Na]$^+$.

tert-Butyl (R)-6-(1-((4-(N,N-diethylsulfamoyl)phenyl)sulfonyl)piperidine-3-carbonyl)-2,6-diazaspiro[3.3]heptane-2-carboxylate (DX3-120)

Using a similar procedure as described for DX2-237 with DX2-235 (20 mg, 0.05 mmol) and tert-butyl 2,6-diazaspiro[3.3]heptane-2-carboxylate (10 mg, 0.05 mmol) in DMF (1 mL), white solid (28 mg, 96%). $^1$H NMR (300 MHz, $CDCl_3$) δ 7.98 (d, J=8.5 Hz, 2H), 7.87 (d, J=8.5 Hz, 2H), 4.42-4.24 (m, 2H), 4.10 (d, J=7.4 Hz, 6H), 3.86 (dt, J=8.7, 5.0 Hz, 2H), 3.30 (q, J=7.1 Hz, 4H), 2.58-2.42 (m, 2H), 2.32-2.20 (m, 1H), 1.91-1.79 (m, 2H), 1.75-1.60 (m, 2H), 1.46 (s, 9H), 1.18 (t, J=7.2 Hz, 6H). LC-MS (ESI) m/z 585.1 [M+H]$^+$.

tert-Butyl (R)-4-(1-((4-(N,N-diethylsulfamoyl)phenyl)sulfonyl)piperidine-3-carbonyl)piperazine-1-carboxylate (DX3-121)

Using a similar procedure as described for DX2-237 with DX2-235 (20 mg, 0.05 mmol) and tert-butyl piperazine-1-carboxylate (9.3 mg, 0.05 mmol) in DMF (1 mL), white solid (26 mg, 91%). $^1$H NMR (300 MHz, $CDCl_3$) δ 7.98 (d, J=8.7 Hz, 2H), 7.89 (d, J=8.7 Hz, 2H), 3.88 (d, J=11.7 Hz, 2H), 3.61-3.40 (m, 8H), 3.30 (q, J=7.2 Hz, 4H), 2.92-2.80 (m, 1H), 2.58 (t, J=11.4 Hz, 1H), 2.35-2.22 (m, 1H), 1.94-1.79 (m, 2H), 1.78-1.68 (m, 1H), 1.63-1.53 (m, 1H), 1.50 (s, 9H), 1.18 (t, J=7.1 Hz, 6H). LC-MS (ESI) m/z 595.2 [M+H]$^+$.

(R)—N,N-Diethyl-4-((3-(morpholine-4-carbonyl)piperidin-1-yl)sulfonyl)benzenesulfonamide (DX3-121B)

Using a similar procedure as described for DX2-237 with DX2-235 (20 mg, 0.05 mmol) and morpholine (4.4 mg, 0.05 mmol) in DMF (1 mL), white solid (23 mg, 97%). $^1$H NMR (300 MHz, $CDCl_3$) δ 7.98 (d, J=8.7 Hz, 2H), 7.89 (d, J=8.7 Hz, 2H), 3.88 (d, J=11.6 Hz, 2H), 3.81-3.49 (m, 8H), 3.30 (q, J=7.1 Hz, 4H), 2.91-2.78 (m, 1H), 2.64-2.53 (m, 1H), 2.36-2.24 (m, 1H), 1.92-1.81 (m, 2H), 1.79-1.64 (m, 1H), 1.55-1.39 (m, 1H), 1.18 (t, J=7.1 Hz, 6H). LC-MS (ESI) m/z 474.1 [M+H]$^+$.

(R)—N,N-Diethyl-4-((3-(piperidine-1-carbonyl)piperidin-1-yl)sulfonyl)benzenesulfonamide (DX3-122)

Using a similar procedure as described for DX2-237 with DX2-235 (20 mg, 0.05 mmol) and piperidine (4.3 mg, 0.05 mmol) in DMF (1 mL), white solid (21 mg, 89%). $^1$H NMR (300 MHz, $CDCl_3$) δ 7.97 (d, J=7.8 Hz, 2H), 7.88 (d, J=8.0 Hz, 2H), 3.87 (d, J=11.5 Hz, 2H), 3.49 (dt, J=24.8, 5.4 Hz, 5H), 3.29 (q, J=7.2 Hz, 4H), 3.16 (d, J=9.1 Hz, 1H), 2.94-2.78 (m, 1H), 2.56 (t, J=11.3 Hz, 1H), 2.34-2.19 (m, 2H), 1.94-1.78 (m, 2H), 1.77-1.38 (m, 5H), 1.17 (t, J=7.1 Hz, 6H). LC-MS (ESI) m/z 472.1 [M+H]$^+$.

tert-Butyl (R)-4-(1-((4-(N,N-diethylsulfamoyl)phenyl)sulfonyl)piperidine-3-carboxamido)piperidine-1-carboxylate (DX3-124)

Using a similar procedure as described for DX2-237 with DX2-235 (20 mg, 0.05 mmol) and tert-butyl 4-aminopiperidine-1-carboxylate (10 mg, 0.05 mmol) in DMF (1 mL), white solid (28 mg, 95%). $^1$H NMR (300 MHz, $CDCl_3$) δ 7.99 (d, J=8.7 Hz, 2H), 7.88 (d, J=8.7 Hz, 2H), 5.77 (d, J=7.9 Hz, 1H), 4.16-4.00 (m, 2H), 3.91 (ddd, J=11.1, 7.5, 3.9 Hz, 1H), 3.68-3.58 (m, 1H), 3.53 (d, J=11.2 Hz, 1H), 3.31 (q, J=7.1 Hz, 4H), 2.97-2.73 (m, 3H), 2.67-2.54 (m, 1H), 2.50-2.35 (m, 1H), 1.99-1.63 (m, 6H), 1.48 (s, 9H), 1.42-1.26 (m, 2H), 1.18 (t, J=7.1 Hz, 6H). LC-MS (ESI) m/z 609.2 [M+Na]$^+$.

tert-Butyl (1S,4S)-5-((R)-1-((4-(N,N-diethylsulfamoyl)phenyl)sulfonyl)piperidine-3-carbonyl)-2,5-diazabicyclo[2.2.1]heptane-2-carboxylate (DX3-126B)

Using a similar procedure as described for DX2-237 with DX2-235 (20 mg, 0.05 mmol) and tert-butyl (1S,4S)-2,5-diazabicyclo[2.2.1]heptane-2-carboxylate (10 mg, 0.05 mmol) in DMF (1 mL), white solid (26 mg, 90%). $^1$H NMR (300 MHz, $CDCl_3$) δ 7.98 (dd, J=8.6, 1.6 Hz, 2H), 7.93-7.83 (m, 2H), 4.93-4.46 (m, 2H), 3.99-3.79 (m, 2H), 3.64-3.35 (m, 4H), 3.30 (q, J=7.2, 6.6 Hz, 4H), 2.75-2.46 (m, 2H), 2.27 (t, J=11.6 Hz, 1H), 2.02-1.64 (m, 5H), 1.50 (s, 9H), 1.18 (t, J=7.1 Hz, 6H). LC-MS (ESI) m/z 585.2 [M+H]$^+$.

tert-Butyl (R)-2-(1-((4-(N,N-diethylsulfamoyl)phenyl)sulfonyl)piperidine-3-carbonyl)-2,6-diazaspiro[3.4]octane-6-carboxylate (DX3-127)

Using a similar procedure as described for DX2-237 with DX2-235 (20 mg, 0.05 mmol) and tert-butyl 2,6-diazaspiro[3.4]octane-6-carboxylate (11 mg, 0.05 mmol) in DMF (1 mL), white solid (27 mg, 90%). $^1$H NMR (300 MHz, $CDCl_3$) δ 7.97 (d, J=8.6 Hz, 2H), 7.87 (d, J=8.8 Hz, 2H), 4.25-4.01 (m, 2H), 3.89 (dt, J=15.6, 9.5 Hz, 4H), 3.62-3.37 (m, 4H), 3.30 (q, J=7.2 Hz, 4H), 2.60-2.40 (m, 2H), 2.26 (t, J=11.6 Hz, 1H), 2.09 (d, J=8.7 Hz, 2H), 1.84 (d, J=12.3 Hz, 2H), 1.68 (d, J=13.2 Hz, 2H), 1.48 (s, 9H), 1.18 (t, J=7.1 Hz, 6H). LC-MS (ESI) m/z 621.2 [M+Na]$^+$.

tert-Butyl 5-((R)-1-((4-(N,N-diethylsulfamoyl)phenyl)sulfonyl)piperidine-3-carbonyl)hexahydropyrrolo[3,4-c]pyrrole-2(1H)-carboxylate (DX3-127B)

Using a similar procedure as described for DX2-237 with DX2-235 (40 mg, 0.10 mmol) and tert-butyl hexahydropyrrolo[3,4-c]pyrrole-2(1H)-carboxylate (22 mg, 0.10 mmol) in DMF (1 mL), white solid (44 mg, 73%). $^1$H NMR (300 MHz, $CDCl_3$) δ 7.98 (dd, J=8.6, 1.6 Hz, 2H), 7.93-7.84 (m, 2H), 3.96-3.56 (m, 6H), 3.53-3.36 (m, 2H), 3.30 (q, J=7.2 Hz, 6H), 3.06-2.95 (m, 1H), 2.96-2.84 (m, 1H), 2.69 (t, J=11.7 Hz, 1H), 2.54 (t, J=11.3 Hz, 1H), 2.28 (t, J=11.8 Hz, 1H), 1.88 (t, J=12.5 Hz, 2H), 1.82-1.62 (m, 2H), 1.49 (d, J=8.6 Hz, 9H), 1.18 (t, J=7.1 Hz, 6H). LC-MS (ESI) m/z 621.2 [M+Na]$^+$.

tert-Butyl (1R,4R)-5-((R)-1-((4-(N,N-diethylsulfamoyl)phenyl)sulfonyl)piperidine-3-carbonyl)-2,5-diazabicyclo[2.2.1]heptane-2-carboxylate (DX3-128B)

Using a similar procedure as described for DX2-237 with DX2-235 (20 mg, 0.05 mmol) and tert-butyl (1R,4R)-2,5-diazabicyclo[2.2.1]heptane-2-carboxylate (10 mg, 0.05 mmol) in DMF (1 mL), white solid (24 mg, 83%). $^1$H NMR (300 MHz, $CDCl_3$) δ 7.97 (dd, J=8.5, 1.8 Hz, 2H), 7.88 (dd, J=8.5, 2.7 Hz, 2H), 4.91-4.43 (m, 2H), 3.96-3.78 (m, 2H), 3.66-3.34 (m, 4H), 3.29 (qd, J=7.2, 1.7 Hz, 4H), 2.76-2.44 (m, 2H), 2.36-2.19 (m, 1H), 2.08-1.64 (m, 5H), 1.51 (s, 9H), 1.17 (t, J=7.3 Hz, 6H). LC-MS (ESI) m/z 585.2 $[M+H]^+$.

tert-butyl (R)-4-((R)-1-((4-(N,N-diethylsulfamoyl)phenyl)sulfonyl)piperidine-3-carbonyl)-3-methylpiperazine-1-carboxylate (DX3-139B)

Using a similar procedure as described for DX2-237 with DX2-235 (20 mg, 0.05 mmol) and tert-butyl (R)-3-methylpiperazine-1-carboxylate (10 mg, 0.05 mmol) in DMF (1 mL), white solid (29 mg, 99%). $^1$H NMR (300 MHz, $CDCl_3$) δ 7.98 (d, J=8.2 Hz, 2H), 7.89 (d, J=8.3 Hz, 2H), 4.80-4.66 (m, 0.5H), 4.34 (d, J=12.6 Hz, 0.5H), 4.24-3.80 (m, 5H), 3.63 (d, J=12.8 Hz, 1H), 3.30 (q, J=7.2 Hz, 4H), 3.07-2.73 (m, 4H), 2.68-2.55 (m, 1H), 2.28 (t, J=11.7 Hz, 1H), 1.93-1.81 (m, 2H), 1.79-1.69 (m, 1H), 1.49 (s, 9H), 1.33 (d, J=6.6 Hz, 1.5H), 1.18 (t, J=7.1 Hz, 6H), 1.13 (d, J=7.0 Hz, 1.5H). LC-MS (ESI) m/z 587.2 $[M+H]^+$.

tert-butyl (S)-4-((R)-1-((4-(N,N-diethylsulfamoyl)phenyl)sulfonyl)piperidine-3-carbonyl)-3-methylpiperazine-1-carboxylate (DX3-141)

Using a similar procedure as described for DX2-237 with DX2-235 (20 mg, 0.05 mmol) and tert-butyl (S)-3-methylpiperazine-1-carboxylate (10 mg, 0.05 mmol) in DMF (1 mL), white solid (26 mg, 89%). $^1$H NMR (300 MHz, $CDCl_3$) δ 7.98 (d, J=8.3 Hz, 2H), 7.89 (d, J=8.2 Hz, 2H), 4.81-4.67 (m, 0.5H), 4.41-4.30 (m, 0.5H), 4.25-3.78 (m, 5H), 3.59 (d, J=11.8 Hz, 0.5H), 3.43 (dd, J=10.6, 3.9 Hz, 0.5H), 3.30 (q, J=7.1 Hz, 4H), 3.16-2.73 (m, 4H), 2.57 (t, J=11.3 Hz, 1H), 2.28 (t, J=11.6 Hz, 1H), 1.86 (d, J=12.6 Hz, 2H), 1.76-1.69 (m, 1H), 1.50 (s, 9H), 1.30 (d, J=7.1 Hz, 1.5H), 1.18 (t, J=7.2 Hz, 7.5H). LC-MS (ESI) m/z 587.2 $[M+H]^+$.

tert-Butyl (R)-4-((R)-1-((4-(N,N-diethylsulfamoyl)phenyl)sulfonyl)piperidine-3-carbonyl)-2-methylpiperazine-1-carboxylate (DX3-141B)

Using a similar procedure as described for DX2-237 with DX2-235 (20 mg, 0.05 mmol) and tert-butyl (R)-2-methylpiperazine-1-carboxylate (10 mg, 0.05 mmol) in DMF (1 mL), white solid (26 mg, 89%). $^1$H NMR (300 MHz, $CDCl_3$) δ 7.98 (d, J=8.0 Hz, 2H), 7.89 (t, J=7.5 Hz, 2H), 4.49-4.23 (m, 2H), 4.04-3.76 (m, 4H), 3.66 (d, J=13.3 Hz, 0.5H), 3.41 (d, J=14.4 Hz, 0.5H), 3.30 (q, J=7.1 Hz, 4H), 3.20-3.10 (m, 1H), 3.09-2.68 (m, 3H), 2.69-2.44 (m, 1H), 2.29 (t, J=11.9 Hz, 1H), 1.95-1.81 (m, 2H), 1.79-1.67 (m, 1H), 1.50 (s, 9H), 1.25-1.08 (m, 9H). LC-MS (ESI) m/z 587.2 $[M+H]^+$.

tert-Butyl (S)-4-((R)-1-((4-(N,N-diethylsulfamoyl)phenyl)sulfonyl)piperidine-3-carbonyl)-2-methylpiperazine-1-carboxylate (DX3-142)

Using a similar procedure as described for DX2-237 with DX2-235 (20 mg, 0.05 mmol) and tert-butyl (S)-2-methylpiperazine-1-carboxylate (10 mg, 0.05 mmol) in DMF (1 mL), white solid (27 mg, 92%). $^1$H NMR (300 MHz, $CDCl_3$) δ 7.98 (d, J=8.2 Hz, 2H), 7.88 (d, J=8.2 Hz, 2H), 4.51-4.24 (m, 2H), 4.04-3.76 (m, 4H), 3.64 (d, J=13.1 Hz, 0.5H), 3.43-3.32 (m, 0.5H), 3.30 (q, J=7.2 Hz, 4H), 3.27-3.17 (m, 0.5H), 3.15-2.96 (m, 1.5H), 2.94-2.53 (m, 4H), 2.28 (t, J=11.8 Hz, 1H), 1.96-1.79 (m, 2H), 1.77-1.67 (m, 1H), 1.49 (s, 9H), 1.24 (d, J=6.8 Hz, 1.5H), 1.18 (t, J=7.1 Hz, 6H), 1.06 (d, J=6.7 Hz, 1.5H). LC-MS (ESI) m/z 587.2 $[M+H]^+$.

tert-Butyl 8-((R)-1-((4-(N,N-diethylsulfamoyl)phenyl)sulfonyl)piperidine-3-carbonyl)-3,8-diazabicyclo[3.2.1]octane-3-carboxylate (DX3-142B)

Using a similar procedure as described for DX2-237 with DX2-235 (20 mg, 0.05 mmol) and tert-butyl (1R,5S)-3,8-diazabicyclo[3.2.1]octane-3-carboxylate (11 mg, 0.05 mmol) in DMF (1 mL), white solid (29 mg, 97%). $^1$H NMR (300 MHz, $CDCl_3$) δ 7.98 (dd, J=8.5, 2.0 Hz, 2H), 7.89 (dd, J=8.3, 5.2 Hz, 2H), 4.75-4.59 (m, 1H), 4.32-4.13 (m, 1H), 4.10-3.73 (m, 4H), 3.30 (q, J=7.1 Hz, 4H), 3.14-2.88 (m, 2H), 2.81-2.68 (m, 1H), 2.68-2.48 (m, 1H), 2.36-2.21 (m, 1H), 2.07-1.70 (m, 8H), 1.48 (d, J=4.4 Hz, 9H), 1.18 (t, J=7.1 Hz, 6H). LC-MS (ESI) m/z 599.2 $[M+H]^+$.

(R)-4-((3-(6-Oxa-2-azaspiro[3.4]octane-2-carbonyl)piperidin-1-yl)sulfonyl)-N,N-diethylbenzenesulfonamide (DX3-149)

Using a similar procedure as described for DX2-237 with DX2-235 (15 mg, 0.037 mmol) and 6-oxa-2-azaspiro[3.4]octane hemioxalate (5.9 mg, 0.037 mmol) in DMF (1 mL), white solid (18 mg, 97%). $^1$H NMR (300 MHz, $CDCl_3$) δ 7.98 (d, J=8.5 Hz, 2H), 7.88 (d, J=8.4 Hz, 2H), 4.28-4.09 (m, 2H), 4.02-3.80 (m, 8H), 3.30 (q, J=7.1 Hz, 4H), 2.59-2.44 (m, 2H), 2.34-2.12 (m, 3H), 1.85 (d, J=12.8 Hz, 2H), 1.78-1.68 (m, 1H), 1.54-1.41 (m, 1H), 1.18 (t, J=7.1 Hz, 6H). LC-MS (ESI) m/z 500.1 $[M+H]^+$.

(R)-4-((3-(2-Oxa-6-azaspiro[3.3]heptane-6-carbonyl)piperidin-1-yl)sulfonyl)-N,N-diethylbenzenesulfonamide (DX3-149B)

Using a similar procedure as described for DX2-237 with DX2-235 (15 mg, 0.037 mmol) and 2-oxa-6-azaspiro[3.3]heptane hemioxalate (5.3 mg, 0.037 mmol) in DMF (1 mL), white solid (11 mg, 61%). $^1$H NMR (300 MHz, $CDCl_3$) δ 7.97 (d, J=8.4 Hz, 2H), 7.87 (d, J=8.5 Hz, 2H), 4.90-4.77 (m, 4H), 4.48-4.30 (m, 2H), 4.15 (s, 2H), 3.91-3.75 (m, 2H), 3.30 (q, J=7.2 Hz, 4H), 2.55-2.42 (m, 2H), 2.32-2.20 (m, 1H), 1.91-1.70 (m, 3H), 1.50-1.39 (m, 1H), 1.18 (t, J=7.1 Hz, 6H). LC-MS (ESI) m/z 486.1 $[M+H]^+$.

(R)-4-((3-(4,4-Difluoropiperidine-1-carbonyl)piperidin-1-yl)sulfonyl)-N,N-diethylbenzenesulfonamide (DX3-184B)

Using a similar procedure as described for DX2-237 with DX2-235 (15 mg, 0.037 mmol) and 4,4-difluoropiperidine (4.5 mg, 0.037 mmol) in DMF (1 mL), white solid (11 mg, 59%). $^1$H NMR (300 MHz, $CDCl_3$) δ 7.99 (d, J=8.2 Hz, 2H), 7.89 (d, J=8.2 Hz, 2H), 3.89 (d, J=11.7 Hz, 2H), 3.79-3.58 (m, 4H), 3.30 (q, J=7.1 Hz, 4H), 2.88 (t, J=12.3 Hz, 1H), 2.58 (t, J=11.4 Hz, 1H), 2.30 (t, J=11.7 Hz, 1H), 2.14-1.94 (m, 4H), 1.93-1.82 (m, 2H), 1.80-1.67 (m, 1H), 1.56-1.42 (m, 1H), 1.18 (t, J=7.1 Hz, 6H). LC-MS (ESI) m/z 508.2 $[M+H]^+$.

(R)-4-((3-(1,1-Dioxidothiomorpholine-4-carbonyl)piperidin-1-yl)sulfonyl)-N,N-diethylbenzenesulfonamide (DX3-185)

Using a similar procedure as described for DX2-237 with DX2-235 (15 mg, 0.037 mmol) and thiomorpholine 1,1-dioxide (5.0 mg, 0.037 mmol) in DMF (1 mL), white solid (14 mg, 73%). $^1$H NMR (300 MHz, $CDCl_3$) δ 7.99 (d, J=8.2 Hz, 2H), 7.89 (d, J=8.2 Hz, 2H), 4.26-3.98 (m, 4H), 3.88 (d, J=11.8 Hz, 2H), 3.31 (q, J=7.1 Hz, 4H), 3.18-3.01 (m, 4H), 2.89 (t, J=11.5 Hz, 1H), 2.59 (t, J=11.4 Hz, 1H), 2.33 (t, J=11.8 Hz, 1H), 1.89 (d, J=12.6 Hz, 2H), 1.81-1.68 (m, 1H), 1.51 (dd, J=14.3, 5.2 Hz, 1H), 1.18 (t, J=7.1 Hz, 6H). LC-MS (ESI) m/z 544.1 $[M+Na]^+$.

(R)—N,N-Diethyl-4-((3-(4-methoxypiperidine-1-carbonyl)piperidin-1-yl)sulfonyl)benzenesulfonamide (DX3-185B)

Using a similar procedure as described for DX2-237 with DX2-235 (15 mg, 0.037 mmol) and 4-methoxypiperidine (4.3 mg, 0.037 mmol) in DMF (1 mL), white solid (13 mg, 70%). $^1$H NMR (300 MHz, $CDCl_3$) δ 7.98 (d, J=8.2 Hz, 2H), 7.89 (d, J=8.2 Hz, 2H), 3.95-3.77 (m, 3H), 3.77-3.65 (m, 1H), 3.52-3.43 (m, 1H), 3.42-3.25 (m, 9H), 2.87 (t, J=11.4 Hz, 1H), 2.57 (dt, J=15.4, 7.7 Hz, 1H), 2.28 (t, J=11.8 Hz, 1H), 1.96-1.79 (m, 4H), 1.76-1.60 (m, 3H), 1.52-1.39 (m, 1H), 1.18 (t, J=7.1 Hz, 6H). LC-MS (ESI) m/z 502.3 $[M+H]^+$.

(R)—N,N-Diethyl-4-((3-(4-hydroxypiperidine-1-carbonyl)piperidin-1-yl)sulfonyl)benzenesulfonamide (DX3-186)

Using a similar procedure as described for DX2-237 with DX2-235 (15 mg, 0.037 mmol) and 4-hydroxypiperidine (3.7 mg, 0.037 mmol) in DMF (1 mL), white solid (15 mg, 83%). $^1$H NMR (300 MHz, $CDCl_3$) δ 7.98 (d, J=8.2 Hz, 2H), 7.89 (d, J=8.2 Hz, 2H), 4.09-3.95 (m, 2H), 3.93-3.73 (m, 3H), 3.29 (p, J=7.2 Hz, 6H), 2.95-2.81 (m, 1H), 2.57 (t, J=11.3 Hz, 1H), 2.29 (t, J=11.8 Hz, 1H), 2.05-1.66 (m, 5H), 1.64-1.38 (m, 3H), 1.18 (t, J=7.1 Hz, 6H).

(R)—N,N-Diethyl-4-((3-(4-(methoxymethyl)piperidine-1-carbonyl)piperidin-1-yl)sulfonyl)benzenesulfonamide (DX3-186B)

Using a similar procedure as described for DX2-237 with DX2-235 (15 mg, 0.037 mmol) and 4-(methoxymethyl)piperidine (4.8 mg, 0.037 mmol) in DMF (1 mL), white solid (16 mg, 84%). $^1$H NMR (300 MHz, $CDCl_3$) δ 7.97 (d, J=8.0 Hz, 2H), 7.89 (d, J=8.2 Hz, 2H), 4.59 (d, J=13.2 Hz, 1H), 3.97-3.81 (m, 3H), 3.41-3.19 (m, 10H), 3.07 (q, J=13.2 Hz, 1H), 2.93-2.77 (m, 1H), 2.66-2.48 (m, 2H), 2.34-2.21 (m, 1H), 1.94-1.68 (m, 7H), 1.52-1.36 (m, 1H), 1.18 (t, J=7.1 Hz, 6H). LC-MS (ESI) m/z 516.3 $[M+H]^+$.

N,N-Diethyl-4-(((R)-3-((R)-3-methoxypyrrolidine-1-carbonyl)piperidin-1-yl)sulfonyl)benzenesulfonamide (DX3-187B)

Using a similar procedure as described for DX2-237 with DX2-235 (15 mg, 0.037 mmol) and (R)-3-methoxypyrrolidine hydrochloride (5.1 mg, 0.037 mmol) in DMF (1 mL), white solid (14 mg, 78%). $^1$H NMR (300 MHz, $CDCl_3$) δ 7.97 (d, J=8.2 Hz, 2H), 7.88 (d, J=8.3 Hz, 2H), 4.10-3.82 (m, 3H), 3.71-3.41 (m, 4H), 3.39-3.22 (m, 7H), 2.80-2.64 (m, 1H), 2.53 (t, J=11.3 Hz, 1H), 2.34-2.00 (m, 1H), 1.98-1.80 (m, 2H), 1.77-1.66 (m, 1H), 1.56-1.42 (m, 1H), 1.18 (t, J=7.1 Hz, 6H). LC-MS (ESI) m/z 488.2 $[M+H]^+$.

N,N-Diethyl-4-(((R)-3-((S)-3-methoxypyrrolidine-1-carbonyl)piperidin-1-yl)sulfonyl)benzenesulfonamide (DX3-188)

Using a similar procedure as described for DX2-237 with DX2-235 (15 mg, 0.037 mmol) and (S)-3-methoxypyrrolidine hydrochloride (5.1 mg, 0.037 mmol) in DMF (1 mL), white solid (14 mg, 78%). $^1$H NMR (300 MHz, $CDCl_3$) δ 7.97 (d, J=8.2 Hz, 2H), 7.88 (d, J=8.3 Hz, 2H), 4.11-3.81 (m, 3H), 3.74-3.39 (m, 4H), 3.38-3.22 (m, 7H), 2.78-2.62 (m, 1H), 2.53 (td, J=11.3, 4.4 Hz, 1H), 2.35-2.13 (m, 1H), 2.08-1.78 (m, 4H), 1.74-1.57 (m, 1H), 1.56-1.39 (m, 1H), 1.17 (t, J=7.1 Hz, 6H). LC-MS (ESI) m/z 488.2 $[M+H]^+$.

(R)—N,N-Diethyl-4-((3-(4-(3-isopropyl-1,2,4-oxadiazol-5-yl)piperidine-1-carbonyl)piperidin-1-yl)sulfonyl)benzenesulfonamide (DX3-193)

Using a similar procedure as described for DX2-237 with DX2-235 (15 mg, 0.037 mmol) and 3-isopropyl-5-(piperidin-4-yl)-1,2,4-oxadiazole (7.2 mg, 0.037 mmol) in DMF (1 mL), white solid (12 mg, 55%). $^1$H NMR (300 MHz, $CDCl_3$) δ 7.98 (d, J=8.2 Hz, 2H), 7.89 (d, J=8.2 Hz, 2H), 4.51-4.38 (m, 1H), 4.01-3.84 (m, 3H), 3.40-3.17 (m, 6H), 3.17-3.04 (m, 1H), 3.02-2.81 (m, 2H), 2.58 (t, J=11.4 Hz, 1H), 2.35-2.05 (m, 4H), 1.97-1.74 (m, 5H), 1.36 (t, J=6.1 Hz, 6H), 1.18 (t, J=7.1 Hz, 6H). LC-MS (ESI) m/z 582.4 $[M+H]^+$.

(R)-1-((4-(N,N-Diethylsulfamoyl)phenyl)sulfonyl)-N-(cis-4-methoxycyclohexyl)piperidine-3-carboxamide (DX3-193B)

Using a similar procedure as described for DX2-237 with DX2-235 (15 mg, 0.037 mmol) and cis-4-methoxycyclohexan-1-amine (6.1 mg, 0.037 mmol) in DMF (1 mL), white solid (12 mg, 63%). $^1$H NMR (300 MHz, $CDCl_3$) δ 7.98 (d, J=8.2 Hz, 2H), 7.89 (d, J=8.2 Hz, 2H), 5.60 (d, J=8.0 Hz, 1H), 3.89-3.69 (m, 2H), 3.63 (d, J=11.5 Hz, 1H), 3.44-3.34 (m, 1H), 3.35-3.25 (m, 7H), 2.68 (t, J=10.8 Hz, 1H), 2.55-2.34 (m, 2H), 1.95-1.77 (m, 4H), 1.77-1.61 (m, 4H), 1.59-1.48 (m, 4H), 1.18 (t, J=7.1 Hz, 6H). LC-MS (ESI) m/z 538.2 $[M+Na]^+$.

(R)-1-((4-(N,N-Diethylsulfamoyl)phenyl)sulfonyl)-N-(trans-4-methoxycyclohexyl)piperidine-3-carboxamide (DX3-194)

Using a similar procedure as described for DX2-237 with DX2-235 (15 mg, 0.037 mmol) and trans-4-methoxycyclohexan-1-amine (6.1 mg, 0.037 mmol) in DMF (1 mL), white solid (10 mg, 53%). $^1$H NMR (300 MHz, $CDCl_3$) δ 7.99 (d, J=8.2 Hz, 2H), 7.88 (d, J=8.2 Hz, 2H), 5.62 (d, J=7.8 Hz, 1H), 3.84-3.70 (m, 1H), 3.67-3.47 (m, 2H), 3.40-3.26 (m, 7H), 3.23-3.11 (m, 1H), 2.79 (t, J=10.6 Hz, 1H), 2.66-2.55 (m, 1H), 2.47-2.33 (m, 1H), 2.13-1.96 (m, 4H), 1.85-1.63 (m, 4H), 1.44-1.23 (m, 4H), 1.18 (t, J=7.1 Hz, 6H). LC-MS (ESI) m/z 516.3 $[M+H]^+$.

(R)-4-((3-(4-(Difluoromethyl)piperidine-1-carbonyl)piperidin-1-yl)sulfonyl)-N,N-diethylbenzenesulfonamide (DX3-198)

Using a similar procedure as described for DX2-237 with DX2-235 (15 mg, 0.037 mmol) and 4-(difluoromethyl)piperidine (6.4 mg, 0.037 mmol) in DMF (1 mL), white solid (22 mg, 63%). $^1$H NMR (300 MHz, $CDCl_3$) δ 7.98 (d, J=8.2 Hz, 2H), 7.89 (d, J=8.2 Hz, 2H), 5.64 (t, J=56.5 Hz, 2H), 4.69 (d, J=13.4 Hz, 1H), 3.99 (d, J=13.7 Hz, 1H), 3.88 (d, J=11.6 Hz, 2H), 3.30 (q, J=7.1 Hz, 4H), 3.10 (q, J=13.5 Hz, 1H), 2.85 (d, J=12.0 Hz, 1H), 2.58 (q, J=12.2 Hz, 2H), 2.29

(t, J=11.7 Hz, 1H), 2.12-1.70 (m, 7H), 1.54-1.31 (m, 4H), 1.18 (t, J=7.1 Hz, 6H). LC-MS (ESI) m/z 522.2 $[M+H]^+$.

(R)—N,N-Diethyl-4-((3-(4-(trifluoromethyl)piperidine-1-carbonyl)piperidin-1-yl)sulfonyl)benzenesulfonamide (DX3-198B)

Using a similar procedure as described for DX2-237 with DX2-235 (15 mg, 0.037 mmol) and 4-(trifluoromethyl) piperidine (5.7 mg, 0.037 mmol) in DMF (1 mL), white solid (10 mg, 50%). $^1$H NMR (300 MHz, $CDCl_3$) δ 7.98 (d, J=8.2 Hz, 2H), 7.89 (d, J=8.2 Hz, 2H), 4.71 (d, J=13.6 Hz, 1H), 4.02 (d, J=13.7 Hz, 1H), 3.88 (d, J=11.6 Hz, 2H), 3.30 (q, J=7.1 Hz, 2H), 3.17-3.00 (m, 1H), 2.86 (t, J=11.8 Hz, 1H), 2.56 (t, J=12.3 Hz, 2H), 2.29 (t, J=11.6 Hz, 2H), 2.09-1.83 (m, 4H), 1.74 (d, J=12.6 Hz, 1H), 1.53-1.41 (m, 2H), 1.18 (t, J=7.1 Hz, 6H). LC-MS (ESI) m/z 540.2 $[M+H]^+$.

1-Methylpiperidin-4-yl (R)-1-((4-(N,N-diethylsulfamoyl)phenyl)sulfonyl)piperidine-3-carboxylate (DX2-260)

To a solution of DX2-235 (40 mg, 0.10 mmol) and EDCI (22 mg, 0.12 mmol) in DCM (2 mL) was added 1-methylpiperidin-4-ol (14 mg, 0.12 mmol) followed by DMAP (6 mg, 0.05 mmol).

The mixture was stirred at room temperature overnight. The mixture was then diluted with EtOAc, washed with brine, dried over anhydrous $Na_2SO_4$, filtered and concentrated. The residue was purified with flash chromatography (30% EtOAc in hexane) to give DX2-260 as a white solid (43 mg, 71%). $^1$H NMR (300 MHz, $CDCl_3$) δ 8.03 (d, J=8.4 Hz, 2H), 7.88 (d, J=8.5 Hz, 2H), 4.16-4.00 (m, 1H), 3.60-3.39 (m, 4H), 3.32 (q, J=7.1 Hz, 5H), 2.88 (d, J=3.3 Hz, 3H), 2.80-2.76 (m, 1H), 2.68-2.61 (m, 2H), 2.45-2.35 (m, 2H), 2.27 (d, J=9.1 Hz, 2H), 2.08-1.95 (m, 1H), 1.54-1.38 (m, 2H), 1.18 (t, J=7.1 Hz, 6H). LC-MS (ESI) m/z 502.2 $[M+H]^+$.

Isopropyl (R)-1-((4-(N,N-diethylsulfamoyl)phenyl)sulfonyl)piperidine-3-carboxylate (DX2-261)

Using a similar procedure as described for DX2-260 with DX2-235 (35 mg, 0.09 mmol) and propan-2-ol (6.2 mg, 0.10 mmol), white solid (30 mg, 75%). $^1$H NMR (300 MHz, $CDCl_3$) δ 7.99 (d, J=8.5 Hz, 2H), 7.90 (d, J=8.4 Hz, 2H), 5.02 (dt, J=12.5, 6.3 Hz, 1H), 3.83 (d, J=8.4 Hz, 1H), 3.68-3.57 (m, 1H), 3.31 (q, J=7.1 Hz, 4H), 2.67-2.53 (m, 2H), 2.50-2.39 (m, 1H), 2.01 (dd, J=17.0, 4.3 Hz, 1H), 1.90-1.78 (m, 1H), 1.73-1.62 (m, 1H), 1.51-1.37 (m, 1H), 1.25 (t, J=5.9 Hz, 6H), 1.17 (t, J=7.1 Hz, 6H). LC-MS (ESI) m/z 447.0 $[M+H]^+$.

Oxetan-3-yl (R)-1-((4-(N,N-diethylsulfamoyl)phenyl)sulfonyl)piperidine-3-carboxylate (DX2-262)

Using a similar procedure as described for DX2-260 with DX2-235 (35 mg, 0.09 mmol) and oxetan-3-ol (7.4 mg, 0.10 mmol), white solid (32 mg, 78%). $^1$H NMR (300 MHz, $CDCl_3$) δ 8.00 (d, J=8.3 Hz, 2H), 7.91 (d, J=8.4 Hz, 2H), 5.45 (q, J=5.8 Hz, 1H), 4.91 (t, J=7.0 Hz, 2H), 4.72-4.56 (m, 2H), 3.87-3.75 (m, 1H), 3.65-3.51 (m, 1H), 3.31 (q, J=7.1 Hz, 4H), 2.78-2.66 (m, 2H), 2.58-2.46 (m, 1H), 2.10-1.96 (m, 1H), 1.93-1.81 (m, 1H), 1.78-1.62 (m, 1H), 1.58-1.44 (m, 1H), 1.17 (t, J=7.2 Hz, 6H). LC-MS (ESI) m/z 461.0 $[M+H]^+$.

Cyclopropyl (R)-1-((4-(N,N-diethylsulfamoyl)phenyl)sulfonyl)piperidine-3-carboxylate (DX2-263)

Using a similar procedure as described for DX2-260 with DX2-235 (35 mg, 0.09 mmol) and cyclopropanol (5.8 mg, 0.10 mmol), white solid (36 mg, 90%). $^1$H NMR (300 MHz, $CDCl_3$) δ 7.99 (d, J=8.6 Hz, 2H), 7.90 (d, J=8.7 Hz, 2H), 4.15 (tt, J=6.6, 3.3 Hz, 1H), 3.80 (d, J=8.5 Hz, 1H), 3.60 (d, J=11.7 Hz, 1H), 3.30 (q, J=7.1 Hz, 4H), 2.69-2.55 (m, 2H), 2.47 (td, J=11.1, 3.2 Hz, 1H), 1.97 (d, J=13.2 Hz, 1H), 1.83 (dt, J=13.7, 3.8 Hz, 1H), 1.73-1.63 (m, 1H), 1.44 (q, J=14.4, 12.2 Hz, 1H), 1.17 (t, J=7.1 Hz, 6H), 0.81-0.67 (m, 4H). LC-MS (ESI) m/z 445.1 $[M+H]^+$.

tert-Butyl (R)-1-((4-(N,N-diethylsulfamoyl)phenyl)sulfonyl)piperidine-3-carboxylate (DX2-266)

Using a similar procedure as described for DX2-260 with DX2-235 (35 mg, 0.09 mmol) and tert-butanol (7.4 mg, 0.10 mmol), white solid (19 mg, 46%). $^1$H NMR (300 MHz, $CDCl_3$) δ 8.03-7.96 (m, 2H), 7.94-7.87 (m, 2H), 3.78 (d, J=10.9 Hz, 1H), 3.59 (d, J=11.7 Hz, 1H), 3.30 (q, J=7.1 Hz, 4H), 2.67-2.39 (m, 3H), 2.04-1.92 (m, 1H), 1.80 (s, 1H), 1.72-1.58 (m, 1H), 1.46 (s, 9H), 1.44-1.32 (m, 1H), 1.17 (t, J=7.1 Hz, 6H). LC-MS (ESI) m/z 461.1 $[M+H]^+$.

Cyclobutyl (R)-1-((4-(N,N-diethylsulfamoyl)phenyl)sulfonyl)piperidine-3-carboxylate (DX2-282)

Using a similar procedure as described for DX2-260 with DX2-235 (35 mg, 0.09 mmol) and cyclobutanol (7.2 mg, 0.10 mmol), white solid (30 mg, 73%). $^1$H NMR (400 MHz, $CDCl_3$) δ 8.02-7.96 (m, 2H), 7.94-7.88 (m, 2H), 5.06-4.93 (m, 1H), 3.91-3.80 (m, 1H), 3.68-3.59 (m, 1H), 3.31 (q, J=7.2 Hz, 4H), 2.67-2.55 (m, 2H), 2.45 (td, J=11.3, 3.1 Hz, 1H), 2.41-2.31 (m, 2H), 2.14-1.98 (m, 3H), 1.91-1.77 (m, 2H), 1.74-1.61 (m, 2H), 1.50-1.39 (m, 1H), 1.18 (t, J=7.1 Hz, 6H). LC-MS (ESI) m/z 459.1 $[M+H]^+$.

Scheme 8

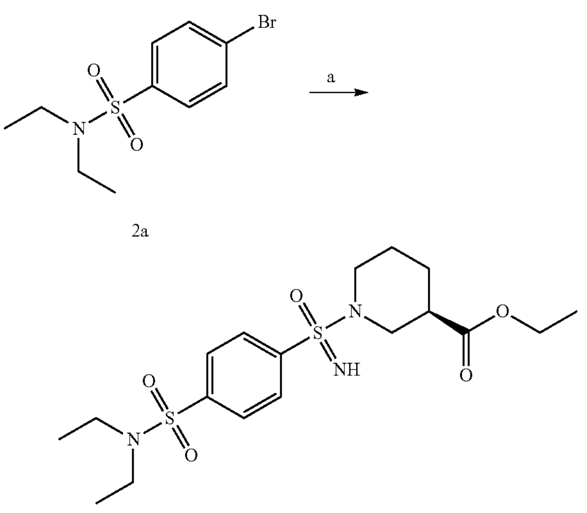

2a

DX2-225

Reagents and conditions: a) i. $^n$BuLi, -78° C., THF; ii. N-Sulfinyltriphenylmethylamine, -78° C.-rt, iii. $^t$BuOCl, 0° C.; iv. ethyl (R)-piperidine-3-carboxylate, $Et_3N$, rt; v. MsOH.

Ethyl (3R)-1-(4-(N,N-diethylsulfamoyl)phenylsulfonimidoyl)piperidine-3-carboxylate (DX2-225)

To a solution of 2a (100 mg, 0.34 mmol) in THF (4 mL) was added $^{n}$BuLi (0.14 mL, 0.34 mmol, 2.5 M in hexane) dropwise and the mixture was stirred at the same temperature for 1 h. N-Sulfinyltriphenylmethylamine (104 mg, 0.34 mmol) was then added as a THF solution dropwise and the mixture was stirred at the same temperature for 25 min before warmed to 0° C. in an ice bath. After stirred for 5 min, BuOCl (39 mg, 0.36 mmol) was added in a darkened hood with aluminum foil covering the flask and stirred for 25 min. Then ethyl (R)-piperidine-3-carboxylate (80 mg, 0.51 mmol) and $Et_3N$ (34 mg, 0.34 mmol) was added, and the mixture was stirred at room temperature overnight and quenched with MsOH (326 mg, 3.40 mmol), diluted with DCM, washed with sat. aq. $NaHCO_3$, brine, dried over anhydrous $Na_2SO_4$, filtered and concentrated. The residue was purified with preparative HPLC to give DX2-225 as a white solid (57 mg, 39%). $^1$H NMR (300 MHz, $CDCl_3$) δ 8.20 (dd, J=6.0, 3.4 Hz, 1H), 8.05 (dd, J=5.9, 3.5 Hz, 1H), 7.68 (dd, J=5.9, 3.4 Hz, 2H), 4.13 (q, J=7.1 Hz, 2H), 3.95 (d, J=13.9 Hz, 1H), 3.83 (d, J=13.4 Hz, 1H), 3.53-3.34 (m, 4H), 2.98 (dd, J=13.0, 10.6 Hz, 1H), 2.91-2.80 (m, 1H), 2.72-2.61 (m, 1H), 2.22-2.03 (m, 1H), 1.85-1.47 (m, 3H), 1.25 (t, J=7.1 Hz, 3H), 1.18 (t, J=7.1 Hz, 6H). LC-MS (ESI) m/z 432.0 $[M+H]^+$.

Scheme 9

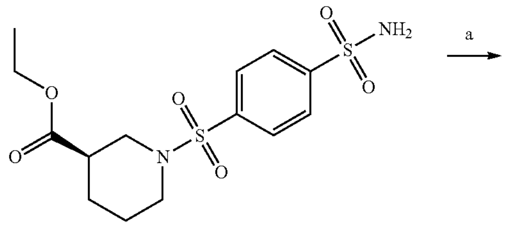

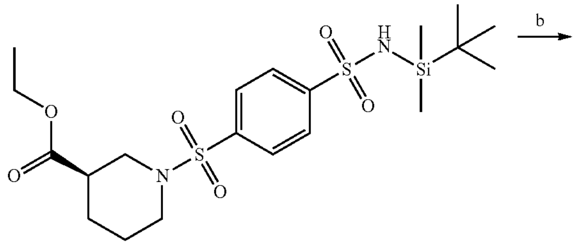

13

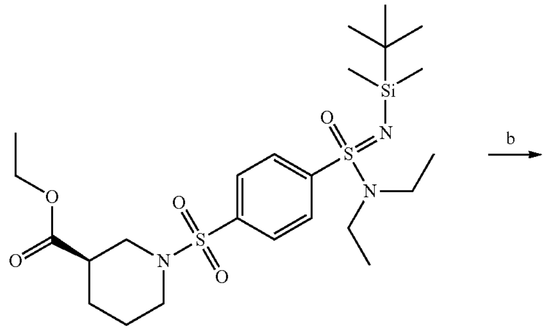

14

-continued

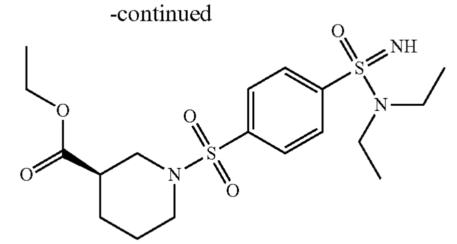

DX3-90

Reagents and conditions: a) TBSCl, NaH, THF, rt; b) i. $Ph_3PCl_2$, $Et_3N$, DCM, 0° C., argon; ii. diethylamine, rt; c) formic acid, $H_2O$, $CH_3CN$.

Ethyl (R)-1-((4-(N-(tert-butyldimethylsilyl)sulfamoyl)phenyl)sulfonyl)piperidine-3-carboxylate (13)

To a solution of DX2-300 (200 mg, 0.54 mmol) in THF was added NaH (32 mg, 0.82 mmol, 60% in mineral oil) at 0° C. portionwise. The resulting mixture was stirred at the same temperature for 15 min and tert-butyldimethylsilyl chloride (100 mg, 0.64 mmol) was added. The mixture was stirred at 0° C. for 5 min and allowed to warm to room temperature and stirred for 3 h. The mixture was quenched by ice-cooled water, extracted by EtOAc, washed by brine, dried over anhydrous $Na_2SO_4$, filtered and purified with flash chromatography (20% EtOAc in hexane) to give 13 as a white solid (165 mg, 62%). $^1$H NMR (300 MHz, $CDCl_3$) δ 8.09-8.01 (m, 2H), 7.90 (dd, J=8.5, 1.6 Hz, 2H), 4.53 (s, 1H), 4.16 (q, J=7.1 Hz, 2H), 3.86 (d, J=8.0 Hz, 1H), 3.64 (d, J=11.8 Hz, 1H), 2.60 (dd, J=12.8, 8.0 Hz, 2H), 2.43 (t, J=11.2 Hz, 1H), 2.03 (d, J=13.4 Hz, 1H), 1.84 (d, J=13.3 Hz, 1H), 1.77-1.60 (m, 1H), 1.53-1.36 (m, 1H), 1.34-1.23 (m, 3H), 0.93 (s, 9H), 0.25 (s, 6H). LC-MS (ESI) m/z 489.3 $[M-H]^-$.

Ethyl (3R)-1-((4-(N'-(tert-butyldimethylsilyl)-N,N-diethylsulfamidimidoyl)phenyl)sulfonyl)piperidine-3-carboxylate (14)

To a suspension of $Ph_3PCl_2$ (30 mg, 0.09 mmol) in $CHCl_3$ (0.3 mL) under argon was added $Et_3N$ (12.4 mg, 0.12 mmol). The mixture was stirred at room temperature for 10 min and light yellow suspension was formed. The mixture was then cooled to 0° C., and 13 (40 mg, 0.08 mmol) in $CHCl_3$ was added. It was stirred at the same temperature for 20 min before a solution of diethylamine (18 mg, 0.24 mmol) in $CHCl_3$ (0.8 mL) was added in one portion. The resulting mixture was stirred at 0° C. for 30 min then room temperature for 1 h. The mixture was concentrated and directly used in the next step without further purification. LC-MS (ESI) m/z 546.4 $[M+H]^+$.

Ethyl (3R)-1-((4-(N,N-diethylsulfamidimidoyl)phenyl)sulfonyl)piperidine-3-carboxylate (DX3-90)

14 (43 mg, 0.08 mmol) was dissolved in $CH_3CN$ (0.5 mL), and formic acid (37 mg 0.80 mmol) and $H_2O$ (0.03 mL) was added. The mixture was stirred at room temperature for 5 h. It was purified with preparative HPLC to give DX3-90 as a white solid (10 mg, 46%). $^1$H NMR (300 MHz, MeOD) (8.17 (d, J=8.6 Hz, 2H), 7.98 (d, J=8.6 Hz, 2H), 4.16 (q, J=7.1 Hz, 2H), 3.66 (dd, J=11.6, 3.9 Hz, 1H), 3.51-3.33 (m, 4H), 3.32-3.20 (m, 1H), 2.80 (t, J=10.5 Hz, 1H), 2.69-2.56 (m, 2H), 1.98-1.77 (m, 2H), 1.71-1.45 (m, 2H), 1.27 (t, J=7.1 Hz, 3H), 1.14 (t, J=7.1 Hz, 6H). LC-MS (ESI) m/z 432.1 $[M+H]^+$.

Scheme 10

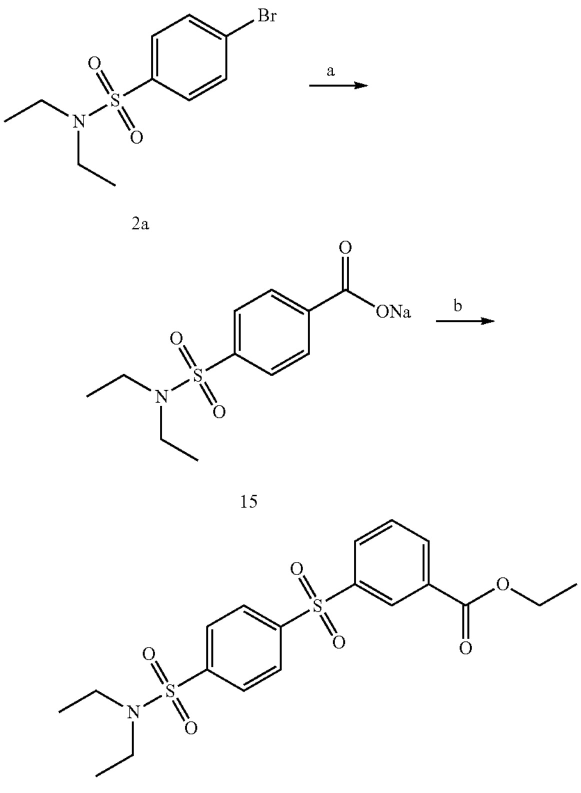

2a

15

DX3-3

Reagents and conditions: a) i. $^nBuLi$, THF, -78° C.; ii. DABSO, -78° C.-rt; b) (3-(ethoxycarbonyl)phenyl)boronic acid, $Cu(OAc)_2$, $Et_3N$, DMSO, rt.

Sodium 4-(N,N-diethylsulfamoyl)benzoate (15)

To a solution of 2a (100 mg, 0.34 mmol) in THF (2 mL) was added $^nBuLi$ (136 μL, 0.34 mmol) dropwise under argon at −78° C. The color turned yellow-brown. The mixture was stirred at the same temperature for 20 min and a suspension of DABSO (82 mg, 0.34 mmol) in THF (1 mL) was added dropwise. The mixture was stirred at the same temperature for another 15 min and stirred at room temperature for 3 h. The mixture was partitioned between $Et_3O$ and 10% $Na_2CO_3$, and the aqueous layer was acidified with 1N HCl and extracted with $Et_2O$. The organic layer was then extracted with 10% $Na_2CO_3$, and the aqueous layer was concentrated and boiled with EtOH (5 mL) for 1 h, filtered and concentrated to give 15 as a white solid (60 mg, 59%). $^1H$ NMR (300 MHz, MeOD) (7.87 (q, J=8.3 Hz, 4H), 3.25 (q, J=7.1 Hz, 4H), 1.13 (t, J=7.1 Hz, 6H). LC-MS (ESI) m/z 276.2 $[M-H]^-$.

Ethyl 3-((4-(N,N-diethylsulfamoyl)phenyl)sulfonyl) benzoate (DX3-3)

A solution of 15 (50 mg, 0.17 mmol), (3-(ethoxycarbonyl) phenyl)boronic acid (32 mg, 0.17 mmol), $Cu(OAc)_2$ (36 mg, 0.20 mmol) and $K_2CO_3$ (46 mg, 0.33 mmol) in DMSO (1.5 mL) was stirred at room temperature for 3 h. The mixture was then diluted with EtOAc, washed with water, brine, dried over anhydrous $Na_2SO_4$, filtered and concentrated. The residue was purified with flash chromatography (10% EtOAc in hexane) to give DX3-3 as a white solid (24 mg, 33%). $^1H$ NMR (400 MHz, $CDCl_3$) δ 8.62 (d, J=1.9 Hz, 1H), 8.30 (dq, J=7.5, 1.2 Hz, 1H), 8.15 (ddt, J=7.9, 2.0, 1.0 Hz, 1H), 8.12-8.06 (m, 2H), 7.99-7.92 (m, 2H), 7.66 (t, J=7.8 Hz, 1H), 4.44 (qd, J=7.1, 0.8 Hz, 2H), 3.31-3.22 (m, 4H), 1.43 (td, J=7.1, 0.8 Hz, 3H), 1.16 (td, J=7.2, 0.8 Hz, 6H). LC-MS (ESI) m/z 426.0 $[M+H]^+$.

Scheme 11

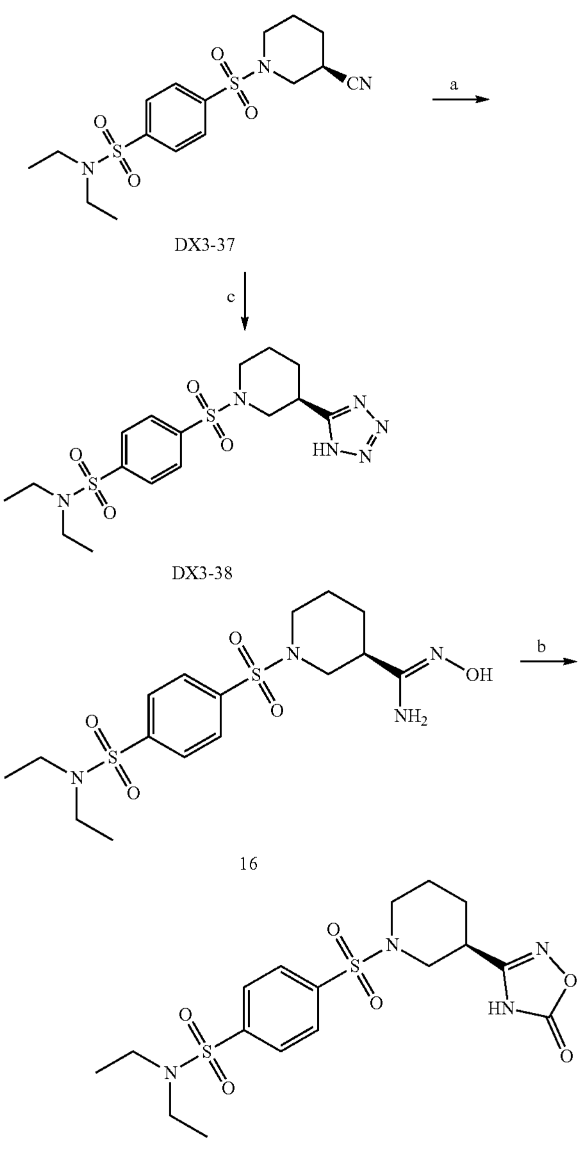

DX3-37

DX3-38

16

DX3-43

Reagents and conditions: a) $NH_2OH$, $H_2O$, EtOH, 75° C.; b) isobutyl chloroformate, pyridine, toluene, 0° C.-rt; c) $TMSN_3$, $AlMe_3$, toluene, 80° C.;

(R)-1-(4-(N,N-Diethylsulfamoyl)phenyl)-N'-hydroxypiperidine-3-carboximidamide (16)

To a solution of DX3-37 (100 mg, 0.26 mmol) in EtOH (0.5 mL) was added $NH_2OH$ aqueous solution (17 mg, 0.52 mmol) and heated under microwave irradiation at 75° C. for 5 h. The mixture was concentrated to give 16 as a white solid (54 mg, 50%) which was used directly in the next step. $^1$H NMR (400 MHz, $CDCl_3$) δ 8.00 (d, J=7.9 Hz, 2H), 7.95-7.87 (m, 2H), 3.70 (d, J=11.3 Hz, 1H), 3.57 (s, 1H), 3.32 (q, J=7.2 Hz, 4H), 2.79 (t, J=10.8 Hz, 1H), 2.66-2.51 (m, 2H), 2.00-1.62 (m, 4H), 1.19 (t, J=7.2 Hz, 6H).

(R)—N,N-Diethyl-4-((3-(5-oxo-4,5-dihydro-1,2,4-oxadiazol-3-yl)piperidin-1-yl)sulfonyl)benzenesulfonamide (DX3-43)

To a solution of 16 (54 mg, 0.13 mmol) and pyridine (12 mg, 0.15 mmol) in DMF (1 mL) was added isobutyl chloroformate (41 mg, 0.13 mmol) dropwise at 0° C. The mixture was stirred for 16 h while slowly warming to room temperature. The reaction was diluted with $H_2O$ and extracted with EtOAc. The combined organic extracts were washed with $H_2O$, brine, dried over $Na_2SO_4$, filtered, and concentrated. The residue was suspended in toluene (1.0 mL) in a microwave vial and stirred at 120° C. for 2 h, then at 140° C. for 5 h. After cooling to room temperature, the mixture was concentrated. Purification by flash chromatography (10% MeOH in DCM) gave DX3-43 as a white solid (19 mg, 38%). $^1$H NMR (300 MHz, $CDCl_3$) δ 8.01 (d, J=8.7 Hz, 2H), 7.91 (d, J=8.8 Hz, 2H), 3.82-3.70 (m, 1H), 3.52 (d, J=11.9 Hz, 1H), 3.31 (q, J=7.1 Hz, 4H), 3.04 (dt, J=9.3, 5.2 Hz, 1H), 2.87 (dd, J=11.8, 8.9 Hz, 1H), 2.76 (t, J=10.1 Hz, 1H), 2.09-1.87 (m, 2H), 1.85-1.63 (m, 2H), 1.18 (t, J=7.1 Hz, 6H). LC-MS (ESI) m/z 443.3 $[M-H]^-$.

(R)-4-(3-(1H-Tetrazol-5-yl)piperidin-1-yl)-N,N-diethylbenzenesulfonamide (DX3-38)

To a solution of DX3-37 (55 mg, 0.14 mmol) in toluene (4 mL) was added $TMSN_3$ (95 mg, 0.83 mmol) and $AlMe_3$ (0.42 mL, 0.83 mmol, 2 M in toluene). The mixture was heated at 80° C. overnight, diluted with EtOAc, washed with water, brine, dried over anhydrous $Na_2SO_4$, filtered, concentrated and purified with preparative HPLC to give DX3-38 as a white solid (6 mg, 10%). $^1$H NMR (400 MHz, $CDCl_3$) δ 8.02 (d, J=8.3 Hz, 2H), 7.93 (d, J=8.3 Hz, 2H), 3.57-3.39 (m, 3H), 3.33 (q, J=7.1 Hz, 4H), 3.28-3.19 (m, 2H), 2.12-2.02 (m, 2H), 1.83-1.72 (m, 2H), 1.20 (t, J=7.1 Hz, 6H). LC-MS (ESI) m/z 429.1 $[M+H]^+$.

Scheme 12

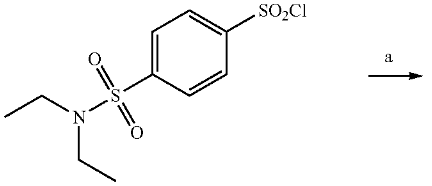

4a

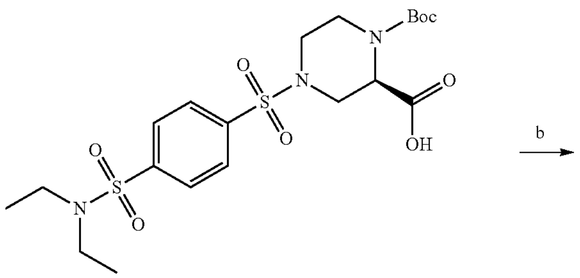

17

-continued

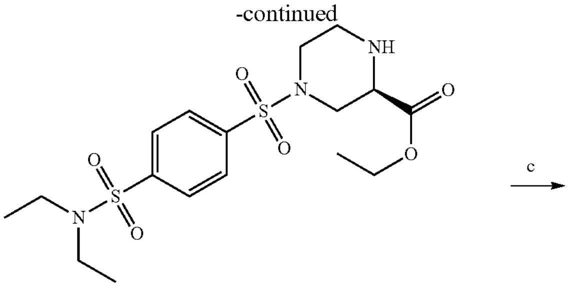

DX3-44B

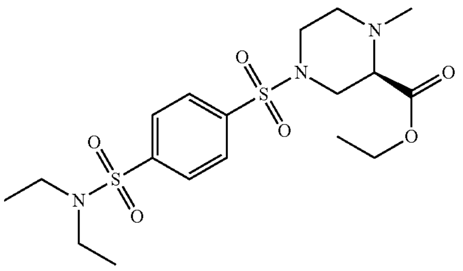

DX3-48B

Reagents and conditions: a)(R)-1-(tert-butoxycarbonyl)piperazine-2-carboxylic acid, $Na_2CO_3$, dioxane, $H_2O$; b) conc. $H_2SO_4$, EtOH, reflux; c) $CH_3I$, $K_2CO_3$, $CH_3CN$, microwave.

(R)-1-(tert-Butoxycarbonyl)-4-((4-(N,N-diethylsulfamoyl)phenyl)sulfonyl)piperazine-2-carboxylic Acid (17)

To a solution of 4a (120 mg, 0.39 mmol) in dioxane (4 mL) and $H_2O$ (2 mL) was added $Na_2CO_3$ (82 mg, 0.77 mmol). The mixture was stirred at room temperature overnight, diluted with EtOAc, washed with water, brine, dried over anhydrous $Na_2SO_4$, filtered, concentrated to give 17 as a white solid (176 mg, 90%). $^1$H NMR (400 MHz, MeOD) (8.07 (d, J=8.5 Hz, 2H), 7.99 (d, J=8.5 Hz, 2H), 4.73 (d, J=23.2 Hz, 1H), 4.37 (s, 1H), 4.30 (t, J=14.2 Hz, 1H), 3.93 (d, J=13.3 Hz, 1H), 3.74 (dd, J=21.8, 11.8 Hz, 1H), 3.32-3.27 (m, 4H), 3.24-3.14 (m, 1H), 2.64-2.56 (m, 1H), 2.37 (t, J=12.0 Hz, 1H), 1.44 (d, J=9.2 Hz, 9H), 1.16 (t, J=7.1 Hz, 6H). LC-MS (ESI) m/z 504.3 $[M-H]^-$.

Ethyl (R)-4-((4-(N,N-diethylsulfamoyl)phenyl)sulfonyl)piperazine-2-carboxylate (DX3-44B)

To a solution of 17 (44 mg, 0.087 mmol) in EtOH (2 mL) was added conc. $H_2SO_4$ (50 μL). The mixture was heated at reflux overnight, concentrated and partitioned between EtOAc and sat. $NaHCO_3$. The organic layer was washed with brine, dried over anhydrous $Na_2SO_4$, filtered, concentrated. The residue was purified with flash chromatography (5% MeOH in DCM) to give DX3-44B as a white solid (16 mg, 42%). $^1$H NMR (300 MHz, $CDCl_3$) δ 8.02-7.97 (m, 2H), 7.90 (d, J=8.8 Hz, 2H), 4.24 (q, J=7.2 Hz, 2H), 3.75-3.68 (m, 1H), 3.59 (dd, J=8.4, 3.4 Hz, 1H), 3.47-3.34 (m, 1H), 3.30 (q, J=7.2 Hz, 4H), 3.19-3.10 (m, 1H), 2.98-2.87 (m, 1H), 2.81 (dd, J=11.2, 8.4 Hz, 1H), 2.75-2.63 (m, 1H), 1.32 (t, J=7.1 Hz, 3H), 1.18 (t, J=7.2 Hz, 6H). LC-MS (ESI) m/z 475.1 $[M+CH_3CN+H]^+$.

Ethyl (R)-4-((4-(N,N-diethylsulfamoyl)phenyl)sulfonyl)-1-methylpiperazine-2-carboxylate (DX3-48B)

To a solution of DX3-44B (20 mg, 0.046 mmol) and $K_2CO_3$ (9.5 mg, 0.069 mmol) in $CH_3CN$ (1 mL) was added $CH_3I$ (13 mg, 0.092 mmol). The mixture was heated at 50° C. under microwave for 2 h. The mixture was diluted with EtOAc, washed with water, brine, dried over anhydrous $Na_2SO_4$, filtered, concentrated. The residue was purified with flash chromatography (50% EtOAc in hexane) to give DX3-48B as a white solid (mg, %). $^1H$ NMR (400 MHz, $CDCl_3$) δ 8.02 (d, J=8.6 Hz, 2H), 7.88 (d, J=8.6 Hz, 2H), 4.44-4.26 (m, 2H), 3.92 (s, 1H), 3.83 (s, 1H), 3.79-3.68 (m, 1H), 3.62-3.50 (m, 1H), 3.41 (d, J=12.4 Hz, 1H), 3.29 (q, J=7.1 Hz, 4H), 3.26-3.17 (m, 1H), 3.05 (d, J=12.1 Hz, 1H), 2.84 (s, 3H), 1.39 (t, J=7.2 Hz, 3H), 1.19 (t, J=7.1 Hz, 6H). LC-MS (ESI) m/z 489.2 $[M+CH_3CN+H]^+$.

Scheme 13

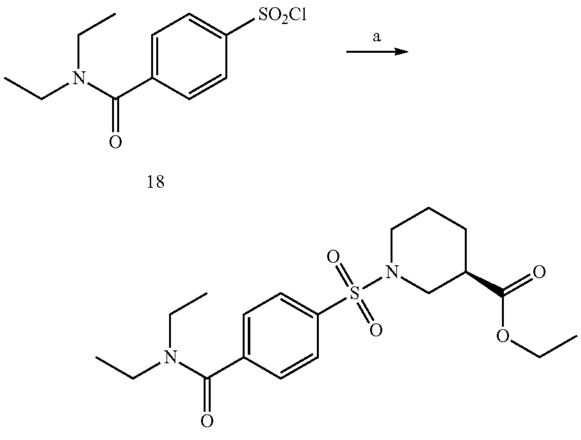

18

DX3-78B

Reagents and conditions: a) ethyl (R)-piperidine-3-carboxylate, $Et_3N$, DCM

Ethyl (R)-1-((4-(diethylcarbamoyl)phenyl)sulfonyl) piperidine-3-carboxylate (DX3-78B)

To a solution of ethyl (R)-piperidine-3-carboxylate (35 mg, 0.22 mmol) and triethylamine (36 mg, 0.36 mmol) in DCM (2 mL) was added 4-(diethylcarbamoyl)benzenesulfonyl chloride (18, 50 mg, 0.18 mmol). The mixture was stirred at room temperature for 3 h. The mixture was concentrated and purified with flash chromatography (20% EtOAc in hexane) to give DX3-78B as a colorless gel (59 mg, 83%). $^1H$ NMR (300 MHz, $CDCl_3$) δ 7.83 (d, J=8.6 Hz, 2H), 7.60-7.51 (m, 2H), 4.16 (q, J=7.1 Hz, 2H), 3.86 (d, J=8.8 Hz, 1H), 3.59 (q, J=9.8, 7.0 Hz, 3H), 3.23 (q, J=6.8 Hz, 2H), 2.70-2.54 (m, 2H), 2.41 (td, J=11.2, 3.1 Hz, 1H), 2.06-1.96 (m, 1H), 1.83 (dt, J=12.9, 3.8 Hz, 1H), 1.74-1.64 (m, 1H), 1.43 (t, J=10.9 Hz, 1H), 1.28 (t, J=7.1 Hz, 6H), 1.14 (t, J=7.0 Hz, 3H). LC-MS (ESI) m/z 397.1 $[M+H]^+$.

Scheme 14

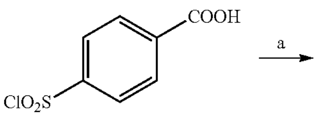

19

-continued

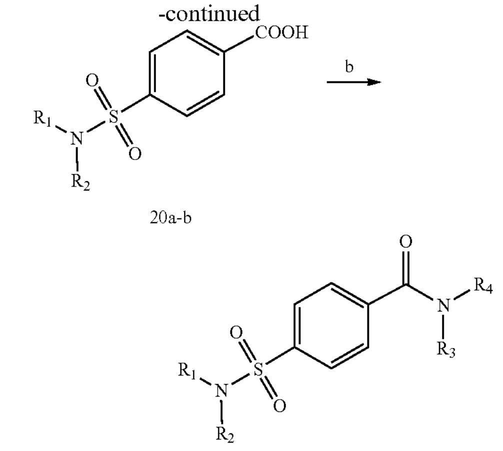

20a-b

Reagents and conditions: a) for 20a, ethyl (R)-piperidine-3-carboxylate, $Et_3N$, THF; b) $R_3$—NH—$R_4$, HATU, DIEA, DMF.

(R)-4-((3-(Ethoxycarbonyl)piperidin-1-yl)sulfonyl) benzoic Acid (20a)

To a solution of ethyl (R)-piperidine-3-carboxylate (426 mg, 2.71 mmol) and $Et_3N$ (457 mg, 4.52 mmol) in THF (10 mL) was added 4-(chlorosulfonyl)benzoic acid (19, 500 mg, 2.26 mmol). The mixture was stirred at room temperature overnight. The mixture was then concentrated, diluted with EtOAc, washed with 1N HCl, brine, dried over anhydrous $Na_2SO_4$, filtered and concentrated to give 20a as a white solid (604 mg, 78%). $^1H$ NMR (400 MHz, $CDCl_3$) δ 12.19 (d, J=8.4 Hz, 2H), 11.85 (d, J=8.4 Hz, 2H), 7.69 (d, J=11.8 Hz, 1H), 7.51-7.41 (m, 1H), 6.63 (dd, J=11.6, 9.8 Hz, 1H), 6.58-6.42 (m, 2H), 5.91 (d, J=13.9 Hz, 1H), 5.83-5.72 (m, 1H), 5.56 (dd, J=13.7, 10.1 Hz, 1H), 5.41 (q, J=13.1, 12.5 Hz, 1H). LC-MS (ESI) m/z 342.1 $[M+H]^+$.

Ethyl (R)-1-((4-(isopropyl(methyl)carbamoyl)phenyl)sulfonyl)piperidine-3-carboxylate (DX3-102B)

To a solution of 20a (25 mg, 0.073 mmol) and HATU (42 mg, 0.11 mmol) in DMF (1 mL) was added N-methylpropan-2-amine (5.3 mg, 0.073 mmol) and DIEA (28 mg, 0.22 mmol). The mixture was stirred at room temperature overnight. The mixture was then diluted with EtOAc, washed with brine, dried over anhydrous $Na_2SO_4$, filtered and concentrated. The residue was purified with flash chromatography (20% EtOAc in hexane) to give DX3-102B as a colorless gel (25 mg, 86%). $^1H$ NMR (300 MHz, $CDCl_3$) δ 7.82 (d, J=8.3 Hz, 2H), 7.60-7.47 (m, 2H), 4.15 (q, J=7.1 Hz, 2H), 3.83 (t, J=8.1 Hz, 2H), 3.62 (d, J=11.7 Hz, 1H), 2.98 (s, 2H), 2.76 (s, 1H), 2.71-2.51 (m, 2H), 2.48-2.33 (m, 1H), 2.01 (dd, J=14.0, 3.9 Hz, 1H), 1.82 (dp, J=11.3, 3.8 Hz, 1H), 1.76-1.57 (m, 1H), 1.51-1.31 (m, 1H), 1.32-1.12 (m, 9H). LC-MS (ESI) m/z 397.1 $[M+H]^+$.

Ethyl (R)-1-((4-(ethyl(propyl)carbamoyl)phenyl) sulfonyl)piperidine-3-carboxylate (DX3-103)

To a solution of 20a (25 mg, 0.073 mmol) and HATU (42 mg, 0.11 mmol) in DMF (1 mL) was added N-ethylpropan-1-amine (6.4 mg, 0.073 mmol) and DIEA (28 mg, 0.22 mmol). The mixture was stirred at room temperature overnight. The mixture was then diluted with EtOAc, washed with brine, dried over anhydrous $Na_2SO_4$, filtered and concentrated. The residue was purified with flash chromatographytography (20% EtOAc in hexane) to give DX3-103 as a colorless gel (20 mg, 67%). $^1$H NMR (300 MHz, $CDCl_3$) δ 7.82 (d, J=8.3 Hz, 2H), 7.53 (d, J=7.9 Hz, 2H), 4.15 (q, J=7.1 Hz, 2H), 3.84 (d, J=8.5 Hz, 1H), 3.60 (t, J=9.8 Hz, 2H), 3.48 (t, J=7.6 Hz, 1H), 3.22 (q, J=7.1 Hz, 1H), 3.12 (t, J=7.6 Hz, 1H), 2.70-2.52 (m, 2H), 2.40 (td, J=11.3, 3.1 Hz, 1H), 2.06-1.94 (m, 1H), 1.82 (dt, J=13.2, 3.8 Hz, 1H), 1.76-1.62 (m, 2H), 1.55 (q, J=8.7 Hz, 1H), 1.49-1.35 (m, 1H), 1.27 (t, J=7.2 Hz, 4.3H), 1.11 (t, J=7.1 Hz, 1.3H), 1.00 (t, J=7.4 Hz, 1.7H), 0.77 (t, J=7.3 Hz, 1.7H). LC-MS (ESI) m/z 433.1 $[M+Na]^+$.

Ethyl (R)-1-(4-(N,N-diethylsulfamoyl)benzoyl)piperidine-3-carboxylate (DX3-79)

To a solution of commercially available 4-(N,N-diethylsulfamoyl)benzoic acid (20b, 50 mg, 0.19 mmol) and HATU (108 mg, 0.29 mmol) in DMF (2 mL) was added ethyl (R)-piperidine-3-carboxylate (37 mg, 0.23 mmol) and DIEA (49 mg, 0.38 mmol). The mixture was stirred at room temperature overnight. The mixture was then diluted with EtOAc, washed with brine, dried over anhydrous $Na_2SO_4$, filtered and concentrated. The residue was purified with flash chromatography (20% EtOAc in hexane) to give DX3-79 as a colorless gel (72 mg, 96%). $^1$H NMR (300 MHz, $CDCl_3$) δ 7.88 (d, J=8.3 Hz, 2H), 7.53 (d, J=7.9 Hz, 2H), 4.74-4.27 (m, 1H), 4.17 (s, 2H), 3.58 (d, J=46.6 Hz, 1H), 3.26 (q, J=7.1 Hz, 6H), 2.54 (dt, J=48.8, 14.7 Hz, 1H), 2.15 (dd, J=15.1, 6.1 Hz, 1H), 1.90-1.71 (m, 2H), 1.35-1.22 (m, 3H), 1.17 (t, J=7.2 Hz, 6H). LC-MS (ESI) m/z 397.1 $[M+H]^+$.

N,N-Diethyl-4-fluorobenzenesulfonamide (22)

To a solution of diethylamine (360 mg, 4.93 mmol) and triethylamine (996 mg, 9.86 mmol) was added 4-fluorobenzenesulfonyl chloride (21, 962 mg, 4.93 mmol) portionwise. The mixture was stirred at room temperature overnight. The mixture was concentrated and purified with flash chromatography (10% EtOAc in hexane) to give 22 as a colorless oil. (940 mg, 83%). $^1$H NMR (400 MHz, $CDCl_3$) δ 7.89-7.80 (m, 2H), 7.24-7.14 (m, 2H), 3.27 (q, J=7.1 Hz, 4H), 1.16 (t, J=7.2 Hz, 6H).

N,N-Diethyl-4-mercaptobenzenesulfonamide (23)

22 (400 mg, 1.74 mmol) and NaSMe (484 mg, 6.92 mmol) was heated in DMF (2 mL) under microwave for 1 h. $Et_2O$ was added and it was extracted with 1N NaOH. The aqueous layer was acidified to pH<4 with 1N HCl and extracted with $Et_2O$. The organic layer was dried with $Na_2SO_4$, filtered and concentrated to give 23 as a white solid (410 mg, 96%). $^1$H NMR (400 MHz, $CDCl_3$) δ 7.68 (d, J=8.8 Hz, 2H), 7.36 (d, J=8.7 Hz, 2H), 3.25 (q, J=7.1 Hz, 4H), 1.15 (t, J=7.1 Hz, 6H).

Ethyl 3-((methylsulfonyl)oxy)cyclohexane-1-carboxylate (25)

To a solution of ethyl 3-hydroxycyclohexane-1-carboxylate (24, 500 mg, 2.91 mmol) and triethylamine (588 mg, 5.82 mmol) was added methanesulfonyl chloride (401 mg, 3.49 mmol) portionwise. The mixture was stirred at room Scheme 15

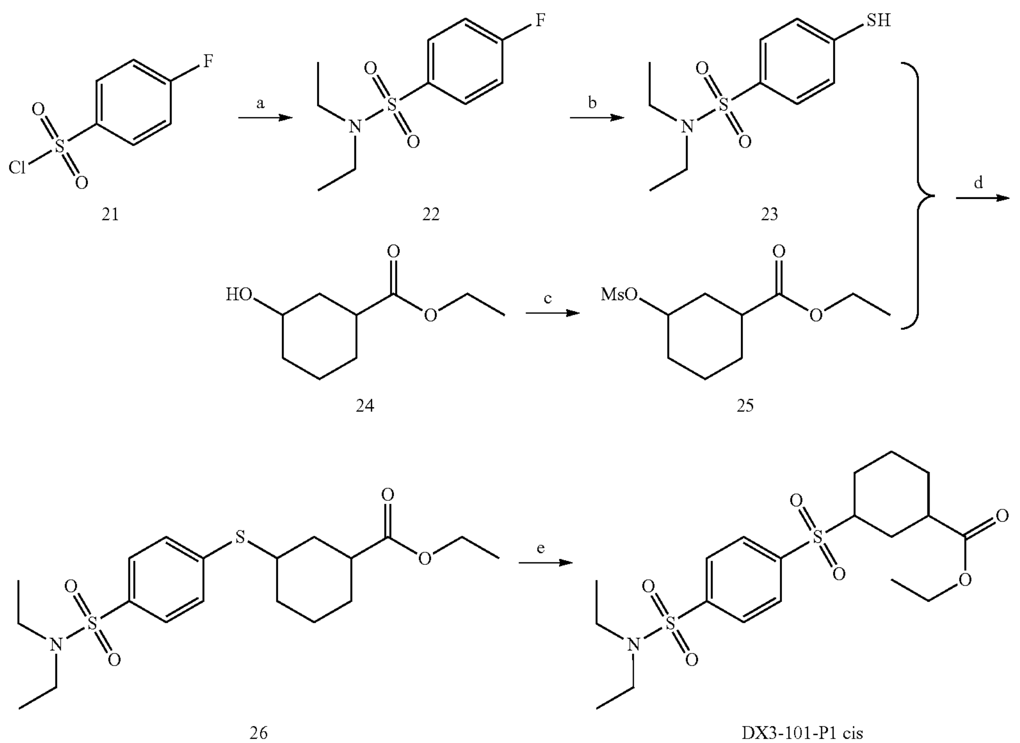

21 22 23 24 25 26 DX3-101-P1 cis DX3-101-P2 trans

Reagents and conditions: a) diethylamine, $Et_3N$, DCM; b) NaSMe, DCM, microwave, 170° C.; c) methanesulfonyl chloride, $Et_3N$, DCM; d) $Cs_2CO_3$, DCM, argon, 75° C.; e) mCPBA, DCM.

temperature for 3 h. The mixture was concentrated and purified with flash chromatography (10% EtOAc in hexane) to give 25 as a. (652 mg, 90%). $^1$H NMR (400 MHz, $CDCl_3$) δ 5.08 (s, 0.4H), 4.65 (td, J=10.9, 5.2 Hz, 0.6H), 4.16 (q, J=7.1 Hz, 2H), 3.05 (d, J=3.0 Hz, 3H), 2.82-2.72 (m, 0.4H), 2.44 (d, J=11.1 Hz, 1H), 2.19 (d, J=12.8 Hz, 1H), 1.96 (d, J=12.7 Hz, 2.6H), 1.78-1.65 (m, 2H), 1.56 (d, J=9.0 Hz, 1H), 1.40 (dd, J=11.9, 9.5 Hz, 1H), 1.28 (t, J=7.2 Hz, 3H).

Ethyl 3-((4-(N,N-diethylsulfamoyl)phenyl)thio)cyclohexane-1-carboxylate (26)

To a solution of 23 (52 mg, 0.21 mmol) and 25 (53 mg, 0.21 mmol) was added $Cs_2CO_3$ (102 mg, 0.32 mmol) portionwise. The mixture was stirred at 75° C. under argon for 5 h. The mixture was concentrated and purified with flash chromatography (30% EtOAc in hexane) to give 26 as a colorless oil. (56 mg, 67%). $^1$H NMR (400 MHz, $CDCl_3$) δ 7.71 (dd, J=8.6, 2.3 Hz, 2H), 7.43 (t, J=8.3 Hz, 2H), 4.16 (dq, J=17.6, 7.1 Hz, 2H), 3.74 (tt, J=7.6, 3.8 Hz, 0.4H), 3.29-3.22 (m, 4H), 3.22-3.16 (s, 0.6H), 2.81 (td, J=7.1, 3.7 Hz, 0.4H), 2.46-2.22 (m, 1.6H), 2.12-1.99 (m, 1H), 1.98-1.90 (m, 1H), 1.80 (dddd, J=16.4, 13.5, 7.4, 4.3 Hz, 2H), 1.71-1.52 (m, 2H), 1.47-1.36 (m, 1H), 1.28 (dt, J=13.2, 7.1 Hz, 3H), 1.15 (td, J=7.1, 1.5 Hz, 6H). LC-MS (ESI) m/z 400.1 [M+H]$^+$.

(cis)-Ethyl 3-((4-(N,N-diethylsulfamoyl)phenyl)sulfonyl)cyclohexane-1-carboxylate (DX3-101-P1) and (trans)-ethyl 3-((4-(N,N-diethylsulfamoyl)phenyl)sulfonyl)cyclohexane-1-carboxylate (DX3-101-P2)

To a solution of 26 (53 mg, 0.14 mmol) in DCM (3 mL) was added mCPBA (91 mg, 0.54 mmol) and stirred at room temperature overnight. Sat. $NaHCO_3$ was added and the mixture was extracted with EtOAc. The organic layer was washed with brine, dried with $Na_2SO_4$, filtered and concentrated. The residue was purified with preparative HPLC to give DX3-101-P1 (10 mg, 21%) and DX3-101-P2 (7 mg, 15%) as white solids. DX3-101-P1 $^1$H NMR (300 MHz, $CDCl_3$) (8.02 (s, 4H), 4.14 (q, J=7.1 Hz, 2H), 3.31 (q, J=7.1 Hz, 4H), 3.07-2.93 (m, 1H), 2.33 (d, J=12.8 Hz, 2H), 2.11 (d, J=11.6 Hz, 1H), 2.01 (d, J=8.0 Hz, 2H), 1.67-1.54 (m, 1H), 1.48-1.31 (m, 3H), 1.26 (t, J=7.1 Hz, 3H), 1.17 (t, J=7.1 Hz, 6H). LC-MS (ESI) m/z 432.0 [M+H]$^+$.

DX3-101-P2 $^1$H NMR (300 MHz, $CDCl_3$) δ 8.03 (d, J=1.2 Hz, 4H), 4.12 (q, J=7.1 Hz, 2H), 3.46 (tt, J=11.4, 3.8 Hz, 1H), 3.30 (q, J=7.1 Hz, 4H), 2.95-2.84 (m, 1H), 2.26 (d, J=13.4 Hz, 1H), 2.12-1.91 (m, 2H), 1.83 (dt, J=13.3, 3.9 Hz, 1H), 1.72 (ddd, J=13.3, 11.5, 4.8 Hz, 1H), 1.65-1.49 (m, 2H), 1.48-1.34 (m, 1H), 1.23 (t, J=7.1 Hz, 3H), 1.16 (t, J=7.2 Hz, 6H). LC-MS (ESI) m/z 432.0 [M+H]$^+$.

Scheme 16

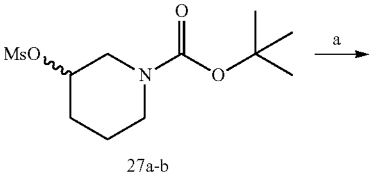

27a-b

-continued

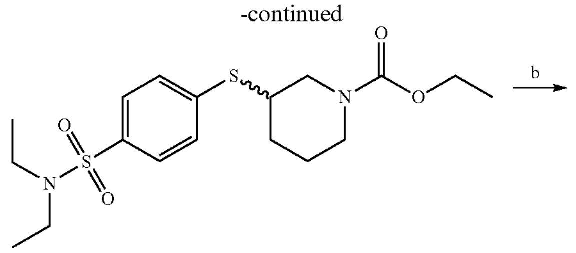

28a-b

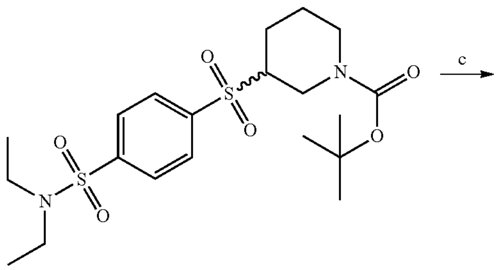

29a-b

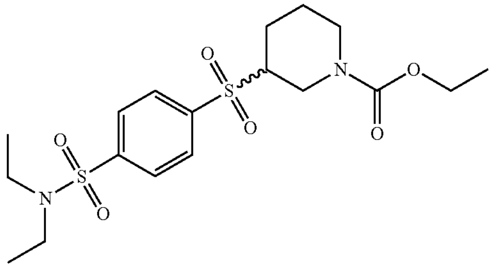

DX3-112B (S)
DX3-114 (R)

Reagents and conditions: a) 23, $Cs_2CO_3$, DMF, microwave, 110° C.; b) mCPBA, DCM; c) TFA, DCM, rt; ii. ethyl chloroformate, $Et_3N$, DCM.

tert-Butyl (S)-3-((4-(N,N-diethylsulfamoyl)phenyl)thio)piperidine-1-carboxylate (28a)

A solution of tert-butyl (R)-3-((methylsulfonyl)oxy)piperidine-1-carboxylate (27a, 137 mg, 0.49 mmol), 23 (120 mg, 0.49 mmol) and $Cs_2CO_3$ (239 mg, 0.74 mmol) in DMF (5 mL) was heated at 110° C. under microwave for 6 h. The mixture was diluted with EtOAc, washed with $H_2O$, brine and dried over anhydrous $Na_2SO_4$, filtered and concentrated. The residue was purified with flash chromatography (5% MeOH in DCM) to give 28a as a white solid (160 mg, 76%). $^1$H NMR (300 MHz, $CDCl_3$) δ 7.72 (d, J=8.5 Hz, 2H), 7.43 (d, J=8.2 Hz, 2H), 3.90 (d, J=13.2 Hz, 1H), 3.39-3.28 (m, 1H), 3.24 (q, J=7.1 Hz, 4H), 3.07-2.83 (m, 2H), 2.21-2.09 (m, 1H), 1.90-1.72 (m, 1H), 1.69-1.53 (m, 3H), 1.45 (s, 9H), 1.15 (t, J=7.1 Hz, 6H). LC-MS (ESI) m/z 451.1 [M+Na]$^+$.

tert-Butyl (S)-3-((4-(N,N-diethylsulfamoyl)phenyl)sulfonyl)piperidine-1-carboxylate (29a)

Using a similar procedure as described for DX3-101-P1 with 28a (80 mg, 0.19 mmol) and mCPBA (129 mg, 0.75 mmol), white solid (80 mg, 93%). $^1$H NMR (300 MHz, $CDCl_3$) δ 8.02 (s, 4H), 4.26 (d, J=12.2 Hz, 1H), 4.06-3.84 (m, 1H), 3.27 (q, J=7.1 Hz, 4H), 2.98 (dt, J=23.3, 7.7 Hz, 2H), 2.77-2.55 (m, 1H), 2.23-2.10 (m, 1H), 1.92-1.66 (m, 2H), 1.52-1.44 (m, 1H), 1.38 (s, 9H), 1.14 (t, J=7.1 Hz, 6H).

Ethyl (S)-3-((4-(N,N-diethylsulfamoyl)phenyl)sulfonyl)piperidine-1-carboxylate (DX3-112B)

To a solution of 29a (40 mg, 0.087 mmol) in DCM (1 mL) was added TFA (0.2 mL) and the resulting mixture was stirred at room temperature for 2 h. It was concentrated and dissolved by DCM (1 mL). $Et_3N$ (18 mg, 0.17 mmol) and ethyl chloroformate (11 mg, 0.10 mmol) were added subsequently. The mixture was stirred for 2 h at room temperature and concentrated. The residue was purified with flash chromatography (50% EtOAc in hexane) to give DX3-112B (16 mg, 43%) as a white solid. $^1$H NMR (300 MHz, $CDCl_3$) δ 8.05 (s, 4H), 4.39 (d, J=11.4 Hz, 1H), 4.18-3.98 (m, 3H), 3.31 (q, J=7.2 Hz, 4H), 3.17-2.97 (m, 2H), 2.86-2.69 (m, 1H), 2.24-2.10 (m, 1H), 1.93-1.70 (m, 2H), 1.56-1.40 (m, 1H), 1.24 (t, J=7.1 Hz, 3H), 1.17 (t, J=7.1 Hz, 6H). LC-MS (ESI) m/z 433.0 $[M+H]^+$.

tert-Butyl (R)-3-((4-(N,N-diethylsulfamoyl)phenyl)thio)piperidine-1-carboxylate (28b)

Using a similar procedure as described for 28a with tert-butyl (S)-3-((methylsulfonyl)oxy)piperidine-1-carboxylate (27b, 80 mg, 0.19 mmol), 23 (120 mg, 0.49 mmol) and $Cs_2CO_3$ (239 mg, 0.74 mmol), white solid (79 mg, 38%). $^1$H NMR (300 MHz, $CDCl_3$) δ 7.72 (d, J=8.5 Hz, 2H), 7.43 (d, J=8.1 Hz, 2H), 3.90 (d, J=13.1 Hz, 1H), 3.39-3.31 (m, 1H), 3.24 (q, J=7.2 Hz, 4H), 3.04-2.84 (m, 2H), 2.21-2.08 (m, 1H), 1.91-1.75 (m, 1H), 1.69-1.50 (m, 3H), 1.45 (s, 9H), 1.16 (t, J=7.1 Hz, 6H).

tert-Butyl (R)-3-((4-(N,N-diethylsulfamoyl)phenyl)sulfonyl)piperidine-1-carboxylate (29b)

Using a similar procedure as described for 29a with 28b (70 mg, 0.16 mmol) and mCPBA (113 mg, 0.65 mmol), white solid (60 mg, 80%). $^1$H NMR (300 MHz, $CDCl_3$) δ 8.03 (s, 4H), 4.28 (d, J=12.3 Hz, 1H), 4.01 (s, 1H), 3.29 (q, J=7.2 Hz, 4H), 3.14-2.88 (m, 1H), 2.81-2.58 (m, 1H), 2.18 (d, J=13.4 Hz, 1H), 1.95-1.64 (m, 2H), 1.54-1.46 (m, 1H), 1.40 (s, 9H), 1.16 (t, J=7.1 Hz, 6H). LC-MS (ESI) m/z 483.1 $[M+Na]^+$.

Ethyl (R)-3-((4-(N,N-diethylsulfamoyl)phenyl)sulfonyl)piperidine-1-carboxylate (DX3-114)

Using a similar procedure as described for DX3-112B with 29b (40 mg, 0.087 mmol), $Et_3N$ (18 mg, 0.17 mmol) and ethyl chloroformate (11 mg, 0.10 mmol), white solid (23 mg, 61%). $^1$H NMR (300 MHz, $CDCl_3$) δ 8.04 (s, 4H), 4.39 (d, J=11.4 Hz, 1H), 4.12 (q, J=7.1 Hz, 3H), 3.31 (q, J=7.1 Hz, 4H), 3.14-2.96 (m, 2H), 2.88-2.67 (m, 1H), 2.24-2.10 (m, 1H), 1.83 (s, 2H), 1.56-1.39 (m, 1H), 1.24 (t, J=7.1 Hz, 3H), 1.17 (t, J=7.1 Hz, 6H). LC-MS (ESI) m/z 433.1 $[M+H]^+$.

Scheme 17
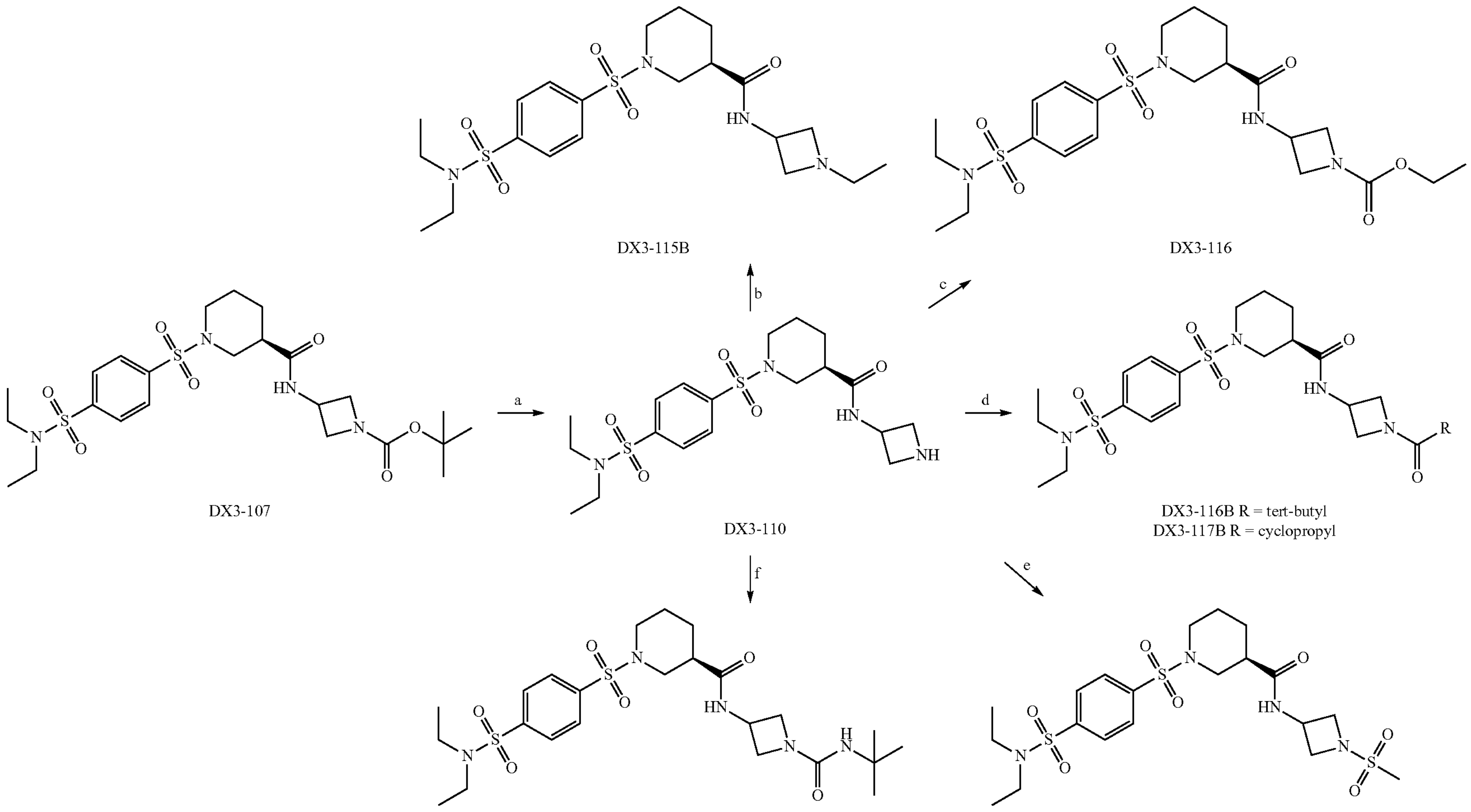
DX3-107
DX3-110
DX3-115B
DX3-116
DX3-116B R = tert-butyl
DX3-117B R = cyclopropyl
DX3-123
DX3-117
Reagents and conditions: a) TFA, DCM, rt; b) acetaldehyde, $NaBH_3CN$, AcOH, MeOH; c) ethyl chloroformate, $Et_3N$, DCM, rt; d) RCOCl, $Et_3N$, DCM, rt; e) methanesulfonyl chloride, $Et_3N$, DCM; f) tert-butyl isocyanate, $Et_3N$, DCM, rt.

(R)—N-(Azetidin-3-yl)-1-((4-(N,N-diethylsulfamoyl)phenyl)sulfonyl)piperidine-3-carboxamide (DX3-110)

To a solution of DX3-107 (27 mg, 0.048 mmol) in DCM (1 mL) was added TFA (0.2 mL). The mixture was stirred at room temperature for 2 h and concentrated. The residue was purified with preparative HPLC to give DX3-110 as a white solid (21 mg, 95%). $^1$H NMR (300 MHz, $CDCl_3$) (9.20 (s, 1H), 8.27 (d, J=7.4 Hz, 1H), 7.98 (d, J=8.3 Hz, 2H), 7.89 (d, J=8.3 Hz, 2H), 4.95-4.77 (m, 1H), 4.47-4.30 (m, 2H), 4.26-4.08 (m, 2H), 3.69 (d, J=10.8 Hz, 1H), 3.54 (d, J=5.9 Hz, 1H), 3.29 (q, J=7.1 Hz, 4H), 2.69 (t, J=10.5 Hz, 1H), 2.63-2.44 (m, 2H), 1.92-1.75 (m, 2H), 1.68-1.45 (m, 2H), 1.16 (t, J=7.1 Hz, 6H). LC-MS (ESI) m/z 459.1 $[M+H]^+$.

(R)-1-((4-(N,N-Diethylsulfamoyl)phenyl)sulfonyl)-N-(1-ethylazetidin-3-yl)piperidine-3-carboxamide (DX3-115B)

To a solution of DX3-110 (15 mg, 0.033 mmol) and acetaldehyde (1.7 mg, 0.039 mmol) in MeOH (1 mL) was added 1 drop of AcOH followed by $NaBH_3CN$ (3.2 mg, 0.05 mmol). The mixture was stirred at room temperature for 5 h and partitioned between EtOAc and sat. $NaHCO_3$ solution. The organic layer was washed with brine, dried over anhydrous $Na_2SO_4$, filtered and concentrated. The residue was purified with flash chromatography (10% MeOH in DCM) to give DX3-115B as a white solid (8.3 mg, 52%). $^1$H NMR (300 MHz, $CDCl_3$) δ 9.04 (d, J=8.3 Hz, 1H), 7.95 (q, J=8.6, 8.2 Hz, 4H), 5.10-4.82 (m, 1H), 4.53-4.03 (m, 4H), 3.76 (d, J=12.1 Hz, 1H), 3.68-3.49 (m, 1H), 3.30 (q, J=7.1 Hz, 4H), 3.17 (dt, J=13.2, 6.9 Hz, 2H), 2.78 (t, J=10.8 Hz, 1H), 2.65-2.48 (m, 2H), 1.99-1.77 (m, 2H), 1.76-1.46 (m, 2H), 1.30 (t, J=7.2 Hz, 3H), 1.17 (t, J=7.1 Hz, 6H). LC-MS (ESI) m/z 487.1 $[M+H]^+$.

Ethyl (R)-3-(1-((4-(N,N-diethylsulfamoyl)phenyl)sulfonyl)piperidine-3-carboxamido)azetidine-1-carboxylate (DX3-116)

To a solution of DX3-110 (20 mg, 0.044 mmol) and $Et_3N$ (9 mg, 0.088 mmol) in DCM (1 mL) was added ethyl chloroformate (5.7 mg, 0.052 mmol). The mixture was stirred at room temperature for 5 h and concentrated. The residue was purified with flash chromatography (10% MeOH in DCM) to give DX3-116 as a white solid (9 mg, 39%). $^1$H NMR (300 MHz, $CDCl_3$) δ 7.99 (d, J=8.5 Hz, 2H), 7.89 (d, J=8.5 Hz, 2H), 6.61 (d, J=7.1 Hz, 1H), 4.73-4.58 (m, 1H), 4.32 (ddd, J=9.3, 7.8, 4.5 Hz, 2H), 4.13 (q, J=7.1 Hz, 2H), 3.83 (dt, J=9.4, 5.9 Hz, 2H), 3.68 (d, J=11.6 Hz, 1H), 3.59 (d, J=11.5 Hz, 1H), 3.31 (q, J=7.1 Hz, 4H), 2.80-2.67 (m, 1H), 2.63-2.43 (m, 2H), 1.91-1.55 (m, 4H), 1.26 (td, J=7.2, 1.2 Hz, 3H), 1.18 (t, J=7.1 Hz, 6H). LC-MS (ESI) m/z 531.1 $[M+H]^+$.

(R)-1-((4-(N,N-Diethylsulfamoyl)phenyl)sulfonyl)-N-(1-pivaloylazetidin-3-yl)piperidine-3-carboxamide (DX3-116B)

To a solution of DX3-110 (20 mg, 0.044 mmol) and $Et_3N$ (9 mg, 0.088 mmol) in DCM (1 mL) was added pivaloyl chloride (6.3 mg, 0.052 mmol). The mixture was stirred at room temperature for 5 h and concentrated. The residue was purified with flash chromatography (10% MeOH in DCM) to give DX3-116B as a white solid (19 mg, 79%). $^1$H NMR (300 MHz, $CDCl_3$) δ 7.99 (d, J=8.5 Hz, 2H), 7.88 (d, J=8.5 Hz, 2H), 6.93 (s, 1H), 4.63 (d, J=6.4 Hz, 2H), 4.49-3.85 (m, 3H)z, 3.66 (dd, J=30.7, 11.5 Hz, 2H), 3.31 (q, J=7.1 Hz, 4H), 2.71 (t, J=10.7 Hz, 1H), 2.54 (d, J=10.4 Hz, 2H), 1.85 (q, J=9.9 Hz, 2H), 1.78-1.56 (m, 2H), 1.25-1.14 (m, 15H). LC-MS (ESI) m/z 543.3 $[M+H]^+$.

(R)—N-(1-(Cyclopropanecarbonyl)azetidin-3-yl)-1-((4-(N,N-diethylsulfamoyl)phenyl)sulfonyl)piperidine-3-carboxamide (DX3-117B)

Using a similar procedure as described for DX3-116B with DX3-110 (20 mg, 0.044 mmol), $Et_3N$ (9 mg, 0.088 mmol) and cyclopropanecarbonyl chloride (5.5 mg, 0.052 mmol), white solid (20 mg, 87%). $^1$H NMR (300 MHz, $CDCl_3$) δ 8.00 (d, J=8.3 Hz, 2H), 7.89 (d, J=8.4 Hz, 2H), 6.69 (dd, J=22.8, 7.0 Hz, 1H), 4.79-4.54 (m, 2H), 4.42-4.30 (m, 1H), 4.14-4.02 (m, 1H), 3.95-3.80 (m, 1H), 3.66 (d, J=12.0 Hz, 1H), 3.56 (dt, J=11.2, 4.6 Hz, 1H), 3.31 (q, J=7.1 Hz, 4H), 2.86-2.69 (m, 1H), 2.69-2.46 (m, 2H), 1.92-1.64 (m, 4H), 1.47-1.36 (m, 1H), 1.18 (t, J=7.1 Hz, 6H), 0.98 (s, 2H), 0.80 (d, J=6.6 Hz, 2H). LC-MS (ESI) m/z 527.2 $[M+H]^+$.

(R)-1-((4-(N,N-Diethylsulfamoyl)phenyl)sulfonyl)-N-(1-(methylsulfonyl)azetidin-3-yl)piperidine-3-carboxamide (DX3-117)

To a solution of DX3-110 (20 mg, 0.044 mmol) and $Et_3N$ (9 mg, 0.088 mmol) in DCM (1 mL) was added methanesulfonyl chloride (6 mg, 0.052 mmol). The mixture was stirred at room temperature for 2 h and concentrated. The residue was purified with flash chromatography (10% MeOH in DCM) and then preparative HPLC to give DX3-117 as a white solid (2.8 mg, 12%). $^1$H NMR (300 MHz, $CDCl_3$) δ 8.00 (d, J=8.2 Hz, 2H), 7.89 (d, J=8.2 Hz, 2H), 6.54 (d, J=7.5 Hz, 1H), 4.69 (q, J=7.2 Hz, 1H), 4.17 (q, J=7.6 Hz, 2H), 3.93 (q, J=6.8 Hz, 2H), 3.63 (d, J=11.9 Hz, 1H), 3.53 (d, J=11.6 Hz, 1H), 3.31 (q, J=7.1 Hz, 4H), 2.94 (s, 3H), 2.81 (t, J=10.5 Hz, 1H), 2.72-2.57 (m, 1H), 2.58-2.44 (m, 1H), 1.89-1.67 (m, 4H), 1.18 (t, J=7.2 Hz, 6H). LC-MS (ESI) m/z 537.0 $[M+H]^+$.

(R)—N-(1-(tert-butylcarbamoyl)azetidin-3-yl)-1-((4-(N,N-diethylsulfamoyl)phenyl)sulfonyl)piperidine-3-carboxamide (DX3-123)

To a solution of DX3-110 (20 mg, 0.044 mmol) and $Et_3N$ (9 mg, 0.088 mmol) in DCM (1 mL) was added tert-butyl isocyanate (5.2 mg, 0.053 mmol). The mixture was stirred at room temperature for 3 h and concentrated. The residue was purified with flash chromatography (10% MeOH in DCM) to give DX3-123 as a white solid (23 mg, 95%). $^1$H NMR (300 MHz, $CDCl_3$) δ 7.99 (d, J=8.6 Hz, 2H), 7.89 (d, J=8.6 Hz, 2H), 6.65 (d, J=6.9 Hz, 1H), 4.61 (q, J=5.9 Hz, 1H), 4.22 (td, J=8.0, 3.6 Hz, 2H), 3.95 (s, 1H), 3.79-3.65 (m, 3H), 3.59 (d, J=11.6 Hz, 1H), 3.31 (q, J=7.1 Hz, 4H), 2.80-2.68 (m, 1H), 2.62-2.46 (m, 2H), 1.91-1.77 (m, 2H), 1.73-1.59 (m, 2H), 1.35 (s, 9H), 1.18 (t, J=7.2 Hz, 6H). LC-MS (ESI) m/z 558.1 $[M+H]^+$.

Scheme 18

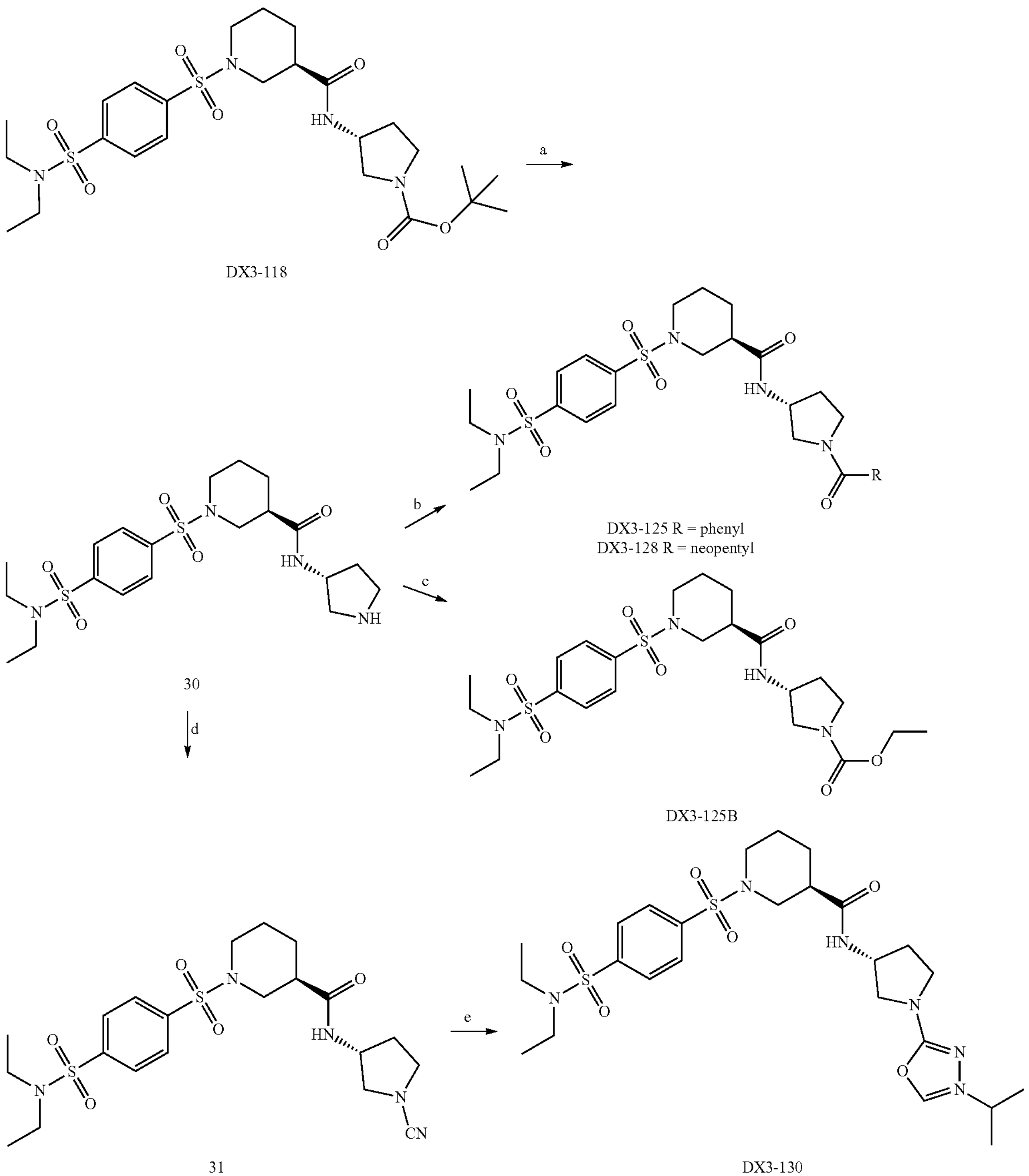

DX3-118

DX3-125 R = phenyl
DX3-128 R = neopentyl

30

DX3-125B

31

DX3-130

Reagents and conditions: a) TFA, DCM, rt; b) RCOCl, $Et_3N$, DCM, rt; c) ethyl chloroformate, $Et_3N$, DCM, rt; d) BrCn, aq. $NaHCO_3$, DCM, rt; e) i. N'-hydroxyisobutyrimidamide, $ZnCl_2$, EtOAc, THF, Ar, rt; ii. 2M HCl, EtOH, 80° C.

(R)-1-((4-(N,N-Diethylsulfamoyl)phenyl)sulfonyl)-N—((R)-pyrrolidin-3-yl)piperidine-3-carboxamide (30)

To a solution of DX3-118 (197 mg, 0.34 mmol) in DCM (4 mL) was added TFA (0.8 mL). The mixture was stirred at room temperature for 2 h and concentrated to give 30 as a colorless gel, which was directly used in the next step without further purification.

(R)—N—((R)-1-Benzoylpyrrolidin-3-yl)-1-((4-(N,N-diethylsulfamoyl)phenyl)sulfonyl)piperidine-3-carboxamide (DX3-125)

To a solution of 30 (20 mg, 0.042 mmol) and $Et_3N$ (13 mg, 0.13 mmol) in DCM (1 mL) was added benzoyl chloride (6 mg, 0.042 mmol). The mixture was stirred at room temperature for 3 h and concentrated. The residue was purified with flash chromatography (10% MeOH in DCM)

to give DX3-125 as a white solid (18 mg, 75%). $^1$H NMR (300 MHz, $CDCl_3$) δ 7.99 (t, J=7.6 Hz, 2H), 7.95-7.81 (m, 2H), 7.53 (t, J=6.2 Hz, 2H), 7.45 (s, 3H), 6.62 (dd, J=82.0, 6.8 Hz, 1H), 4.66-4.37 (m, 1H), 4.01-3.72 (m, 2H), 3.70-3.46 (m, 3H), 3.39-3.22 (m, 4H), 2.85-2.66 (m, 1H), 2.66-2.38 (m, 2H), 2.34-2.12 (m, 1H), 2.02-1.88 (m, 1H), 1.87-1.53 (m, 5H), 1.18 (t, J=7.1 Hz, 6H). LC-MS (ESI) m/z 577.2 $[M+H]^+$.

(R)-1-((4-(N,N-Diethylsulfamoyl)phenyl)sulfonyl)-N—((R)-1-(3,3-dimethylbutanoyl)pyrrolidin-3-yl)piperidine-3-carboxamide (DX3-128)

To a solution of 30 (20 mg, 0.042 mmol) and $Et_3N$ (13 mg, 0.13 mmol) in DCM (1 mL) was added 3,3-dimethylbutanoyl chloride (5.2 mg, 0.042 mmol). The mixture was stirred at room temperature for 3 h and concentrated. The residue was purified with flash chromatography (10% MeOH in DCM) to give DX3-128 as a white solid (18 mg, 75%). $^1$H NMR (300 MHz, $CDCl_3$) δ 7.99 (d, J=8.3 Hz, 2H), 7.88 (d, J=8.5 Hz, 2H), 6.31 (dd, J=26.1, 6.9 Hz, 1H), 4.56-4.39 (m, 1H), 3.86-3.69 (m, 1H), 3.69-3.37 (m, 5H), 3.31 (q, J=7.2 Hz, 4H), 2.87-2.75 (m, 1H), 2.72-2.57 (m, 1H), 2.57-2.43 (m, 1H), 2.33-2.12 (m, 3H), 2.03-1.63 (m, 5H), 1.18 (t, J=7.1 Hz, 6H), 1.09 (s, 9H). LC-MS (ESI) m/z 571.2 $[M+H]^+$.

Ethyl (R)-3-((R)-1-((4-(N,N-diethylsulfamoyl)phenyl)sulfonyl)piperidine-3-carboxamido)pyrrolidine-1-carboxylate (DX3-125B)

To a solution of 30 (20 mg, 0.042 mmol) and $Et_3N$ (13 mg, 0.13 mmol) in DCM (1 mL) was added ethyl chloroformate (4.6 mg, 0.042 mmol). The mixture was stirred at room temperature for 3 h and concentrated. The residue was purified with flash chromatography (10% MeOH in DCM) to give DX3-125B as a white solid (15 mg, 63%). $^1$H NMR (300 MHz, $CDCl_3$) δ 7.99 (d, J=8.6 Hz, 2H), 7.89 (d, J=8.5 Hz, 2H), 6.02 (d, J=7.2 Hz, 1H), 4.46 (dd, J=12.0, 6.0 Hz, 1H), 4.17 (q, J=7.1 Hz, 2H), 3.70 (dd, J=11.4, 6.2 Hz, 1H), 3.62 (d, J=11.6 Hz, 1H), 3.60-3.43 (m, 3H), 3.31 (q, J=7.2 Hz, 5H), 2.86-2.72 (m, 1H), 2.61 (dd, J=13.6, 8.3 Hz, 1H), 2.54-2.38 (m, 1H), 2.28-2.11 (m, 1H), 1.95-1.63 (m, 6H), 1.30 (t, J=7.1 Hz, 3H), 1.18 (t, J=7.1 Hz, 6H). LC-MS (ESI) m/z 545.2 $[M+H]^+$.

(R)—N—((R)-1-Cyanopyrrolidin-3-yl)-1-((4-(N,N-diethylsulfamoyl)phenyl)sulfonyl)piperidine-3-carboxamide (31)

A solution of 30 (51 mg, 0.11 mmol) in DCM (3 mL) was stirred at 0° C. A solution of $NaHCO_3$ (46 mg, 0.55 mmol) in $H_2O$ (1 mL) was added, followed by a solution of cyanogen bromide (14 mg, 0.13 mmol) in DCM (3 mL). The mixture was stirred at 0° C. for 30 min and room temperature for 3 h. The organic layer was separated and washed with sat. $NaHCO_3$, dried over $Na_2SO_4$, filtered and concentrated. The residue was purified with flash chromatography (50% EtOAc in DCM) to give 31 as a white solid (41 mg, 75%). $^1$H NMR (300 MHz, $CDCl_3$) δ 8.00 (d, J=8.1 Hz, 2H), 7.90 (d, J=8.1 Hz, 2H), 6.75 (d, J=7.0 Hz, 1H), 4.47 (s, 1H), 3.75-3.48 (m, 5H), 3.40-3.24 (m, 5H), 2.74 (t, J=10.7 Hz, 1H), 2.63-2.45 (m, 2H), 2.27-2.08 (m, 1H), 2.00-1.76 (m, 3H), 1.73-1.54 (m, 2H), 1.18 (t, J=7.1 Hz, 6H). LC-MS (ESI) m/z 498.1 $[M+H]^+$.

(R)-1-((4-(N,N-Diethylsulfamoyl)phenyl)sulfonyl)-N—((R)-1-(3-isopropyl-1,2,4-oxadiazol-5-yl)pyrrolidin-3-yl)piperidine-3-carboxamide (DX3-130)

To a solution of 31 (16 mg, 0.032 mmol) and N-hydroxy-isobutyrimidamide (4.2 mg, 0.042 mmol) in EtOAc (0.5 mL) and THF (0.5 mL) was added a suspension of $ZnCl_2$ (4.4 mg, 0.032 mmol) in $Et_2O$ (0.032 mL) dropwise under argon. The mixture was then stirred at room temperature for 3 h and concentrated. The residue was taken up by EtOH (0.5 mL) and 2M HCl (0.035 mL) was added. The mixture was stirred at 80° C. for 3 h and concentrated. The residue was purified with flash chromatography (10% DCM in MeOH) to give DX3-130 as a white solid (11 mg, 59%). $^1$H NMR (300 MHz, $CDCl_3$) δ 8.00 (d, J=8.4 Hz, 2H), 7.88 (d, J=8.5 Hz, 2H), 4.68-4.60 (m, 1H), 3.91 (dd, J=11.2, 5.9 Hz, 1H), 3.85-3.70 (m, 2H), 3.59 (dd, J=11.2, 3.9 Hz, 1H), 3.44 (d, J=11.9 Hz, 1H), 3.31 (q, J=7.1 Hz, 5H), 3.07-2.92 (m, 2H), 2.83 (dd, J=11.8, 8.7 Hz, 1H), 2.59-2.49 (m, 1H), 2.35 (dt, J=13.8, 6.5 Hz, 1H), 2.16-2.05 (m, 1H), 1.83-1.63 (m, 4H), 1.33 (d, J=7.0 Hz, 6H), 1.18 (t, J=7.1 Hz, 6H). LC-MS (ESI) m/z 583.2 $[M+H]^+$.

Scheme 19

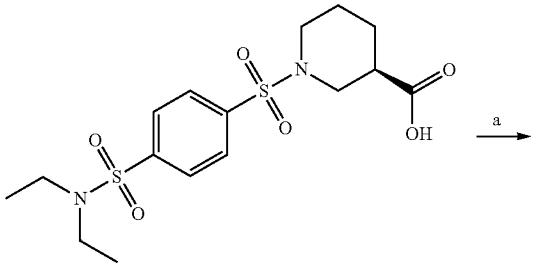

DX2-235

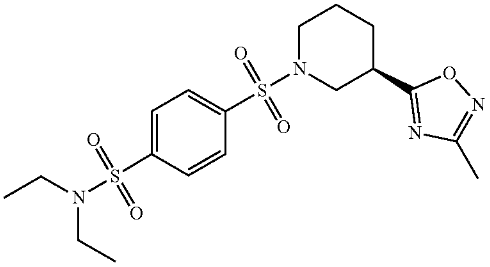

DX3-122B

Reagents and conditions: a) N-hydroxyacetimidamide, HATU, DIEA, DMF, 60° C.

(R)—N,N-Diethyl-4-((3-(3-methyl-1,2,4-oxadiazol-5-yl)piperidin-1-yl)sulfonyl)benzenesulfonamide (DX3-122B)

To a solution of DX2-235 (60 mg, 0.15 mmol) and HATU (87 mg, 0.23 mmol) in DMF (2 mL) was added N-hydroxyacetimidamide (13 mg, 0.18 mmol) and DIEA (58 mg, 0.45 mmol). The mixture was stirred at room temperature for 3 h and then 60° C. overnight. The mixture was diluted with EtOAc, washed with $H_2O$, brine, dried over anhydrous $Na_2SO_4$, filtered and concentrated. The residue was purified with preparative HPLC to give DX3-122B as a white solid (11 mg, 17%). $^1H$ NMR (300 MHz, $CDCl_3$) δ 8.00 (d, J=8.2 Hz, 2H), 7.92 (d, J=8.3 Hz, 2H), 4.14-4.02 (m, 1H), 3.78 (d, J=11.9 Hz, 1H), 3.38-3.26 (m, 4H), 3.30-3.18 (m, 1H), 2.80-2.66 (m, 1H), 2.50 (td, J=11.4, 3.1 Hz, 1H), 2.40 (s, 3H), 2.29-2.16 (m, 1H), 2.00-1.71 (m, 2H), 1.71-1.52 (m, 1H), 1.25-1.12 (m, 6H). LC-MS (ESI) m/z 443.0 $[M+H]^+$.

Scheme 20

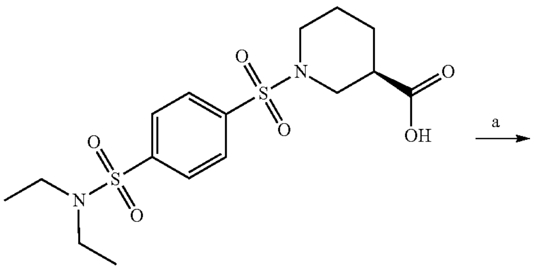

DX2-235

-continued

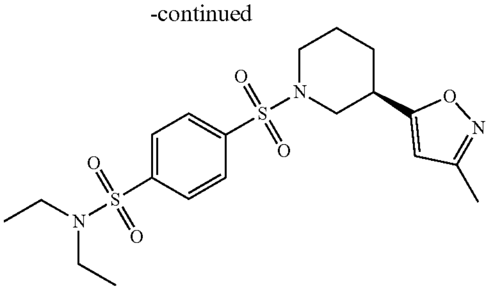

DX3-123B

Reagents and conditions: a) i. acetone oxime, $^n$BuLi, THF, 0° C.; ii. conc. $H_2SO_4$, THF, $H_2O$, 100° C.

(R)—N,N-Diethyl-4-((3-(3-methylisoxazol-5-yl)piperidin-1-yl)sulfonyl)benzenesulfonamide (DX3-123B)

Acetone oxime (11 mg, 0.30 mmol) was dissolved under argon in THF (2 mL), and the solution was cooled to 0° C. Butyllithium (0.12 mL, 0.60 mmol, 2.5 M in hexane) was added dropwise, and the solution was stirred at 0° C. for 2 h. a solution of DX2-235 (50 mg, 0.12 mmol) in THF (2 mL) was added dropwise. The mixture was allowed to warm to room temperature and stirred overnight and concentrated. The residue was re-dissolved in THF (3 mL) and $H_2O$ (1 mL) and concentrated $H_2SO_4$ (0.04 mL) was added. The resulting mixture was heated at 100° C. for 30 min and diluted with EtOAc, washed with sat. $NaHCO_3$, brine, dried over anhydrous $Na_2SO_4$, filtered and concentrated. The residue was purified with flash chromatography (10% MeOH in DCM) to give DX3-123B as a white solid (11 mg, 22%). $^1H$ NMR (300 MHz, $CDCl_3$) δ 7.99 (d, J=8.2 Hz, 2H), 7.89 (d, J=8.1 Hz, 2H), 5.97 (s, 1H), 3.79 (d, J=11.8 Hz, 1H), 3.62-3.50 (m, 1H), 3.31 (q, J=7.1 Hz, 4H), 3.20-3.08 (m, 1H), 2.69 (dt, J=23.1, 10.8 Hz, 2H), 2.30 (s, 3H), 2.10-1.95 (m, 1H), 1.92-1.60 (m, 3H), 1.17 (t, J=7.1 Hz, 6H). LC-MS (ESI) m/z 442.0 $[M+H]^+$.

Scheme 21
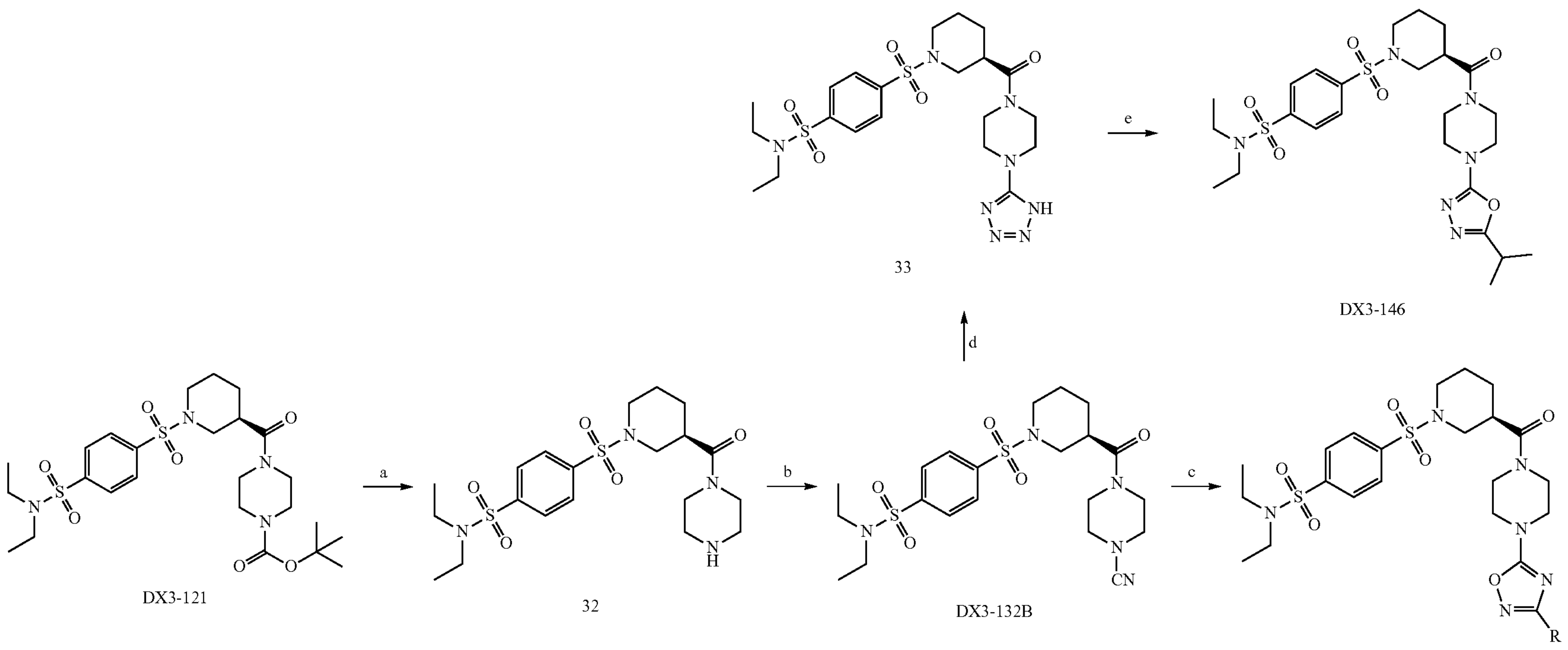
DX3-121
32
DX3-132B
33
DX3-146
DX3-134 R = —$CH_3$
DX3-134B R = —$CH(CH_3)_2$
DX3-140 R = —$CF_3$
Reagents and conditions: a) TFA, DCM, rt; b) BrCN, aq. $NaHCO_3$, DCM, rt; c) i. N'-hydroxyimidamides, $ZnCl_2$, EtOAc, THF, Ar, rt; ii. 2M HCl, EtOH, 80° C.; d) $NaN_3$, $Et_3N$•HCl, toluene, Ar, 80° C.; e) isobutyric anhydride, DIEA, chlorobenzene, Ar, 130° C.

(R)—N,N-Diethyl-4-((3-(piperazine-1-carbonyl)piperidin-1-yl)sulfonyl)benzenesulfonamide (32)

To a solution of DX3-121 (200 mg, 0.35 mmol) in DCM (4 mL) was added TFA (0.8 mL). The mixture was stirred at room temperature for 2 h and concentrated to give 32 as a colorless gel, which was directly used in the next step without further purification. LC-MS (ESI) m/z 473.1 $[M+H]^+$.

(R)-4-((3-(4-Cyanopiperazine-1-carbonyl)piperidin-1-yl)sulfonyl)-N,N-diethylbenzenesulfonamide (DX3-132B)

Using a similar procedure as described for 31 with 32 (120 mg, 0.25 mmol) and cyanogen bromide (29 mg, 0.28 mmol), white solid (110 mg, 88%). $^1H$ NMR (300 MHz, $CDCl_3$) δ 7.99 (d, J=8.6 Hz, 1H), 7.88 (d, J=8.7 Hz, 1H), 3.95-3.82 (m, 3H), 3.68 (d, J=19.2 Hz, 5H), 3.31 (q, J=7.2 Hz, 4H), 2.89-2.75 (m, 1H), 2.65-2.50 (m, 1H), 2.38-2.24 (m, 1H), 1.91-1.81 (m, 2H), 1.79-1.63 (m, 1H), 1.56-1.38 (m, 1H), 1.18 (t, J=7.1 Hz, 6H). LC-MS (ESI) m/z 498.1 $[M+H]^+$.

(R)—N,N-Diethyl-4-((3-(4-(3-methyl-1,2,4-oxadiazol-5-yl)piperazine-1-carbonyl)piperidin-1-yl)sulfonyl)benzenesulfonamide (DX3-134)

Using a similar procedure as described for DX3-130 with DX3-132B (30 mg, 0.06 mmol) and N-hydroxyacetimidamide (5.8 mg, 0.078 mmol), white solid (23 mg, 69%). $^1H$ NMR (300 MHz, $CDCl_3$) δ 7.99 (d, J=8.7 Hz, 2H), 7.89 (d, J=8.7 Hz, 2H), 3.89 (d, J=11.6 Hz, 2H), 3.77-3.56 (m, 8H), 3.30 (q, J=7.2 Hz, 4H), 2.88 (t, J=11.3 Hz, 1H), 2.66-2.54 (m, 1H), 2.36-2.28 (m, 1H), 2.26 (s, 3H), 1.94-1.83 (m, 2H), 1.82-1.69 (m, 1H), 1.55-1.41 (m, 1H), 1.18 (t, J=7.1 Hz, 6H). LC-MS (ESI) m/z 555.1 $[M+H]^+$.

(R)—N,N-Diethyl-4-((3-(4-(3-isopropyl-1,2,4-oxadiazol-5-yl)piperazine-1-carbonyl)piperidin-1-yl)sulfonyl)benzenesulfonamide (DX3-134B)

Using a similar procedure as described for DX3-130 with DX3-132B (30 mg, 0.06 mmol) and N-hydroxyisobutyrimidamide (8 mg, 0.078 mmol), white solid (23 mg, 66%). $^1H$ NMR (300 MHz, $CDCl_3$) δ 7.99 (d, J=8.1 Hz, 2H), 7.89 (d, J=8.1 Hz, 2H), 3.89 (d, J=11.9 Hz, 2H), 3.78-3.55 (m, 8H), 3.31 (q, J=7.1 Hz, 4H), 3.01-2.81 (m, 2H), 2.60 (t, J=11.2 Hz, 1H), 2.31 (t, J=11.7 Hz, 1H), 1.89 (d, J=13.4 Hz, 2H), 1.82-1.71 (m, 1H), 1.56-1.41 (m, 1H), 1.31 (d, J=6.9 Hz, 6H), 1.18 (t, J=7.1 Hz, 6H). LC-MS (ESI) m/z 583.2 $[M+H]^+$.

(R)—N,N-Diethyl-4-((3-(4-(3-(trifluoromethyl)-1,2,4-oxadiazol-5-yl)piperazine-1-carbonyl)piperidin-1-yl)sulfonyl)benzenesulfonamide (DX3-140)

Using a similar procedure as described for DX3-130 with DX3-132B (30 mg, 0.06 mmol) and 2,2,2-trifluoro-N-hydroxyacetimidamide (10 mg, 0.078 mmol), and purified with prep-HPLC (10-95% $CH_3CN$ in $H_2O$ with 0.05% TFA, 25 min), white solid (3.4 mg, 9%). $^1H$ NMR (300 MHz, $CDCl_3$) δ 7.99 (d, J=8.3 Hz, 2H), 7.89 (d, J=8.3 Hz, 2H), 3.89 (d, J=11.5 Hz, 2H), 3.73 (d, J=14.7 Hz, 8H), 3.31 (q, J=7.2 Hz, 4H), 2.95-2.82 (m, 1H), 2.61 (t, J=11.3 Hz, 1H), 2.32 (t, J=11.9 Hz, 1H), 1.96-1.85 (m, 2H), 1.78 (d, J=7.0 Hz, 1H), 1.51-1.42 (m, 1H), 1.18 (t, J=7.1 Hz, 6H). LC-MS (ESI) m/z 609.1 $[M+H]^+$.

(R)-4-((3-(4-(1H-Tetrazol-5-yl)piperazine-1-carbonyl)piperidin-1-yl)sulfonyl)-N,N-diethylbenzenesulfonamide (33)

To a suspension of DX3-132B (30 mg, 0.06 mmol) and $NaN_3$ (7.8 mg, 0.12 mmol) in toluene (1 mL) under argon was added $Et_3N{\cdot}HCl$ (16.5 mg, 0.12 mmol) and heated at 80° C. for 5 h. The mixture was then concentrated and EtOAc and $H_2O$ was added. The organic layer was separated, washed with brine, dried over anhydrous $Na_2SO_4$, filtered and concentrated. The residue was directly used in the next step without further purification. LC-MS (ESI) m/z 541.1 $[M+H]^+$.

(R)—N,N-Diethyl-4-((3-(4-(5-isopropyl-1,3,4-oxadiazol-2-yl)piperazine-1-carbonyl)piperidin-1-yl)sulfonyl)benzenesulfonamide (DX3-146)

To an ice cooled solution of 33 (10.8 mg, 0.02 mmol) and DIEA (5.2 mg, 0.04 mmol) in chlorobenzene (1 mL) was added isobutyric anhydride (4.7 mg, 0.03 mmol) under argon. The mixture was heated at 130° C. for 20 h and concentrated. The residue was purified with prep-HPLC (10-95% $CH_3CN$ in $H_2O$ with 0.05% TFA, 25 min) to give a white solid (3.2 mg, 27%). $^1H$ NMR (300 MHz, $CDCl_3$) δ 7.99 (d, J=6.1 Hz, 2H), 7.89 (d, J=8.0 Hz, 2H), 3.89 (d, J=11.8 Hz, 2H), 3.81-3.45 (m, 8H), 3.31 (q, J=6.6, 5.5 Hz, 4H), 3.19-2.97 (m, 1H), 2.97-2.82 (m, 1H), 2.60 (t, J=11.6 Hz, 1H), 2.31 (t, J=12.0 Hz, 1H), 1.89 (d, J=13.6 Hz, 2H), 1.81-1.68 (m, 1H), 1.57-1.46 (m, 1H), 1.37 (d, J=6.7 Hz, 6H), 1.19 (t, J=6.8 Hz, 6H). LC-MS (ESI) m/z 583.2 $[M+H]^+$.

Scheme 22

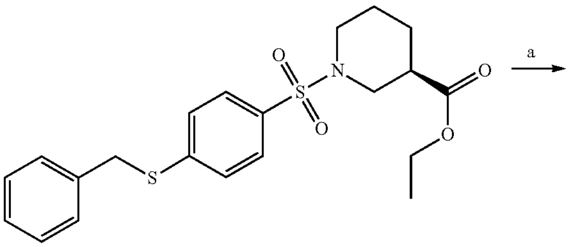

3b

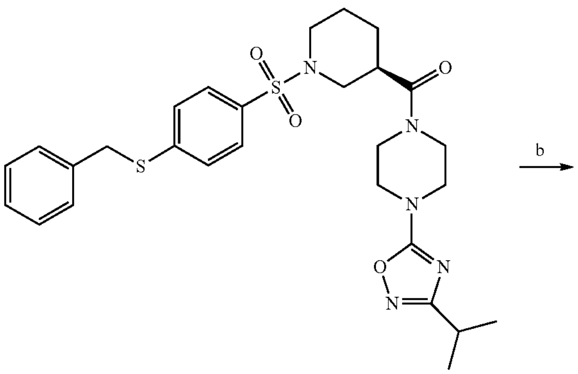

34

-continued

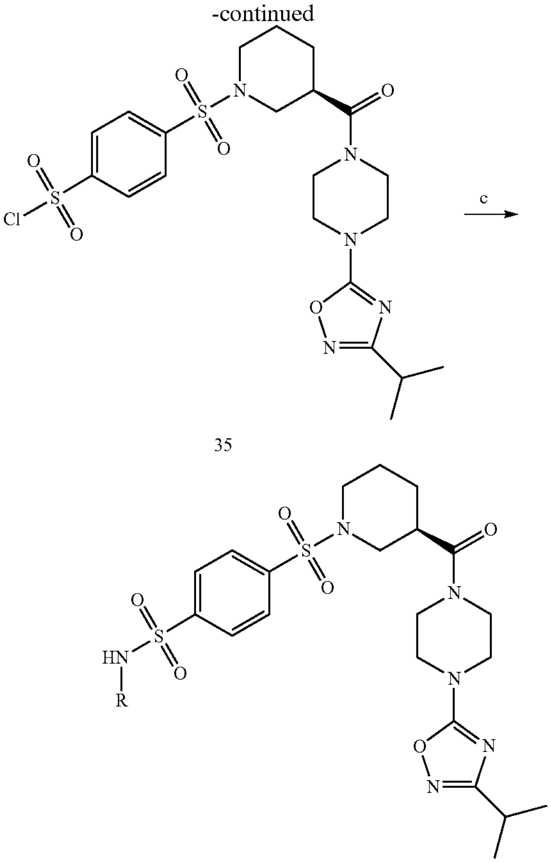

35

Reagents and conditions: a) i. LiOH, THF, $H_2O$, rt; ii. 3-isopropyl-5-(piperazin-1-yl)-1,2,4-oxadiazole, HATU, DIEA, DMF, rt; b) 1,3-dichloro-5,5-dimethylimidazolidine-2,4-dione, $CH_3CN$, $CH_3COOH$, $H_2O$, 0° C.; c) $RNH_2$, $Et_3N$, DCM, rt.

(R)-(1-((4-(Benzylthio)phenyl)sulfonyl)piperidin-3-yl)(4-(3-isopropyl-1,2,4-oxadiazol-5-yl)piperazin-1-yl)methanone (34)

To a solution of 69b (583 mg, 1.39 mmol) in THF (5 mL) and $H_2O$ (5 mL) was added $LiOH{\cdot}H_2O$ (290 mg, 6.94 mmol) at 0° C. and stirred at room temperature for 5 h. The mixture was then diluted with $H_2O$, and the pH was adjusted to 3 by 1N HCl solution. It was extracted with EtOAc, and the organic layer was washed with brine, dried over anhydrous $Na_2SO_4$, filtered and concentrated to give (R)-1-((4-(benzylthio)phenyl)sulfonyl)piperidine-3-carboxylic acid as a white solid (480 mg, 88%), which was directly used in the next step. To a solution of (R)-1-((4-(benzylthio)phenyl)sulfonyl)piperidine-3-carboxylic acid as a white solid (300 mg, 0.77 mmol) and HATU (439 mg, 1.16 mmol) in DMF (8 mL) was added 3-isopropyl-5-(piperazin-1-yl)-1,2,4-oxadiazole (150 mg, 0.77 mmol) and DIEA (298 mg, 2.31 mmol). The mixture was stirred at room temperature overnight. The mixture was then diluted with EtOAc, washed with brine, dried over anhydrous $Na_2SO_4$, filtered and concentrated. The residue was purified with flash chromatography (10% MeOH in DCM) to give 34 as a white solid (343 mg, 78%). $^1H$ NMR (300 MHz, $CDCl_3$) δ 7.62 (d, J=8.2 Hz, 2H), 7.44-7.28 (m, 7H), 4.24 (s, 2H), 3.83 (d, J=11.7 Hz, 2H), 3.75-3.56 (m, 8H), 2.99-2.81 (m, 2H), 2.49 (t, J=11.3 Hz, 1H), 2.23 (t, J=11.5 Hz, 1H), 1.93-1.64 (m, 3H), 1.56-1.41 (m, 1H), 1.31 (d, J=6.9 Hz, 6H). LC-MS (ESI) m/z 570.3 $[M+H]^+$.

(R)-4-((3-(4-(3-Isopropyl-1,2,4-oxadiazol-5-yl)piperazine-1-carbonyl)piperidin-1-yl)sulfonyl)benzenesulfonyl chloride (35)

Using a similar procedure as described for 4a with 34 (100 mg, 0.18 mmol), white solid (98 mg, 100% crude). LC-MS (ESI) m/z 546.3, 548.1 $[M+H]^+$.

(R)—N-ethyl-4-((3-(4-(3-isopropyl-1,2,4-oxadiazol-5-yl)piperazine-1-carbonyl)piperidin-1-yl)sulfonyl)benzenesulfonamide (DX3-167)

Using a similar procedure as described for DX2-201 with 35 (20 mg, 0.037 mmol) and ethylamine (5.0 mg, 0.11 mmol), white solid (6 mg, 29%). $^1H$ NMR (300 MHz, $CDCl_3$) δ 8.04 (d, J=8.1 Hz, 2H), 7.91 (d, J=8.1 Hz, 2H), 4.68-4.56 (m, 1H), 3.94-3.83 (m, 2H), 3.78-3.61 (m, 7H), 3.17-3.03 (m, 2H), 3.02-2.83 (m, 2H), 2.60 (t, J=11.2 Hz, 1H), 2.32 (t, J=11.8 Hz, 1H), 1.95-1.68 (m, 3H), 1.55-1.43 (m, 1H), 1.36-1.26 (m, 6H), 1.18 (t, J=7.2 Hz, 3H). LC-MS (ESI) m/z 555.2 $[M+H]^+$. Purity: 96.3%.

(R)—N-Isopropyl-4-((3-(4-(3-isopropyl-1,2,4-oxadiazol-5-yl)piperazine-1-carbonyl)piperidin-1-yl)sulfonyl)benzenesulfonamide (DX3-166B)

Using a similar procedure as described for DX2-201 with 35 (20 mg, 0.037 mmol) and isopropylamine (6.5 mg, 0.11 mmol), white solid (4 mg, 19%). $^1H$ NMR (300 MHz, $CDCl_3$) δ 8.06 (d, J=8.5 Hz, 2H), 7.91 (d, J=8.5 Hz, 2H), 4.52 (d, J=7.7 Hz, 1H), 3.89 (d, J=11.7 Hz, 2H), 3.82-3.49 (m, 9H), 3.03-2.81 (m, 2H), 2.60 (t, J=11.3 Hz, 1H), 2.39-2.28 (m, 1H), 1.95-1.82 (m, 2H), 1.81-1.69 (m, 1H), 1.57-1.43 (m, 1H), 1.32 (d, J=7.0 Hz, 6H), 1.14 (d, J=6.5 Hz, 6H). LC-MS (ESI) m/z 569.2 $[M+H]^+$. Purity: 95.6%.

(R)—N-Cyclopropyl-4-((3-(4-(3-isopropyl-1,2,4-oxadiazol-5-yl)piperazine-1-carbonyl)piperidin-1-yl)sulfonyl)benzenesulfonamide (DX3-179B)

Using a similar procedure as described for DX2-201 with 35 (20 mg, 0.037 mmol) and cyclopropanamine (6.3 mg, 0.11 mmol), white solid (5 mg, 24%). $^1H$ NMR (300 MHz, $CDCl_3$) δ 8.09 (d, J=8.6 Hz, 2H), 7.93 (d, J=8.7 Hz, 2H), 5.11 (s, 1H), 3.90 (d, J=11.6 Hz, 2H), 3.78-3.57 (m, 8H), 3.01-2.82 (m, 2H), 2.68-2.57 (m, 1H), 2.39-2.24 (m, 2H), 1.89 (d, J=13.3 Hz, 2H), 1.82-1.66 (m, 1H), 1.58-1.43 (m, 1H), 1.31 (d, J=6.9 Hz, 6H), 0.74-0.62 (m, 4H). LC-MS (ESI) m/z 567.2 $[M+H]^+$. Purity: 95.2%.

(R)—N-Cyclobutyl-4-((3-(4-(3-isopropyl-1,2,4-oxadiazol-5-yl)piperazine-1-carbonyl)piperidin-1-yl)sulfonyl)benzenesulfonamide (DX3-167B)

Using a similar procedure as described for DX2-201 with 35 (20 mg, 0.037 mmol) and cyclobutanamine (7.8 mg, 0.11 mmol), white solid (3.4 mg, 16%). $^1H$ NMR (300 MHz, $CDCl_3$) (8.03 (d, J=8.3 Hz, 2H), 7.90 (d, J=8.3 Hz, 2H), 4.84 (d, J=8.6 Hz, 1H), 3.99-3.80 (m, 3H), 3.79-3.59 (m, 8H), 3.02-2.83 (m, 2H), 2.59 (t, J=11.3 Hz, 1H), 2.34-2.15 (m, 3H), 1.97-1.74 (m, 5H), 1.75-1.59 (m, 2H), 1.57-1.42 (m, 1H), 1.31 (d, J=6.9 Hz, 6H). LC-MS (ESI) m/z 581.2 $[M+H]^+$. Purity: 96.5%.

(R)—N-(tert-Butyl)-4-((3-(4-(3-isopropyl-1,2,4-oxadiazol-5-yl)piperazine-1-carbonyl)piperidin-1-yl)sulfonyl)benzenesulfonamide (DX3-178)

Using a similar procedure as described for DX2-201 with 35 (20 mg, 0.037 mmol) and 2-methylpropan-2-amine (8.0 mg, 0.11 mmol), white solid (8 mg, 37%). $^1$H NMR (300 MHz, $CDCl_3$) δ 8.07 (d, J=8.3 Hz, 2H), 7.89 (d, J=8.3 Hz, 2H), 4.64 (s, 1H), 3.90 (d, J=11.6 Hz, 2H), 3.78-3.59 (m, 8H), 3.03-2.82 (m, 2H), 2.61-2.56 (m, 1H), 2.31 (t, J=11.7 Hz, 1H), 1.94-1.70 (m, 3H), 1.57-1.45 (m, 1H), 1.36-1.24 (m, 15H). LC-MS (ESI) m/z 583.2 [M+H]$^+$. Purity: 95.3%.

Scheme 23

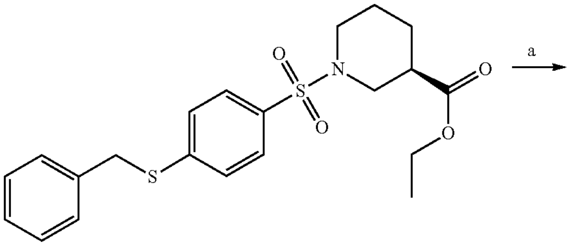

3b

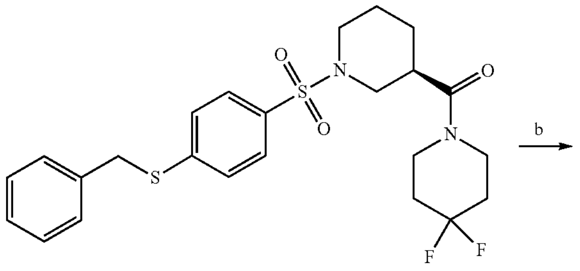

36

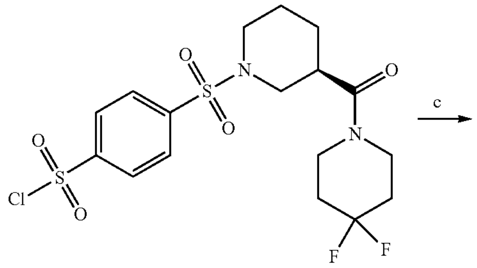

37

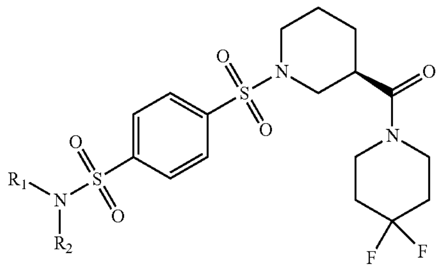

Reagents and conditions: a) i. LiOH, THF, $H_2O$, rt; ii. 4,4-difluoropiperidine, HATU, DIEA, DMF, rt; b) 1,3-dichloro-5,5-dimethylimidazolidine-2,4-dione, $CH_3CN$, $CH_3COOH$, $H_2O$, 0° C.; c) $RNH_2$, $Et_3N$, DCM, rt.

(R)-(1-((4-(Benzylthio)phenyl)sulfonyl)piperidin-3-yl)(4,4-difluoropiperidin-1-yl)methanone (36)

To a solution of 3b (139 mg, 0.33 mmol) in THF (2 mL) and $H_2O$ (2 mL) was added LiOH·$H_2O$ (69 mg, 1.65 mmol) at 0° C. and stirred at room temperature for 5 h. The mixture was then diluted with $H_2O$, and the pH was adjusted to 3 by TN HCl solution. It was extracted with EtOAc, and the organic layer was washed with brine, dried over anhydrous $Na_2SO_4$, filtered and concentrated to give the corresponding carboxylic acid. It was directly dissolved in DMF (5 mL). Then HATU (190 mg, 0.50 mmol), 4,4-difluoropiperidine (40 mg, 0.33 mmol) and DIEA (129 mg, 1.0 mmol) was added subsequently. The mixture was stirred at room temperature overnight. The mixture was then diluted with EtOAc, washed with brine, dried over anhydrous $Na_2SO_4$, filtered and concentrated. The residue was purified with flash chromatography (20% EtOAc in hexane) to give 36 as a light yellow gel (145 mg, 90%).

(R)-4-((3-(4,4-Difluoropiperidine-1-carbonyl)piperidin-1-yl)sulfonyl)benzenesulfonyl chloride (37)

Using a similar procedure as described for 4a with 36 (50 mg, 0.10 mmol), colorless gel (47 mg, 100% crude). $^1$H NMR (300 MHz, $CDCl_3$) δ 8.21 (d, J=8.6 Hz, 2H), 8.00 (d, J=8.5 Hz, 2H), 3.88 (d, J=11.2 Hz, 2H), 3.77-3.55 (m, 4H), 2.95-2.83 (m, 1H), 2.59 (t, J=11.3 Hz, 1H), 2.33 (td, J=11.9, 2.8 Hz, 1H), 2.05-1.68 (m, 8H).

(R)-4-((3-(4,4-Difluoropiperidine-1-carbonyl)piperidin-1-yl)sulfonyl)-N-isopropylbenzenesulfonamide (DX3-195B)

To a solution of isopropylamine (3 mg, 0.05 mmol) and triethylamine (15 mg, 0.15 mmol) was added 37 (24 mg, 0.05 mmol) portionwise. The mixture was stirred at room temperature overnight. The mixture was concentrated and purified with flash chromatography (10% MeOH in DCM) to give DX3-195B as a white solid (10 mg, 37%). $^1$H NMR (300 MHz, $CDCl_3$) δ 8.05 (d, J=8.4 Hz, 2H), 7.90 (d, J=8.3 Hz, 2H), 4.67 (d, J=7.7 Hz, 1H), 3.88 (d, J=11.6 Hz, 2H), 3.77-3.49 (m, 5H), 2.96-2.82 (m, 1H), 2.58 (t, J=11.3 Hz, 1H), 2.37-2.22 (m, 1H), 2.09-1.82 (m, 6H), 1.80-1.65 (m, 1H), 1.56-1.42 (m, 1H), 1.13 (d, J=6.5 Hz, 6H). LC-MS (ESI) m/z 494.2 [M+H]$^+$.

(R)-4-((3-(4,4-Difluoropiperidine-1-carbonyl)piperidin-1-yl)sulfonyl)-N,N-dimethylbenzenesulfonamide (DX3-201B)

Using a similar procedure as described for DX3-195B with 37 (50 mg, 0.10 mmol) and dimethyl amine (2.3 mg, 0.05 mmol), white solid (14 mg, 58%). $^1$H NMR (300 MHz, $CDCl_3$) δ 7.95 (s, 4H), 3.90 (d, J=11.8 Hz, 2H), 3.78-3.58 (m, 4H), 2.89 (t, J=11.3 Hz, 1H), 2.79 (s, 6H), 2.60 (t, J=11.3 Hz, 1H), 2.38-2.27 (m, 1H), 2.10-1.83 (m, 6H), 1.80-1.69 (m, 1H), 1.55-1.43 (m, 1H). LC-MS (ESI) m/z 502.1 [M+Na]$^+$.

Scheme 24.

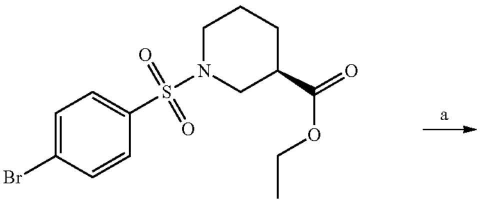

2b

-continued

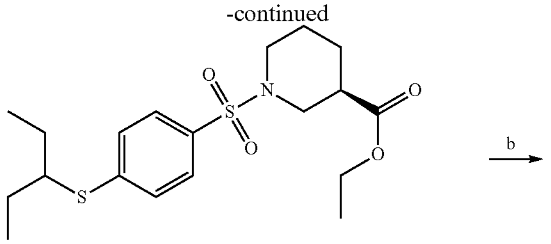

38

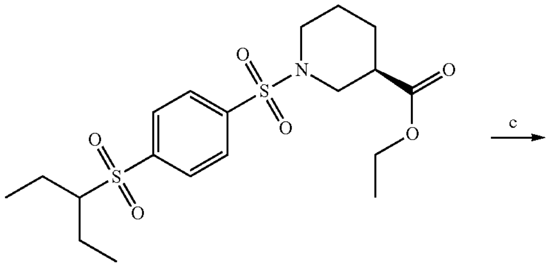

39

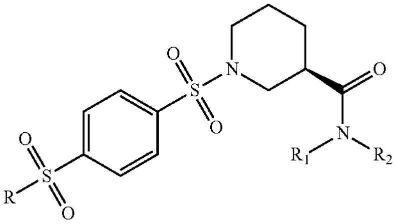

Reagents and conditions: a) 2-propanethiol, $Pd_2(dba)_3$, XantPhos, DIEA, dioxane, reflux; b) mCPBA, DCM, rt; c) i. LiOH, THF, $H_2O$, rt; ii) 3-isopropyl-5-(piperazin-1-yl)-1,2,4-oxadiazole, HATU, DIEA, DMF, rt.

Ethyl (R)-1-((4-(pentan-3-ylthio)phenyl)sulfonyl) piperidine-3-carboxylate (38)

Using a similar procedure as described for 3a with 2b (80 mg, 0.21 mmol) and pentane-3-thiol (22 mg, 0.21 mmol), light yellow solid (78 mg, 92%). LC-MS (ESI) m/z 400.0 $[M+H]^+$.

Ethyl (R)-1-((4-(pentan-3-ylsulfonyl)phenyl)sulfonyl)piperidine-3-carboxylate (39)

To a solution of 38 (44 mg, 0.11 mmol) in DCM (2 mL) was added mCPBA (76 mg, 0.44 mmol) and stirred at room temperature overnight. Sat. $NaHCO_3$ was added and the mixture was extracted with EtOAc. The organic layer was washed with brine, dried with $Na_2SO_4$, filtered and concentrated. The residue was purified with silica chromatography (50% EtOAc in hexane) to give 39 as a white solid (20 mg, 42%). $^1H$ NMR (300 MHz, $CDCl_3$) δ 8.08 (d, J=8.3 Hz, 2H), 7.97 (d, J=8.4 Hz, 2H), 4.17 (q, J=7.1 Hz, 2H), 3.95-3.80 (m, 1H), 3.66 (d, J=11.7 Hz, 1H), 2.89 (ddd, J=11.9, 7.2, 4.9 Hz, 1H), 2.71-2.58 (m, 2H), 2.46 (td, J=11.3, 3.2 Hz, 1H), 2.04 (d, J=13.4 Hz, 1H), 1.87 (ddd, J=15.6, 7.7, 4.9 Hz, 3H), 1.72 (dq, J=20.9, 6.9, 6.4 Hz, 4H), 1.53-1.39 (m, 1H), 1.28 (t, J=7.1 Hz, 3H), 1.05 (t, J=7.5 Hz, 6H). LC-MS (ESI) m/z 432.1 $[M+H]^+$.

(R)-(4-(3-Isopropyl-1,2,4-oxadiazol-5-yl)piperazin-1-yl)(1-((4-(pentan-3-ylsulfonyl)phenyl)sulfonyl) piperidin-3-yl)methanone (DX3-210)

Using a similar procedure as described for 34 with 39 (15 mg, 0.037 mmol) and 3-isopropyl-5-(piperazin-1-yl)-1,2,4-oxadiazole (7.3 mg, 0.037 mmol), white solid (12 mg, 55%). $^1H$ NMR (300 MHz, $CDCl_3$) δ 8.07 (d, J=8.0 Hz, 2H), 7.95 (d, J=8.1 Hz, 2H), 3.90 (d, J=11.8 Hz, 2H), 3.78-3.55 (m, 8H), 2.99-2.81 (m, 3H), 2.62 (t, J=11.3 Hz, 1H), 2.32 (t, J=11.6 Hz, 1H), 1.98-1.68 (m, 7H), 1.58-1.42 (m, 1H), 1.31 (d, J=6.9 Hz, 6H), 1.05 (t, J=7.5 Hz, 6H). LC-MS (ESI) m/z 582.3 $[M+H]^+$.

(R)-Morpholino(1-((4-(pentan-3-ylsulfonyl)phenyl) sulfonyl)piperidin-3-yl)methanone (DX3-209B)

Using a similar procedure as described for 34 with 39 (15 mg, 0.037 mmol) and morpholine (3.2 mg, 0.037 mmol), white solid (10 mg, 57%). $^1H$ NMR (300 MHz, $CDCl_3$) δ 8.07 (d, J=8.5 Hz, 2H), 7.95 (d, J=8.3 Hz, 2H), 3.89 (d, J=11.5 Hz, 2H), 3.80-3.45 (m, 8H), 2.94-2.77 (m, 2H), 2.60 (t, J=11.4 Hz, 1H), 2.31 (td, J=12.0, 2.8 Hz, 1H), 1.96-1.82 (m, 4H), 1.82-1.65 (m, 3H), 1.49 (td, J=12.2, 3.4 Hz, 1H), 1.05 (t, J=7.5 Hz, 6H).

Scheme 25.

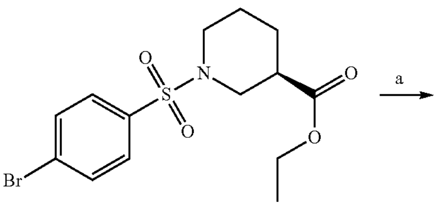

2b

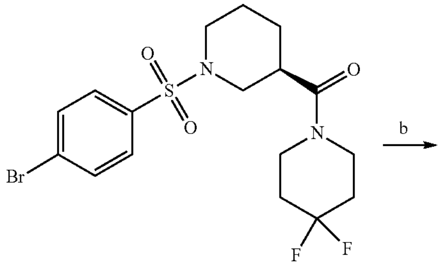

40

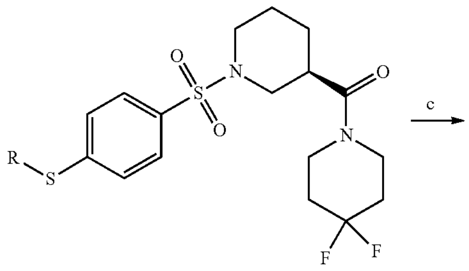

41a R = isobutyl
41b R = cyclopropyl
41c R = cyclobutyl
41d R = oxetanyl

-continued

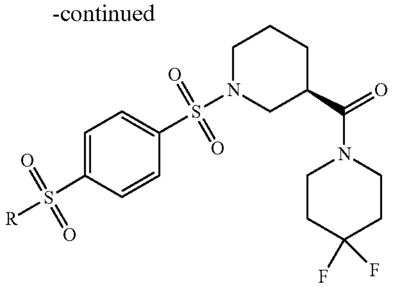

Reagents and conditions: a) i. LiOH, THF, $H_2O$, rt; ii. 4,4-difluoropiperidine, HATU, DIEA, DMF, rt; b) RSH, $Pd_2(dba)_3$, XantPhos, DIEA, dioxane, reflux, 0° C.; c) mCPBA, DCM, rt.

(R)-(1-((4-Bromophenyl)sulfonyl)piperidin-3-yl)(4,4-difluoropiperidin-1-yl)methanone (40)

Using a similar procedure as described for 3a from 40 (188 mg, 0.50 mmol) and (4,4-difluoropiperidine (67 mg, 0.55 mmol), white solid (205 mg, 91%). $^1$H NMR (300 MHz, $CDCl_3$) (7.70 (d, J=8.3 Hz, 2H), 7.63 (d, J=8.4 Hz, 2H), 3.84 (d, J=11.6 Hz, 2H), 3.77-3.57 (m, 4H), 2.88 (t, J=11.6 Hz, 1H), 2.50 (t, J=11.3 Hz, 1H), 2.25 (t, J=11.8 Hz, 1H), 2.15-1.79 (m, 6H), 1.79-1.66 (m, 1H), 1.54-1.39 (m, 1H).

(R)-(4,4-Difluoropiperidin-1-yl)(1-((4-(isobutylthio)phenyl)sulfonyl)piperidin-3-yl)methanone (41a)

Using a similar procedure as described for 3a from 40 (50 mg, 0.11 mmol) and 2-methylpropane-1-thiol (10 mg, 0.11 mmol), white solid (43 mg, 85%). $^1$H NMR (300 MHz, $CDCl_3$) δ 7.63 (d, J=8.2 Hz, 2H), 7.36 (d, J=8.2 Hz, 2H), 3.83 (d, J=11.7 Hz, 2H), 3.78-3.58 (m, 4H), 2.89 (d, J=6.9 Hz, 3H), 2.48 (t, J=11.4 Hz, 1H), 2.24 (t, J=11.7 Hz, 1H), 2.12-1.89 (m, 5H), 1.90-1.66 (m, 3H), 1.53-1.38 (m, 1H), 1.10 (d, J=6.7 Hz, 6H). LC-MS (ESI) m/z 461.0 $[M+H]^+$.

(R)-(1-((4-(Cyclopropylthio)phenyl)sulfonyl)piperidin-3-yl)(4,4-difluoropiperidin-1-yl)methanone (41b)

Using a similar procedure as described for 3a from 40 (40 mg, 0.089 mmol) and 0cyclopropanethiol (6.6 mg, 0.089 mmol), white solid (26 mg, 65%). $^1$H NMR (300 MHz, $CDCl_3$) δ 7.63 (d, J=7.0 Hz, 2H), 7.47 (d, J=8.3 Hz, 2H), 3.89-3.76 (m, 2H), 3.77-3.56 (m, 4H), 2.88 (t, J=11.6 Hz, 1H), 2.47 (t, J=11.1 Hz, 1H), 2.28-2.17 (m, 2H), 2.10-1.88 (m, 4H), 1.89-1.67 (m, 3H), 1.52-1.34 (m, 1H), 1.18 (d, J=6.9 Hz, 2H), 0.80-0.70 (m, 2H).

(R)-(1-((4-(Cyclobutylthio)phenyl)sulfonyl)piperidin-3-yl)(4,4-difluoropiperidin-1-yl)methanone (41c)

Using a similar procedure as described for 3a from 40 (40 mg, 0.089 mmol) and cyclobutanethiol (7.8 mg, 0.089 mmol), white solid (36 mg, 88%). $^1$H NMR (300 MHz, $CDCl_3$) δ 7.59 (d, J=8.5 Hz, 2H), 7.24 (d, J=8.5 Hz, 2H), 4.05-3.94 (m, 1H), 3.86-3.75 (m, 2H), 3.74-3.58 (m, 4H), 2.93-2.78 (m, 1H), 2.64-2.51 (m, 1H), 2.45 (t, J=11.3 Hz, 1H), 2.26-1.92 (m, 10H), 1.87-1.64 (m, 3H), 1.48-1.37 (m, 1H).

(R)-(4,4-Difluoropiperidin-1-yl)(1-((4-(oxetan-3-ylthio)phenyl)sulfonyl)piperidin-3-yl)methanone (41d)

Using a similar procedure as described for 3a from 40 (40 mg, 0.089 mmol) and oxetane-3-thiol (8.0 mg, 0.089 mmol), white solid (16 mg, 39%). $^1$H NMR (300 MHz, $CDCl_3$) δ 7.64 (d, J=8.4 Hz, 2H), 7.20 (d, J=8.4 Hz, 2H), 5.15 (t, J=6.6 Hz, 2H), 4.69 (t, J=6.3 Hz, 2H), 4.65-4.58 (m, 1H), 3.90-3.58 (m, 6H), 2.94-2.83 (m, 1H), 2.47 (t, J=11.3 Hz, 1H), 2.22 (td, J=11.8, 2.7 Hz, 1H), 2.12-1.89 (m, 4H), 1.88-1.66 (m, 3H), 1.50-1.35 (m, 1H).

(R)-(4,4-Difluoropiperidin-1-yl)(1-((4-(isobutylsulfonyl)phenyl)sulfonyl)piperidin-3-yl)methanone (DX3-218)

To a solution of 41a (21 mg, 0.046 mmol) in DCM (3 mL) was added mCPBA (32 mg, 0.182 mmol) and stirred at room temperature overnight. Sat. $NaHCO_3$ was added and the mixture was extracted with EtOAc. The organic layer was washed with brine, dried with $Na_2SO_4$, filtered and concentrated. The residue was purified with silica chromatography (50% EtOAc in hexane) to give DX3-218 (8 mg, 35%) as a white solid. $^1$H NMR (300 MHz, $CDCl_3$) δ 8.10 (d, J=8.2 Hz, 2H), 7.96 (d, J=8.4 Hz, 2H), 3.89 (d, J=11.8 Hz, 2H), 3.79-3.59 (m, 4H), 3.05 (d, J=6.5 Hz, 2H), 2.89 (t, J=11.4 Hz, 1H), 2.58 (t, J=11.4 Hz, 1H), 2.40-2.24 (m, 2H), 2.16-1.82 (m, 6H), 1.81-1.66 (m, 1H), 1.56-1.41 (m, 1H), 1.12 (d, J=6.7 Hz, 6H). LC-MS (ESI) m/z 491.3 $[M-H]^-$. Purity: 96.4%.

(R)-(1-((4-(Cyclopropylsulfonyl)phenyl)sulfonyl)piperidin-3-yl)(4,4-difluoropiperidin-1-yl)methanone (DX3-221)

Using a similar procedure as described for DX3-218 from 41b (26 mg, 0.058 mmol), white solid (18 mg, 64%). $^1$H NMR (300 MHz, $CDCl_3$) δ 8.09 (d, J=8.5 Hz, 2H), 7.95 (d, J=8.3 Hz, 2H), 3.99-3.83 (m, 2H), 3.80-3.57 (m, 4H), 2.90 (t, J=11.5 Hz, 1H), 2.66-2.46 (m, 2H), 2.39-2.24 (m, 1H), 2.14-1.82 (m, 6H), 1.73 (t, J=13.0 Hz, 1H), 1.56-1.37 (m, 3H), 1.20-1.08 (m, 2H).

(R)-(1-((4-(Cyclobutylsulfonyl)phenyl)sulfonyl)piperidin-3-yl)(4,4-difluoropiperidin-1-yl)methanone (DX3-220B)

Using a similar procedure as described for DX3-218 from 41c (18 mg, 0.039 mmol), white solid (13 mg, 68%). $^1$H NMR (300 MHz, $CDCl_3$) δ 8.06 (d, J=8.3 Hz, 2H), 7.94 (d, J=8.4 Hz, 2H), 3.96-3.80 (m, 3H), 3.77-3.55 (m, 4H), 2.89 (t, J=11.6 Hz, 1H), 2.74-2.51 (m, 3H), 2.35-2.19 (m, 3H), 2.10-1.86 (m, 8H), 1.80-1.69 (m, 1H), 1.52-1.40 (m, 1H).

(R)-(4,4-Difluoropiperidin-1-yl)(1-((4-(oxetan-3-ylsulfonyl)phenyl)sulfonyl)piperidin-3-yl)methanone (DX3-219B)

Using a similar procedure as described for DX3-218 from 41d (16 mg, 0.035 mmol), white solid (10 mg, 59%). $^1$H NMR (300 MHz, $CDCl_3$) δ 8.09 (d, J=8.2 Hz, 2H), 7.98 (d, J=8.4 Hz, 2H), 5.07-4.97 (m, 2H), 4.87 (td, J=7.7, 3.5 Hz, 2H), 4.52 (tt, J=7.9, 6.1 Hz, 1H), 3.95-3.82 (m, 2H), 3.79-3.58 (m, 4H), 2.89 (t, J=11.5 Hz, 1H), 2.59 (t, J=11.3 Hz, 1H), 2.32 (td, J=11.9, 2.7 Hz, 1H), 2.14-1.81 (m, 6H), 1.81-1.62 (m, 1H), 1.53-1.38 (m, 1H). LC-MS (ESI) m/z 493.1 $[M+H]^+$. Purity: 98.4%

Scheme 26.

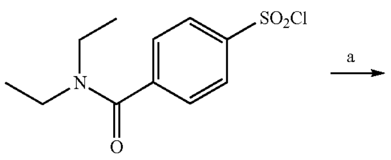

42

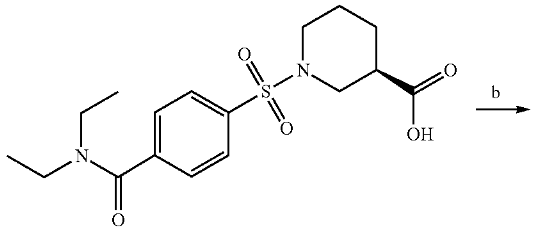

43

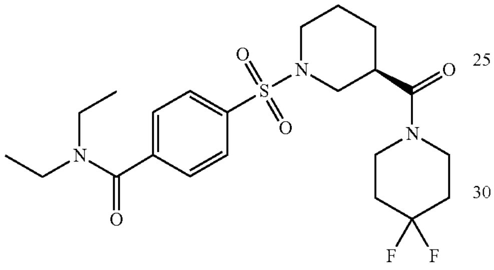

DX3-203

Reagents and conditions: a) (R)-piperidine-3-carboxylic acid, $Na_2CO_3$, THF, $H_2O$, rt; b) 4,4-difluoropiperidine, HATU, DIEA, DMF, rt;

(R)-1-((4-(Diethylcarbamoyl)phenyl)sulfonyl)piperidine-3-carboxylic acid (43)

To a solution of 42 (100 mg, 0.36 mmol) and $Na_2CO_3$ (114 mg, 1.08 mmol) in $H_2O$ (1.5 mL) was added a solution of (R)-piperidine-3-carboxylic acid (47 mg, 0.36 mmol) in THF (1.5 mL) dropwise at 0° C. and stirred at room temperature for 3 h. THF was removed by evaporation and the pH was adjusted to 3 by 1N HCl solution. It was extracted with EtOAc, and the organic layer was washed with brine, dried over anhydrous $Na_2SO_4$, filtered and concentrated to give 43 as a white solid (130 mg, 98%). $^1H$ NMR (300 MHz, $CDCl_3$) δ 7.83 (d, J=8.0 Hz, 2H), 7.55 (d, J=7.9 Hz, 2H), 3.85 (d, J=11.1 Hz, 1H), 3.67-3.51 (m, 3H), 3.24 (q, J=6.7 Hz, 2H), 2.73-2.49 (m, 2H), 2.49-2.36 (m, 1H), 2.01 (d, J=13.5 Hz, 1H), 1.88-1.76 (m, 1H), 1.68 (q, J=13.9, 12.4 Hz, 1H), 1.47-1.35 (m, 1H), 1.29 (t, J=7.1 Hz, 3H), 1.14 (t, J=6.9 Hz, 3H).

(R)-4-((3-(4,4-difluoropiperidine-1-carbonyl)piperidin-1-yl)sulfonyl)-N,N-diethylbenzamide (DX3-203)

To a solution of 43 (25 mg, 0.068 mmol) and HATU (39 mg, 0.102 mmol) in DMF (1 mL) was added 4,4-difluoropiperidine (8.2 mg, 0.068 mmol) and DIEA (26 mg, 0.204 mmol). The mixture was stirred at room temperature overnight. The mixture was then diluted with EtOAc, washed with brine, dried over anhydrous $Na_2SO_4$, filtered and concentrated. The residue was purified with flash chromatography (10% MeOH in DCM) to give DX3-203 as a white solid (18 mg, 32%). $^1H$ NMR (300 MHz, $CDCl_3$) δ 7.81 (d, J=8.1 Hz, 2H), 7.54 (d, J=8.2 Hz, 2H), 3.93-3.81 (m, 2H), 3.78-3.52 (m, 6H), 3.30-3.16 (m, 2H), 2.86 (tt, J=11.2, 3.4 Hz, 1H), 2.56 (t, J=11.4 Hz, 1H), 2.29 (td, J=11.9, 2.8 Hz, 1H), 2.13-1.79 (m, 6H), 1.78-1.64 (m, 1H), 1.55-1.37 (m, 1H), 1.28 (t, J=7.1 Hz, 3H), 1.14 (t, J=7.1 Hz, 3H).

Scheme 27.

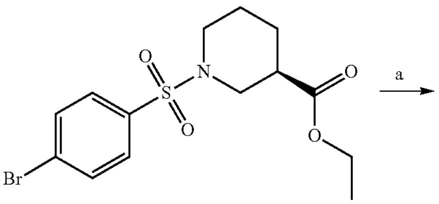

2b

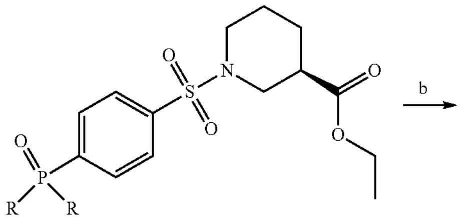

44a R = Me
44b R = Et

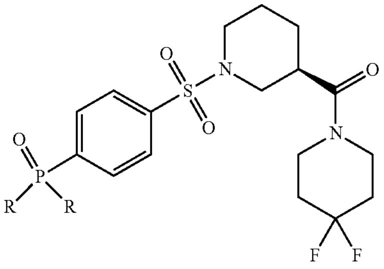

30 R = Me
31 R = Et

Reagents and conditions: a) dimethylphosphine oxide or diethylphosphine oxide, $Pd(OAc)_2$, XantPhos, $K_3PO_4$, DMF, 120° C.; b) i. LiOH, THF, $H_2O$, rt; ii. 4,4-difluoropiperidine, HATU, DIEA, DMF, rt.

Ethyl (R)-1-((4-(dimethylphosphoryl)phenyl)sulfonyl)piperidine-3-carboxylate (44a)

To a suspension of 2b (60 mg, 0.16 mmol), dimethylphosphine oxide (14 mg, 0.18 mmol) and $K_3PO_4$ (0.19 mmol) in DMF (4 mL) was added $Pd(OAc)_2$ (1.8 mg, 0.008 mmol) and XantPhos (5.6 mg, 0.0096 mmol) under argon. The mixture was heated at 120° C. under argon for 5 h. The mixture was then partitioned between EtOAc and water, and the organic layer was separated, washed with brine, dried over anhydrous $Na_2SO_4$, filtered and concentrated. The residue was purified with silica chromatography (DCM: MeOH=10:1) to give 44a as a white solid (51 mg, 88%). $^1H$ NMR (300 MHz, $CDCl_3$) δ 7.86-7.66 (m, 4H), 3.97 (q, J=7.1 Hz, 2H), 3.64 (d, J=7.4 Hz, 1H), 3.43 (dt, J=11.8, 4.1 Hz, 1H), 2.53-2.36 (m, 2H), 2.27 (td, J=11.2, 3.0 Hz, 1H), 1.64 (d, J=13.1 Hz, 7H), 1.58-1.37 (m, 1H), 1.35-1.16 (m, 1H), 1.09 (t, J=7.1 Hz, 3H). LC-MS (ESI) m/z 396.0 $[M+Na]^+$.

Ethyl (R)-1-((4-(diethylphosphoryl)phenyl)sulfonyl) piperidine-3-carboxylate (44b)

Using a similar procedure as described for 44a from 2b (80 mg, 0.21 mmol) and diethylphosphine oxide (25 mg, 0.23 mmol), white solid (80 mg, 95%). $^1$H NMR (300 MHz, $CDCl_3$) δ 7.88 (d, J=6.2 Hz, 4H), 4.13 (q, J=7.1 Hz, 2H), 3.85 (d, J=8.5 Hz, 1H), 3.70-3.58 (m, 1H), 2.67-2.53 (m, 2H), 2.41 (td, J=11.4, 3.1 Hz, 1H), 2.12-1.85 (m, 5H), 1.89-1.75 (m, 1H), 1.75-1.56 (m, 1H), 1.50-1.34 (m, 1H), 1.25 (t, J=7.1 Hz, 3H), 1.21-1.05 (m, 6H). LC-MS (ESI) m/z 424.1 $[M+Na]^+$.

(R)-(4,4-Difluoropiperidin-1-yl)(1-((4-(dimethylphosphoryl)phenyl)sulfonyl)piperidin-3-yl)methanone (DX3-214)

Using a similar procedure as described for 34 from 44a (19 mg, 0.052 mmol) and 4,4-difluoropiperidine (7.6 mg, 0.063 mmol), white solid (19 mg, 83%). $^1$H NMR (300 MHz, $CDCl_3$) δ 7.99-7.86 (m, 4H), 3.87 (t, J=11.3 Hz, 2H), 3.80-3.59 (m, 4H), 2.90 (t, J=11.7 Hz, 1H), 2.53 (t, J=11.3 Hz, 1H), 2.29 (td, J=11.8, 2.7 Hz, 1H), 2.14-1.90 (m, 4H), 1.89-1.72 (m, 9H), 1.51-1.40 (m, 1H). LC-MS (ESI) m/z 470.9 $[M+Na]^+$. Purity: 97.3%.

(R)-(1-((4-(diethylphosphoryl)phenyl)sulfonyl)piperidin-3-yl)(4,4-difluoropiperidin-1-yl)methanone (DX3-216)

Using a similar procedure as described for 34 from 44b (16 mg, 0.040 mmol) and 4,4-difluoropiperidine (5.8 mg, 0.048 mmol), white solid (18 mg, 95%). $^1$H NMR (300 MHz, $CDCl_3$) δ 7.89 (d, J=6.2 Hz, 4H), 3.96-3.83 (m, 2H), 3.78-3.60 (m, 4H), 3.51-3.42 (m, 1H), 2.96-2.83 (m, 1H), 2.56 (t, J=11.3 Hz, 1H), 2.30 (t, J=11.8 Hz, 1H), 2.18-1.87 (m, 9H), 1.79-1.70 (m, 1H), 1.55-1.41 (m, 1H), 1.26-1.06 (m, 6H). LC-MS (ESI) m/z 499.0 $[M+Na]^+$. Purity: 99.1%.

Example II

MTT Assay for the Evaluation of Cancer Cell Growth Inhibition

Measurement of cancer cell growth inhibition of the compounds of invention Cytotoxicity of the compounds was assessed by MTT assay. In brief, MIA PaCa-2 cells or BxPc3 cells were seeded in 96-well microtitre plates at density of 200 cells/well. After overnight attachment, cells were treated with compounds at indicated concentration. After 7 days of treatment, MTT solution (3 mg/ml, 20 μl) was added to each well and cells were incubated for 3 h at 37° C. After incubation, media from each well was removed and the dark blue formazan crystals formed by live cells were dissolved in DMSO (100 ml per well). The absorbance intensity was measured at 570 nm on a microplate reader (Molecular Devices, Sunnyvale, CA, USA). The half maximal inhibitory concentration ($IC_{50}$) value were calculated using 4 or 6 dots curve plotted with Cumulative Gaussian equation or Log(inhibitor) vs. response equation in GraphPad Prism. The results are listed in Table 2.

TABLE 2

| Compound | MiaPaCa $IC_{50}$ (μM) | BxPC-3 $IC_{50}$ (μM) |
|---|---|---|
| DX2-201 | 0.37 ± 0.06 | 0.63 ± 0.24 |
| DX2-202 | 6.08 ± 0.76 | 6.8 ± 2.1 |

TABLE 2-continued

| Compound | MiaPaCa $IC_{50}$ (μM) | BxPC-3 $IC_{50}$ (μM) |
|---|---|---|
| DX2-225 | 12.09 ± 3.85 | 13.35 ± 4.58 |
| DX2-230 | 3.92 ± 0.89 | 3.88 ± 0.57 |
| DX2-242 | 2.34 ± 1.01 | 13.82 ± 3.58 |
| DX2-263 | 0.3 ± 0.13 | 0.35 ± 0.06 |
| DX2-265 | 2.87 ± 0.49 | 3.29 ± 0.74 |
| DX2-275 | 0.93 ± 0.36 | 1.61 ± 0.37 |
| DX2-293 | 1.3 ± 0.45 | 1.37 ± 0.52 |
| DX3-3 | 4.12 ± 2.44 | 2.29 ± 0.7 |
| DX3-14B-P1 | 1.35 ± 0.59 | 3.29 ± 0.06 |
| DX3-39 | 5.1 ± 1.29 | 6.3 ± 1.44 |
| DX3-44 | 4.7 ± 1.92 | 6.77 ± 0.52 |
| DX3-47 | 2.94 ± 0.32 | 4.92 ± 1.94 |
| DX3-49B | 3.65 ± 1.68 | 8.27 ± 2.52 |
| DX3-78B | 0.28 | 0.62 |
| DX3-90 | 2.55 ± 0.15 | 3.59 ± 1.39 |
| DX3-107B | 0.75 ± 0.08 | 2.27 ± 0.61 |
| DX3-115 | 1.04 ± 0.45 | 1.23 ± 0.79 |
| DX3-119 | 0.13 ± 0.04 | 0.33 ± 0.12 |
| DX3-120 | 0.43 ± 0.18 | 1.1 ± 0.16 |
| DX3-122B | 4.12 ± 1.16 | 2.86 ± 3.14 |
| DX3-121B | 0.35 ± 0.02 | 0.79 ± 40.1 |
| DX3-125 | 0.94 | 3.72 |

Example III

Nascent RNA sequencing (Bru-seq) results showed genes in metabolism pathways clustered after 4 hours of DX2-201 treatment. The glycolysis pathway was dramatically upregulated and the oxidative phosphorylation was significantly downregulated. Consistent with this observation, there are also massive metabolite pathways influenced including starch and sucrose metabolism, glycolysis and gluconeogenesis, purine metabolism, pyrimidine metabolism, N-glycan biosynthesis, etc. The overall metabolism change suggested the suppression on oxidative phosphorylation and upregulation in glycolysis upon DX2-201 treatment, subsequently causing the imbalanced ATP and biomass production. As a result of that, DNA repair and mismatch repair gene sets were downregulated, which might be related to the shortage of biomass. In addition, myc target gene sets and E2F target gene set were downregulated, reflecting DX2-201's inhibition on cell growth.

Several other disease related gene sets were also significantly changed, including Parkinson's disease, Huntington's disease and Alzheimer's diseases, which might be also related to the metabolism change, suggesting these compounds' potential to treat certain neurodegenerative diseases.

Proteomic results also showed TCA cycle suppressed while hypoxia pathways, bile acid metabolism, cholesterol homoeostasis and glycolysis upregulated after DX2-201 treatment. Several proteins participating in energy metabolism were dramatically changed. Glycerol kinase is the top upregulated gene with 3-fold change in 24 hours indicating the upregulated usage of glycerol as alternative energy source. Serine protease 23, nuclear receptor family 2 group F member 6, protein NDRG1 were all upregulated. Interestingly, an important enzyme involved in TCA cycle, dihydrolilpoyl dehudrogenase, was downregulated with a fold change of 0.684, suggesting the TCA cycle function was impaired by DX2-201 treatment.

TABLE 3

| Top 25 protein-coding genes downregulated in UM16 cell line treated with DX2-201 (5 μM, 4 hours, Bru-seq) | | |
|---|---|---|
| Genes | Fold change | Comments |
| ARRDC4 | 0.431505 | arrestin domain containing 4 |
| SCARNA5 | 0.43758 | small Cajal body-specific RNA 5; small Cajal body-specific RNA 6 |
| INTS5 | 0.45152 | integrator complex subunit 5 |
| G0S2 | 0.466649 | G0/G1switch 2 |
| HLF | 0.472697 | Hepatic Leukemia Factor |
| POLR2J4 | 0.477451 | polymerase (RNA) II (DNA directed) polypeptide J4, pseudogene |
| TXNIP | 0.499674 | Thioredoxin Interacting Protein |
| DGAT2 | 0.512885 | diacylglycerol O-acyltransferase homolog 2 |
| SNHG21 | 0.549732 | Small Nucleolar RNA Host Gene 21 |
| FAM200A | 0.55948 | chromosome 7 open reading frame 38 |
| RRS1 | 0.568556 | Ribosome biogenesis regulatory protein homolog |
| PCED1A | 0.576043 | PC-esterase domain containing 1A |
| A2ML1 | 0.582029 | alpha-2-macroglobulin like 1 |
| PLLP | 0.584318 | plasma membrane proteolipid (plasmolipin) |
| FAM86HP | 0.594645 | family with sequence similarity 86 member H |
| SNORA62 | 0.596836 | small nucleolar RNA, H/ACA box 62; small nucleolar RNA, H/ACA box 6 |
| GGCT | 0.601165 | gamma-glutamyl cyclotransferase |
| SNORA71C | 0.602279 | small nucleolar RNA, H/ACA box 71C |
| DPAGT1 | 0.603372 | dolichyl-phosphate (UDP-N-acetylglucosamine) N-acetylglucosaminephosphotransferase 1 (GlcNAc-1-P transferase) |
| BDKRB2 | 0.604389 | Bradykinin Receptor B2 |
| FAM86C1 | 0.605286 | Family With Sequence Similarity 86 Member C1 |
| FOXA2 | 0.607488 | Forkhead Box A2 |
| TMED1 | 0.623178 | Transmembrane P24 Trafficking Protein 1 |
| SLC5A6 | 0.623446 | Solute Carrier Family 5 Member 6 |
| L3HYPDH | 0.630135 | Trans-L-3-Hydroxyproline Dehydratase |

TABLE 4

| Top 25 protein-coding genes upregulated in UM16 cell line treated with DX2-201 (5 μM, 4 hours, Bru-seq) | | |
|---|---|---|
| Genes | Fold change | Comments |
| NDRG1 | 2.874353 | N-myc downstream regulated 1 |
| ARG2 | 2.569327 | arginase, type 11 |
| KLHL24 | 2.336295 | kelch-like 24 (Drosophila) |
| ANKRD37 | 2.182391 | ankyrin repeat domain 37 |
| FOXO6 | 1.954496 | forkhead box protein O6 |
| RNF122 | 1.914821 | ring finger protein 122 |
| SOX12 | 1.90308 | SRY (sex determining region Y)-box 12 |
| MXD4 | 1.81177 | MAX dimerization protein 4 |
| HDAC5 | 1.811478 | histone deacetylase 5 |
| MXI1 | 1.78479 | MAX interactor 1 |
| PDK1 | 1.778718 | pyruvate dehydrogenase kinase, isozyme 1 |
| ERRFI1 | 1.770078 | ERBB receptor feedback inhibitor 1 |
| ZNF546 | 1.756829 | zinc finger protein 546 |
| PRDM1 | 1.748233 | PR domain containing 1, with ZNF domain |
| VLDLR | 1.741318 | very low density lipoprotein receptor |
| UPRT | 1.740434 | uracil phosphoribosyltransferase (FUR1) homolog (*S. cerevisiae*) |
| LOXL4 | 1.730349 | lysyl oxidase-like 4 |
| ARHGAP30 | 1.72799 | Rho GTPase activating protein 30 |
| BNIP3L | 1.72291 | BCL2/adenovirus E1B 19 kDa interacting protein 3-like |
| ARRDC3 | 1.707402 | arrestin domain containing 3 |
| YPEL1 | 1.70622779 | Yippee Like 1 |
| PPP1R3C | 1.69920866 | Protein Phosphatase 1 Regulatory Subunit 3C |

TABLE 4-continued

| Top 25 protein-coding genes upregulated in UM16 cell line treated with DX2-201 (5 μM, 4 hours, Bru-seq) | | |
|---|---|---|
| Genes | Fold change | Comments |
| CREBRF | 1.67605395 | CREB3 Regulatory Factor |
| SEMA3B | 1.66808745 | Semaphorin 3B |
| CCNG2 | 1.66756367 | Cyclin G2 |

TABLE 5

| Top 25 non-coding RNA downregulated in UM16 cell line treated with DX2-201 (5 μM, 4 hours, Bru-seq) | | |
|---|---|---|
| Genes | Fold change | Comments |
| AL096870.2 | 0.024652 | processed_transcript |
| Y_RNA | 0.028761 | misc_RNA |
| RNU6-398P | 0.034513 | snRNA |
| RNU6-122P | 0.043142 | snRNA |
| TERC | 0.043142 | lincRNA |
| RNU6-548P | 0.057523 | snRNA |
| MIR5000 | 0.057523 | miRNA |
| RNU1-73P | 0.093812 | snRNA |
| RNU1-19P | 0.156354 | snRNA |
| RNU6-519P | 0.156354 | snRNA |
| AC092916.2 | 0.170566 | processed_pseudogene |
| C1orf50 | 0.187622 | proteincoding |
| MIR545 | 0.187622 | miRNA |
| Z99127.3 | 0.187622 | processed_pseudogene |
| BX679664.2 | 0.187622 | processed_pseudogene |
| RN7SL128P | 0.187622 | misc_RNA |
| AC008521.2 | 0.187622 | processed_pseudogene |
| RN7SL388P | 0.208469 | misc_RNA |
| RN7SL589P | 0.216487 | misc_RNA |
| AC091133.4 | 0.234527 | processed_pseudogene |
| AC019257.2 | 0.234527 | lincRNA |
| SNORA73 | 0.234528 | snoRNA |
| ZBTB40-IT1 | 0.234528 | sense_intronic |
| RN7SL833P | 0.234528 | misc_RNA |
| AC106037.1 | 0.234528 | sense_intronic |

TABLE 6

| Top 25 non-coding RNA upregulated in UM16 cell line treated with DX2-201(5 μM, 4 hours, Bru-seq) | | |
|---|---|---|
| Genes | Fold change | Comments |
| RNU6-1272P | 25.49882 | snRNA |
| RNU6-182P | 20.39897 | snRNA |
| Y_RNA | 15.29913 | misc_RNA |
| DPRXP4 | 3.189539 | processed_pseudogene |
| RNA5SP379 | 2.81426 | rRNA |
| RNU6-564P | 2.81426 | snRNA |
| RNU6-531P | 2.81426 | snRNA |
| AC034198.2 | 2.345256 | antisense_RNA |
| AC007952.4 | 2.345252 | lincRNA |
| AL136982.3 | 2.217333 | sense_intronic |
| AP001527.2 | 2.217333 | lincRNA |
| HMGN1P15 | 2.110723 | processed_pseudogene |
| AC139887.1 | 2.06382 | antisense_RNA |
| AC008687.3 | 2.032552 | lincRNA |
| AC007686.1 | 2.010217 | processed_pseudogene |
| AL161729.3 | 1.993466 | lincRNA |
| EIF5AP3 | 1.876207 | processed_pseudogene |
| AL645939.5 | 1.876196 | lincRNA |
| SNORD124 | 1.876191 | snoRNA |
| RNY3P2 | 1.876182 | misc_RNA |

TABLE 6-continued

Top 25 non-coding RNA upregulated in UM16 cell line treated with DX2-201(5 μM, 4 hours, Bru-seq)

| Genes | Fold change | Comments |
|---|---|---|
| RNU6-396P | 1.876182 | snRNA |
| AL627171.1 | 1.841464 | lincRNA |
| AC105020.4 | 1.782395 | antisense_RNA |
| AP003168.2 | 1.688585 | sense_intronic |
| AP001619.1 | 1.620359 | sense_intronic |

TABLE 7

GSEA results of the upregulated hallmark pathways in UM16 cell line treated with DX2-201 (5 μM, 4 hours, Bru-seq)

| NAME | SIZE | ES | NES | NOM p-val | FDR q-val | FWER p-val |
|---|---|---|---|---|---|---|
| HALLMARK_HYPOXIA | 131 | 0.6294 | 2.8139 | 0 | 0.0000 | 0 |
| HALLMARK_CHOLESTEROL_HOMEOSTASIS | 58 | 0.4969 | 1.9354 | 0 | 0.0043 | 0.005 |
| HALLMARK_GLYCOLYSIS | 152 | 0.4109 | 1.8782 | 0 | 0.0054 | 0.009 |
| HALLMARK_APOPTOSIS | 119 | 0.3812 | 1.6931 | 0 | 0.0232 | 0.056 |
| HALLMARK_UV_RESPONSE_DN | 110 | 0.3784 | 1.6434 | 0 | 0.0304 | 0.091 |
| HALLMARK_HEME_METABOLISM | 137 | 0.3641 | 1.6288 | 0 | 0.0296 | 0.104 |
| HALLMARK_P53_PATHWAY | 156 | 0.3403 | 1.5682 | 0 | 0.0408 | 0.16 |
| HALLMARK_ESTROGEN_RESPONSE_LATE | 133 | 0.3437 | 1.5630 | 0 | 0.0370 | 0.166 |
| HALLMARK_IL2_STAT5_SIGNALING | 122 | 0.3402 | 1.5174 | 0.0027 | 0.0488 | 0.24 |
| HALLMARK_MYOGENESIS | 81 | 0.3657 | 1.5149 | 0.0160 | 0.0449 | 0.246 |
| HALLMARK_TNFA_SIGNALING_VIA_NFKB | 146 | 0.3199 | 1.4745 | 0.0026 | 0.0556 | 0.32 |
| HALLMARK_MITOTIC_SPINDLE | 190 | 0.3104 | 1.4709 | 0.0026 | 0.0530 | 0.33 |
| HALLMARK_KRAS_SIGNALING_DN | 45 | 0.3965 | 1.4318 | 0.0539 | 0.0675 | 0.415 |
| HALLMARK_HEDGEHOG_SIGNALING | 17 | 0.4848 | 1.3854 | 0.0981 | 0.0884 | 0.538 |
| HALLMARK_ANDROGEN_RESPONSE | 84 | 0.3155 | 1.3002 | 0.0550 | 0.1543 | 0.77 |
| HALLMARK_FATTY_ACID_METABOLISM | 114 | 0.2942 | 1.2729 | 0.0622 | 0.1755 | 0.831 |
| HALLMARK_INFLAMMATORY_RESPONSE | 91 | 0.2995 | 1.2667 | 0.0855 | 0.1740 | 0.847 |
| HALLMARK_XENOBIOTIC_METABOLISM | 105 | 0.2890 | 1.2573 | 0.0829 | 0.1775 | 0.87 |
| HALLMARK_BILE_ACID_METABOLISM | 57 | 0.3249 | 1.2479 | 0.1200 | 0.1785 | 0.883 |
| HALLMARK_MTORC1_SIGNALING | 177 | 0.2680 | 1.2451 | 0.0554 | 0.1726 | 0.887 |
| HALLMARK_ALLOGRAFT_REJECTION | 82 | 0.2962 | 1.2241 | 0.1200 | 0.1877 | 0.916 |

NES = Normalized Enrichment Score, FDR = False Discovery Rate, FWER = Family-Wise Error Rate.

Cutoff: FDR < 0.2

TABLE 8

GSEA results of the downregulated hallmark pathways in UM16 cell line treated with DX2-201 (5 μM, 4 hours, Bru-seq)

| NAME | SIZE | ES | NES | NOM p-val | FDR q-val | FWER p-val |
|---|---|---|---|---|---|---|
| HALLMARK_MYC_TARGETS_V1 | 189 | −0.5426 | −2.4192 | 0.0000 | 0.0000 | 0 |
| HALLMARK_MYC_TARGETS_V2 | 53 | −0.6265 | −2.2565 | 0.0000 | 0.0000 | 0 |
| HALLMARK_DNA_REPAIR | 127 | −0.4085 | −1.7322 | 0.0016 | 0.0104 | 0.049 |
| HALLMARK_E2F_TARGETS | 195 | −0.3804 | −1.7010 | 0.0000 | 0.0103 | 0.065 |
| HALLMARK_OXIDATIVE_PHOSPHORYLATION | 176 | −0.3812 | −1.6882 | 0.0000 | 0.0092 | 0.073 |
| HALLMARK_ANGIOGENESIS | 16 | −0.5078 | −1.4124 | 0.0852 | 0.0973 | 0.635 |
| HALLMARK_UNFOLDED_PROTEIN_RESPONSE | 97 | −0.3254 | −1.3390 | 0.0521 | 0.1481 | 0.832 |

NES = Normalized Enrichment Score, FDR = False Discovery Rate, FWER = Family-Wise Error Rate.

Cutoff: FDR < 0.2

TABLE 9

GSEA results of the upregulated KEGG pathways in UM16 cell line treated with DX2-201 (5 μM, 4 hours, Bru-seq)

| NAME | SIZE | ES | NES | NOM p-val | FDR q-val | FWER p-val |
|---|---|---|---|---|---|---|
| KEGG_STARCH_AND_SUCROSE_METABOLISM | 17 | 0.7356 | 2.1177 | 0.0000 | 0.0026 | 0.002 |
| KEGG_DORSO_VENTRAL_AXIS_FORMATION | 17 | 0.6614 | 1.9145 | 0.0000 | 0.0296 | 0.044 |
| KEGG_GLYCOLYSIS_GLUCONEOGENESIS | 33 | 0.5362 | 1.8482 | 0.0069 | 0.0432 | 0.095 |
| KEGG_REGULATION_OF_AUTOPHAGY | 18 | 0.5972 | 1.7250 | 0.0151 | 0.1086 | 0.276 |
| KEGG_LEISHMANIA_INFECTION | 31 | 0.5017 | 1.6760 | 0.0097 | 0.1288 | 0.382 |
| KEGG_TYPE_II_DIABETES_MELLITUS | 22 | 0.5316 | 1.6335 | 0.0178 | 0.1482 | 0.495 |
| KEGG_RENAL_CELL_CARCINOMA | 53 | 0.4210 | 1.6054 | 0.0069 | 0.1615 | 0.577 |

NES = Normalized Enrichment Score, FDR = False Discovery Rate, FWER = Family-Wise Error Rate.
Cutoff: FDR < 0.2

TABLE 10

GSEA results of the downregulated KEGG pathways in UM16 cell line treated with DX2-201 (5 μM, 4 hours, Bru-seq)

| NAME | SIZE | ES | NES | NOM p-val | FDR q-val | FWER p-val |
|---|---|---|---|---|---|---|
| KEGG_RIBOSOME | 83 | −0.6266 | −2.4526 | 0.0000 | 0.0000 | 0.0000 |
| KEGG_PURINE_METABOLISM | 95 | −0.4914 | −2.0380 | 0.0000 | 0.0011 | 0.0030 |
| KEGG_RNA_POLYMERASE | 25 | −0.6348 | −1.9613 | 0.0018 | 0.0027 | 0.0100 |
| KEGG_DNA_REPLICATION | 34 | −0.5795 | −1.9358 | 0.0000 | 0.0029 | 0.0150 |
| KEGG_PYRIMIDINE_METABOLISM | 77 | −0.4987 | −1.9279 | 0.0000 | 0.0028 | 0.0180 |
| KEGG_PROTEASOME | 36 | −0.5628 | −1.9164 | 0.0000 | 0.0030 | 0.0240 |
| KEGG_MISMATCH_REPAIR | 21 | −0.6381 | −1.8751 | 0.0018 | 0.0053 | 0.0480 |
| KEGG_SPLICEOSOME | 113 | −0.4510 | −1.8728 | 0.0000 | 0.0048 | 0.0500 |
| KEGG_N_GLYCAN_BIOSYNTHESIS | 40 | −0.5360 | −1.8440 | 0.0000 | 0.0063 | 0.0740 |
| KEGG_OXIDATIVE_PHOSPHORYLATION | 87 | −0.4451 | −1.7650 | 0.0000 | 0.0144 | 0.1780 |
| KEGG_PARKINSONS_DISEASE | 82 | −0.4446 | −1.7382 | 0.0000 | 0.0173 | 0.2340 |
| KEGG_HUNTINGTONS_DISEASE | 126 | −0.4035 | −1.7040 | 0.0000 | 0.0215 | 0.3030 |
| KEGG_ALZHEIMERS_DISEASE | 108 | −0.3872 | −1.6021 | 0.0000 | 0.0524 | 0.5950 |
| KEGG_NUCLEOTIDE_EXCISION_REPAIR | 41 | −0.4603 | −1.5835 | 0.0175 | 0.0579 | 0.6550 |
| KEGG_VIBRIO_CHOLERAE_INFECTION | 37 | −0.4430 | −1.4689 | 0.0290 | 0.1376 | 0.9260 |
| KEGG_AMINOACYL_TRNA_BIOSYNTHESIS | 39 | −0.4260 | −1.4417 | 0.0430 | 0.1593 | 0.9680 |

NES = Normalized Enrichment Score, FDR = False Discovery Rate, FWER = Family-Wise Error Rate.
Cutoff: FDR < 0.2

TABLE 11

GSEA results of the upregulated GO pathways in UM16 cell line treated with DX2-201 (5 μM, 4 hours, Bru-seq)

| NAME | SIZE | ES | NES | NOM p-val | FDR q-val | FWER p-val |
|---|---|---|---|---|---|---|
| GO_NUCLEOTIDE_PHOSPHORYLATION | 33 | 0.5920 | 2.0727 | 0.0000 | 0.0224 | 0.131 |
| GO_RIBONUCLEOSIDE_DIPHOSPHATE_METABOLIC_PROCESS | 41 | 0.5746 | 2.0919 | 0.0000 | 0.0225 | 0.1 |
| GO_NADH_METABOLIC_PROCESS | 24 | 0.6704 | 2.0814 | 0.0023 | 0.0235 | 0.121 |
| GO_ATP_GENERATION_FROM_ADP | 23 | 0.6848 | 2.0929 | 0.0000 | 0.0270 | 0.1 |
| GO_ADP_METABOLIC_PROCESS | 29 | 0.6343 | 2.1062 | 0.0000 | 0.0271 | 0.081 |
| GO_GLUCOSE_CATABOLIC_PROCESS | 18 | 0.7209 | 2.1191 | 0.0023 | 0.0273 | 0.062 |
| GO_PYRUVATE_METABOLIC_PROCESS | 36 | 0.6035 | 2.1281 | 0.0000 | 0.0324 | 0.049 |
| GO_HEXOSE_CATABOLIC_PROCESS | 26 | 0.6548 | 2.1301 | 0.0000 | 0.0622 | 0.047 |
| GO_MONOSACCHARIDE_CATABOLIC_PROCESS | 32 | 0.5791 | 1.9771 | 0.0000 | 0.0716 | 0.385 |
| GO_RESPONSE_TO_OXYGEN_LEVELS | 179 | 0.4230 | 1.9612 | 0.0000 | 0.0782 | 0.449 |
| GO_NEGATIVE_REGULATION_OF_FAT_CELL_DIFFERENTIATION | 23 | 0.6098 | 1.9052 | 0.0000 | 0.0995 | 0.676 |

NES = Normalized Enrichment Score, FDR = False Discovery Rate, FWER = Family-Wise Error Rate.
Cutoff: FDR < 0.1.

TABLE 12

GSEA results of the top 25 downregulated GO pathways in UM16 cell line treated with DX2-201 (5 μM, 4 hours, Bru-seq)

| NAME | SIZE | ES | NES | NOM p-val | FDR q-val | FWER p-val |
|---|---|---|---|---|---|---|
| GO_RIBOSOME_BIOGENESIS | 270 | −0.616 | −2.869 | 0 | 0 | 0 |
| GO_NCRNA_PROCESSING | 329 | −0.594 | −2.802 | 0 | 0 | 0 |
| GO_RRNA_METABOLIC_PROCESS | 226 | −0.604 | −2.757 | 0 | 0 | 0 |
| GO_RIBONUCLEOPROTEIN_COMPLEX_BIOGENESIS | 383 | −0.552 | −2.663 | 0 | 0 | 0 |
| GO_RIBOSOME | 186 | −0.589 | −2.626 | 0 | 0 | 0 |
| GO_NCRNA_METABOLIC_PROCESS | 439 | −0.528 | −2.591 | 0 | 0 | 0 |
| GO_CYTOSOLIC_RIBOSOME | 99 | −0.626 | −2.548 | 0 | 0 | 0 |
| GO_TRANSLATIONAL_INITIATION | 134 | −0.590 | −2.521 | 0 | 0 | 0 |
| GO_RIBOSOMAL_SUBUNIT | 142 | −0.581 | −2.491 | 0 | 0 | 0 |
| GO_ESTABLISHMENT_OF_PROTEIN_LOCAL-IZATION_TO_ENDOPLASMIC_RETICULUM | 97 | −0.589 | −2.417 | 0 | 0 | 0 |
| GO_STRUCTURAL_CONSTITUENT_OF_RIBOSOME | 172 | −0.539 | −2.395 | 0 | 0 | 0 |
| GO_MULTI_ORGANISM_METABOLIC_PROCESS | 132 | −0.557 | −2.388 | 0 | 0 | 0 |
| GO_RIBOSOMAL_SMALL_SUBUNIT_BIOGENESIS | 51 | −0.653 | −2.377 | 0 | 0 | 0 |
| GO_CYTOSOLIC_PART | 170 | −0.537 | −2.371 | 0 | 0 | 0 |
| GO_RRNA_BINDING | 50 | −0.650 | −2.367 | 0 | 0 | 0 |
| GO_PRERIBOSOME | 54 | −0.648 | −2.348 | 0 | 0 | 0 |
| GO_PROTEIN_LOCALIZATION_TO_ENDOPLASMIC_RETICULUM | 111 | −0.563 | −2.329 | 0 | 0 | 0 |
| GO_LARGE_RIBOSOMAL_SUBUNIT | 83 | −0.585 | −2.298 | 0 | 0 | 0 |
| GO_CYTOSOLIC_LARGE_RIBOSOMAL_SUBUNIT | 56 | −0.629 | −2.298 | 0 | 0 | 0 |
| GO_NUCLEOLAR_PART | 51 | −0.630 | −2.294 | 0 | 0 | 0 |
| GO_TRNA_PROCESSING | 89 | −0.559 | −2.240 | 0 | 3.79E−05 | 0.001 |
| GO_NUCLEAR_TRANSCRIBED_MRNA_CATABOLIC_PRO-CESS_NONSENSE_MEDIATED_DECAY | 113 | −0.539 | −2.231 | 0 | 3.62E−05 | 0.001 |
| GO_PEPTIDE_METABOLIC_PROCESS | 413 | −0.461 | −2.222 | 0 | 3.46E−05 | 0.001 |
| GO_MATURATION_OF_SSU_RRNA | 38 | −0.642 | −2.206 | 0 | 6.60E−05 | 0.002 |
| GO_AMIDE_BIOSYNTHETIC_PROCESS | 389 | −0.454 | −2.193 | 0 | 1.55E−04 | 0.005 |

NES = Normalized Enrichment Score, FDR = False Discovery Rate, FWER = Family-Wise Error Rate.
Cutoff: FDR < 0.1.

TABLE 13

GSEA results of the top 25 upregulated transcription factors in UM16 cell line treated with DX2-201 (5 μM, 4 hours, Bru-seq)

| NAME | SIZE | ES | NES | NOM p-val | FDR q-val | FWER p-val |
|---|---|---|---|---|---|---|
| FOXO4_01 | 134 | 0.464 | 2.069 | 0.000 | 0.014 | 0.007 |
| FOXO1_02 | 146 | 0.459 | 2.057 | 0.000 | 0.007 | 0.007 |
| FOXO4_02 | 128 | 0.454 | 2.000 | 0.000 | 0.007 | 0.011 |
| FREAC2_01 | 134 | 0.440 | 1.964 | 0.000 | 0.008 | 0.016 |
| AAAYWAACM_HFH4_01 | 122 | 0.431 | 1.896 | 0.000 | 0.013 | 0.033 |
| FOXO3_—01 | 126 | 0.417 | 1.860 | 0.000 | 0.015 | 0.046 |
| RTAAACA_FREAC2_01 | 499 | 0.344 | 1.816 | 0.000 | 0.025 | 0.083 |
| FAC1_01 | 124 | 0.394 | 1.751 | 0.000 | 0.043 | 0.157 |
| AP4_Q5 | 124 | 0.393 | 1.743 | 0.000 | 0.043 | 0.173 |
| HFH3_01 | 99 | 0.401 | 1.733 | 0.000 | 0.042 | 0.190 |
| FOXO1_01 | 126 | 0.384 | 1.732 | 0.000 | 0.039 | 0.191 |
| ATF1_Q6 | 122 | 0.383 | 1.701 | 0.000 | 0.053 | 0.264 |
| OCT_Q6 | 121 | 0.381 | 1.697 | 0.000 | 0.051 | 0.274 |
| TTANWNANTGGM_UNKNOWN | 27 | 0.511 | 1.686 | 0.007 | 0.051 | 0.295 |
| PAX2_02 | 132 | 0.374 | 1.664 | 0.000 | 0.061 | 0.366 |
| NKX62_Q2 | 102 | 0.387 | 1.663 | 0.003 | 0.058 | 0.368 |
| FREAC3_01 | 121 | 0.375 | 1.657 | 0.000 | 0.058 | 0.389 |
| E47_01 | 131 | 0.363 | 1.646 | 0.003 | 0.060 | 0.418 |
| YWATTWNNRGCT_UNKNOWN | 34 | 0.482 | 1.641 | 0.007 | 0.059 | 0.430 |
| AP4_Q6 | 92 | 0.377 | 1.607 | 0.000 | 0.078 | 0.537 |
| RYCACNNRNNRNCAG_UNKNOWN | 38 | 0.462 | 1.606 | 0.012 | 0.075 | 0.542 |
| HNF3_Q6 | 79 | 0.392 | 1.604 | 0.005 | 0.073 | 0.547 |
| FOXJ2_02 | 106 | 0.364 | 1.582 | 0.010 | 0.090 | 0.648 |
| OCT1_Q5_01 | 118 | 0.357 | 1.574 | 0.003 | 0.094 | 0.674 |
| AREB6_04 | 134 | 0.346 | 1.566 | 0.003 | 0.098 | 0.708 |

NES = Normalized Enrichment Score, FDR = False Discovery Rate, FWER = Family-Wise Error Rate.
Cutoff: FDR < 0.1

TABLE 14

GSEA results of the downregulated transcription factors in UM16 cell line treated with DX2-201 (5 µM, 4 hours, Bru-seq)

| NAME | SIZE | ES | NES | NOM p-val | FDR q-val | FWER p-val |
|---|---|---|---|---|---|---|
| MYCMAX_01 | 164 | −0.425 | −1.853 | 0.000 | 0.018 | 0.044 |
| MYC_Q2 | 115 | −0.429 | −1.792 | 0.000 | 0.022 | 0.107 |
| YY1_Q6 | 184 | −0.372 | −1.643 | 0.000 | 0.072 | 0.518 |
| E2F_Q6 | 173 | −0.352 | −1.565 | 0.002 | 0.078 | 0.833 |
| GGAANCGGAANY_UNKNOWN | 92 | −0.409 | −1.661 | 0.000 | 0.080 | 0.453 |
| E2F1_Q6 | 175 | −0.355 | −1.568 | 0.002 | 0.085 | 0.822 |
| E2F1_Q6_01 | 180 | −0.352 | −1.578 | 0.000 | 0.086 | 0.78 |
| NMYC_01 | 176 | −0.350 | −1.545 | 0.006 | 0.087 | 0.892 |
| E2F_03 | 178 | −0.360 | −1.597 | 0.000 | 0.097 | 0.704 |
| SGCGSSAAA_E2F1DP2_01 | 126 | −0.373 | −1.581 | 0.002 | 0.098 | 0.773 |

NES = Normalized Enrichment Score, FDR = False Discovery Rate, FWER = Family-Wise Error Rate.
Cutoff: FDR < 0.1

TABLE 15 cMap analysis results of top 25 similar compounds (5 µM, 4 hours, Bru-seq)

| Score | Name | Description |
|---|---|---|
| 99.68 | PAC-1 | Caspase activator |
| 99.65 | hinokitiol | Tyrosinase inhibitor |
| 99.47 | BMS-536924 | IGF-1 inhibitor |
| 99.44 | PP-30 | RAF inhibitor |
| 99.4 | WAY-170523 | Metalloproteinase inhibitor |
| 99.26 | AZ-628 | RAF inhibitor |
| 99.26 | SA-1478088 | −666 |
| 99.12 | TW-37 | BCL inhibitor |
| 99.08 | selumetinib | MEK inhibitor |
| 99.05 | VU-0418946-1 | HIF modulator |
| 98.98 | APHA-compound-8 | HDAC inhibitor |
| 98.91 | ISOX | HDAC inhibitor |
| 98.87 | NCH-51 | HDAC inhibitor |
| 98.87 | pyroxamide | HDAC inhibitor |
| 98.8 | geldanamycin | HSP inhibitor |
| 98.8 | PI-103 | MTOR inhibitor |
| 98.8 | WYE-354 | MTOR inhibitor |
| 98.77 | latrunculin-b | Actin polymerization inhibitor |
| 98.77 | WZ-3146 | EGFR inhibitor |
| 98.77 | ZSTK-474 | PI3K inhibitor |
| 98.73 | trichostatin-a | HDAC inhibitor |
| 98.73 | WT-171 | HDAC inhibitor |
| 98.73 | GSK-1059615 | PI3K inhibitor |
| 98.7 | U-0126 | MEK inhibitor |
| 98.7 | QL-XI-92 | DDR1 inhibitor |

TABLE 16 cMap analysis results of top 25 opposing compounds (5 µM, 4 hours, Bru-seq)

| Score | Name | Description |
|---|---|---|
| −99.89 | rucaparib | PARP inhibitor |
| −99.86 | SB-216763 | Glycogen synthase kinase inhibitor |
| −99.86 | PKCbeta-inhibitor | PKC inhibitor |
| −99.82 | kenpaullone | CDK inhibitor |
| −99.41 | androstenol | GABA receptor modulator |
| −99.33 | ascorbyl-palmitate | antioxidant |
| −99.3 | acetyl-geranygeranyl-cysteine | Inhibitor of methyl esterification of geranylgeranylated proteins |
| −99.22 | enzastaurin | PKC inhibitor |
| −99.13 | nifedipine | Calcium channel blocker |
| −99.12 | prostaglandin-a1 | HSP inducer |
| −99.01 | VX-222 | HCV inhibitor |
| −99.01 | danoprevir | HCV inhibitor |

TABLE 16-continued cMap analysis results of top 25 opposing compounds (5 µM, 4 hours, Bru-seq)

| Score | Name | Description |
|---|---|---|
| −98.81 | 2-aminopurine | Serine/threonine kinase inhibitor |
| −98.66 | maraviroc | CC chemokine receptor antagonist |
| −98.66 | valproic-acid | HDAC inhibitor |
| −98.63 | AT-9283 | JAK inhibitor |
| −98.29 | thiazolopyrimidine | CDC inhibitor |
| −97.96 | orantinib | FGFR inhibitor |
| −97.74 | GSK-3-inhibitor-IX | Glycogen synthase kinase inhibitor |
| −97.36 | SB-415286 | Glycogen synthase kinase inhibitor |
| −96.94 | olomoucine | CDK inhibitor |
| −96.83 | GW-843682X | PLK inhibitor |
| −96.79 | RHO-kinase-inhibitor-III[rockout] | Rho associated kinase inhibitor |
| −96.75 | esmolol | Adrenergic receptor antagonist |
| −99.89 | rucaparib | PARP inhibitor |

TABLE 17 cMap analysis results of top 25 predicted gene knockdown (similar) (5 µM, 4 hours, Bru-seq)

| Score | Name | Description |
|---|---|---|
| 99.95 | ATP6V0C | ATPases/V-type |
| 99.95 | MYC | Basic helix-loop-helix proteins |
| 99.92 | SMC1A | Structural maintenance of chromosomes proteins |
| 99.76 | MST1R | Type X RTKs: HGF (hepatocyte growth factor) receptor family |
| 99.68 | SFPQ | RNA binding motif (RRM) containing |
| 99.68 | STK3 | MST subfamily |
| 99.66 | SERINC3 | — |
| 99.63 | ME1 | — |
| 99.44 | RRM1 | Ribonucleoside-diphosphate reductases |
| 99.37 | TESK1 | TESK subfamily |
| 99.25 | ADAM15 | ADAM metallopeptidase domain containing |
| 99.21 | PXN | — |
| 99.12 | MDH2 | — |
| 99.08 | OGG1 | — |
| 98.95 | AP2M1 | — |
| 98.69 | RANBP9 | — |
| 98.5 | NCOA3 | Histone acetyltransferases |
| 98.46 | NCOA4 | — |

TABLE 17-continued

| cMap analysis results of top 25 predicted gene knockdown (similar) (5 μM, 4 hours, Bru-seq) | | |
|---|---|---|
| Score | Name | Description |
| 98.31 | ARID4B | — |
| 98.25 | PTP4A1 | Protein tyrosine phosphatases/ Class I Cys-based PTPs:PRLs |
| 97.93 | CCND3 | — |
| 97.77 | TNFAIP1 | BTB/POZ domain containing |
| 97.77 | COX4I1 | Mitochondrial respiratory chain complex |
| 97.76 | TTR | — |
| 97.55 | MYD88 | — |

TABLE 18

| cMap analysis results of top 25 predicted knockdown (opposing) (5 μM, 4 hours, Bru-seq) | | |
|---|---|---|
| Score | Name | Description |
| −99.92 | DHX8 | DEAH-boxes |
| −99.87 | IFNGR1 | Interferon receptor family |
| −99.71 | LOXL1 | — |
| −99.68 | SIAH2 | — |
| −99.58 | SLC16A6 | SLC16 family of monocarboxylate transporters |
| −99.48 | PAFAH1B2 | — |
| −99.34 | ADAM10 | ADAM metallopeptidase domain containing |
| −99.32 | RPS6KB2 | p70 subfamily |
| −99.13 | BMI1 | Polycomb group ring fingers |
| −99.03 | ATF1 | basic leucine zipper proteins |
| −98.95 | ABCA5 | ATP binding cassette transporters/subfamily A |
| −98.86 | CP | — |
| −98.44 | INS | — |
| −98.24 | TNFRSF19 | Tumour necrosis factor (TNF) receptor family |
| −98.11 | RASSF5 | — |
| −97.98 | RCHY1 | RING-type (C3HC4) zinc fingers |
| −97.84 | CREBBP | Chromatin-modifying enzymes/ K-acetyltransferases |
| −97.77 | TCF7L2 | — |
| −97.76 | RPL7 | L ribosomal proteins |
| −97.75 | DNAJC15 | Heat shock proteins/DNAJ (HSP40) |
| −97.62 | KBTBD2 | BTB/POZ domain containing |
| −97.55 | PAFAH1B1 | WD repeat domain containing |
| −97.54 | RASD1 | — |
| −97.46 | NIPSNAP1 | — |
| −97.4 | SCAP | WD repeat domain containing |

TABLE 19

| cMap analysis results of top 25 predicted gene overexpression (similar) (5 μM, 4 hours, Bru-seq) | | |
|---|---|---|
| Score | Name | Description |
| 99.72 | EBF1 | — |
| 99.49 | LIG1 | — |
| 99.26 | PAX8 | Paired boxes |
| 98.94 | KLF6 | Kruppel-like transcription factors |
| 98.33 | IFNB1 | Interferons |
| 98.15 | TAF13 | — |
| 98.02 | MEIS2 | Homeoboxes/TALE class |
| 97.93 | CDX2 | Homeoboxes/ANTP class: HOXL subclass |
| 97.92 | OVOL2 | Zinc fingers, C2H2-type |
| 97.87 | UGCG | Glycosyltransferase family 2 domain containing |

TABLE 19-continued

| cMap analysis results of top 25 predicted gene overexpression (similar) (5 μM, 4 hours, Bru-seq) | | |
|---|---|---|
| Score | Name | Description |
| 97.69 | SOX2 | SRY (sex determining region Y)-boxes |
| 97.22 | SATB2 | Homeoboxes/CUT class |
| 96.78 | ELK1 | ETS Transcription Factors |
| 95.94 | HOXC9 | Homeoboxes/ANTP class: HOXL subclass |
| 95.9 | HOXB13 | Homeoboxes/ANTP class: HOXL subclass |
| 95.83 | EIF4E3 | Translation Initiation Factor 4E |
| 95.45 | MXD3 | Basic helix-loop-helix proteins |
| 95.36 | VGLL4 | — |
| 95.32 | DUSP28 | Protein tyrosine phosphatases/ Class I Cys-based PTPs: Atypical dual specificity phosphatases |
| 94.75 | ESR1 | Estrogen receptors |
| 94.15 | VPS28 | — |
| 93.66 | TRIP10 | — |
| 92.82 | SOX10 | SRY (sex determining region Y)-boxes |
| 92.64 | DUSP6 | Protein tyrosine phosphatases/ Class I Cys-based PTPs:MAP kinase phosphatases |
| 92.56 | FBXW7 | F-boxes/WD-40 domains |

TABLE 20

| cMap analysis results of top 25 predicted gene overexpression (opposing) (5 μM, 4 hours, Bru-seq) | | |
|---|---|---|
| Score | Name | Description |
| −96.49 | TSPAN8 | Tetraspanins |
| −96.34 | CETN3 | EF-hand domain containing |
| −96.2 | PDGFRA | Type III RTKs: PDGFR, CSFR, Kit, FLT3 receptor family |
| −92.63 | CPD | Carboxypeptidase A |
| −92.05 | PHF13 | Zinc fingers, PHD-type |
| −91.81 | STX4 | — |
| −91.8 | UGT1A9 | UDP glucuronosyltransferases |
| −90.66 | FCGR2A | CD molecules |
| −90.09 | ENOSF1 | — |
| −87.85 | RUFY1 | Zinc fingers, FYVE domain containing |
| −86.48 | MMP14 | Matrix metallopeptidase |
| −85.99 | SSX3 | — |
| −85.63 | ERGIC2 | — |
| −85.06 | TMEM174 | — |
| −84.94 | PSMA3 | Proteasome subunits |
| −84.42 | EIF4EBP2 | — |
| −84.14 | PIAS1 | Zinc fingers, MIZ-type |
| −83.9 | PSMD3 | Proteasome (prosome, macropain) subunits |
| −83.39 | SRSF4 | RNA binding motif (RRM) containing |
| −83.36 | FOXR1 | Forkhead boxes |
| −83.2 | BRF2 | — |
| −82.18 | RNF5 | RING-type (C3HC4) zinc fingers |
| −82.17 | GNA11 | — |
| −81.78 | LAGE3 | — |
| −81.78 | TMEM5 | — |

TABLE 21

| cMap analysis results of top 25 sets of compound or genetic perturbagens (Similar) (5 μM, 4 hours, Bru-seq) | | |
|---|---|---|
| Score | Name | Description |
| 99.6 | IGF-1 inhibitor | — |
| 99.55 | HIF activator | — |
| 99.5 | HDAC inhibitor | — |
| 99.47 | PI3K inhibitor | — |
| 99.44 | Bromodomain Inhibitor | — |
| 99.43 | MTOR inhibitor | — |
| 99.37 | SRC inhibitor | — |
| 99.33 | DNA dependent protein kinase inhibitor | — |
| 98.98 | MEK inhibitor | — |
| 98.63 | Mitochondrial complex IV LOF | Genetic, loss of function |
| 98.63 | HSP inhibitor | — |
| 98.25 | V type ATPases LOF | Genetic, loss of function |
| 98.09 | Aurora kinase inhibitor | — |
| 97.72 | FLT3 inhibitor | — |
| 97.63 | T-type calcium channel blocker | — |
| 97.09 | EGFR inhibitor | — |
| 96.77 | Lysine acetyltransferases LOF | Genetic, loss of function |
| 96.73 | PDGFR/KIT inhibitor | — |
| 95.93 | Dopamine receptor antagonist | — |
| 95.14 | Estrogen receptor antagonist | — |
| 94.74 | JAK inhibitor | — |
| 93.84 | RAF inhibitor | — |
| 92.36 | Homeobox Gene GOF | Genetic, gain of function |
| 91.2 | Leucine rich repeat kinase inhibitor | — |
| 88.75 | VEGFR inhibitor | — |

TABLE 22

| cMap analysis results of top 25 sets of compound or genetic perturbagens (opposing) (5 μM, 4 hours, Bru-seq) | | |
|---|---|---|
| Score | Name | Description |
| −99.03 | Glycogen synthase kinase inhibitor | — |
| −92.69 | MDM inhibitor | — |
| −92.06 | Bile acid | — |
| −77.08 | Tubulin inhibitor | — |
| −71.93 | Retinoid receptor agonist | — |
| −67.82 | Integrin subunits beta LOF | Genetic, loss of function |
| −64.42 | TGF beta receptor inhibitor | — |
| −62.94 | Phospholipases LOF | Genetic, loss of function |
| −62.25 | Aromatase inhibitor | — |
| −58.57 | PI3K Signaling LOF | Genetic, loss of function |
| −56.89 | X linked mental retardation group 1 LOF | Genetic, loss of function |
| −56.68 | Bacterial 30S ribosomal subunit inhibitor | — |
| −55.23 | Serpin peptidase inhibitors LOF | Genetic, loss of function |
| −52.83 | FXR antagonist | — |
| −52.14 | NADH ubiquinone oxidoreductase supernumerary subunits LOF | Genetic, loss of function |
| −52.09 | Lipocalins GOF | Genetic, gain of function |
| −50.12 | PPAR receptor agonist | — |
| −45.51 | Tumor necrosis factor superfamily LOF | Genetic, loss of function |

TABLE 22-continued

| cMap analysis results of top 25 sets of compound or genetic perturbagens (opposing) (5 μM, 4 hours, Bru-seq) | | |
|---|---|---|
| Score | Name | Description |
| −43.05 | Thymidylate synthase inhibitor | — |
| −31.62 | Estrogen receptor agonist | — |
| −31.13 | Poly ADP ribose polymerases LOF | Genetic, loss of function |
| −29.32 | HIV protease inhibitor | — |
| −29.22 | S100 calcium binding proteins LOF | Genetic, loss of function |
| −27.81 | Adenosine receptor agonist | — |
| −23.72 | Non Homologous End Joining LOF | Genetic, loss of function |

TABLE 23

| Top 25 proteins upregulated in UMI 6 cell line treated with DX2-201 (5 μM, 24 hours) | | |
|---|---|---|
| Genes | Fold change | Description |
| gk | 3.009 | Glycerol kinase GK |
| PRSS23 | 1.844 | Serine protease 23 PRSS23 |
| NR2F6 | 1.842 | Nuclear receptor subfamily 2 group F member 6 NR2F6 |
| CMTM4 | 1.678 | CKLF-like MARVEL transmembrane domain-containing protein 4 CMTM4 |
| TMEM55B | 1.664 | Type 1 phosphatidylinositol 4,5-bisphosphate 4-phosphatase TMEM55B |
| BTBD10 | 1.651 | BTB/POZ domain-containing protein 10 BTBD10 |
| CCNT2 | 1.65 | Cyclin-T2 CCNT2 |
| CYP51A1 | 1.636 | Lanosterol 14-alpha demethylase CYP51A1 |
| UQCC3 | 1.635 | Ubiquinol-cytochrome-c reductase complex assembly factor 3 UQCC3 |
| NDRG1 | 1.55 | Protein NDRG1 NDRG1 |
| CDC42BPA | 1.514 | Serine/threonine-protein kinase MRCK alpha CDC42BPA |
| scaf8 | 1.508 | Protein SCAF8 SCAF8 |
| KIAA0355 | 1.48 | Uncharacterized protein KIAA0355 KIAA0355 |
| APBB1IP | 1.458 | Amyloid beta A4 precursor protein-binding family B member 1-interacting protein APBB1IP |
| TADA3 | 1.45 | Transcriptional adapter 3 TADA3 |
| RCCD1 | 1.443 | RCC1 domain-containing protein 1 RCCD1 |
| RDH13 | 1.429 | Retinol dehydrogenase 13 RDH13 |
| OSTC | 1.418 | Oligosaccharyltransferase complex subunit OSTC OSTC |
| RRM2B | 1.395 | Ribonucleoside-diphosphate reductase subunit M2 B RRM2B |
| ALAS1 | 1.393 | 5-aminolevulinate synthase, nonspecific, mitochondrial ALAS1 |
| MROH1 | 1.386 | Maestro heat-like repeat-containing protein family member 1 MROH1 PE = 2 |
| krt17 | 1.386 | Keratin, type 1 cytoskeletal 17 KRT17 |
| DHTKD1 | 1.384 | Probable 2-oxoglutarate dehydrogenase E1 component DHKTD1, mitochondrial DHTKD1 |
| TCEAL1 | 1.382 | Transcription elongation factor A protein-like 1 TCEAL1 |
| NAA35 | 1.377 | N-alpha-acetyltransferase 35, NatC auxiliary subunit NAA35 |

TABLE 24

| Top 25 proteins downregulated in UM 16 cell line treated with DX2-201 (5 μM, 24 hours) | | |
|---|---|---|
| Genes | Fold change | Description |
| DLD | 0.684 | Dihydrolipoyl dehydrogenase, mitochondrial DLD |
| Hist1h1d | 0.703 | Histone H1.3 HIST1H1D |
| ZBTB21 | 0.709 | Zinc finger and BTB domain-containing protein 21 ZBTB21 |

TABLE 24-continued

| Top 25 proteins downregulated in UM 16 cell line treated with DX2-201 (5 μM, 24 hours) | | |
|---|---|---|
| Genes | Fold change | Description |
| SCAMP2 | 0.729 | Secretory carrier-associated membrane protein 2 SCAMP2 |
| DOLPP1 | 0.731 | Dolichyldiphosphatase 1 DOLPP1 PE = 2 SV = 1 |
| pop7 | 0.736 | Ribonuclease P protein subunit p20 POP7 |
| FAU | 0.742 | 40S ribosomal protein S30 FAU |
| PDCL | 0.752 | Phosducin-like protein PDCL |
| OGFOD2 | 0.754 | 2-oxoglutarate and iron-dependent oxygenase domain-containing protein 2 OGFOD2 |
| CDCA5 | 0.761 | Sororin CDCA5 |
| PLP2 | 0.763 | Proteolipid protein 2 PLP2 |
| RUSC1 | 0.771 | RUN and SH3 domain-containing protein 1 RUSC1 |
| NOL8 | 0.771 | Nucleolar protein 8 NOL8 |
| ANKH | 0.777 | Progressive ankylosis protein homolog ANKH |
| ABTB2 | 0.778 | Ankyrin repeat and BTB/POZ domain-containing protein 2 ABTB2 |
| AP2S1 | 0.781 | AP-2 complex subunit sigma AP2S1 |
| FAH | 0.785 | Fumarylacetoacetase FAH |
| CCDC88C | 0.785 | Protein Daple CCDC88C |
| MED27 | 0.79 | Mediator of RNA polymerase II transcription subunit 27 MED27 |
| AP1S2 | 0.792 | AP-1 complex subunit sigma-2 AP1S2 |
| DTNBP1 | 0.794 | Dysbindin DTNBP1 |
| NRGN | 0.795 | Neurogranin NRGN |
| SLC25A15 | 0.796 | Mitochondrial ornithine transporter 1 SLC25A15 |
| DOPEY2 | 0.797 | Protein dopey-2 DOPEY2 |
| ANKRD54 | 0.799 | Ankyrin repeat domain-containing protein 54 ANKRD54 |

TABLE 25

GSEA results of the top 20 upregulated HALLMARK pathways in UM16 cell line treated with DX2-201(5 μM, 24 hours, proteomics)

| NAME | SIZE | ES | NES | NOM p-val | FDR q-val | FWER p-val |
|---|---|---|---|---|---|---|
| HALLMARK_HYPOXIA | 74 | 0.595 | 1.851 | 0.000 | 0.003 | 0.004 |
| HALLMARK_COAGULATION | 40 | 0.636 | 1.813 | 0.004 | 0.004 | 0.009 |
| HALLMARK_BILE_ACID_METABOLISM | 35 | 0.523 | 1.465 | 0.058 | 0.245 | 0.589 |
| HALLMARK_CHOLESTEROL_HOMEOSTASIS | 37 | 0.493 | 1.407 | 0.059 | 0.314 | 0.785 |
| HALLMARK_COMPLEMENT | 72 | 0.401 | 1.235 | 0.153 | 0.425 | 0.994 |
| HALLMARK_DNA_REPAIR | 100 | 0.381 | 1.239 | 0.127 | 0.454 | 0.994 |
| HALLMARK_EPITHELIAL_MESENCHYMAL_TRANSITION | 48 | 0.449 | 1.312 | 0.103 | 0.456 | 0.968 |
| HALLMARK_TNFA_SIGNALING_VIA_NFKB | 54 | 0.448 | 1.335 | 0.096 | 0.457 | 0.943 |
| HALLMARK_XENOBIOTIC_METABOLISM | 81 | 0.393 | 1.244 | 0.146 | 0.488 | 0.993 |
| HALLMARK_GLYCOLYSIS | 105 | 0.399 | 1.281 | 0.076 | 0.489 | 0.984 |
| HALLMARK_UV_RESPONSE_DN | 50 | 0.433 | 1.256 | 0.146 | 0.510 | 0.991 |
| HALLMARK_MITOTIC_SPINDLE | 144 | 0.348 | 1.170 | 0.180 | 0.529 | 0.999 |
| HALLMARK_IL2_STAT5_SIGNALING | 60 | 0.384 | 1.176 | 0.228 | 0.552 | 0.999 |
| HALLMARK_HEME_METABOLISM | 73 | 0.376 | 1.150 | 0.250 | 0.552 | 0.999 |
| KEGG_MELANOGENESIS | 21 | 0.534 | 1.369 | 0.105 | 0.638 | 1 |
| HALLMARK_ADIPOGENESIS | 109 | 0.317 | 1.025 | 0.436 | 0.644 | 1 |
| HALLMARK_PEROXISOME | 57 | 0.347 | 1.037 | 0.414 | 0.645 | 1 |
| KEGG_GLYCEROLIPID_METABOLISM | 17 | 0.572 | 1.376 | 0.088 | 0.663 | 1 |
| HALLMARK_APOPTOSIS | 75 | 0.335 | 1.042 | 0.403 | 0.666 | 1 |
| KEGG_ARGININE_AND_PROLINE_METABOLISM | 25 | 0.543 | 1.389 | 0.087 | 0.668 | 0.999 |

NES = Normalized Enrichment Score, FDR = False Discovery Rate, FWER = Family-Wise Error Rate.

TABLE 26

GSEA results of the downregulated HALLMARK pathways in UM16 cell line treated with DX2-201(5 μM, 24 hours, proteomics)

| NAME | SIZE | ES | NES | NOM p-val | FDR q-val | FWER p-val |
|---|---|---|---|---|---|---|
| HALLMARK_MYC_TARGETS_V1 | 186 | −0.424 | −1.975 | 0.000 | 0.006 | 0.003 |
| HALLMARK_E2F_TARGETS | 157 | −0.349 | −1.559 | 0.000 | 0.077 | 0.076 |
| HALLMARK_UNFOLDED_PROTEIN_RESPONSE | 76 | −0.372 | −1.517 | 0.008 | 0.070 | 0.102 |
| HALLMARK_G2M_CHECKPOINT | 139 | −0.313 | −1.421 | 0.000 | 0.107 | 0.195 |
| HALLMARK_P53_PATHWAY | 78 | −0.323 | −1.338 | 0.015 | 0.146 | 0.315 |
| HALLMARK_MYC_TARGETS_V2 | 47 | −0.329 | −1.215 | 0.135 | 0.264 | 0.565 |
| HALLMARK_ALLOGRAFT_REJECTION | 54 | −0.287 | −1.082 | 0.309 | 0.521 | 0.874 |
| HALLMARK_MYOGENESIS | 48 | −0.285 | −1.077 | 0.323 | 0.467 | 0.878 |
| HALLMARK_TGF_BETA_SIGNALING | 25 | −0.296 | −0.944 | 0.538 | 0.771 | 0.978 |
| HALLMARK_OXIDATIVE_PHOSPHORYLATION | 159 | −0.214 | −0.938 | 0.620 | 0.711 | 0.98 |
| HALLMARK_PROTEIN_SECRETION | 79 | −0.207 | −0.842 | 0.869 | 0.862 | 0.995 |
| HALLMARK_SPERMATOGENESIS | 33 | −0.229 | −0.803 | 0.768 | 0.851 | 0.998 |

NES = Normalized Enrichment Score, FDR = False Discovery Rate, FWER = Family-Wise Error Rate.

TABLE 27

GSEA results of the top 20 upregulated KEGG pathways in UM16 cell line treated with DX2-201 (5 μM, 24 hours, proteomics)

| NAME | SIZE | ES | NES | NOM p-val | FDR q-val | FWER p-val |
|---|---|---|---|---|---|---|
| KEGG_B_CELL_RECEPTOR_SIGNALING_PATHWAY | 37 | 0.504 | 1.432 | 0.058 | 0.813 | 0.995 |
| HALLMARK_ESTROGEN_RESPONSE_EARLY | 69 | 0.301 | 0.929 | 0.614 | 0.813 | 1 |
| KEGG_ERBB_SIGNALING_PATHWAY | 44 | 0.488 | 1.410 | 0.051 | 0.821 | 0.997 |
| KEGG_FC_EPSILON_RI_SIGNALING_PATHWAY | 29 | 0.593 | 1.623 | 0.011 | 0.825 | 0.539 |
| KEGG_NUCLEOTIDE_EXCISION_REPAIR | 32 | 0.469 | 1.271 | 0.142 | 0.829 | 1 |
| KEGG_VIRAL_MYOCARDITIS | 23 | 0.497 | 1.292 | 0.159 | 0.832 | 1 |
| KEGG_PEROXISOME | 38 | 0.459 | 1.302 | 0.134 | 0.839 | 1 |
| KEGG_INOSITOL_PHOSPHATE_METABOLISM | 19 | 0.520 | 1.277 | 0.167 | 0.852 | 1 |
| KEGG_PATHWAYS_IN_CANCER | 119 | 0.324 | 1.074 | 0.341 | 0.858 | 1 |
| KEGG_INSULIN_SIGNALING_PATHWAY | 66 | 0.352 | 1.077 | 0.357 | 0.872 | 1 |
| KEGG_PROPANOATE_METABOLISM | 21 | 0.424 | 1.079 | 0.385 | 0.889 | 1 |
| KEGG_GLYCOLYSIS_GLUCONEOGENESIS | 35 | 0.394 | 1.086 | 0.354 | 0.889 | 1 |
| KEGG_NON_SMALL_CELL_LUNG_CANCER | 27 | 0.415 | 1.092 | 0.368 | 0.894 | 1 |
| KEGG_GAP_JUNCTION | 31 | 0.386 | 1.041 | 0.409 | 0.898 | 1 |
| KEGG_CARDIAC_MUSCLE_CONTRACTION | 21 | 0.469 | 1.177 | 0.269 | 0.900 | 1 |
| KEGG_ADIPOCYTOKINE_SIGNALING_PATHWAY | 28 | 0.390 | 1.046 | 0.427 | 0.903 | 1 |
| KEGG_CYTOSOLIC_DNA_SENSING_PATHWAY | 19 | 0.469 | 1.166 | 0.287 | 0.907 | 1 |
| KEGG_PURINE_METABOLISM | 72 | 0.331 | 1.023 | 0.448 | 0.909 | 1 |
| KEGG_LYSINE_DEGRADATION | 23 | 0.381 | 1.007 | 0.449 | 0.914 | 1 |
| HALLMARK_ANDROGEN_RESPONSE | 52 | 0.259 | 0.760 | 0.846 | 0.915 | 1 |

NES = Normalized Enrichment Score, FDR = False Discovery Rate, FWER = Family-Wise Error Rate.

TABLE 28

GSEA results of the downregulated KEGG pathways in UM16 cell line treated with DX2-201 (5 μM, 24 hours, proteomics)

| NAME | SIZE | ES | NES | NOM p-val | FDR q-val | FWER p-val |
|---|---|---|---|---|---|---|
| KEGG_RIBOSOME | 79 | −0.520 | −2.132 | 0.000 | 0.003 | 0.004 |
| KEGG_CITRATE_CYCLE_TCA_CYCLE | 25 | −0.445 | −1.416 | 0.045 | 0.422 | 0.79 |
| KEGG_SPLICEOSOME | 110 | −0.310 | −1.319 | 0.033 | 0.541 | 0.942 |
| KEGG_PROTEASOME | 40 | −0.401 | −1.425 | 0.025 | 0.605 | 0.776 |
| KEGG_PROTEIN_EXPORT | 18 | −0.376 | −1.116 | 0.326 | 0.625 | 0.998 |
| KEGG_N_GLYCAN_BIOSYNTHESIS | 26 | −0.366 | −1.160 | 0.246 | 0.658 | 0.994 |
| KEGG_RNA_DEGRADATION | 42 | −0.342 | −1.228 | 0.158 | 0.672 | 0.988 |
| KEGG_BASAL_TRANSCRIPTION_FACTORS | 17 | −0.389 | −1.121 | 0.278 | 0.687 | 0.998 |
| KEGG_PARKINSONS_DISEASE | 74 | −0.290 | −1.180 | 0.148 | 0.702 | 0.994 |
| KEGG_VIBRIO_CHOLERAE_INFECTION | 22 | −0.335 | −1.044 | 0.395 | 0.754 | 1 |
| KEGG_ANTIGEN_PROCESSING_AND_PRESENTATION | 27 | −0.285 | −0.917 | 0.576 | 0.792 | 1 |
| KEGG_B_CELL_RECEPTOR_SIGNALING_PATHWAY | 37 | 0.504 | 1.432 | 0.058 | 0.813 | 0.995 |
| KEGG_ERBB_SIGNALING_PATHWAY | 44 | 0.488 | 1.410 | 0.051 | 0.821 | 0.997 |
| KEGG_FC_EPSILON_RISIGNALING_PATHWAY | 29 | 0.593 | 1.623 | 0.011 | 0.825 | 0.539 |
| KEGG_CELL_CYCLE | 71 | −0.246 | −0.995 | 0.490 | 0.828 | 1 |
| KEGG_NUCLEOTIDE_EXCISION_REPAIR | 32 | 0.469 | 1.271 | 0.142 | 0.829 | 1 |
| KEGG_VIRAL_MYOCARDITIS | 23 | 0.497 | 1.292 | 0.159 | 0.832 | 1 |
| KEGG_PEROXISOME | 38 | 0.459 | 1.302 | 0.134 | 0.839 | 1 |
| KEGG_DNA_REPLICATION | 30 | −0.273 | −0.919 | 0.577 | 0.844 | 1 |

NES = Normalized Enrichment Score, FDR = False Discovery Rate, FWER = Family-Wise Error Rate.

REFERENCES (1) Roesch, A.; Vultur, A.; Bogeski, I.; Wang, H.; Zimmermann, K. M.; Speicher, D.; Korbel, C.; Laschke, M. W.; Gimotty, P. A.; Philipp, S. E.; Krause, E.; Patzold, S.; Villanueva, J.; Krepler, C.; Fukunaga-Kalabis, M.; Hoth, M.; Bastian, B. C.; Vogt, T.; Herlyn, M. Overcoming intrinsic multidrug resistance in melanoma by blocking the mitochondrial respiratory chain of slow-cycling JARID1B(high) cells. *Cancer Cell* 2013, 23, 811-25.

(2) Hu, J.; Locasale, J. W.; Bielas, J. H.; O'Sullivan, J.; Sheahan, K.; Cantley, L. C.; Vander Heiden, M. G.; Vitkup, D. Heterogeneity of tumor-induced gene expression changes in the human metabolic network. *Nat Biotechnol* 2013, 31, 522-9.

(3) Sriskanthadevan, S.; Jeyaraju, D. V.; Chung, T. E.; Prabha, S.; Xu, W.; Skrtic, M.; Jhas, B.; Hurren, R.; Gronda, M.; Wang, X.; Jitkova, Y.; Sukhai, M. A.; Lin, F. H.; Maclean, N.; Laister, R.; Goard, C. A.; Mullen, P. J.; Xie, S.; Penn, L. Z.; Rogers, I. M.; Dick, J. E.; Minden, M. D.; Schimmer, A. D. AML cells have low spare reserve capacity in their respiratory chain that renders them susceptible to oxidative metabolic stress. *Blood* 2015, 125, 2120-30.

(4) Birsoy, K.; Wang, T.; Chen, W. W.; Freinkman, E.; Abu-Remaileh, M.; Sabatini, D. M. An Essential Role of the Mitochondrial Electron Transport Chain in Cell Proliferation Is to Enable Aspartate Synthesis. *Cell* 2015, 162, 540-51.

(5) Sullivan, L. B.; Gui, D. Y.; Hosios, A. M.; Bush, L. N.; Freinkman, E.; Vander Heiden, M. G. Supporting Aspartate Biosynthesis Is an Essential Function of Respiration in Proliferating Cells. *Cell* 2015, 162, 552-63.

(6) Birsoy, K.; Possemato, R.; Lorbeer, F. K.; Bayraktar, E. C.; Thiru, P.; Yucel, B.; Wang, T.; Chen, W. W.; Clish, C. B.; Sabatini, D. M. Metabolic determinants of cancer cell sensitivity to glucose limitation and biguanides. *Nature* 2014, 508, 108-+.

(7) Lissanu Deribe, Y.; Sun, Y.; Terranova, C.; Khan, F.; Martinez-Ledesma, J.; Gay, J.; Gao, G.; Mullinax, R. A.; Khor, T.; Feng, N.; Lin, Y. H.; Wu, C. C.; Reyes, C.; Peng, Q.; Robinson, F.; Inoue, A.; Kochat, V.; Liu, C. G.; Asara, J. M.; Moran, C.; Muller, F.; Wang, J.; Fang, B.; Papadimitrakopoulou, V.; Wistuba, II; Rai, K.; Marszalek, J.; Futreal, P. A. Mutations in the SWI/SNF complex induce a targetable dependence on oxidative phosphorylation in lung cancer. *Nat Med* 2018, 24, 1047-1057.

(8) Sancho, P.; Bameda, D.; Heeschen, C. Hallmarks of cancer stem cell metabolism. *British Journal of Cancer* 2016, 114, 1305-1312.

(9) Kuntz, E. M.; Baquero, P.; Michie, A. M.; Dunn, K.; Tardito, S.; Holyoake, T. L.; Helgason, G. V.; Gottlieb, E. Targeting mitochondrial oxidative phosphorylation eradicates therapy-resistant chronic myeloid leukemia stem cells. *Nature Medicine* 2017, 23, 1234-+.

(10) Viale, A.; Pettazzoni, P.; Lyssiotis, C. A.; Ying, H.; Sanchez, N.; Marchesini, M.; Carugo, A.; Green, T.; Seth, S.; Giuliani, V.; Kost-Alimova, M.; Muller, F.; Colla, S.; Nezi, L.; Genovese, G.; Deem, A. K.; Kapoor, A.; Yao, W.; Brunetto, E.; Kang, Y.; Yuan, M.; Asara, J. M.; Wang, Y. A.; Heffernan, T. P.; Kimmelman, A. C.; Wang, H.; Fleming, J. B.; Cantley, L. C.; DePinho, R. A.; Draetta, G. F. Oncogene ablation-resistant pancreatic cancer cells depend on mitochondrial function. *Nature* 2014, 514, 628-32.

(11) Lee, K. M.; Giltnane, J. M.; Balko, J. M.; Schwarz, L. J.; Guerrero-Zotano, A. L.; Hutchinson, K. E.; Nixon, M. J.; Estrada, M. V.; Sanchez, V.; Sanders, M. E.; Lee, T.; Gomez, H.; Lluch, A.; Perez-Fidalgo, A.; Wolf, M. M.; Andrejeva, G.; Rathmell, J. C.; Fesik, S. W.; Arteaga, C. L. MYC and MCL1 Cooperatively Promote Chemotherapy-Resistant Breast Cancer Stem Cells via Regulation of Mitochondrial Oxidative Phosphorylation. *Cell Metabolism* 2017, 26, 633-+.

(12) Vazquez, F.; Lim, J. H.; *Chim*, H.; Bhalla, K.; Gimun, G.; Pierce, K.; Clish, C. B.; Granter, S. R.; Widlund, H. R.; Spiegelman, B. M.; Puigserver, P. PGC1 alpha Expression Defines a Subset of Human Melanoma Tumors with Increased Mitochondrial Capacity and Resistance to Oxidative Stress. *Cancer Cell* 2013, 23, 287-301.

(13) Farge, T.; Saland, E.; de Toni, F.; Aroua, N.; Hosseini, M.; Perry, R.; Bosc, C.; Sugita, M.; Stuani, L.; Fraisse, M.; Scotland, S.; Larrue, C.; Boutzen, H.; Feliu, V.; Nicolau-Travers, M. L.; Cassant-Sourdy, S.; Broin, N.; David, M.; Serhan, N.; Sarry, A.; Tavitian, S.; Kaoma, T.; Vallar, L.; Iacovoni, J.; Linares, L. K.; Montersino, C.; Castellano, R.; Griessinger, E.; Collette, Y.; Duchamp, O.; Barreira, Y.; Hirsch, P.; Palama, T.; Gales, L.; Delhommeau, F.; Garmy-Susini, B. H.; Portais, J. C.; Vergez, F.; Selak, M.; Danet-Desnoyers, G.; Carroll, M.; Recher, C.; Sarry, J. E. Chemotherapy-Resistant Human Acute Myeloid Leukemia Cells Are Not Enriched for Leukemic Stem Cells but Require Oxidative Metabolism. *Cancer Discovery* 2017, 7, 716-735.

(14) Zhang, L.; Yao, Y. X.; Zhang, S. J.; Liu, Y.; Guo, H.; Ahmed, M.; Bell, T.; Zhang, H.; Han, G. C.; Lorence, E.; Badillo, M.; Zhou, S. H.; Sun, Y. T.; Di Francesco, M. E.; Feng, N. P.; Haun, R.; Lan, R.; Mackintosh, S. G.; Mao, X. Z.; Song, X. Z.; Zhang, J. H.; Pham, L. V.; Lorenzi, P. L.; Marszalek, J.; Heffernan, T.; Draetta, G.; Jones, P.; Futreal, A.; Nomie, K.; Wang, L. H.; Wang, M. Metabolic reprogramming toward oxidative phosphorylation identifies a therapeutic target for mantle cell lymphoma. *Science Translational Medicine* 2019, 11.

(15) Wheaton, W. W.; Weinberg, S. E.; Hamanaka, R. B.; Soberanes, S.; Sullivan, L. B.; Anso, E.; Glasauer, A.; Dufour, E.; Mutlu, G. M.; Budigner, G. S.; Chandel, N. S. Metformin inhibits mitochondrial complex I of cancer cells to reduce tumorigenesis. *Elife* 2014, 3, e02242.

(16) Dykens, J. A.; Jamieson, J.; Marroquin, L.; Nadanaciva, S.; Billis, P. A.; Will, Y. Biguanide-induced mitochondrial dysfunction yields increased lactate production and cytotoxicity of aerobically-poised HepG2 cells and human hepatocytes in vitro. *Toxicol Appl Pharmacol* 2008, 233, 203-10.

(17) Matsuzaki, S.; Humphries, K. M. Selective inhibition of deactivated mitochondrial complex I by biguanides. *Biochemistry* 2015, 54, 2011-21.

(18) Bridges, H. R.; Jones, A. J.; Pollak, M. N.; Hirst, J. Effects of metformin and other biguanides on oxidative phosphorylation in mitochondria. *Biochem J* 2014, 462, 475-87.

(19) Shi, Y.; Lim, S. K.; Liang, Q.; Iyer, S. V.; Wang, H. Y.; Wang, Z.; Xie, X.; Sun, D.; Chen, Y. J.; Tabar, V.; Gutin, P.; Williams, N.; De Brabander, J. K.; Parada, L. F. Gboxin is an oxidative phosphorylation inhibitor that targets glioblastoma. *Nature* 2019, 567, 341-346.

(20) Molina, J. R.; Sun, Y.; Protopopova, M.; Gera, S.; Bandi, M.; Bristow, C.; McAfoos, T.; Morlacchi, P.; Ackroyd, J.; Agip, A. A.; Al-Atrash, G.; Asara, J.; Bardenhagen, J.; Carrillo, C. C.; Carroll, C.; Chang, E.; Ciurea, S.; Cross, J. B.; Czako, B.; Deem, A.; Daver, N.; de Groot, J. F.; Dong, J. W.; Feng, N.; Gao, G.; Gay, J.; Do, M. G.; Greer, J.; Giuliani, V.; Han, J.; Han, L.; Henry, V. K.; Hirst, J.; Huang, S.; Jiang, Y.; Kang, Z.; Khor, T.; Konoplev, S.; Lin, Y. H.; Liu, G.; Lodi, A.; Lofton, T.; Ma, H.; Mahendra, M.; Matre, P.; Mullinax, R.; Peoples, M.; Petrocchi, A.; Rodriguez-Canale, J.; Serreli, R.; Shi, T.; Smith, M.; Tabe, Y.; Theroff, J.; Tiziani, S.; Xu, Q.; Zhang, Q.; Muller, F.; DePinho, R. A.; Toniatti, C.; Draetta, G. F.; Heffernan, T. P.; Konopleva, M.; Jones, P.; Di Francesco, M. E.; Marszalek, J. R. An inhibitor of oxidative phosphorylation exploits cancer vulnerability. *Nat Med* 2018, 24, 1036-1046.

(21) Salmond, R. J. mTOR Regulation of Glycolytic Metabolism in T Cells. *Frontiers in Cell and Developmental Biology* 2018, 6.

(22) Diskin, C.; Palsson-McDermott, E. M. Metabolic Modulation in Macrophage effector Function. *Frontiers in Immunology* 2018, 9.

(23) Kumar, V.; Patel, S.; Tcyganov, E.; Gabrilovich, D. I. The Nature of Myeloid-Derived Suppressor Cells in the Tumor Microenvironment. *Trends in Immunology* 2016, 37, 208-220.

(24) Vats, D.; Mukundan, L.; Odegaard, J. I.; Zhang, L.; Smith, K. L.; Morel, C. R.; Wagner, R. A.; Greaves, D. R.; Murray, P. J.; Chawla, A. Oxidative metabolism and PGC-lbeta attenuate macrophage-mediated inflammation. *Cell Metab* 2006, 4, 13-24.

(25) Beier, U. H.; Angelin, A.; Akimova, T.; Wang, L.; Liu, Y.; Xiao, H.; Koike, M. A.; Hancock, S. A.; Bhatti, T. R.; Han, R.; Jiao, J.; Veasey, S. C.; Sims, C. A.; Baur, J. A.; Wallace, D. C.; Hancock, W. W. Essential role of mitochondrial energy metabolism in Foxp3(+) T-regulatory cell function and allograft survival. *FASEB J* 2015, 29, 2315-26.

(26) Gatza, E.; Wahl, D. R.; Opipari, A. W.; Sundberg, T. B.; Reddy, P.; Liu, C.; Glick, G. D.; Ferrara, J. L. Manipulating the bioenergetics of alloreactive T cells causes their selective apoptosis and arrests graft-versus-host disease. *Sci Transl Med* 2011, 3, 67ra8.

(27) Glick, G. D.; Rossignol, R.; Lyssiotis, C. A.; Wahl, D.; Lesch, C.; Sanchez, B.; Liu, X.; Hao, L. Y.; Taylor, C.; Hurd, A.; Ferrara, J. L.; Tkachev, V.; Byersdorfer, C. A.; Boros, L.; Opipari, A. W. Anaplerotic metabolism of alloreactive T cells provides a metabolic approach to treat graft-versus-host disease. *J Pharmacol Exp Ther* 2014, 351, 298-307.

(28) Wahl, D. R.; Petersen, B.; Warner, R.; Richardson, B. C.; Glick, G. D.; Opipari, A. W. Characterization of the metabolic phenotype of chronically activated lymphocytes. *Lupus* 2010, 19, 1492-501.

What is claimed is:

1. A compound described by

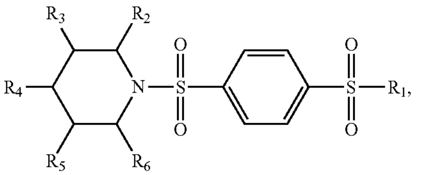

or a pharmaceutically acceptable form thereof;

wherein $R_1$ is selected from the group consisting of:

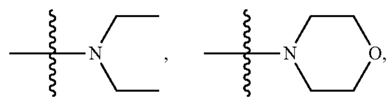

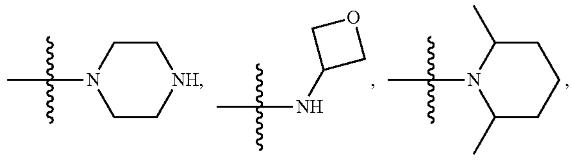

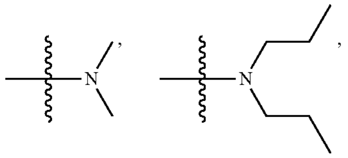

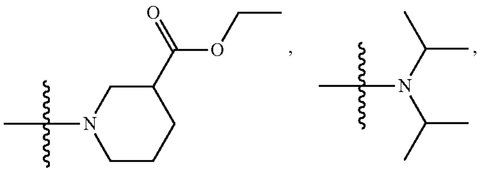

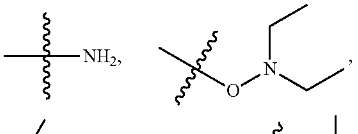

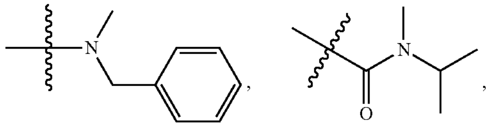

-continued

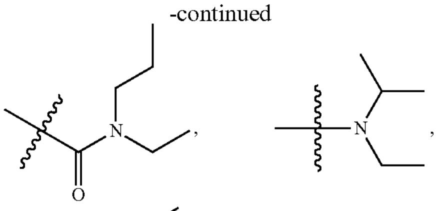

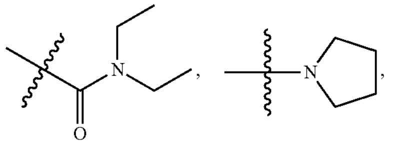

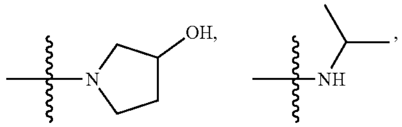

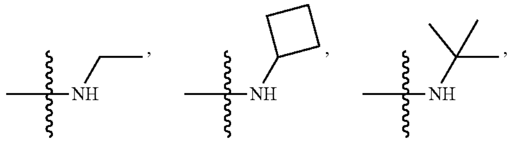

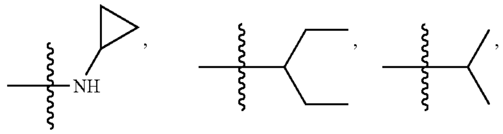

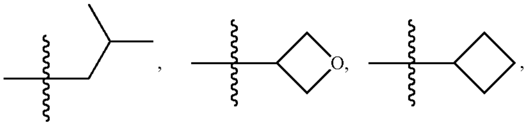

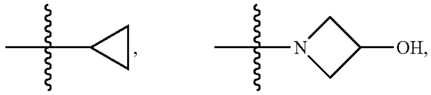

and $CH_3$;

wherein $R_2$, $R_4$, and $R_6$ are independently selected from the group consisting of: hydrogen,

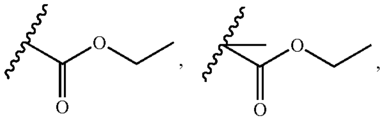

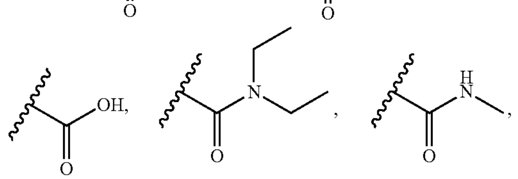

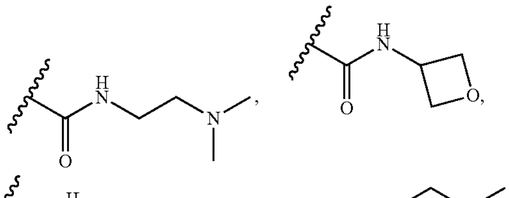

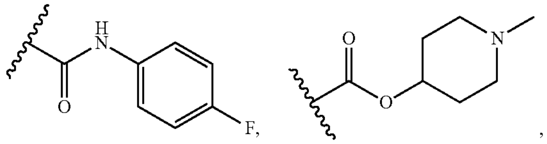

-continued
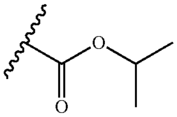,
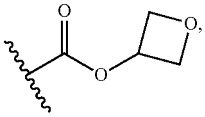
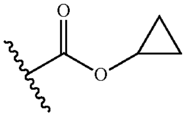
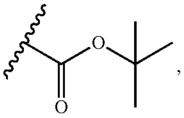,
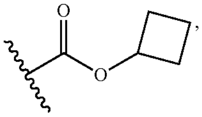
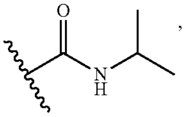,
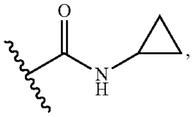
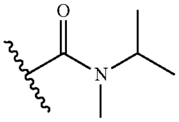,
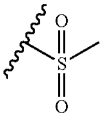,
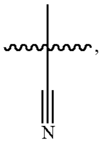,
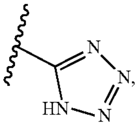
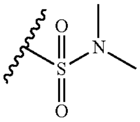,
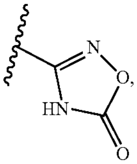
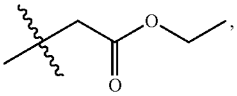,
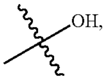
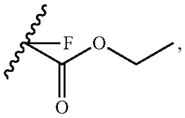
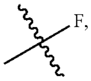
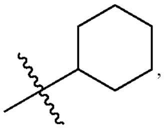
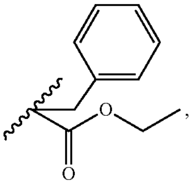
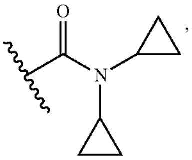,
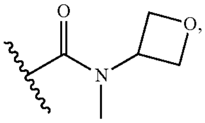
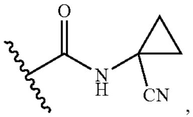,
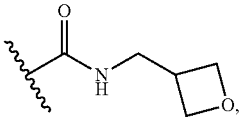
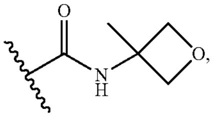
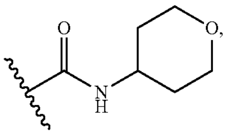
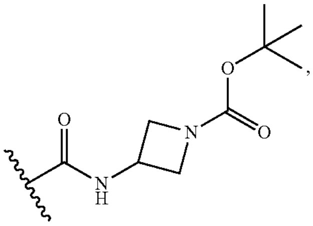
-continued
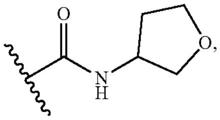
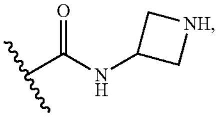
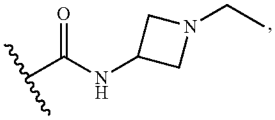
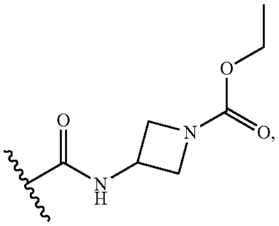
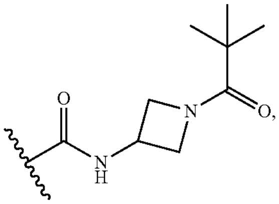
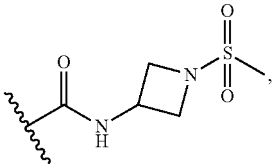
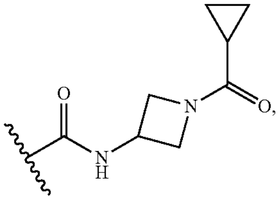
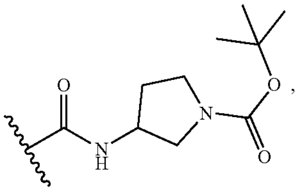
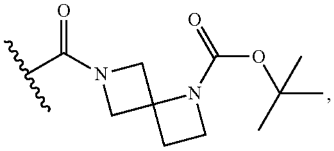
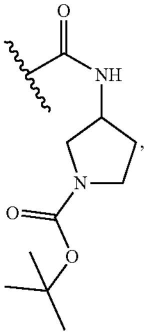
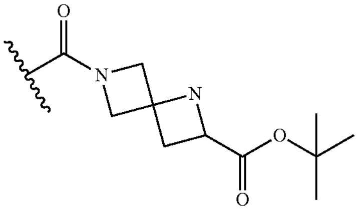
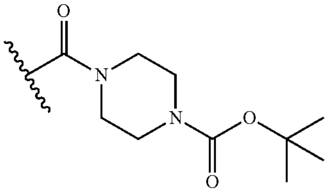
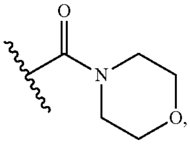

-continued
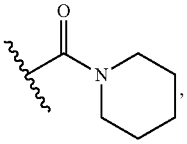
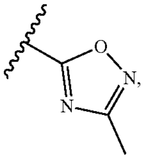
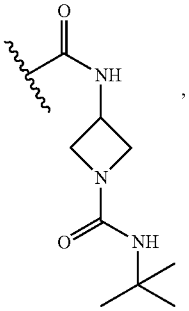
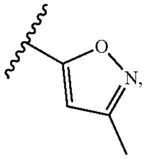
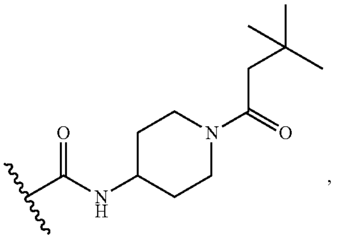
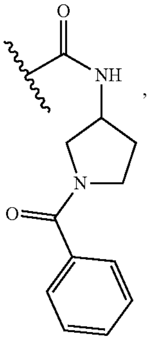
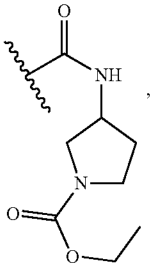
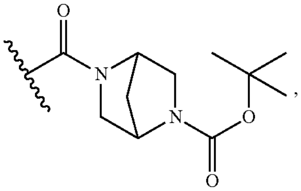
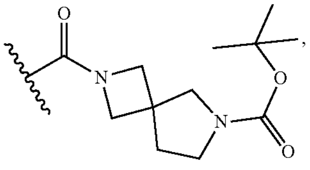
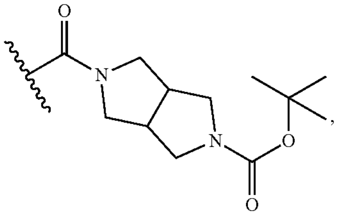
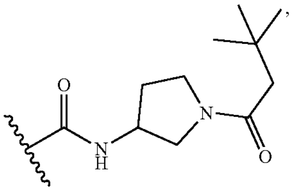
-continued
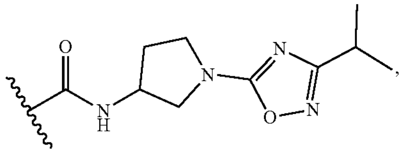
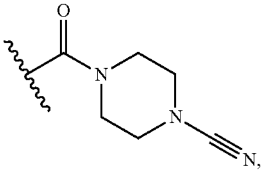
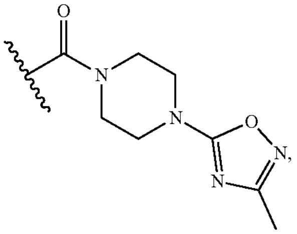
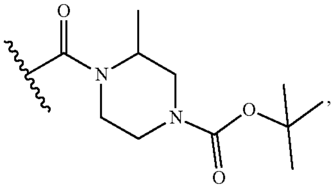
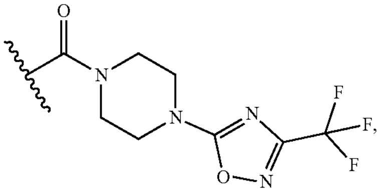
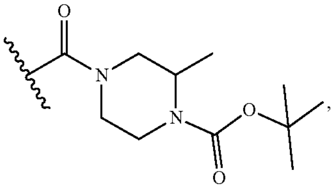
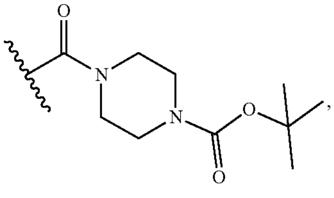
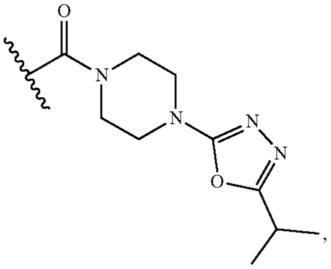
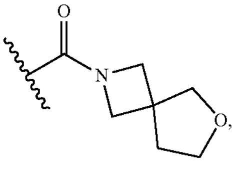
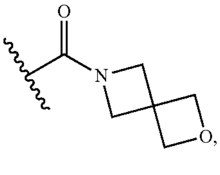

-continued
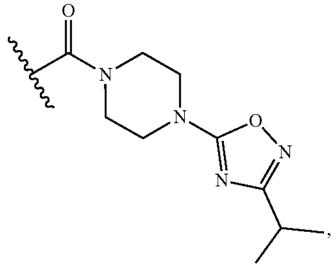,
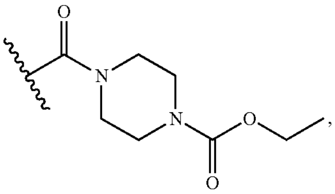, 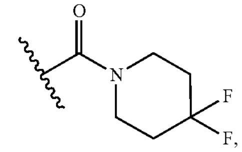,
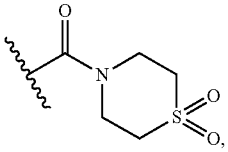, 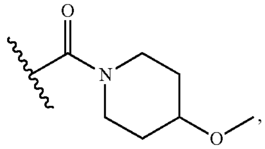,
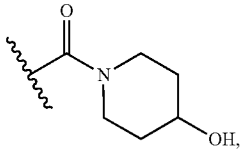, 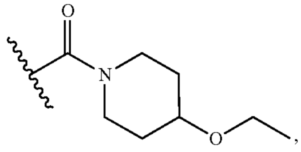,
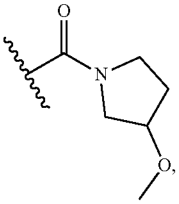, 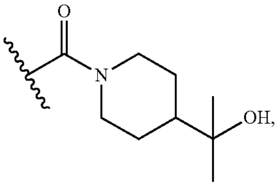,
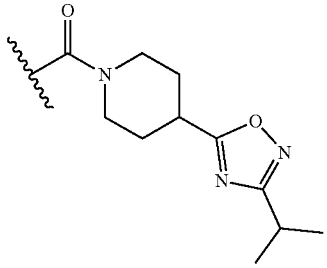,
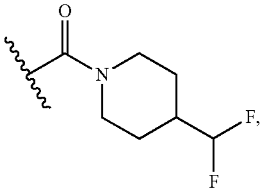, 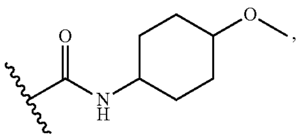,
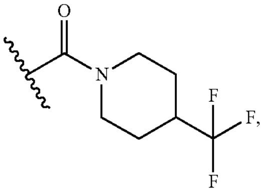 and
-continued
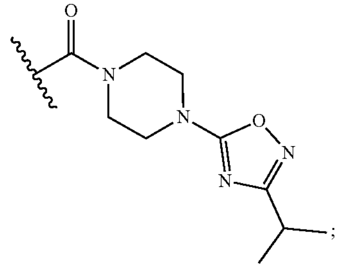;
wherein $R_3$ and $R_5$ are independently selected from the group consisting of: hydrogen
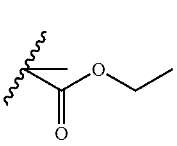, 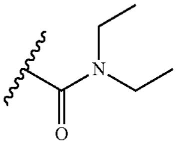, 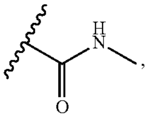,
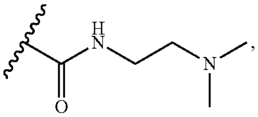, 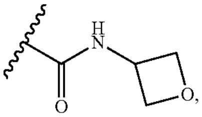,
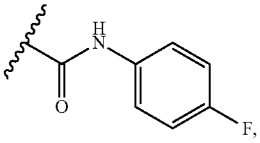, 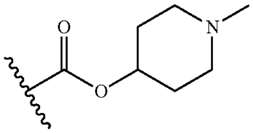,
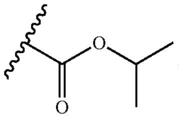, 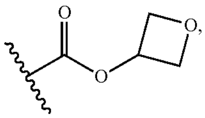,
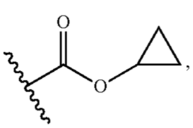, 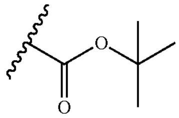,
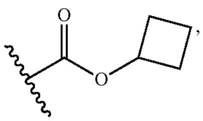, 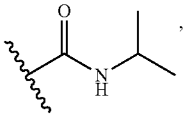,
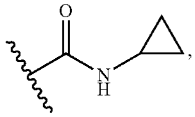, 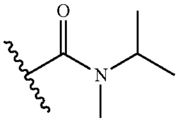, 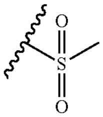,
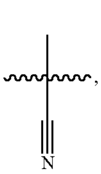, 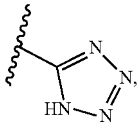, 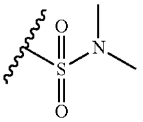, 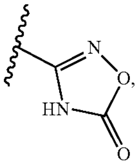,
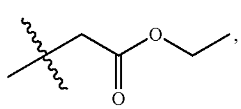, 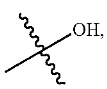, 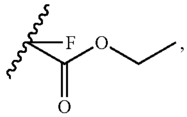, -continued
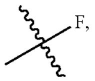
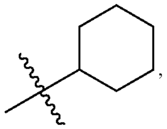
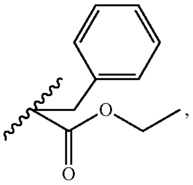
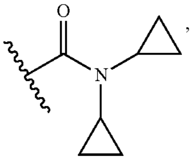
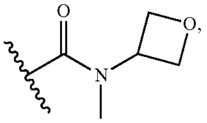
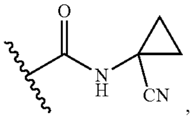
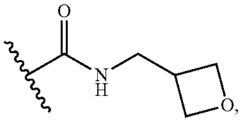
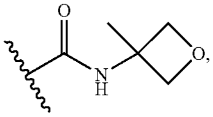
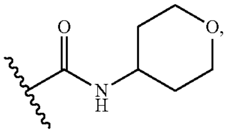
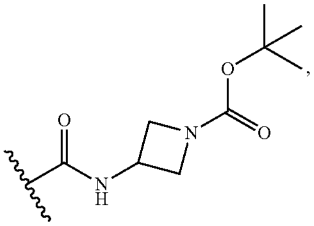
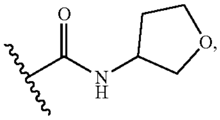
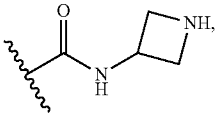
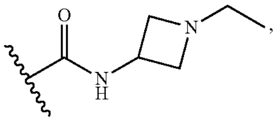
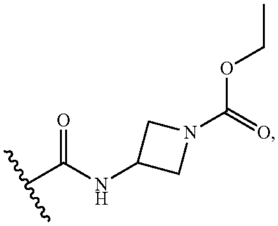
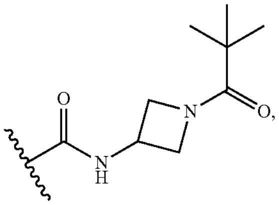
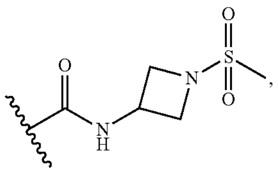
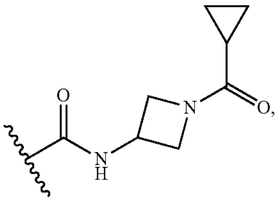
-continued
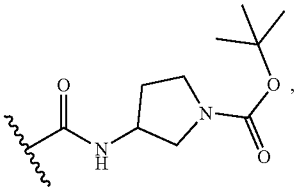
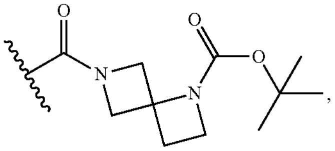
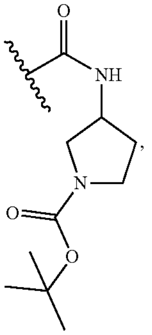
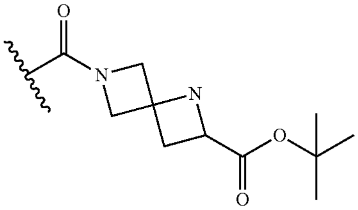
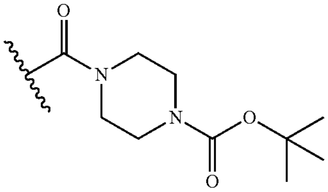
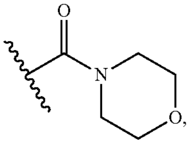
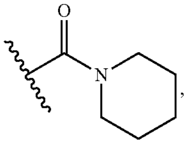
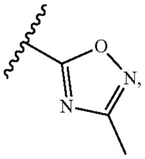
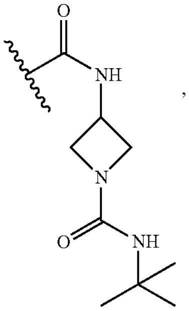
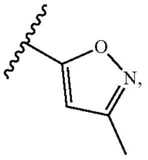
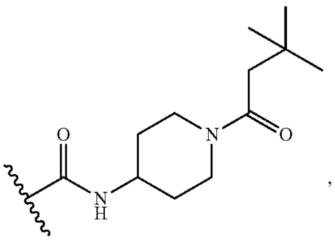

-continued
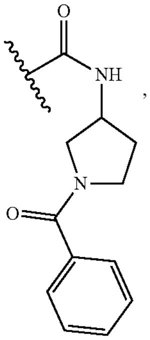
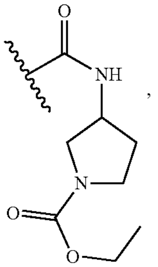
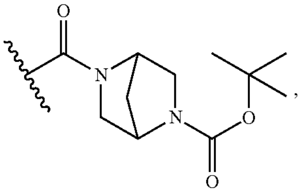
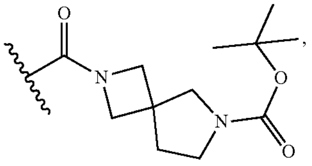
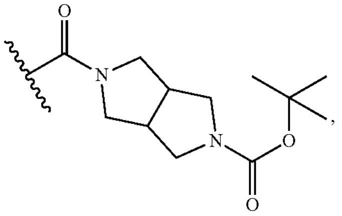
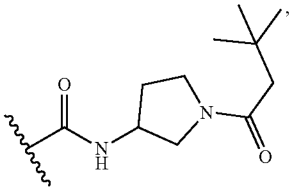
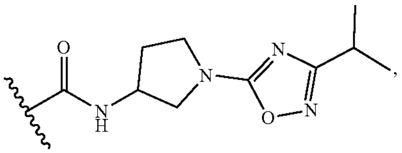
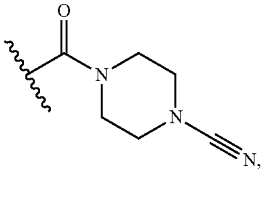
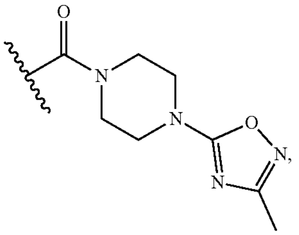
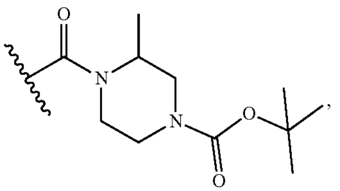
-continued
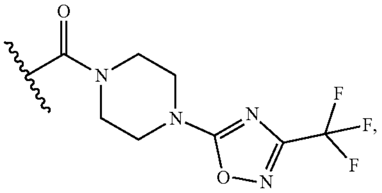
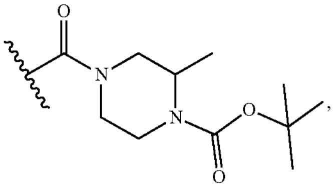
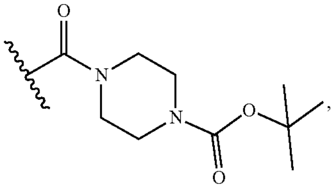
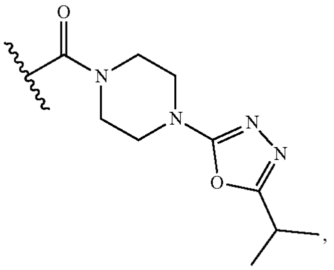
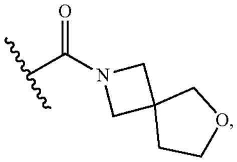
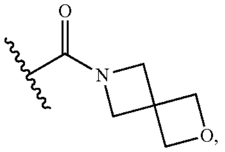
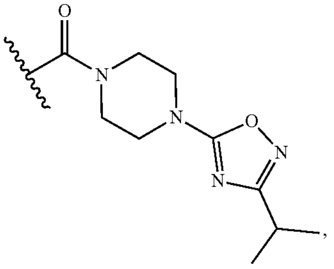
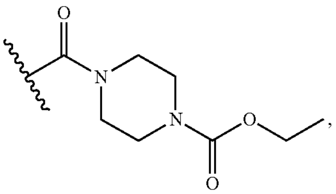
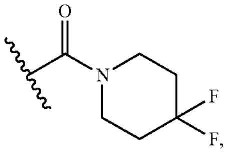
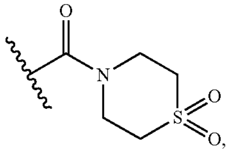
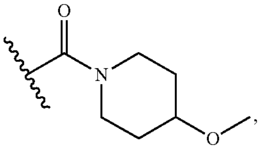

-continued
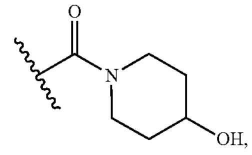
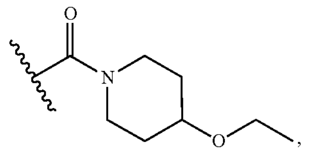
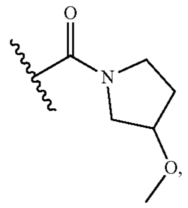
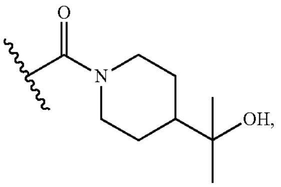
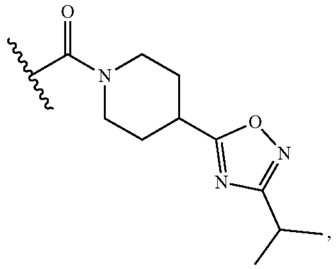
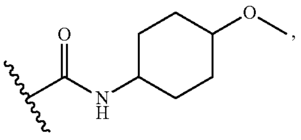
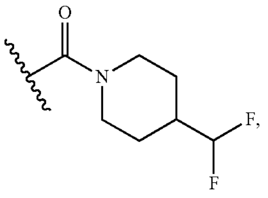
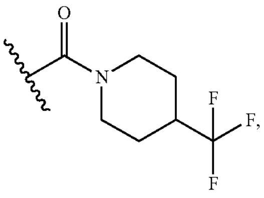
and
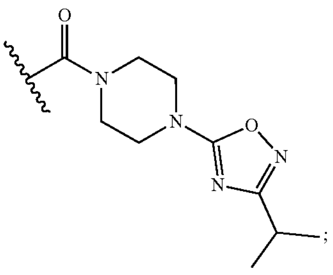
wherein four of R2, R3, R4, R5, and R6 must be hydrogen.
2. The compound of claim 1, wherein the compound is selected from the group consisting of:
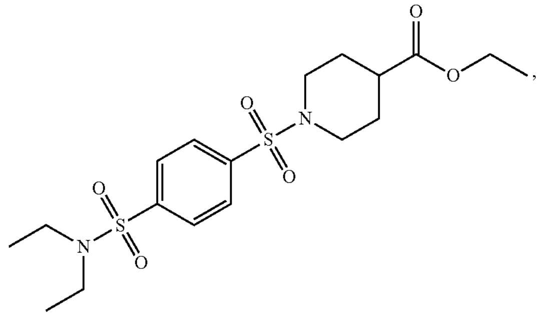
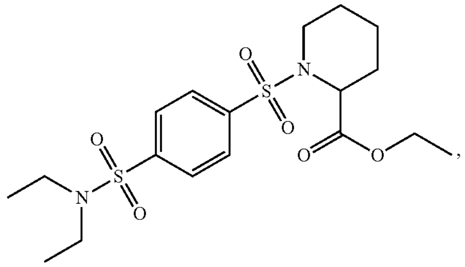
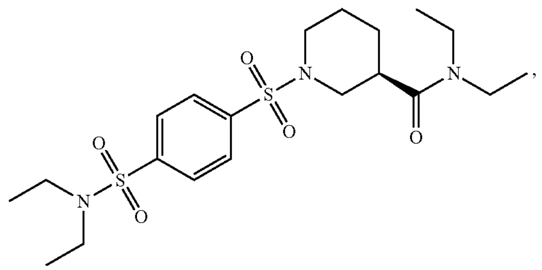
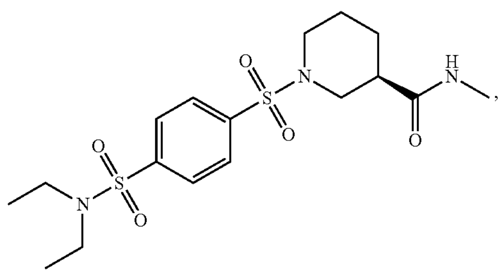
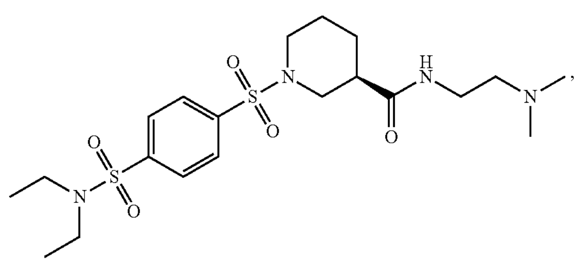
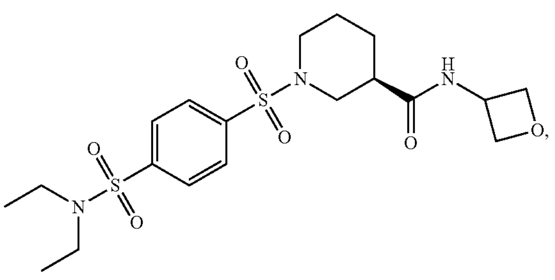

-continued
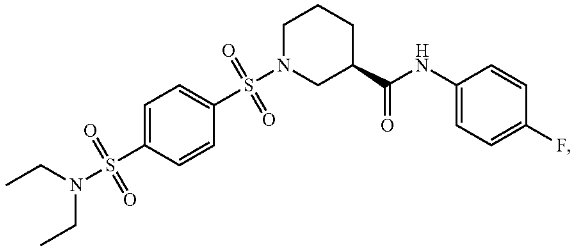
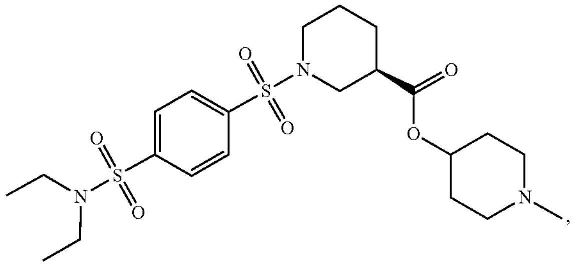
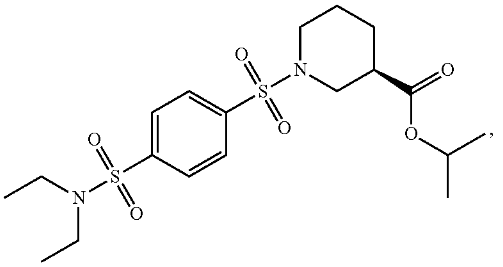
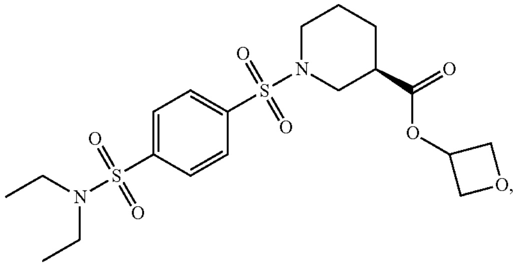
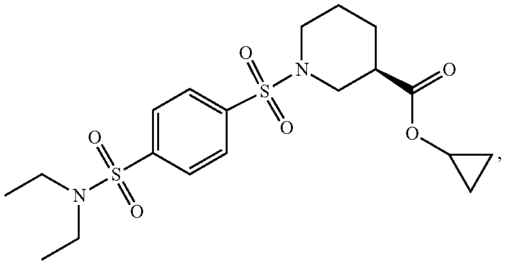
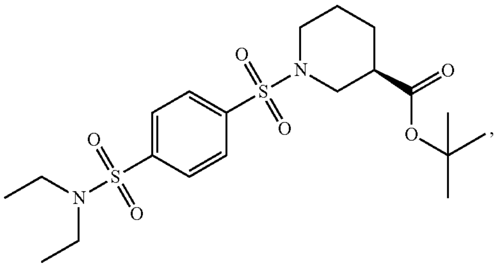
-continued
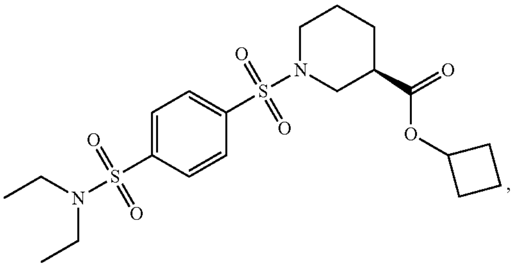
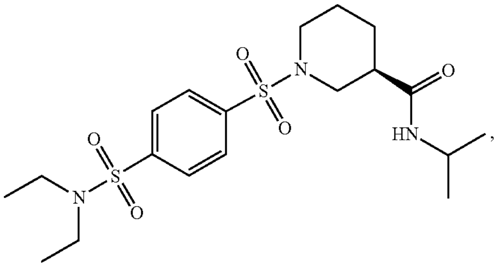
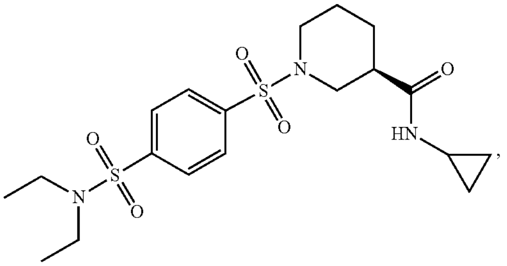
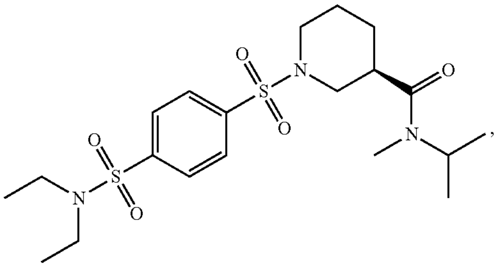
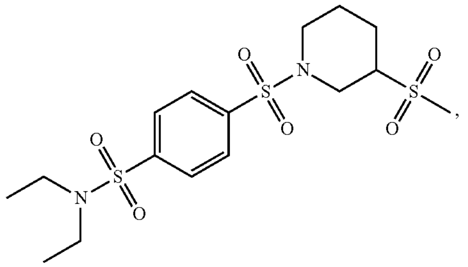
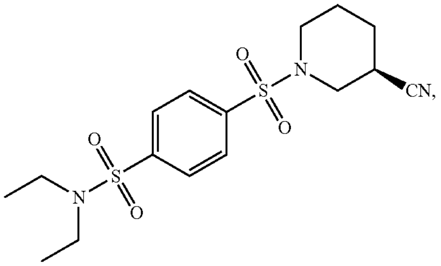

-continued
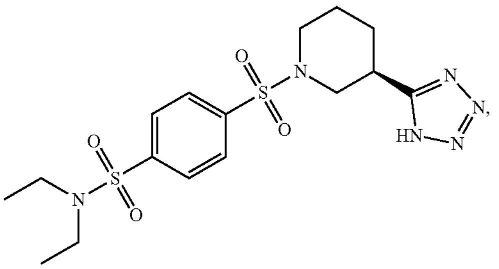
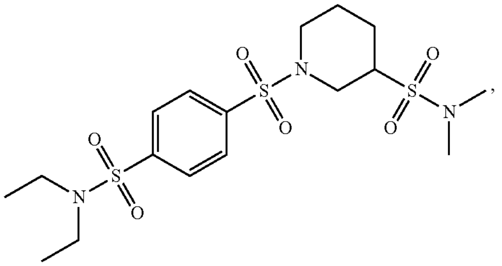
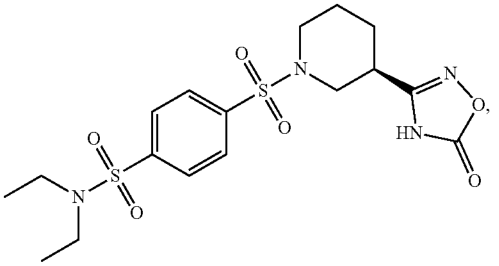
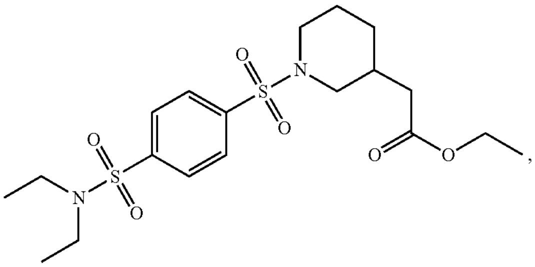
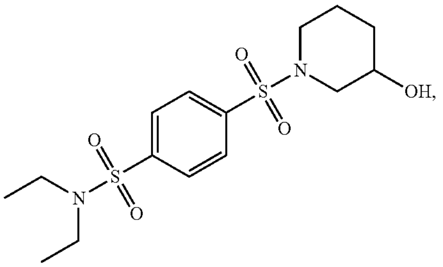
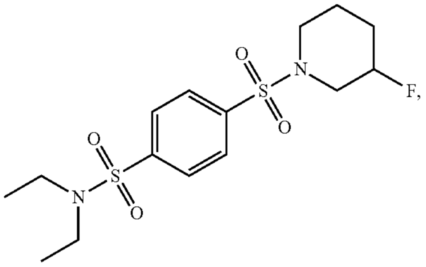
-continued
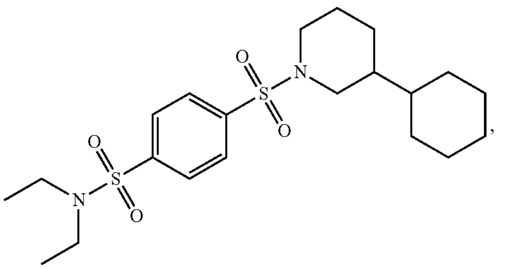
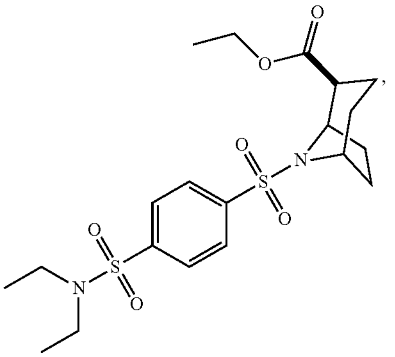
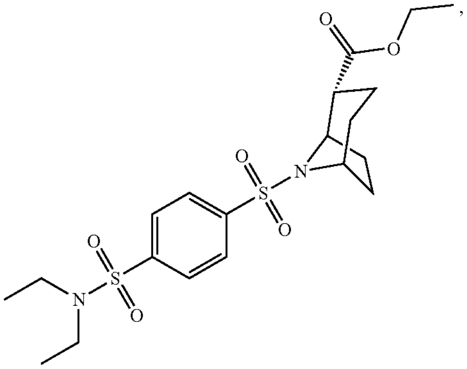
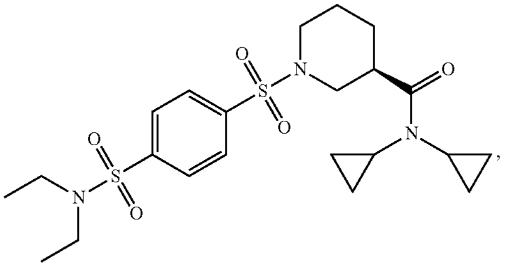
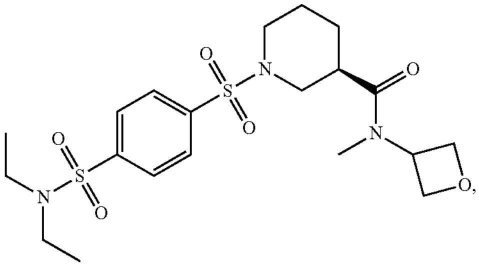

-continued
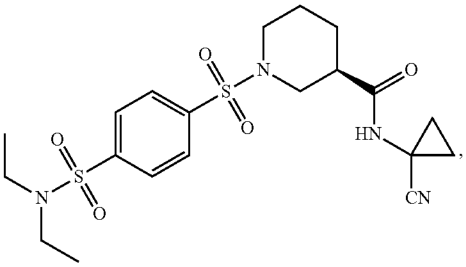
,
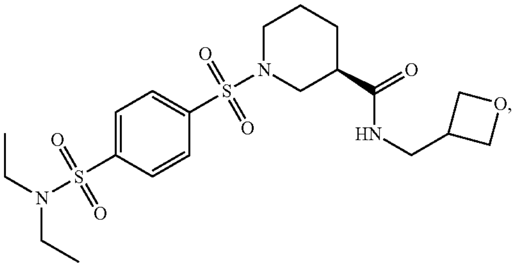
,
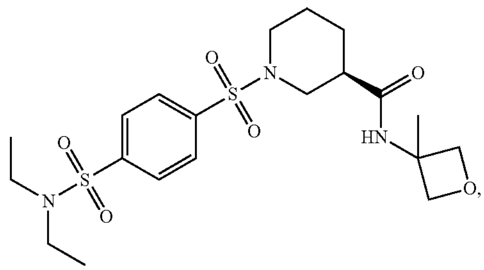
,
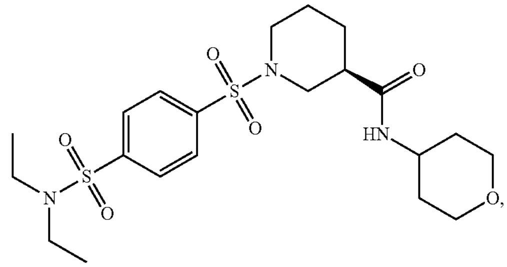
,
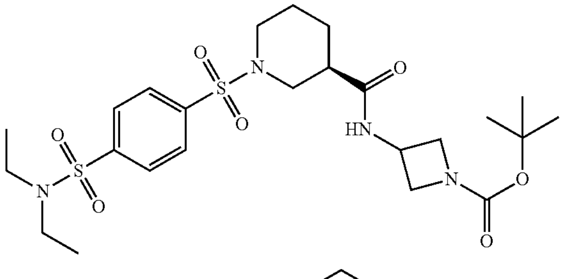
,
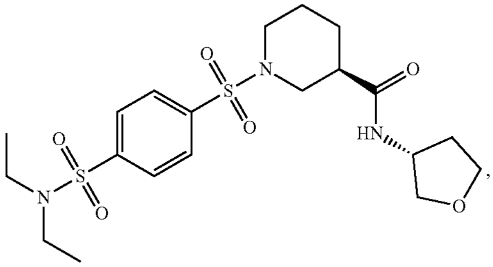
,
-continued
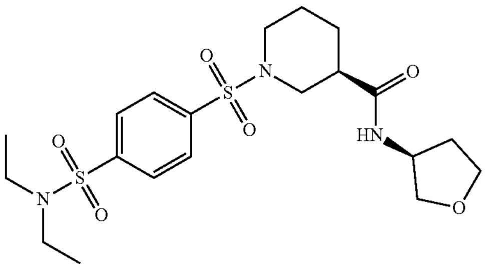
,
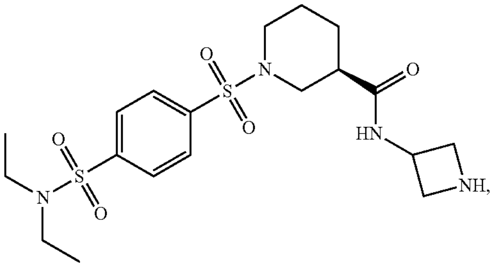
,
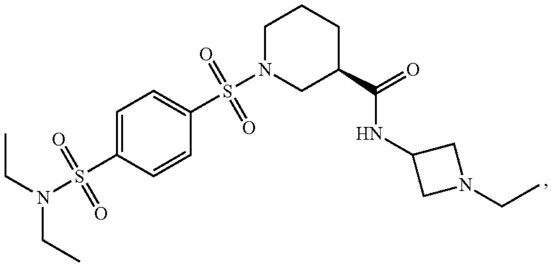
,
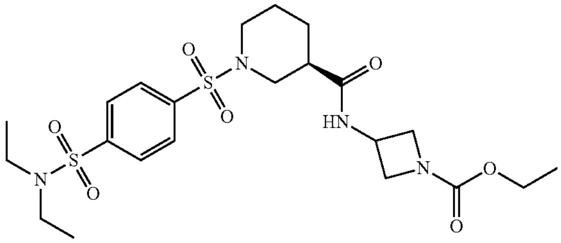
,
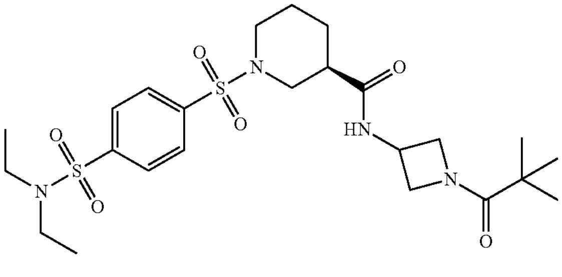
,
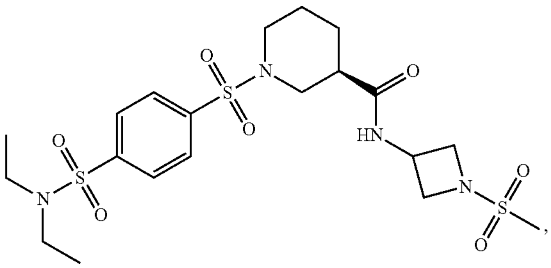
, -continued
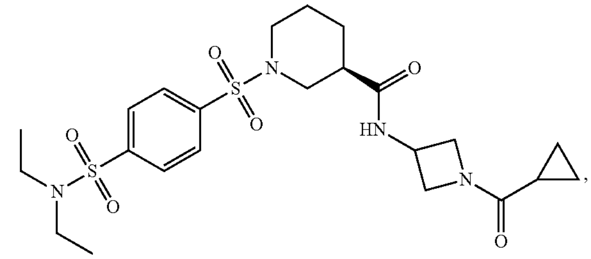
,
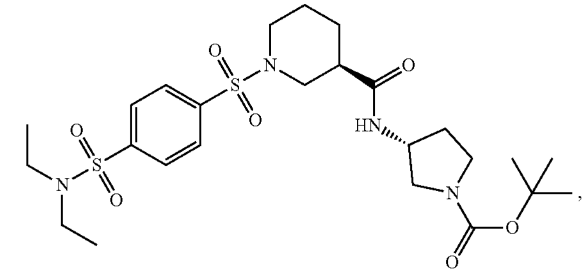
,
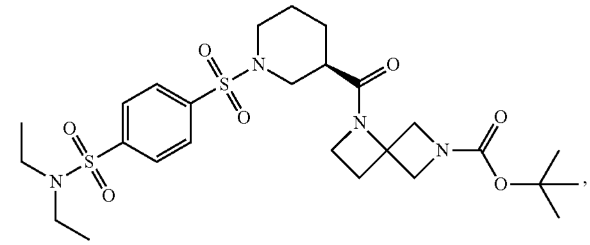
,
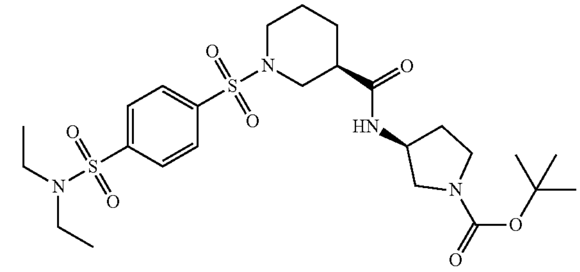
,
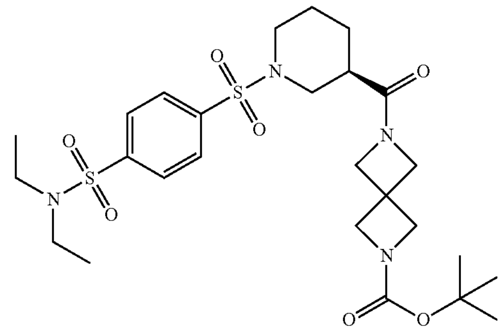
,
-continued
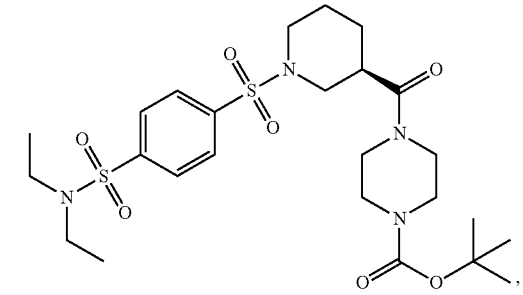
,
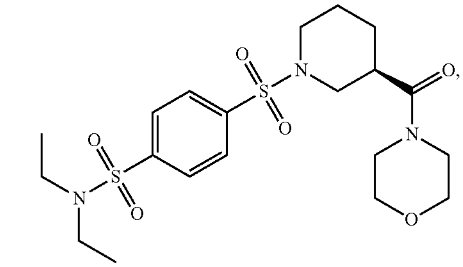
,
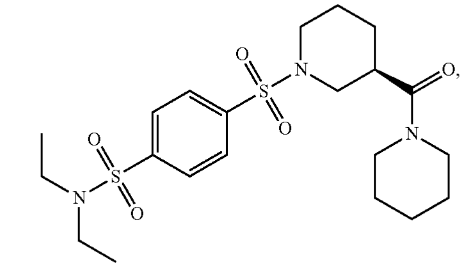
,
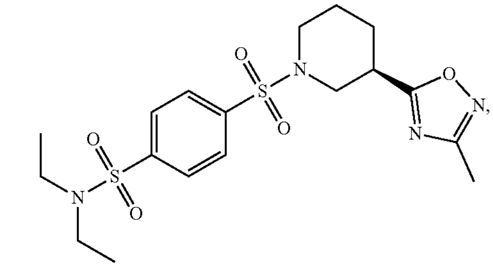
,
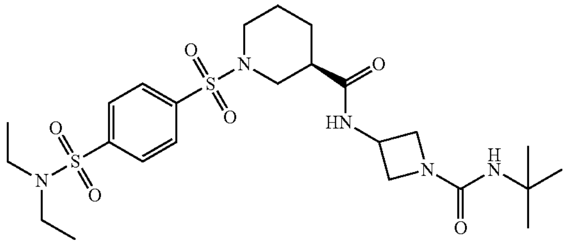
,
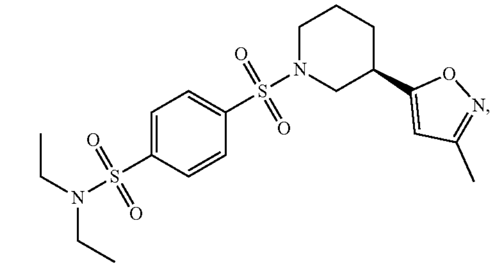
, -continued
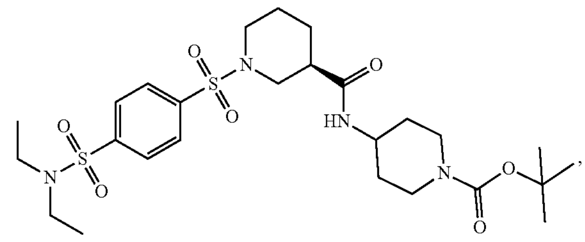,
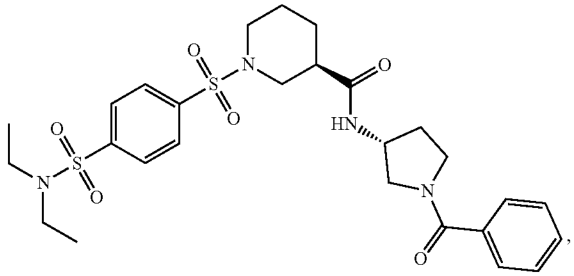,
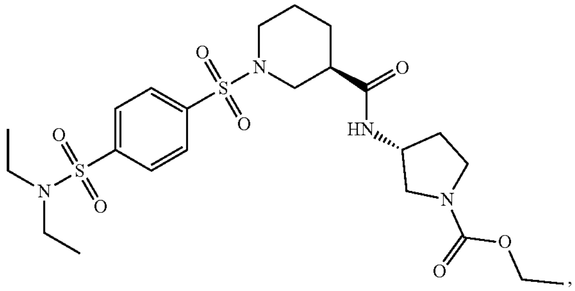,
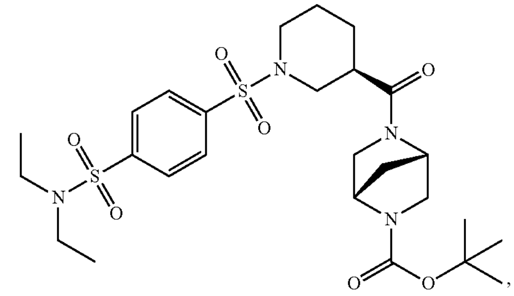,
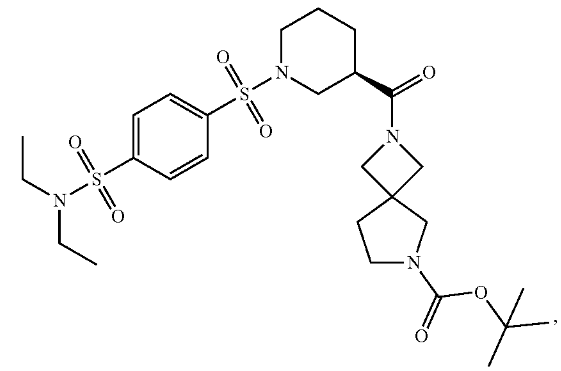,
-continued
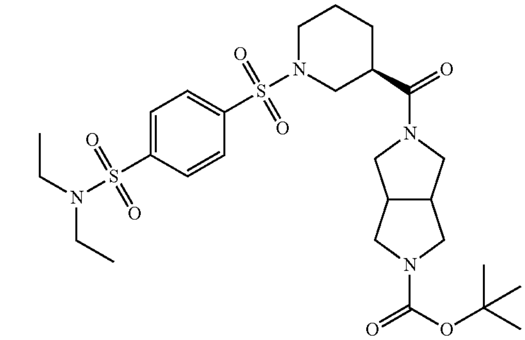,
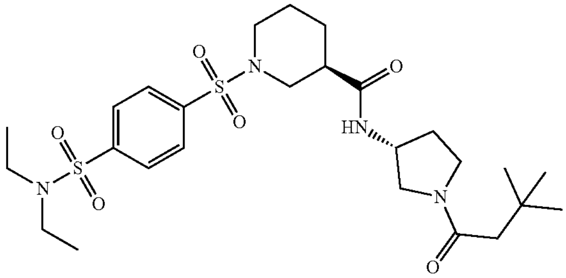,
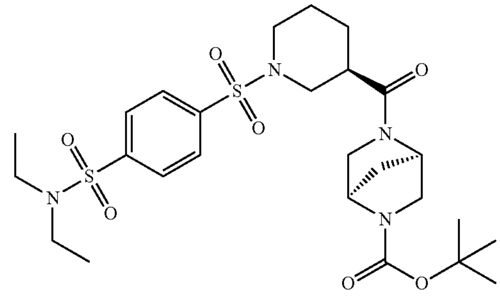,
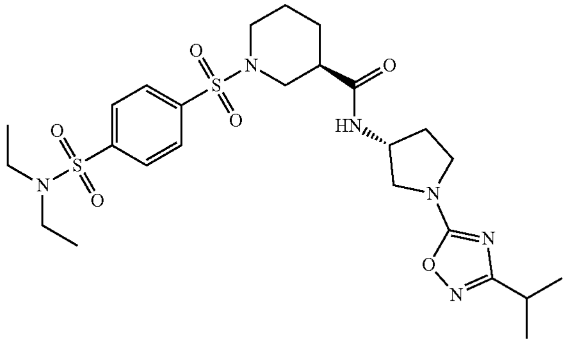,
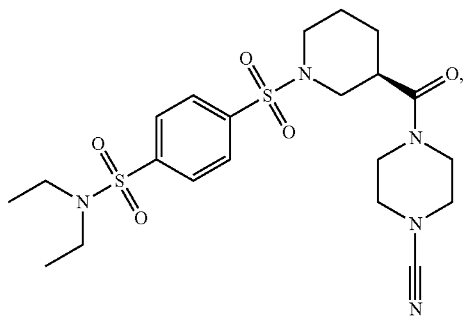, -continued
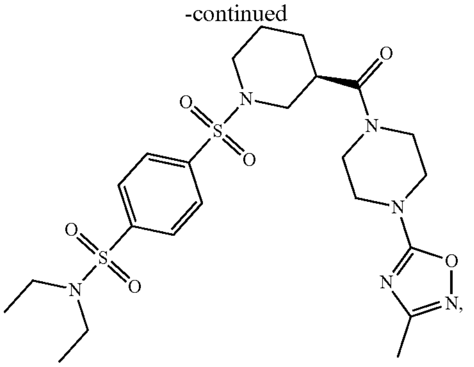
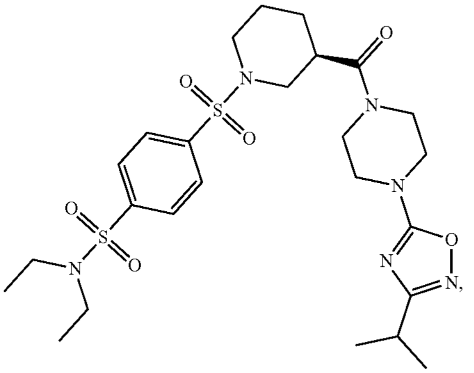
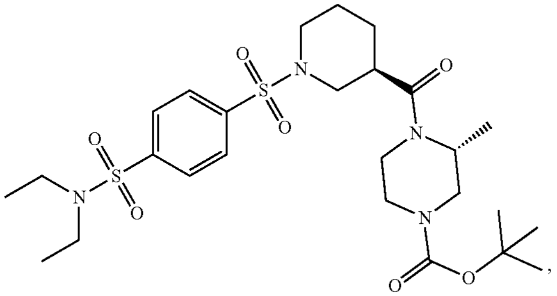
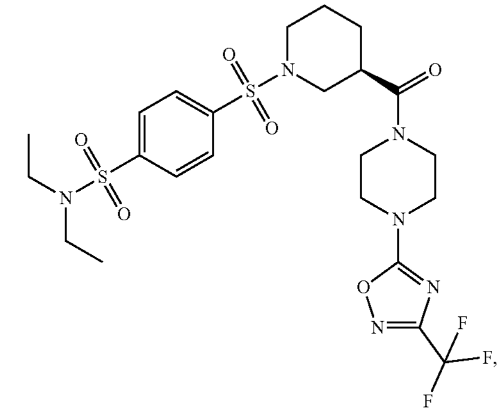
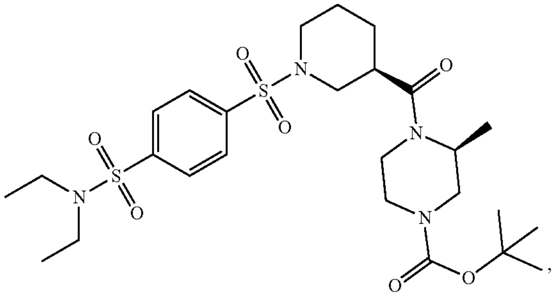
-continued
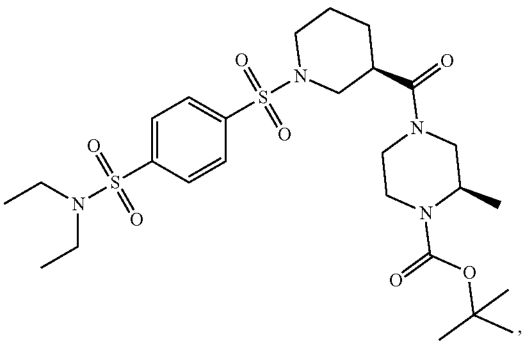
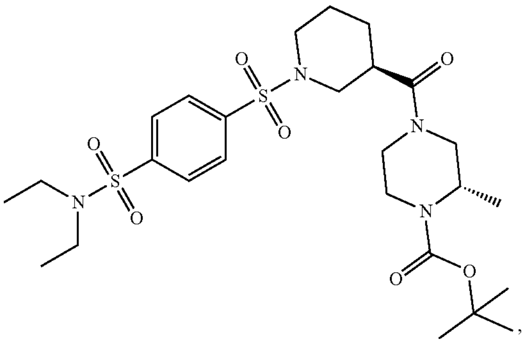
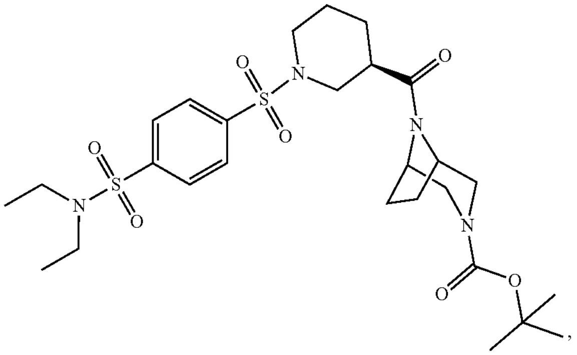
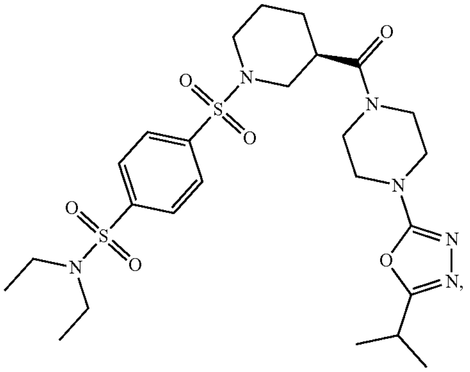

-continued
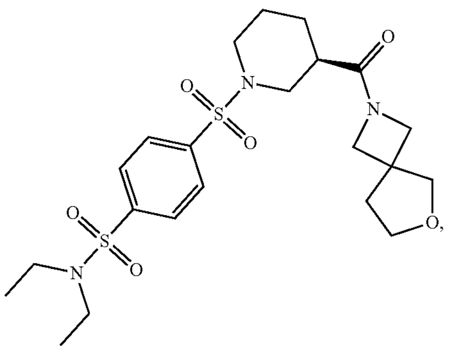
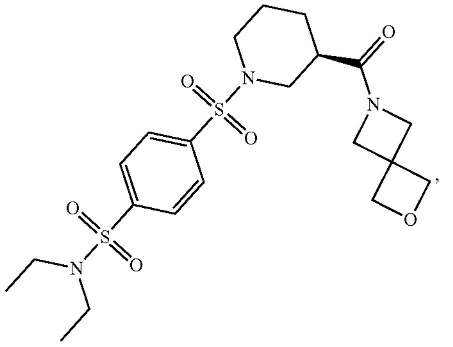
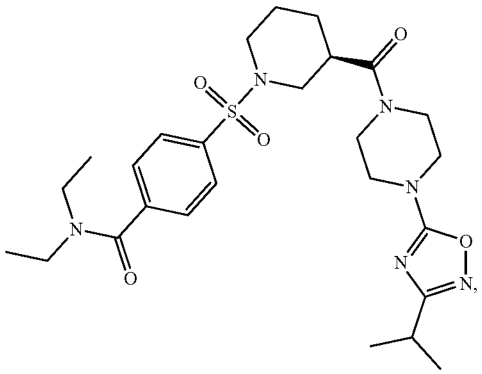
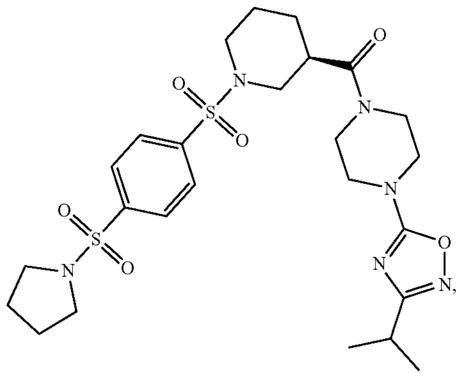
-continued
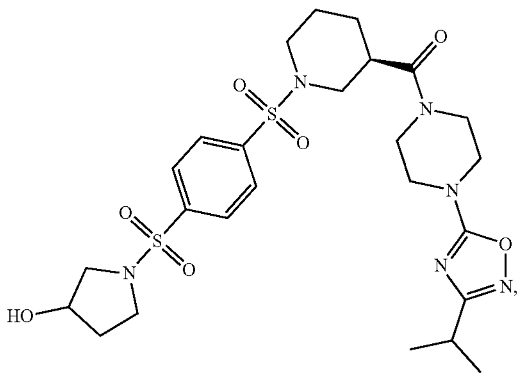
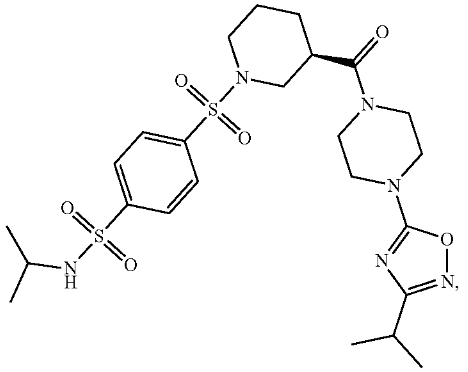
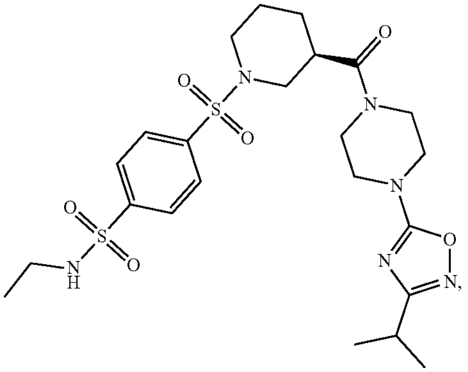
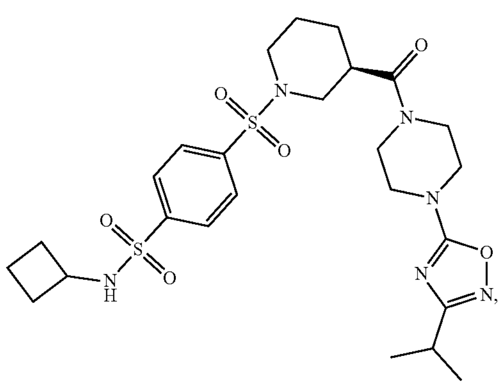

-continued
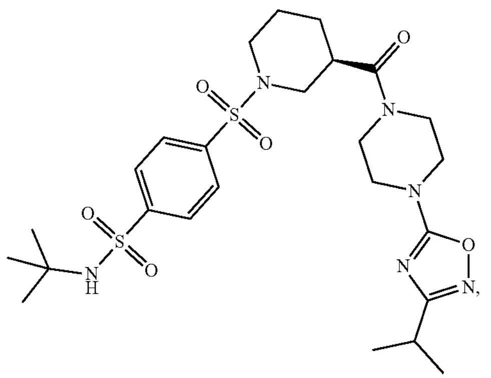
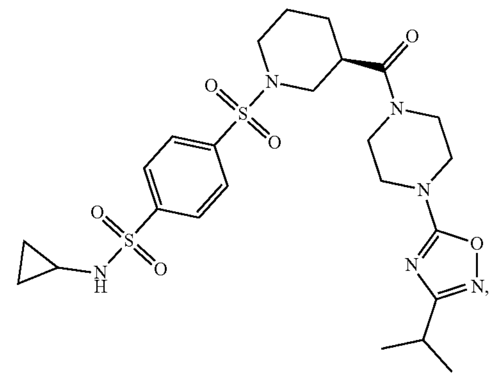
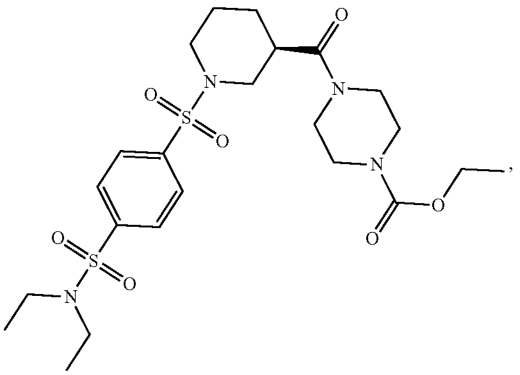
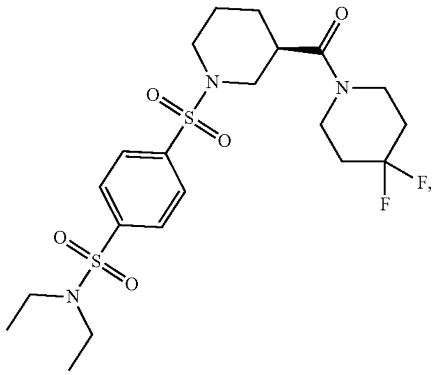
-continued
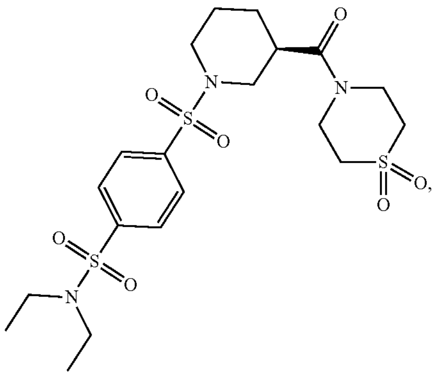
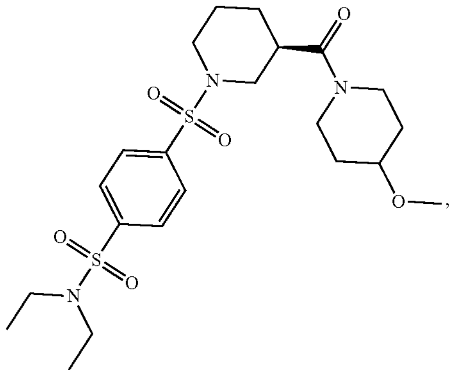
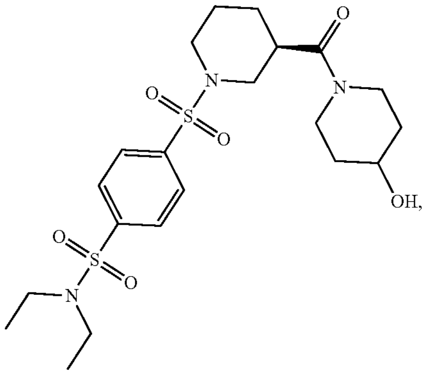
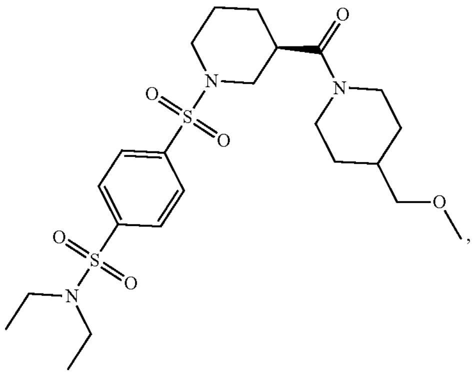

-continued
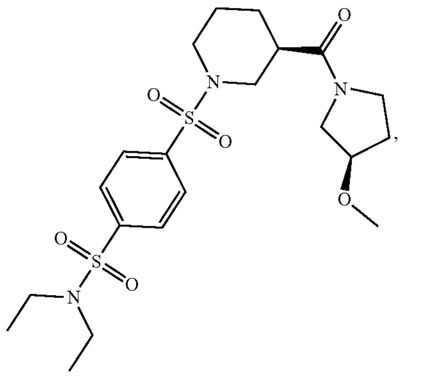
,
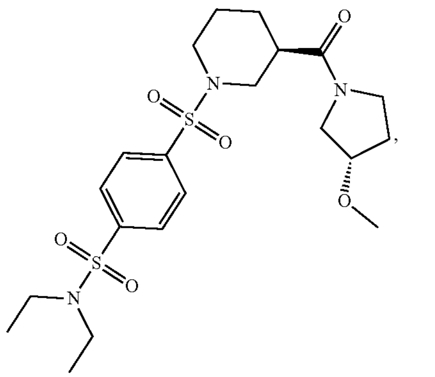
,
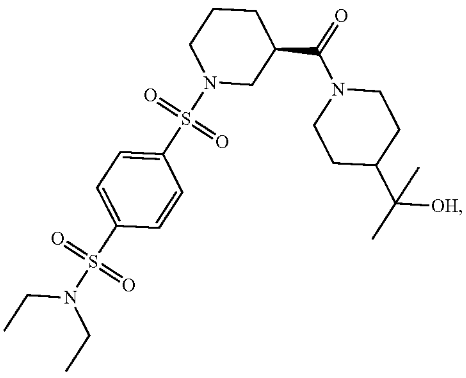
,
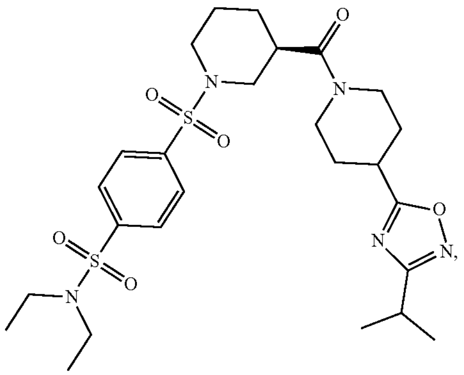
,
-continued
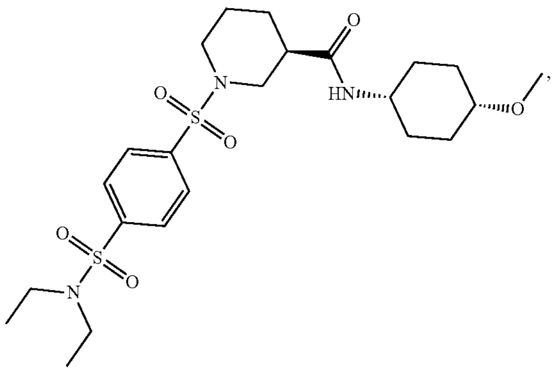
,
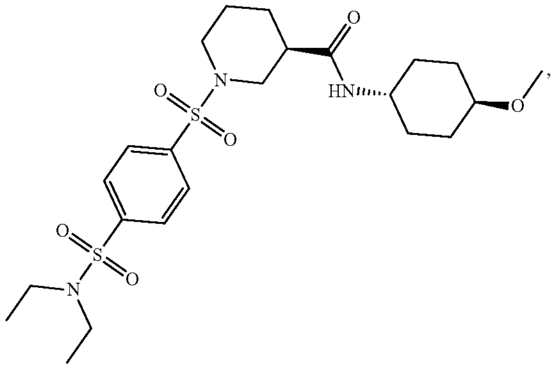
,
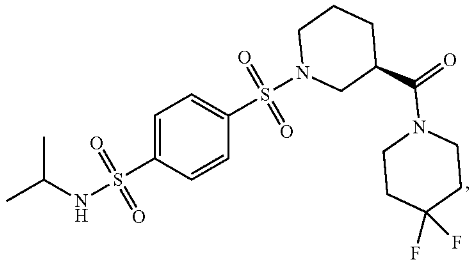
,
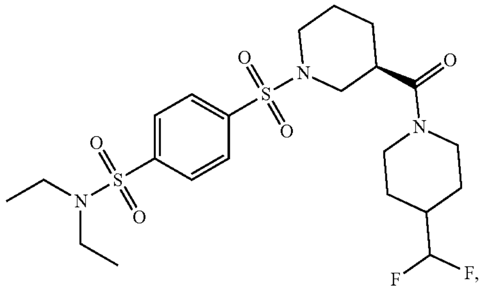
,
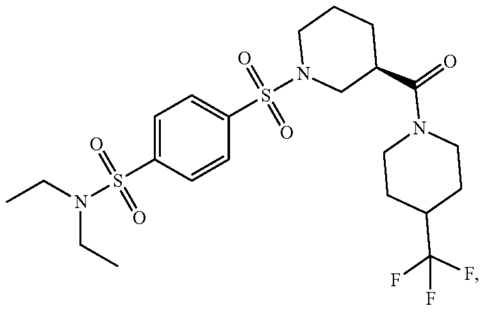
, -continued
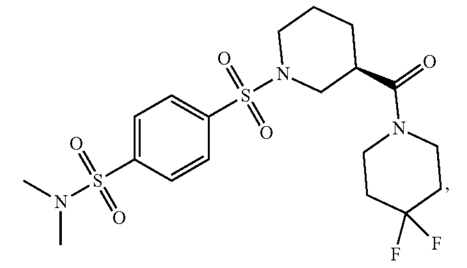
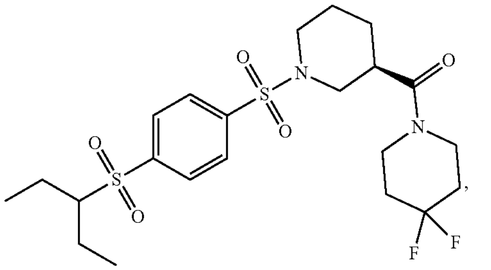
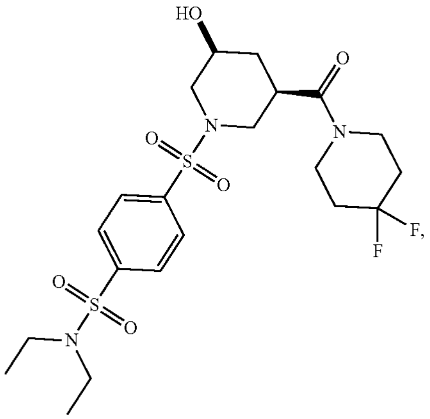
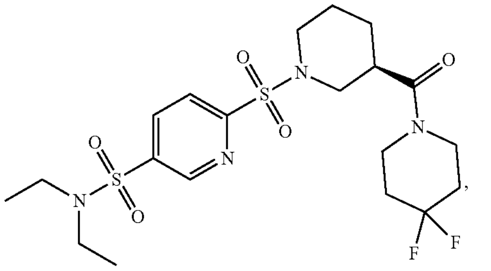
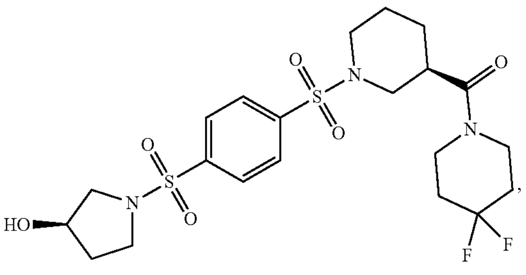
-continued
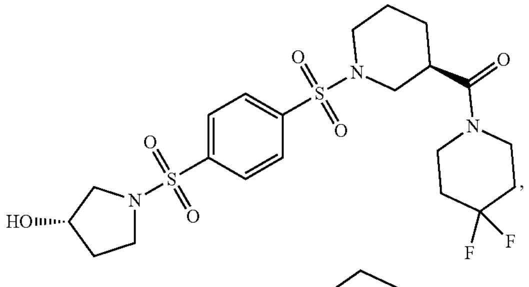
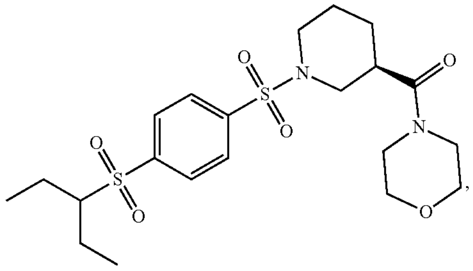
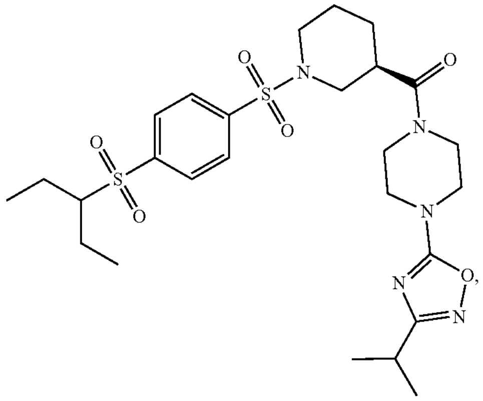
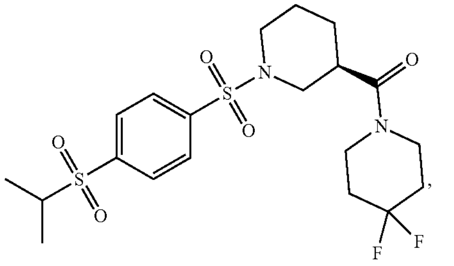
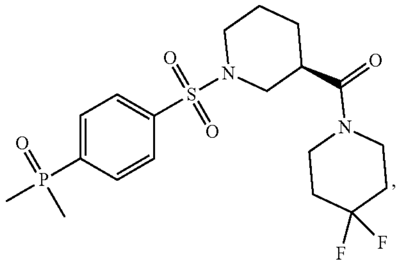
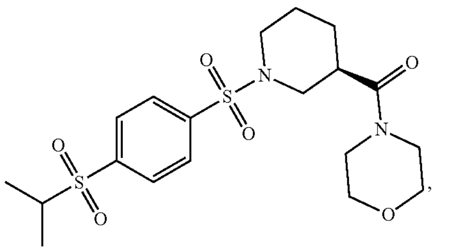

-continued
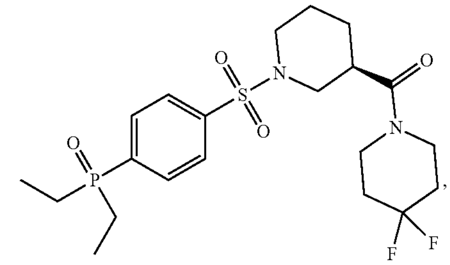
,
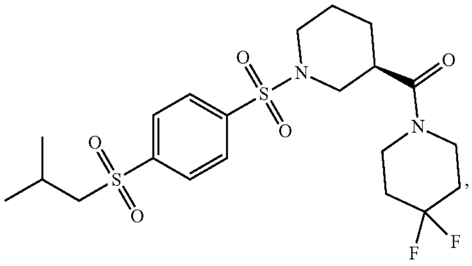
,
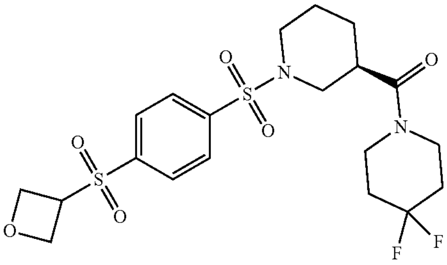
,
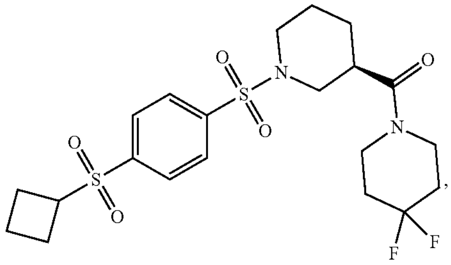
,
-continued
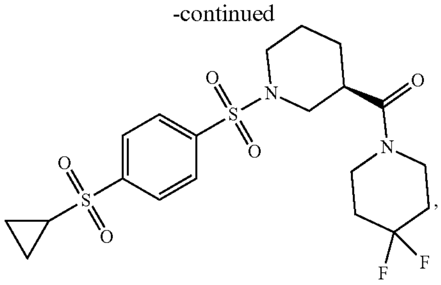
,
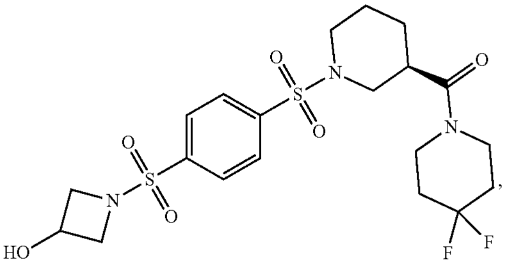
,
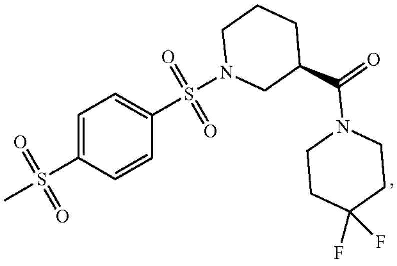
, and
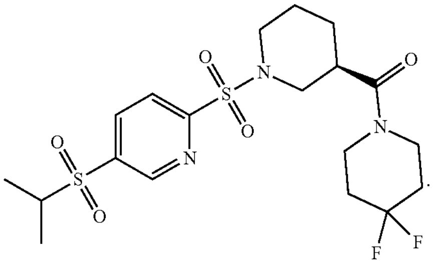
.
* * * * *